US009993520B2

(12) United States Patent
Kenney et al.

(10) Patent No.: US 9,993,520 B2
(45) Date of Patent: *Jun. 12, 2018

(54) VASOPRESSIN FORMULATIONS FOR USE IN TREATMENT OF HYPOTENSION

(71) Applicant: Par Pharmaceutical, Inc., Chestnut Ridge, NY (US)

(72) Inventors: Matthew Kenney, New Haven, MI (US); Vinayagam Kannan, Rochester, MI (US); Sunil Vandse, Basking Ridge, NJ (US); Suketu Sanghvi, Kendall Park, NJ (US)

(73) Assignee: Par Pharmaceutical, Inc., Chestnut Ridge, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/688,334

(22) Filed: Aug. 28, 2017

(65) Prior Publication Data

US 2018/0000891 A1    Jan. 4, 2018

Related U.S. Application Data

(63) Continuation of application No. 15/612,649, filed on Jun. 2, 2017, which is a continuation-in-part of application No. 15/426,693, filed on Feb. 7, 2017, now Pat. No. 9,744,209, which is a continuation-in-part of application No. 15/289,640, filed on Oct. 10, 2016, now Pat. No. 9,687,526, which is a continuation-in-part of application No. 14/717,877, filed on May 20, 2015, now Pat. No. 9,744,239, which is a continuation of application No. 14/610,499, filed on Jan. 30, 2015, now abandoned.

(51) Int. Cl.
| | |
|---|---|
| *A61K 38/11* | (2006.01) |
| *A61K 47/12* | (2006.01) |
| *A61K 47/10* | (2017.01) |
| *A61K 9/08* | (2006.01) |
| *A61K 31/045* | (2006.01) |
| *G01N 30/74* | (2006.01) |
| *A61K 9/00* | (2006.01) |
| *G01N 30/02* | (2006.01) |

(52) U.S. Cl.
CPC ............ *A61K 38/11* (2013.01); *A61K 9/0019* (2013.01); *A61K 9/08* (2013.01); *A61K 31/045* (2013.01); *A61K 47/10* (2013.01); *A61K 47/12* (2013.01); *G01N 30/74* (2013.01); *G01N 2030/027* (2013.01)

(58) Field of Classification Search
None
See application file for complete search history.

(56) References Cited

U.S. PATENT DOCUMENTS

| | | |
|---|---|---|
| 4,542,124 A | 9/1985 | Huffman et al. |
| 4,604,378 A | 8/1986 | Callahan et al. |
| 4,684,622 A | 8/1987 | Ali et al. |
| 4,746,508 A | 5/1988 | Carey et al. |
| 4,762,820 A | 8/1988 | Gavras |
| 4,764,378 A | 8/1988 | Keith et al. |
| 4,781,871 A | 11/1988 | West, III et al. |
| 5,042,975 A | 8/1991 | Chien et al. |
| 5,124,315 A | 6/1992 | Ceschel et al. |
| 5,192,741 A | 3/1993 | Orsolini et al. |
| 5,204,112 A | 4/1993 | Hope et al. |
| 5,225,212 A | 7/1993 | Martin et al. |
| 5,250,022 A | 10/1993 | Chien et al. |
| 5,252,263 A | 10/1993 | Hope et al. |
| 5,288,497 A | 2/1994 | Stanley et al. |
| 5,288,498 A | 2/1994 | Stanley et al. |
| 5,359,030 A | 10/1994 | Ekwuribe |
| 5,424,068 A | 6/1995 | Filip |
| 5,482,931 A | 1/1996 | Harris et al. |
| 5,698,516 A | 12/1997 | Nilsson et al. |
| 5,702,717 A | 12/1997 | Cha et al. |
| 5,770,559 A | 6/1998 | Manning et al. |
| 5,776,885 A | 7/1998 | Orsolini et al. |
| 5,785,989 A | 7/1998 | Stanley et al. |
| 5,811,399 A | 9/1998 | Khavinson et al. |
| 5,889,110 A | 3/1999 | Hutchinson |
| 5,902,790 A | 5/1999 | Green et al. |
| 5,972,894 A | 10/1999 | Sinackevich et al. |
| 5,981,474 A | 11/1999 | Manning et al. |
| 5,989,857 A | 11/1999 | Mundschenk |
| 6,004,573 A | 12/1999 | Rathi et al. |
| 6,034,175 A | 3/2000 | Hutchinson |
| 6,086,918 A | 7/2000 | Stern et al. |
| 6,117,949 A | 9/2000 | Rathi et al. |
| 6,143,722 A | 11/2000 | Melin et al. |
| 6,174,547 B1 | 1/2001 | Dong et al. |

(Continued)

OTHER PUBLICATIONS

FDA Label for Vasostrict® (vasopressin injection) downloaded from www.fda.gov, published May 7, 2015.*
FDA label for Vasostrict® (vasopressin injection) downloaded from www.fda.gov,published on Dec. 21, 2016.*
Center for Drug Evaluation and Research, Application No. 204485Orig1s000, Other Action Letters, Jul. 19, 2013, pp. 1-7, downloaded from www.accessdatafda.gov/drugsatfda_docs/nda/2014/204485Orig1s000Otheractionltrs.pdf on Feb. 12, 2018 (Year: 2013).*
FDA Label for VASOSTRICT(R) (Vasopressin injection, USP) revised Dec. 2016, downloaded from www.accessdata.fda.gov/drugsatfda_docs/label/2016/204485s004lbl.pdf on Feb. 12, 2018 (Year: 2016).*
AHFS Drug Information. Vasopressin. Pituitary. 2011; 68:28, 3261-3263.

(Continued)

*Primary Examiner* — Christina Bradley
(74) *Attorney, Agent, or Firm* — Wilson Sonsini Goodrich & Rosati

(57) ABSTRACT

Provided herein are peptide formulations comprising polymers as stabilizing agents. The peptide formulations can be more stable for prolonged periods of time at temperatures higher than room temperature when formulated with the polymers. The polymers used in the present invention can decrease the degradation of the constituent peptides of the peptide formulations.

14 Claims, 62 Drawing Sheets

(56) References Cited

U.S. PATENT DOCUMENTS

| | | |
|---|---|---|
| 6,180,608 B1 | 1/2001 | Gefter et al. |
| 6,187,756 B1 | 2/2001 | Lee et al. |
| 6,201,072 B1 | 3/2001 | Rathi et al. |
| 6,264,981 B1 | 7/2001 | Zhang et al. |
| 6,287,588 B1 | 9/2001 | Shih et al. |
| 6,589,549 B2 | 7/2003 | Shih et al. |
| 6,592,894 B1 | 7/2003 | Zarif et al. |
| 6,630,486 B1 | 10/2003 | Royer |
| 6,720,001 B2 | 4/2004 | Chen et al. |
| 6,740,333 B2 | 5/2004 | Beckett et al. |
| 6,811,689 B2 | 11/2004 | Zhang et al. |
| 6,814,870 B2 | 11/2004 | Zhang et al. |
| 6,821,249 B2 | 11/2004 | Casscells et al. |
| 6,841,617 B2 | 1/2005 | Jeong et al. |
| 6,949,509 B2 | 9/2005 | Woodrow |
| 6,967,028 B2 | 11/2005 | Dulieu et al. |
| 6,991,798 B1 | 1/2006 | Gschneidner et al. |
| 6,998,137 B2 | 2/2006 | Shih et al. |
| 7,074,775 B2 | 7/2006 | Miller et al. |
| 7,087,244 B2 | 8/2006 | Jeong et al. |
| 7,135,190 B2 | 11/2006 | Piao et al. |
| 7,151,084 B2 | 12/2006 | Miller et al. |
| 7,157,421 B2 | 1/2007 | Miller et al. |
| 7,186,414 B2 | 3/2007 | Gschneidner et al. |
| 7,402,652 B2 | 7/2008 | Miller et al. |
| 7,498,044 B2 | 3/2009 | Petereit et al. |
| 7,504,407 B2 | 3/2009 | Castelhano et al. |
| 7,538,092 B2 | 5/2009 | Orlando et al. |
| 7,713,705 B2 | 5/2010 | Buechler et al. |
| 7,714,918 B2 | 5/2010 | Kuroda |
| 7,744,910 B2 | 6/2010 | Gschneidner et al. |
| 7,767,656 B2 | 8/2010 | Shoichet et al. |
| 7,807,397 B2 | 10/2010 | Bergmann et al. |
| 7,833,546 B2 | 11/2010 | Petereit et al. |
| 7,840,263 B2 | 11/2010 | Girouard et al. |
| 7,884,079 B2 | 2/2011 | Miller et al. |
| 7,899,527 B2 | 3/2011 | Yun et al. |
| 7,960,336 B2 | 6/2011 | Castillo et al. |
| 7,964,219 B2 | 6/2011 | Li et al. |
| 8,030,297 B2 | 10/2011 | Lichter et al. |
| 8,075,916 B2 | 12/2011 | Song et al. |
| 8,075,919 B2 | 12/2011 | Brown et al. |
| 8,093,207 B2 | 1/2012 | Stern |
| 8,183,004 B2 | 5/2012 | Bergmann et al. |
| 8,202,838 B2 | 6/2012 | Yeomans et al. |
| 8,252,745 B2 | 8/2012 | Yeomans et al. |
| 8,257,740 B1 | 9/2012 | Sung et al. |
| 8,263,125 B2 | 9/2012 | Vaya et al. |
| 8,268,352 B2 | 9/2012 | Vaya et al. |
| 8,277,830 B2 | 10/2012 | De Juan, Jr. et al. |
| 8,283,317 B1 | 10/2012 | Sung et al. |
| 8,287,888 B2 | 10/2012 | Song et al. |
| 8,293,726 B2 | 10/2012 | Habib et al. |
| 8,354,506 B2 | 1/2013 | Bergmann et al. |
| 8,361,022 B2 | 1/2013 | Ameri et al. |
| 8,399,006 B2 | 3/2013 | De Juan, Jr. et al. |
| 8,513,188 B2 | 8/2013 | Botti |
| 8,518,444 B2 | 8/2013 | Kissel et al. |
| 8,663,155 B2 | 3/2014 | Cormier et al. |
| 8,679,540 B2 | 3/2014 | Bonnet-Gonnet et al. |
| 8,764,733 B2 | 7/2014 | Imran |
| 8,846,606 B2 | 9/2014 | Quintin |
| 8,846,770 B2 | 9/2014 | Lichter et al. |
| 8,889,366 B2 | 11/2014 | Struck et al. |
| 8,920,817 B2 | 12/2014 | Armeri et al. |
| 9,375,478 B1 | 6/2016 | Kenney et al. |
| 9,687,526 B2 | 6/2017 | Kenney et al. |
| 9,744,209 B2 | 8/2017 | Kenney et al. |
| 9,744,239 B2 | 8/2017 | Kenney et al. |
| 9,750,785 B2 | 9/2017 | Kenney et al. |
| 2002/0198315 A1 | 12/2002 | Hutchinson |
| 2003/0051266 A1 | 3/2003 | Serafini |
| 2003/0106074 A1 | 6/2003 | Serafini |
| 2003/0121067 A1 | 6/2003 | Brennan et al. |
| 2003/0139427 A1 | 7/2003 | Castelhano |
| 2003/0147812 A1 | 8/2003 | Ueberle |
| 2003/0157717 A1 | 8/2003 | Draghia-Akli |
| 2003/0216302 A1 | 11/2003 | Bhowmick et al. |
| 2003/0228355 A1 | 12/2003 | Zarif et al. |
| 2004/0013609 A1 | 1/2004 | Trier |
| 2004/0043076 A1 | 3/2004 | Dulieu et al. |
| 2004/0077540 A1 | 4/2004 | Quay |
| 2004/0086494 A1 | 5/2004 | John |
| 2004/0146551 A1 | 7/2004 | Mannino et al. |
| 2004/0219208 A1 | 11/2004 | Kawamura et al. |
| 2005/0013854 A1 | 1/2005 | Mannino et al. |
| 2005/0089873 A1 | 4/2005 | Tai et al. |
| 2005/0143378 A1 | 6/2005 | Yun et al. |
| 2005/0148029 A1 | 7/2005 | Buechler et al. |
| 2005/0164238 A1 | 7/2005 | Valkirs et al. |
| 2005/0186265 A1 | 8/2005 | Zarif et al. |
| 2005/0272815 A1 | 12/2005 | Leone-Bay et al. |
| 2005/0282896 A1 | 12/2005 | Lopaschuk et al. |
| 2006/0034889 A1 | 2/2006 | Jo et al. |
| 2006/0093658 A1 | 5/2006 | Sathyan et al. |
| 2006/0193825 A1 | 8/2006 | Musso et al. |
| 2006/0194878 A1 | 8/2006 | Lopaschuk et al. |
| 2006/0293243 A1 | 12/2006 | Puri et al. |
| 2007/0054843 A1 | 3/2007 | Yeomans et al. |
| 2007/0059285 A1 | 3/2007 | Samaritani et al. |
| 2007/0092911 A1 | 4/2007 | Buechler et al. |
| 2007/0154482 A1 | 7/2007 | Sukhatme et al. |
| 2007/0190047 A1 | 8/2007 | Brych et al. |
| 2007/0292391 A1 | 12/2007 | Samaritani et al. |
| 2008/0015265 A1 | 1/2008 | Rubin et al. |
| 2008/0026014 A1 | 1/2008 | Michel |
| 2008/0125361 A1 | 5/2008 | Ludvigsen et al. |
| 2008/0152675 A1 | 6/2008 | Pouliquen |
| 2008/0188449 A1 | 8/2008 | Crews et al. |
| 2008/0193545 A1 | 8/2008 | Richard et al. |
| 2008/0194942 A1 | 8/2008 | Cumpson et al. |
| 2008/0221039 A1 | 9/2008 | Gibson et al. |
| 2009/0022683 A1 | 1/2009 | Song et al. |
| 2009/0192177 A1 | 7/2009 | Castelhano et al. |
| 2009/0220455 A1 | 9/2009 | Chilkoti |
| 2009/0280103 A1 | 11/2009 | Flueck |
| 2009/0280169 A1 | 11/2009 | Leonard |
| 2009/0298711 A1 | 12/2009 | Russell et al. |
| 2009/0306137 A1 | 12/2009 | Wolfgang et al. |
| 2010/0062981 A1 | 3/2010 | Jeppsson et al. |
| 2010/0221243 A1 | 9/2010 | Sukhatme et al. |
| 2010/0234276 A1 | 9/2010 | Mizushima et al. |
| 2010/0273709 A1 | 10/2010 | Aston et al. |
| 2010/0311642 A1 | 12/2010 | J-M.Riviere et al. |
| 2011/0008911 A1 | 1/2011 | Bergmann et al. |
| 2011/0071216 A1 | 3/2011 | Fowers et al. |
| 2011/0114087 A1 | 5/2011 | Djupesland et al. |
| 2011/0237508 A1 | 9/2011 | Amorij et al. |
| 2011/0297147 A1 | 12/2011 | Lick et al. |
| 2011/0303871 A1 | 12/2011 | Burba et al. |
| 2012/0093866 A1 | 4/2012 | Burger et al. |
| 2012/0121517 A1 | 5/2012 | Song et al. |
| 2012/0282227 A1 | 11/2012 | Katz |
| 2013/0011378 A1 | 1/2013 | Yang et al. |
| 2013/0028930 A1 | 1/2013 | Plumridge et al. |
| 2013/0040884 A1 | 2/2013 | Lau et al. |
| 2013/0041241 A1 | 2/2013 | Felts et al. |
| 2013/0115231 A1 | 5/2013 | Hong et al. |
| 2013/0122515 A1 | 5/2013 | Bergmann et al. |
| 2013/0189230 A1 | 7/2013 | Shoichet et al. |
| 2013/0224248 A1 | 8/2013 | Taylor et al. |
| 2013/0296324 A1 | 11/2013 | Held |
| 2014/0051628 A1 | 2/2014 | Castillo et al. |
| 2014/0161892 A1 | 6/2014 | Salman et al. |
| 2014/0171369 A1 | 6/2014 | Moberg et al. |
| 2014/0206752 A1 | 7/2014 | Afeyan et al. |
| 2014/0207104 A1 | 7/2014 | Vouillamoz et al. |
| 2014/0220063 A1 | 8/2014 | Asari et al. |
| 2014/0221442 A1 | 8/2014 | Bacha et al. |
| 2014/0249083 A1 | 9/2014 | Shingel et al. |
| 2014/0249484 A1 | 9/2014 | Jones et al. |
| 2014/0251859 A1 | 9/2014 | Weikart et al. |

(56) References Cited

U.S. PATENT DOCUMENTS

| | | |
|---|---|---|
| 2014/0329747 A1 | 11/2014 | Tidmarsh et al. |
| 2017/0157203 A1 | 6/2017 | Kenney et al. |

OTHER PUBLICATIONS

Alten, et al. Early initiation of arginine vasopressin infusion in neonates after complex cardiac surgery. Pediatr Crit Care Med. May 2012;13(3):300-4. doi: 10.1097/PCC.0b013e31822f1753.

Angus, et al. Epidemiology of severe sepsis in the United States: analysis of incidence, outcome, and associated costs of care. Crit Care Med. Jul. 2001;29(7):1303-10.

Argenziano, et al. A prospective randomized trial of arginine vasopressin in the treatment of vasodilatory shock after left ventricular assist device placement. Circulation. Nov. 4, 1997;96(9 Suppl):II-286-90.

Argenziano, et al. Arginine vasopressin in the management of vasodilatory hypotension after cardiac transplantation. J Heart Lung Transplant. Aug. 1999;18(8):814-7.

Argenziano, et al. Management of vasodilatory shock after cardiac surgery: identification of predisposing factors and use of a novel pressor agent. J Thorac Cardiovasc Surg. Dec. 1998; 116(6):973-80.

Barr, et al. Similarity of arterial and intravenous vasopressin on portal and systemic hemodynamics. Gastroenterology. Jul. 1975;69(1):13-9.

Bauer, et al. Arginine vasopressin for the treatment of septic shock in adults. Pharmacotherapy. Oct. 2010;30(10):1057-71. doi: 10.1592/phco.30.10.1057.

Bauer, et al. Effect of corticosteroids on arginine vasopressin-containing vasopressor therapy for septic shock: a case control study. J Crit Care. Dec. 2008;23(4):500-6. doi: 10.1016/j.jcrc.2008.04.002. Epub Jun. 30, 2008.

Benedini, et al. New antianginal nitro esters with reduced hypotensive activity. Synthesis and pharmacological evaluation of 3-[(nitrooxy)alkyl]-2H-1,3-benzoxazin-4(3H)-ones. J Med Chem. Jan. 6, 1995;38(1):130-6.

Botox Preparation,storage and injection technique, Jul. 23, 2003.

Breslow, et al. Quantitative effects of antihydrophobic agents on binding constants and solubilities in water. Proc Natl Acad Sci U S A. Aug. 1, 1992;89(15):6916-8.

Brierley, et al. Clinical practice parameters for hemodynamic support of pediatric and neonatal septic shock: 2007 update from the American College of Critical Care Medicine. Crit Care Med. Feb. 2009;37(2):666-88. doi: 10.1097/CCM.0b013e31819323c6.

Brun-Buisson. The epidemiology of the systemic inflammatory response. Intensive Care Med. 2000;26 Suppl 1:S64-74.

Buck, M. Low-dose Vasopressin Infusions for Vasodilatory Shock, Pediatric Pharmacotherapy, A Monthly Newsletter for Health Care Professionals from the Children's Medical Center at the University of Virginia, (2003), 9(9), pp. 1-4.

Burbach, et al. Difference in susceptibility of arginine-vasopressin and oxytocin to aminopeptidase activity in brain synaptic membranes. Biochem Biophys Res Commun. Oct. 15, 1982;108(3):1165-71.

Cetrotide® Cetrorelix acetate Consumer Medicine Information, Apr. 2011.

Chang, et al., Practical approaches to protein formulation development, Rational Design of stable protein in formulations, edited by Carpenter and Manning. Kluwer Academic/Plenum Publishers, New York, 2002, pp. 1-25.

Choong, et al. Vasopressin in pediatric shock and cardiac arrest. Pediatr Crit Care Med. Jul. 2008;9(4):372-9. doi: 10.1097/PCC.0b013e318172d7c8.

Choong, et al. Vasopressin in pediatric vasodilatory shock: a multicenter randomized controlled trial. Am J Respir Crit Care Med. Oct. 1, 2009;180(7):632-9. doi: 10.1164/rccm.200902-0221OC. Epub Jul. 16, 2009.

Co-pending U.S. Appl. No. 14/610,488, filed Jan. 30, 2015.
Co-pending U.S. Appl. No. 14/610,499, filed Jan. 30, 2015.
Co-pending U.S. Appl. No. 14/610,579, filed Jan. 30, 2015.
Co-pending U.S. Appl. No. 14/610,594, filed Jan. 30, 2015.
Co-pending U.S. Appl. No. 15/606,442, filed May 26, 2017.
Co-pending U.S. Appl. No. 15/612,649, filed Jun. 2, 2017.
Co-pending U.S. Appl. No. 15/688,305, filed Aug. 28, 2017.
Co-pending U.S. Appl. No. 15/688,314, filed Aug. 28, 2017.
Co-pending U.S. Appl. No. 15/688,322, filed Aug. 28, 2017.
Co-pending U.S. Appl. No. 15/688,326, filed Aug. 28, 2017.
Co-pending U.S. Appl. No. 15/688,330, filed Aug. 28, 2017.
Co-pending U.S. Appl. No. 15/688,336, filed Aug. 28, 2017.
Co-pending U.S. Appl. No. 15/688,338, filed Aug. 28, 2017.
Co-pending U.S. Appl. No. 15/688,341, filed Aug. 28, 2017.

Czaczkes, et al. Physiologic Studies of Antidiuretic Hormone by Its Direct Measurement in Human Plasma. J Clin Invest. Aug. 1964;43:1625-40.

Dahlborn, et al. Effects of dehydration and arginine vasopressin infusions on the production of milk and the morphology of the goat udder. J Dairy Res. Nov. 1990;57(4):479-87.

Davison, et al. Changes in the metabolic clearance of vasopressin and in plasma vasopressinase throughout human pregnancy. J Clin Invest. Apr. 1989;83(4):1313-8.

Dellinger, et al. Surviving Sepsis Campaign: international guidelines for management of severe sepsis and septic shock: 2008. Crit Care Med. Jan. 2008;36(1):296-327.

Dunser, et al. Arginine vasopressin in advanced vasodilatory shock: a prospective, randomized, controlled study. Circulation. May 13, 2003;107(18):2313-9. Epub May 5, 2003.

Dunser, et al. Cardiac performance during vasopressin infusion in postcardiotomy shock. Intensive Care Med. Jun. 2002;28(6):746-51. Epub Apr. 30, 2002.

Eden, et al. Ventricular arrhythmia induced by vasopressin: torsade de pointes related to vasopressin-induced bradycardia. Mt Sinai J Med. Jan.-Feb. 1983;50(1):49-51.

Edwards, et al. Renal microvascular effects of vasopressin and vasopressin antagonists. Am J Physiol. Feb. 1989;256(2 Pt 2):F274-8.

Emsley, et al. Impaired water excretion and elevated plasma vasopressin in patients with alcohol-withdrawal symptoms. Q J Med. Aug. 1987;64(244):671-8.

Epstein, et al. Coronary revascularization trends in the United States, 2001-2008. JAMA. May 4, 2011;305(17):1769-76. doi: 10.1001/jama.2011.551.

Ermisch, et al. Improved behavioral performance of rats after pre- and postnatal administration of vasopressin. Exp Clin Endocrinol. Aug. 1987;90(1):17-25.

Ertmer, et al. Methylprednisolone reverses vasopressin hyporesponsiveness in ovine endotoxemia. Shock. Mar. 2007;27(3):281-8.

Fabian, et al. The clearance and antidiuretic potency of neurohypophysial hormones in man, and their plasma binding and stability. J Physiol. Oct. 1969;204(3):653-68.

Faigel, et al. Torsade de pointes complicating the treatment of bleeding esophageal varices: association with neuroleptics, vasopressin, and electrolyte imbalance. Am J Gastroenterol. May 1995;90(5):822-4.

Forsling, et al. Permeability of the foetal guinea-pig placenta to arginine-vasopressin. Endocrinol. Mar. 1977;72(3):409-10.

Forsling, et al. The role of the pineal in the control of the daily patterns of neurohypophysial hormone secretion. J Pineal Res. Jan. 1993;14(1):45-51.

Gibson, et al. Ovine fetal cardiovascular, renal, and fluid balance responses to 3 days of high arginine vasopressin levels. Am J Physiol. Apr. 1997;272(4 Pt 2):R1069-76.

Ginsburg, et al. The clearance of injected vasopressin from the circulation and its fate in the body. J Endocrinol. Jul. 1953;9(3):283-91.

Gordon, et al. The effects of vasopressin on acute kidney injury in septic shock. Intensive Care Med. Jan. 2010;36(1):83-91. doi: 10.1007/500134-009-1687-x. Epub Oct. 20, 2009.

Graybiel, et al. Circulatory effects following the intravenous administration of pitressin in normal persons and in patients with hypertension and angina pectoris. Boston, Mass. 1941; 481-489.

(56) References Cited

OTHER PUBLICATIONS

Grollman, et al. The cardiovascular and metabolic reactions of man to the intramuscular injection of posterior pituitary lquid (pituitrin), pi-tressin and pitocin. Johns Hopkins Univeristy School of Medicine. May 25, 1932; 447-460.

Groszmann, et al. Nitroglycerin improves the hemodynamic response to vasopressin in portal hypertension. Hepatology. Nov.-Dec. 1982;2(6):757-62.

Hartley, et al. Plasma vasopressin concentrations and Fos protein expression in the supraoptic nucleus following osmotic stimulation or hypovolaemia in the ovariectomized rat: effect of oestradiol replacement. J Neuroendocrinol. Mar. 2004;16(3):191-7.

Hartley, et al. Renal response to arginine vasopressin during the oestrous cycle in the rat: comparison of glucose and saline infusion using physiological doses of vasopressin. Exp Physiol. Jan. 2002;87(1):9-15.

Hasija, et al. Prophylactic vasopressin in patients receiving the angiotensin-converting enzyme inhibitor ramipril undergoing coronary artery bypass graft surgery. J Cardiothorac Vasc Anesth. Apr. 2010;24(2):230-8. doi: 10.1053/j.jvca.2009.08.001. Epub Oct. 28, 2009.

Havel, et al. Vasopressors for hypotensive shhock (review). The Cochrane Library, 2011 Issue 5. 76 pages.

Hiramatsu, et al. Antagonizing substances obtained from whale heart extract to vasopressin induced myocardial hypoxia. Jpn J Pharmacol. Sep. 1970;20(3):313-24.

Hirata, et al. Effect of JTV-506, a novel vasodilator, on experimental angina model in rats. J Cardiovasc Pharmacol. Feb. 1998;31(2):322-6.

Holmes, et al. Arginine vasopressin in the treatment of vasodilatory septic shock. Best Pract Res Clin Anaesthesiol. Jun. 2008;22(2):275-86.

Holmes, et al. Physiology of vasopressin relevant to management of septic shock. Chest. Sep. 2001;120(3):989-1002.

Holmes, et al. Science review: Vasopressin and the cardiovascular system part 1—receptor physiology. Crit Care. Dec. 2003;7(6):427-34. Epub Jun. 26, 2003.

Holmes, et al. Science Review: Vasopressin and the cardiovascular system part 2—clinical physiology. Crit Care. Feb. 2004;8(1):15-23. Epub Jun. 26, 2003.

Holmes, et al. The effects of vasopressin on hemodynamics and renal function in severe septic shock: a case series. Intensive Care Med. Aug. 2001;27(8):1416-21.

Iwashyna, et al. Long-term cognitive impairment and functional disability among survivors of severe sepsis. JAMA. Oct. 27, 2010;304(16):1787-94. doi: 10.1001/jama.2010.1553.

Jackson. Vasopressin and other agents affecting the renal conservation of water. The Pharmacological Basis of Therapeutics. Chapter 29. 2006; 771-788.

Karasawa, et al. Antianginal effects of the new calcium antagonist benidipine hydrochloride in anesthetized rats and spontaneously hypertensive rats. Electrocardiographic study. Arzneimittelforschung. Nov. 1988;38(11A):1702-7.

Karmazyn, et al. Changes of vascular reactivity induced by low vasopressin concentrations: interactions with cortisol and lithium and possible involvement of prostaglandins. Endocrinology. Apr. 1978;102(4):1230-6.

Kelly, et al. Vasopressin provocation of ventricular dysrhythmia. Ann Intern Med. Feb. 1980;92(2 Pt 1):205-6.

King, et al. Pharmacokinetics of vasopressin and atrial natriuretic peptide in anesthetized rabbits. Endocrinology. Jan. 1989;124(1):77-83.

Kristeller, et al. Transient diabetes insipidus after discontinuation of therapeutic vasopressin. Pharmacotherapy. Apr. 2004;24(4):541-5.

Kupferschmidt, et al. [Clinico-pharmacological case (2). Bradycardia and ventricular tachycardia of the torsades de pointes type as a side effect of vasopressin: 3 case reports]. Praxis (Bern 1994). Mar. 12, 1996;85(11):340-3. (in German with English abstract).

Label for Angiomax® (bivalirudin) for Injection, 2000.

Label for Oxytocin for Injection, Dec. 2000.

Label for Vasotrict (vasopressin injection) for intravenous use, downloaded from www.fda.gov on Mar. 21, 2017.

"Lam, et al. Lack of an effect of body mass on the hemodynamic response to arginine vasopressin during septic shock. Pharmacotherapy. May 2008;28(5):591-9. doi: 10.1592/phco.28.5.591."

Landry, et al. The pathogenesis of vasodilatory shock. N Engl J Med. Aug. 23, 2001;345(8):588-95.

Landry, et al. Vasopressin deficiency contributes to the vasodilation of septic shock. Circulation. Mar. 4, 1997;95(5):1122-5.

Lauzier, et al. Vasopressin or norepinephrine in early hyperdynamic septic shock: a randomized clinical trial. Intensive Care Med. Nov. 2006;32(11):1782-9. Epub Sep. 22, 2006.

Lechner, et al. Arginine-vasopressin in neonates with vasodilatory shock after cardiopulmonary bypass. Eur J Pediatr. Dec. 2007;166(12):1221-7. Epub Jan. 16, 2007.

Levin, et al. Early on-cardiopulmonary bypass hypotension and other factors associated with vasoplegic syndrome. Circulation. Oct. 27, 2009;120(17):1664-71. doi: 10.1161/CIRCULATIONAHA.108.814533. Epub Oct. 12, 2009.

Levin, et al. Methylene blue reduces mortality and morbidity in vasoplegic patients after cardiac surgery. Ann Thorac Surg. Feb. 2004;77(2):496-9.

Levy, et al. 2001 SCCM/ESICM/ACCP/ATS/SIS International Sepsis Definitions Conference. Crit Care Med. Apr. 2003;31(4):1250-6.

Little, et al. Vasopressin alone or with epinephrine may be superior to epinephrine in a clinically relevant porcine model of pulseless electrical activity cardiac arrest. Am J Emerg Med. Nov. 2006;24(7):810-4.

Luckner, et al. Arginine vasopressin in 316 patients with advanced vasodilatory shock. Crit Care Med. Nov. 2005;33(11):2659-66.

Luckner, et al. Comparison of two dose regimens of arginine vasopressin in advanced vasodilatory shock. Crit Care Med. Oct. 2007;35(10):2280-5.

Malay, et al. Low-dose vasopressin in the treatment of vasodilatory septic shock. J Trauma. Oct. 1999;47(4):699-703; discussion 703-5.

Mander, et al. Fluid balance, vasopressin and withdrawal symptoms during detoxification from alcohol. Drug Alcohol Depend. Dec. 1989;24(3):233-7.

Martin, et al. The epidemiology of sepsis in the United States from 1979 through 2000. N Engl J Med. Apr. 17, 2003;348(16):1546-54.

Mauro, et al. Torsade de pointes in a patient receiving intravenous vasopressin. Crit Care Med. Feb. 1988;16(2):200-1.

Mayr, et al. Infection rate and acute organ dysfunction risk as explanations for racial differences in severe sepsis. JAMA. Jun. 23, 2010;303(24):2495-503. doi: 10.1001/jama.2010.851.

Mekontso-Dessap, et al. Risk factors for post-cardiopulmonary bypass vasoplegia in patients with preserved left ventricular function. Ann Thorac Surg. May 2001;71(5):1428-32.

Meyer, et al. Effects of Conformation on the Chemical Stability of Pharmaceutically Relevant Polypeptides. Chapter 4 in Rational Design of Stable Protein Formulations, Ed. Carpenter and Manning, 2002, pp. 85-107.

Meyer, et al. Vasopressin in catecholamine-refractory shock in children. Anaesthesia. Mar. 2008;63(3):228-34. Epub Dec. 13, 2007.

Miyake, et al. Cardiovascular responses to norepinephrine and arginine vasopressin infusion in chronically catheterized fetal lambs. J Reprod Med. Oct. 1991;36(10):735-40.

Miyazaki, et al. Bioavailability assessment of arginine-vasopressin (AVP) using pharmacokinetic-pharmacodynamic (PK-PD) modeling in the rat. Biol Pharm Bull. Jan. 2000;23(1):87-96.

Morales, et al. Arginine vasopressin in the treatment of 50 patients with postcardiotomy vasodilatory shock. Ann Thorac Surg. Jan. 2000;69(1):102-6.

Morales, et al. Reversal by vasopressin of intractable hypotension in the late phase of hemorrhagic shock. Circulation. Jul. 20, 1999;100(3):226-9.

Mori, et al. Pharmacological profile of semotiadil fumarate, a novel calcium antagonist, in rat experimental angina model. Br J Pharmacol. Sep. 1995;116(1):1668-72.

(56) References Cited

OTHER PUBLICATIONS

Moses, et al. Urinary and metabolic clearances of arginine vasopressin in normal subjects. Am J Physiol. Aug. 1986;251(2 Pt 2):R365-70.
Notice of allowance dated May 4, 2016 for U.S. Appl. No. 14/717,882.
Notice of Allowance dated May 12, 2017 for U.S. Appl. No. 15/289,640.
Notice of Allowance dated Jul. 11, 2017 for U.S. Appl. No. 14/717,877.
Notice of Allowance dated Jul. 11, 2017 for U.S. Appl. No. 15/426,693.
Notice of Allowance dated Jul. 20, 2017 for U.S. Appl. No. 15/426,703.
Nygren, et al. Vasopressin decreases intestinal mucosal perfusion: a clinical study on cardiac surgery patients in vasodilatory shock. Acta Anaesthesiol Scand. May 2009;53(5):581-8. doi: 10.1111/j.1399-6576.2008.01900.x. Epub Feb. 23, 2009.
Octreotide acetate 100 mcg/mL injection solution product information from Kaiser Permanente, Mar. 2013.
Office action dated Jan. 11, 2016 for U.S. Appl. No. 14/717,877.
Office action dated Feb. 2, 2016 for U.S. Appl. No. 14/717,882.
Office Action dated Feb. 22, 2017 for U.S. Appl. No. 15/289,640.
Office action dated Mar. 18, 2015 for U.S. Appl. No. 14/610,488.
Office action dated Mar. 23, 2015 for U.S. Appl. No. 14/610,499.
Office action dated Mar. 24, 2015 for U.S. Appl. No. 14/610,594.
Office action dated Mar. 25, 2015 for U.S. Appl. No. 14/610,579.
Office Action dated Mar. 29, 2017 for U.S. Appl. No. 15/426,693.
Office action dated May 12, 2016 for U.S. Appl. No. 14/717,877.
Office action dated Jun. 5, 2015 for U.S. Appl. No. 14/717,877.
Office action dated Jun. 8, 2015 for U.S. Appl. No. 14/717,882.
Office action dated Jul. 20, 2015 for U.S. Appl. No. 14/610,499.
Office action dated Jul. 28, 2015 for U.S. Appl. No. 14/610,579.
Office action dated Jul. 28, 2015 for U.S. Appl. No. 14/610,594.
Office action dated Jul. 31, 2015 for U.S. Appl. No. 14/610,488.
Office action dated Sep. 2, 2015 for U.S. Appl. No. 14/610,499.
Office action dated Oct. 21, 2015 for U.S. Appl. No. 14/717,877.
Office action dated Oct. 22, 2015 for U.S. Appl. No. 14/717,882.
Office Action dated Nov. 22, 2016 for U.S. Appl. No. 14/717,877.
Office Action dated Mar. 29, 2017 for U.S. Appl. No. 15/426,703.
Oliver, et al. On the Physiological Action of Extracts of Pituitary Body and certain other Glandular Organs: Preliminary Communication. J Physiol. Jul. 18, 1895;18(3):277-9.
Olsson, et al. Vasopressin increases milk flow and milk fat concentration in the goat. Acta Physiol Scand. Feb. 2003;177(2):177-84.
Oosterbaan, et al. Amniotic oxytocin and vasopressin in relation to human fetal development and labour. Early Hum Dev. Jul. 1989;19(4):253-62.
Papadopoulos, et al. Perioperative infusion of low- dose of vasopressin for prevention and management of vasodilatory vasoplegic syndrome in patients undergoing coronary artery bypass grafting—A double-blind randomized study. J Cardiothorac Surg. Mar. 28, 2010;5:17. doi: 10.1186/1749-8090-5-17.
Patel, et al. Beneficial effects of short-term vasopressin infusion during severe septic shock. Anesthesiology. Mar. 2002;96(3):576-82.
Pharmaceutical Partners of Canada, Inc. "Vasopressin Injection, USP" Jun. 2009.
Pinsky. Septic Shock. Medscape review. Updated Aug. 13, 2012. 22 pages.
Prengel, et al. Effects of combined administration of vasopressin, epinephrine, and norepinephrine during cardiopulmonary resuscitation in pigs. Crit Care Med. Nov. 2005;33(11):2587-91.
Product Information for Liraglutide Victoza®, May 15, 2013.
Product Insert for Pitressin. Vasopressin injection. Par Pharmaceuticals. Revised Nov. 2014.
Product Insert for Vasopressin Injection. American Regent. Revised Aug. 2011.
Product Insert for Vasopressin Injection. Fresenius Kabi. Revised Apr. 2014.
Product Insert for Vasopressin Injection. Fresenius Kabi. Revised Jul. 2014.
Public Assessment Report of the Medicines Evaluation Board in the Netherlands, Gonapeptyl 0.1 mg/1 ml, solution for injection, Ferring B.V., the Netherlands, triptorelin acetate, Feb. 2, 2010.
Rideout, et al. Hydrophobic acceleration of Diels-Alder reactions. J. Am. Chem. Soc. 1980; 102:7816-7817.
Risberg, et al. Plasma vasopressin, oxytocin, estradiol, and progesterone related to water and sodium excretion in normal pregnancy and gestational hypertension. Acta Obstet Gynecol Scand. 2009;88(6):639-46. doi: 10.1080/00016340902919002.
Rodriguez-Nunez, et al. Terlipressin continuous infusion: please mind the solvent! Current Drug Targets. 2009; 10(6):577.
Rosenzweig, et al. Intravenous arginine-vasopressin in children with vasodilatory shock after cardiac surgery. Circulation. Nov. 9, 1999;100(19 Suppl):II182-6.
Ross, et al. Amniotic fluid ionic concentration in response to chronic fetal vasopressin infusion. Am J Physiol. Sep. 1985;249(3 Pt 1):E287-91.
Russell, et al. Interaction of vasopressin infusion, corticosteroid treatment, and mortality of septic shock. Crit Care Med. Mar. 2009;37(3):811-8. doi: 10.1097/CCM.0b013e3181961ace.
Russell, et al. Vasopressin versus norepinephrine infusion in patients with septic shock. N Engl J Med. Feb. 28, 2008;358(9):877-87. doi: 10.1056/NEJMoa067373.
Russell, et al. Vasopressin versus norepinephrine infusion in patients with septic shock. N Engl J Med. Feb. 28, 2008;358(9):877-87. doi: 10.1056/NEJMoa067373. Supplemental materials.
Russell. Vasopressin in vasodilatory and septic shock. Curr Opin Crit Care. Aug. 2007; 13(4):383-91.
Rysa, et al. Early left ventricular gene expression profile in response to increase in blood pressure. Blood Press. 2006;15(6):375-83.
Sasaki, et al. Antianginal effects of lercanidipine on the vasopressin or methacholine induced anginal model in rats. Biot Pharm Bull. May 2005;28(5):811-6.
Satoh, et al. Effects of Rho-kinase inhibitor on vasopressin-induced chronic myocardial damage in rats. Life Sci. Nov. 22, 2002;72(1):103-12.
Schrier. Systemic arterial vasodilation, vasopressin, and vasopressinase in pregnancy. J Am Soc Nephrol. Apr. 2010;21(4):570-2. doi: 10.1681/ASN.2009060653. Epub Dec. 3, 2009.
Scott. Making the Medicine. BioProcess International, Mar. 2006, supplement, p. 42-56.
Singh, et al. Effect of buffer pH, buffer concentration and skin with or without enzyme inhibitors on the stability of [Arg8]-vasopressin. International Journal of Pharmaceuticals. 2000; 197:87-93.
Snijdewint, et al. Body and brain growth following continuous perinatal administration of arginine- and lysine-vasopressin to the homozygous Brattleboro rat. Brain Res. Oct. 1985;354(2):269-77.
Studer, et al. Resuscitation from cardiac arrest with adrenaline/epinephrine or vasopressin: effects on intestinal mucosal tonometer pCO(2) during the postresuscitation period in rats. Resuscitation. May 2002;53(2):201-7.
Sun, et al. Effect of peripheral injection of arginine vasopressin and its receptor antagonist on burn shock in the rat. Neuropeptides. Sep. 1990;17(1):17-22.
Swenson, et al. Prenatal exposure to AVP or caffeine but not oxytocin alters learning in female rats. Peptides. Sep.-Oct. 1990;11(5):927-32.
Taivainen, et al. Role of plasma vasopressin in changes of water balance accompanying acute alcohol intoxication. Alcohol Clin Exp Res. Jun. 1995;19(3):759-62.
Tesamorelin EGRIFTA prescribing information. Last revised Nov. 2010. 40 pages.
Tinius, et al. Prenatal administration of arginine vasopressin impairs memory retrieval in adult rats. Peptides. May-Jun. 1987;8(3):493-9.
Tomita, et al. Vasopressin dose-response effects on fetal vascular pressures, heart rate, and blood volume. Am J Physiol. Nov. 1985;249(5 Pt 2):H974-80.
Torgersen, et al. Comparing two different arginine vasopressin doses in advanced vasodilatory shock: a randomized, controlled, open-label trial. Intensive Care Med. Jan. 2010;36(1):57-65. doi: 10.1007/s00134-009-1630-1. Epub Sep. 15, 2009.

(56) References Cited

OTHER PUBLICATIONS

Trabert, et al. Inappropriate vasopressin secretion in severe alcohol withdrawal. Acta Psychiatr Scand. May 1992;85(5):376-9.
Treschan, et al. The Vasopressin System. Anesthesiology. 2006; 105:599-612.
Tsukada, et al. Pharmacological characterization of YM471, a novel potent vasopressin V(1A) and V(2) receptor antagonist. Eur J Pharmacol. Jun. 20, 2002;446(1-3):129-38.
Varlinskaya, et al. Behavioral effects of centrally administered arginine vasopressin in the rat fetus. Behav Neurosci. Apr. 1994;108(2):395-409.
Vasostrict FDA label prescribing information. Published Apr. 2014. 9 pages.
Vasostrict prescribing information. For intravenous infusion. Par Pharmaceutical Companies. 2014.
Walley. Shock. Principles of Critical Care. 3rd Ed. 2005; Chapter 21. 249-265.
Wang. Instability, stabilization, and formulation of liquid protein pharmaceuticals. International Journal of Pharmaceutics. 1999; 185:129-188.
Wenzel, et al. Employing vasopressin during cardiopulmonary resuscitation and vasodilatory shock as a lifesaving vasopressor. Cardiovasc Res. Aug. 15, 2001;51(3):529-41.
Wube, et al. A differential response in the reproductive system and energy balance of spiny mice Acomys populations to vasopressin treatment. Comp Biochem Physiol A Mol Integr Physiol. Dec. 2008;151(4):499-504. doi: 10.1016/j.cbpa.2008.06.027. Epub Jun. 29, 2008.
Xie, et al. Remodeling of capillary network in left ventricular subendocardial tissues induced by intravenous vasopressin administration. Microcirculation. Jun. 1997;4(2):261-6.
Young, P. Drug Manual. Wellington regional hospital, intensive care unit. 2013. p. 421-422.
Buffers (downloaded from www.med.unc.edu/pharm/sondeklab/files/resource-files/protein-purification-handbooks/buffers_calbiochem.pdf, published 2006).
Co-pending U.S. Appl. No. 15/864,593, filed Jan. 8, 2018.
Co-pending U.S. Appl. No. 15/864,597, filed Jan. 8, 2018.
"Entry on acetic acid, preparatorychemistry.com/Bishop_weak_acid_Equilibrium.htm, downloaded Oct. 16, 2017 (Year 2017)".
FDA label for Vasostrict® (vasopressin injection) published on Sep. 18, 2014; downlaoded from www.fda.gov (Year: 2014).
Notice of Allowance dated Jan. 17, 2018 for U.S. Appl. No. 15/606,442.
Notice of Allowance dated Jan. 18, 2018 for U.S. Appl. No. 15/688,338.
Office Action dated Sep. 19, 2017 for U.S. Appl. No. 15/612,649.
Office Action dated Oct. 17, 2017 for U.S. Appl. No. 15/688,330.
"Office Action dated Oct. 27, 2017 for U.S. Appl. No. 15/688,305".
Office Action dated Oct. 27, 2017 for U.S. Appl. No. 15/688,314.
Office Action dated Oct. 27, 2017 for U.S. Appl. No. 15/688,322.
Office Action dated Oct. 27, 2017 for U.S. Appl. No. 15/688,326.
Office Action dated Oct. 27, 2017 for U.S. Appl. No. 15/688,336.
"Office Action dated Nov. 1, 2017 for U.S. Appl. No. 15/688,338".
Office Action dated Sep. 18, 2017 for U.S. Appl. No. 15/606,442.
Southworth and Fine, "FDA Information on Vasostrict Storage" published May 2015; downloaded from www.fda.gov (Year: 2015).

\* cited by examiner

SEQUENCE LISTING

```
<160> NUMBER OF SEQ ID NOS: 17

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 1

Cys Tyr Phe Gln Asn Cys Pro Arg Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Tyr Phe Gln Asn Cys Pro Arg Gly
1               5

<210> SEQ ID NO 3
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 3

Cys Tyr Phe Gln Asp Cys Pro Arg Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 4

Cys Tyr Phe Glu Asn Cys Pro Arg Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Tyr Phe Glu Asn Cys Pro Arg Gly
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 6

Cys Tyr Phe Gln Asp Cys Pro Arg Gly
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 7

Cys Tyr Phe Gln Asn Cys Pro Arg Gly
1               5
```

```
<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 8

Cys His Phe Gln Asn Cys Pro Arg Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 9

Cys Tyr Phe Gln Asn Cys Leu Arg Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Asn
<220> FEATURE:
<223> OTHER INFORMATION: C-term NH2

<400> SEQUENCE: 10

Cys Tyr Phe Gln Asn Cys Pro Arg Gly
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<223> OTHER INFORMATION: C-term NH2

<400> SEQUENCE: 11

Cys Tyr Phe Gln Asn Cys Pro Arg Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: D-Tyr
<220> FEATURE:
<223> OTHER INFORMATION: C-term NH2

<400> SEQUENCE: 12

Cys Tyr Phe Gln Asn Cys Pro Arg Gly
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 13

Cys Tyr Phe Gln Asn Cys Pro Arg Gly
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Gln
<220> FEATURE:
<223> OTHER INFORMATION: C-term NH2

<400> SEQUENCE: 14

Cys Tyr Phe Gln Asn Cys Pro Arg Gly
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Cys
<220> FEATURE:
<223> OTHER INFORMATION: C-term NH2

<400> SEQUENCE: 15

Cys Tyr Phe Gln Asn Cys Pro Arg Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<221> NAME/KEY: MOD_RES
<222> LOCATION: (7)..(7)
<223> OTHER INFORMATION: D-Pro
<220> FEATURE:
<223> OTHER INFORMATION: C-term NH2

<400> SEQUENCE: 16

Cys Tyr Phe Gln Asn Cys Pro Arg Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-Arg
<220> FEATURE:
<223> OTHER INFORMATION: C-term NH2

<400> SEQUENCE: 17

Cys Tyr Phe Gln Asn Cys Pro Arg Gly
1               5
```

US 9,993,520 B2

VASOPRESSIN FORMULATIONS FOR USE IN TREATMENT OF HYPOTENSION

CROSS REFERENCE

This application is a continuation of U.S. application Ser. No. 15/612,649, filed Jun. 2, 2017, which is a continuation-in-part of U.S. application Ser. No. 15/426,693, filed Feb. 7, 2017, which is a continuation-in-part of U.S. application Ser. No. 15/289,640, filed Oct. 10, 2016, which is a continuation-in-part of U.S. application Ser. No. 14/717,877, filed May 20, 2015, which is a continuation of U.S. application Ser. No. 14/610,499, filed Jan. 30, 2015, each of which is incorporated herein by reference in its entirety.

BACKGROUND

Vasopressin is a potent endogenous hormone, responsible for maintaining plasma osmolality and volume in most mammals. Vasopressin can be used clinically in the treatment of sepsis and cardiac conditions, and in the elevation of patient's suffering from low blood pressure. Current formulations of vasopressin suffer from poor long-term stability.

INCORPORATION BY REFERENCE

Each patent, publication, and non-patent literature cited in the application is hereby incorporated by reference in its entirety as if each was incorporated by reference individually.

SEQUENCE LISTING

The instant application contains a Sequence Listing which has been submitted electronically in ASCII format and is hereby incorporated by reference in its entirety. Said ASCII copy, created on Aug. 25, 2017, is named 47956702308_SL.txt and is 5260 bytes in size.

SUMMARY OF THE INVENTION

In some embodiments, the invention provides a pharmaceutical composition comprising, in a unit dosage form: a) from about 0.01 mg/mL to about 0.07 mg/mL of vasopressin, or a pharmaceutically-acceptable salt thereof; and b) a polymeric pharmaceutically-acceptable excipient in an amount that is from about 1% to about 10% by mass of the unit dosage form or the pharmaceutically-acceptable salt thereof, wherein the unit dosage form exhibits from about 5% to about 10% less degradation of the vasopressin or the pharmaceutically-acceptable salt thereof after storage for about 1 week at about 60° C. than does a corresponding unit dosage form, wherein the corresponding unit dosage form consists essentially of: A) vasopressin, or a pharmaceutically-acceptable salt thereof; and B) a buffer having acidic pH.

In some embodiments, the invention provides a method of increasing blood pressure in a human in need thereof, the method comprising: intravenously administering to the human a pharmaceutical composition that consists essentially of, in a unit dosage form: i) from about 0.1 µg/mL to about 2 µg/mL of vasopressin or a pharmaceutically-acceptable salt thereof; ii) dextrose; iii) acetic acid, sodium acetate, or a combination thereof; and iv) optionally hydrochloric acid or sodium hydroxide, wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

In some embodiments, the invention provides a method of increasing blood pressure in a human in need thereof, the method comprising: a) storing at 5° C. for at least about one month a pharmaceutical composition for intravenous administration comprising, in a unit dosage form: i) from about 0.1 µg/mL to about 2 µg/mL of vasopressin or a pharmaceutically-acceptable salt thereof; ii) dextrose; and iii) acetic acid, sodium acetate, or a combination thereof, wherein the pharmaceutical composition exhibits no more than about 1% degradation of vasopressin or the pharmaceutically-acceptable salt thereof after the storage at 5° C. for about one month; and b) administering to the human the pharmaceutical composition, wherein the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

In some embodiments, the invention provides a method of increasing blood pressure in a human in need thereof, the method comprising: a) storing at 25° C. for at least about one month a pharmaceutical composition for intravenous administration comprising, in a unit dosage form: i) from about 0.1 µg/mL to about 2 µg/mL of vasopressin or a pharmaceutically-acceptable salt thereof; ii) dextrose; and iii) acetic acid, sodium acetate, or a combination thereof, wherein the pharmaceutical composition exhibits no more than about 2% degradation of vasopressin or the pharmaceutically-acceptable salt thereof after the storage at 25° C. for about one month; and b) administering to the human the pharmaceutical composition, wherein the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

DETAILED DESCRIPTION

Figure 1:
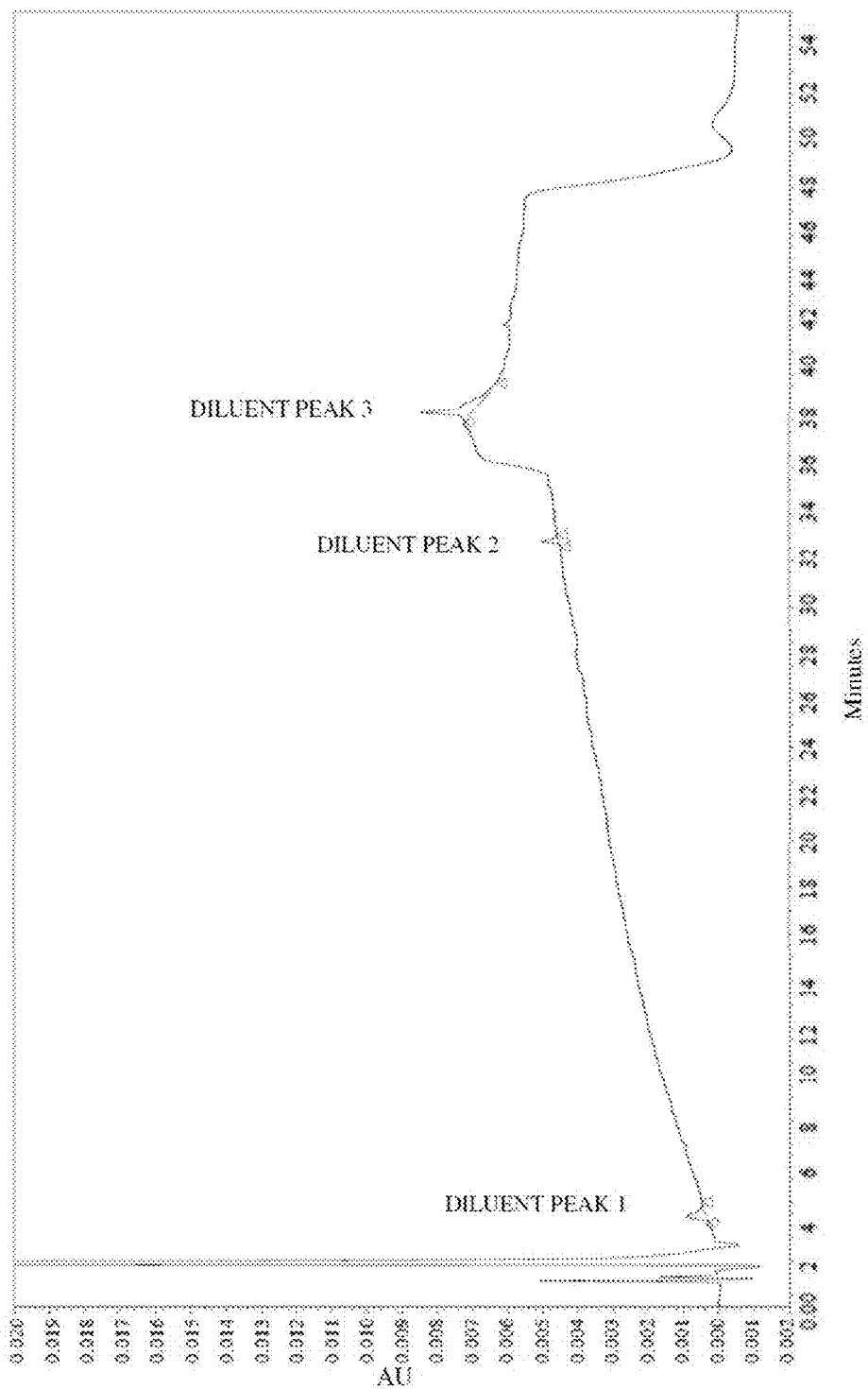
FIG. 1 is a chromatogram of a diluent used in vasopressin assay.

Vasopressin and Peptides of the Invention.

Vasopressin, a peptide hormone, acts to regulate water retention in the body and is a neurotransmitter that controls circadian rhythm, thermoregulation, and adrenocorticotrophic hormone (ACTH) release. Vasopressin is synthesized as a pro-hormone in neurosecretory cells of the hypothalamus, and is subsequently transported to the pituitary gland for storage. Vasopressin is released upon detection of hyperosmolality in the plasma, which can be due to dehydration of the body. Upon release, vasopressin increases the permeability of collecting ducts in the kidney to reduce renal excretion of water. The decrease in renal excretion of water leads to an increase in water retention of the body and an increase in blood volume. At higher concentrations, vasopressin raises blood pressure by inducing vasoconstriction.

Vasopressin acts through various receptors in the body including, for example, the V1, V2, V3, and oxytocin-type (OTR) receptors. The V1 receptors occur on vascular smooth muscle cells, and the major effect of vasopressin action on the V1 receptor is the induction of vasoconstriction via an increase of intracellular calcium. V2 receptors occur on the collecting ducts and the distal tubule of the kidney. V2 receptors play a role in detection of plasma volume and osmolality. V3 receptors occur in the pituitary gland and can cause ACTH release upon vasopressin binding. OTRs can be found on the myometrium and vascular smooth muscle. Engagement of OTRs via vasopressin leads to an increase of intracellular calcium and vasoconstriction.

Vasopressin is a nonapeptide, illustrated below (SEQ ID NO. 1):

depend on primary sequence of the protein, three-dimensional structure of the protein, and solution properties including, for example, pH, temperature, ionic strength, and buffer ions. Deamidation can be catalyzed by acidic conditions. Under physiological conditions, deamidation of asparagine occurs via the formation of a five-membered succinimide ring intermediate by a nucleophilic attack of the nitrogen atom in the following peptide bond on the carbonyl group of the asparagine side chain. Acetylation is a peptide modification whereby an acetyl group is introduced into an amino acid, such as on the N-terminus of the peptide.

Vasopressin can also form dimers in solution and in vivo. The vasopressin dimers can occur through the formation of disulfide bridges that bind a pair of vasopressin monomers together. The dimers can form between two parallel or anti-parallel chains of vasopressin.

Vasopressin and associated degradation products or peptides are listed in TABLE 1 below. All amino acids are L-stereoisomers unless otherwise denoted.

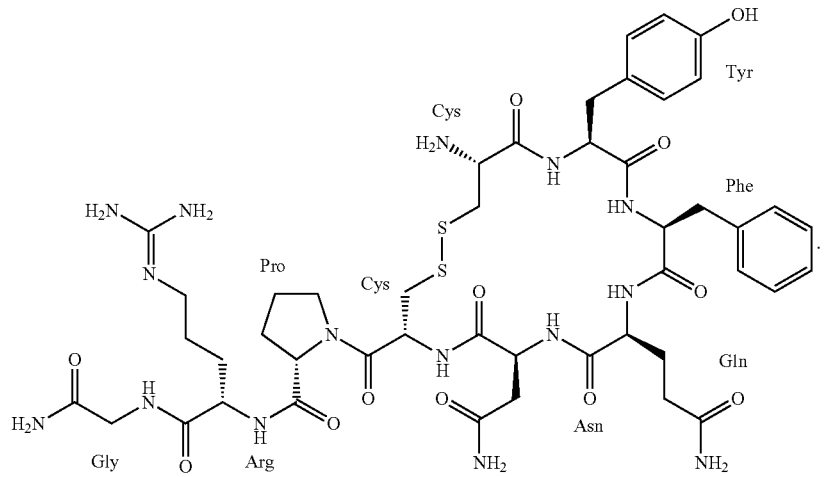 [SMILES: NC(=O)CC[C@@H]1NC(=O)[C@H](Cc2ccccc2)NC(=O)[C@H](Cc2ccc(O)cc2)NC(=O)[C@@H](N)CSSC[C@@H](C(=O)N2CCC[C@H]2C(=O)N[C@@H](CCCN=C(N)N)C(=O)NCC(N)=O)NC(=O)[C@H](CC(N)=O)NC1=O]

At neutral to acidic pH, the two basic groups of vasopressin, the N-terminal cysteine, and the arginine at position eight, are protonated, and can each carry an acetate counterion. The amide groups of the N-terminal glycine, the glutamine at position four, and the asparagine at position five, are susceptible to modification when stored as clinical formulations, such as unit dosage forms. The glycine, glutamine, and asparagine residues can undergo deamidation to yield the parent carboxylic acid and several degradation products as detailed in EXAMPLE 1 and TABLE 1 below.

Deamidation is a peptide modification during which an amide group is removed from an amino acid, and can be associated with protein degradation, apoptosis, and other regulatory functions within the cell. Deamidation of asparagine and glutamine residues can occur in vitro and in vivo, and can lead to perturbation of the structure and function of the affected proteins. The susceptibility to deamidation can

TABLE 1

| Name | Sequence | SEQ ID NO. |
|---|---|---|
| Vasopressin (AVP; arginine vasopressin) | CYFQNCPRG-NH$_2$ | 1 |
| Gly9-vasopressin (Gly9-AVP) | CYFQNCPRG | 2 |
| Asp5-vasopressin (Asp5-AVP) | CYFQDCPRG-NH$_2$ | 3 |
| Glu4-vasopressin (Glu4-AVP) | CYFENCPRG-NH$_2$ | 4 |
| Glu4Gly9-vasopressin (Glu4Gly9-AVP) | CYFENCPRG | 5 |
| AcetylAsp5-vasopressin (AcetylAsp5-AVP) | Ac-CYFQDCPRG-NH$_2$ | 6 |
| Acetyl-vasopressin (Acetyl-AVP) | Ac-CYFQNCPRG-NH$_2$ | 7 |
| His2-vasopressin (His2-AVP) | CHFQNCPRG-NH$_2$ | 8 |
| Leu7-vasopressin (Leu7-AVP) | CYFQNCLRG-NH$_2$ | 9 |
| D-Asn-vasopressin (DAsn-AVP) | CYFQ(D-Asn)CPRG-NH$_2$ | 10 |
| D-Cys1-vasopressin | (D-Cys)YFQNCPRG-NH$_2$ | 11 |
| D-Tyr-vasopressin | C(D-Tyr)FQNCPRG-NH$_2$ | 12 |

TABLE 1-continued

| Name | Sequence | SEQ ID NO. |
|---|---|---|
| D-Phe-vasopressin | CY(D-Phe)QNCPRG-NH$_2$ | 13 |
| D-Gln-vasopressin | CYF(D-Gln)NCPRG-NH$_2$ | 14 |
| D-Cys6-vasopressin | CYFQN(D-cys)PRG-NH$_2$ | 15 |
| D-Pro-vasopressin | CYFQNC(D-pro)RG-NH$_2$ | 16 |
| D-Arg-vasopressin | CYFQNCP(D-Arg)G-NH$_2$ | 17 |

Therapeutic Uses.

A formulation of vasopressin can be used to regulate plasma osmolality and volume and conditions related to the same in a subject. Vasopressin can be used to modulate blood pressure in a subject, and can be indicated in a subject who is hypotensive despite treatment with fluid and catecholamines.

Vasopressin can be used in the treatment of, for example, vasodilatory shock, post-cardiotomy shock, sepsis, septic shock, cranial diabetes insipidus, polyuria, nocturia, polydypsia, bleeding disorders, Von Willebrand disease, haemophilia, platelet disorders, cardiac arrest, liver disease, liver failure, hypovolemia, hemorrhage, oesophageal variceal haemorrhage, hypertension, pulmonary hypertension, renal disease, polycystic kidney disease, blood loss, injury, hypotension, meniere disease, uterine myomas, brain injury, mood disorder. Formulations of vasopressin can be administered to a subject undergoing, for example, surgery or hysterectomy.

Plasma osmolality is a measure of the plasma's electrolyte-water balance and relates to blood volume and hydration of a subject. Normal plasma osmolality in a healthy human subject range from about 275 milliosmoles/kg to about 295 milliosmoles/kg. High plasma osmolality levels can be due to, for example, diabetes insipidus, hyperglycemia, uremia, hypernatremia, stroke, and dehydration. Low plasma osmolality can be due to, for example, vasopressin oversecretion, improper functioning of the adrenal gland, lung cancer, hyponatremia, hypothyroidism, and over-consumption of water or other fluids.

Septic shock can develop due to an extensive immune response following infection and can result in low blood pressure. Causes of sepsis can include, for example, gastrointestinal infections, pneumonia, bronchitis, lower respiratory tract infections, kidney infection, urinary tract infections, reproductive system infections, fungal infections, and viral infections. Risk factors for sepsis include, for example, age, prior illness, major surgery, long-term hospitalization, diabetes, intravenous drug use, cancer, use of steroidal medications, and long-term use of antibiotics. The symptoms of sepsis can include, for example, cool arms and legs, pale arms and legs, extreme body temperatures, chills, light-headedness, decreased urination, rapid breathing, edema, confusion, elevated heart rate, high blood sugar, metabolic acidosis, respiratory alkalosis, and low blood pressure.

Vasopressin can also be administered to regulate blood pressure in a subject. Blood pressure is the measure of force of blood pushing against blood vessel walls. Blood pressure is regulated by the nervous and endocrine systems and can be used as an indicator of a subject's health. Chronic high blood pressure is referred to as hypertension, and chronic low blood pressure is referred to as hypotension. Both hypertension and hypotension can be harmful if left untreated.

Blood pressure can vary from minute to minute and can follow the circadian rhythm with a predictable pattern over a 24-hour period. Blood pressure is recorded as a ratio of two numbers: systolic pressure (mm Hg), the numerator, is the pressure in the arteries when the heart contracts, and diastolic pressure (mm Hg), the denominator, is the pressure in the arteries between contractions of the heart. Blood pressure can be affected by, for example, age, weight, height, sex, exercise, emotional state, sleep, digestion, time of day, smoking, alcohol consumption, salt consumption, stress, genetics, use of oral contraceptives, and kidney disease.

Blood pressure for a healthy human adult between the ages of 18-65 can range from about 90/60 to about 120/80. Hypertension can be a blood pressure reading above about 120/80 and can be classified as hypertensive crisis when there is a spike in blood pressure and blood pressure readings reach about 180/110 or higher. Hypertensive crisis can be precipitated by, for example, stroke, myocardial infarction, heart failure, kidney failure, aortic rupture, drug-drug interactions, and eclampsia. Symptoms of hypertensive crisis can include, for example, shortness of breath, angina, back pain, numbness, weakness, dizziness, confusion, change in vision, nausea, and difficulty speaking.

Vasodilatory shock can be characterized by low arterial blood pressure due to decreased systemic vascular resistance. Vasodilatory shock can lead to dangerously low blood pressure levels and can be corrected via administration of catecholamines or vasopressin formulations. Vasodilatory shock can be caused by, for example, sepsis, nitrogen intoxication, carbon monoxide intoxication, hemorrhagic shock, hypovolemia, heart failure, cyanide poisoning, metformin intoxication, and mitochondrial disease.

Post-cardiotomy shock can occur as a complication of cardiac surgery and can be characterized by, for example, inability to wean from cardiopulmonary bypass, poor hemodynamics in the operating room, development of poor hemodynamics post-surgery, and hypotension.

Pharmaceutical Formulations.

Methods for the preparation of compositions comprising the compounds described herein can include formulating the compounds with one or more inert, pharmaceutically-acceptable excipients. Liquid compositions include, for example, solutions in which a compound is dissolved, emulsions comprising a compound, or a solution containing liposomes, micelles, or nanoparticles comprising a compound as disclosed herein. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, anti-adherents, anti-static agents, surfactants, anti-oxidants, coloring agents, flavoring agents, plasticizers, preservatives, suspending agents, emulsifying agents, plant cellulosic material and spheronization agents, and any combination thereof.

Vasopressin can be formulated as an aqueous formulation or a lyophilized powder, which can be diluted or reconstituted just prior to use. Upon dilution or reconstitution, the vasopressin solution can be refrigerated for long-term stability for about one day. Room temperature incubation or prolonged refrigeration can lead to the generation of degradation products of vasopressin.

In some embodiments, a pharmaceutical composition of the invention can be formulated for long-term storage of vasopressin at room temperature in the presence of a suitable pharmaceutically-acceptable excipient. The pharmaceutically-acceptable excipient can increase the half-life of vasopressin when stored at any temperature, such as room temperature. The presence of the pharmaceutical excipient can decrease the rate of decomposition of vasopressin at any temperature, such as room temperature.

In some embodiments, a pharmaceutical composition has a shelf life of at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 25 months, at least about 26 months, at least about 27 months, at least about 28 months, at least about 29 months, or at least about 30 months. The shelf life can be at any temperature, including, for example, room temperature and refrigeration (i.e., 2-8° C.). As used herein, "shelf life" means the period beginning from manufacture of a formulation beyond which the formulation cannot be expected beyond reasonable doubt to yield the therapeutic outcome approved by a government regulatory agency In some embodiments, a vasopressin formulation of the invention comprises a pharmaceutically-acceptable excipient, and the vasopressin has a half-life that is at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 150%, at least about 200%, at least about 250%, at least about 300%, at least about 350%, at least about 400%, at least about 450%, at least about 500%, at least about 600%, at least about 700%, at least about 800%, at least about 900%, or at least about 1000% greater than the half-life of vasopressin in a corresponding formulation that lacks the pharmaceutically-acceptable excipient.

In some embodiments, a vasopressin formulation of the invention has a half-life at about 5° C. to about 8° C. that is no more than about 1%, no more than about 5%, no more than about 10%, no more than about 15%, no more than about 20%, no more than about 25%, no more than about 30%, no more than about 35%, no more than about 40%, no more than about 45%, no more than about 50%, no more than about 55%, no more than about 60%, no more than about 65%, no more than about 70%, no more than about 75%, no more than about 80%, no more than about 85%, no more than about 90%, no more than about 95%, no more than about 100%, no more than about 150%, no more than about 200%, no more than about 250%, no more than about 300%, no more than about 350%, no more than about 400%, no more than about 450%, no more than about 500%, no more than about 600%, no more than about 700%, no more than about 800%, no more than about 900%, or no more than about 1000% greater than the half-life of the formulation at another temperature, such as room temperature.

The half-life of the compounds of the invention in a formulation described herein at a specified temperature can be, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, or about one week.

A formulation described herein can be stable for or be stored for, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years prior to administration to a subject.

A unit dosage form described herein can be stable for or be stored for, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years prior to administration to a subject.

A diluted unit dosage form described herein can be stable for or be stored for, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years prior to administration to subject.

The stability of a formulation described herein can be measured after, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years.

A formulation or unit dosage form described herein can exhibit, for example, about 0.1%, about 0.2%, about 0.3%, about 0.4%, about 0.5%, about 0.6%, about 0.7%, about 0.8%, about 0.9% about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, or about 10% degradation over a specified period of time. The degradation of a formulation or a unit dosage form disclosed herein can be assessed after about 24 hours, about 36 hours, about 72 hours, about 96 hours, about 1 week, about 2 weeks, about 3 weeks, about 4 weeks, about 5 weeks, about 6 weeks, about 2 months, about 3 months, about 4 months, about 5 months, about 6 months, about 8 months, about 10 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years of storage. The degradation of a formulation or a unit dosage form disclosed herein can be assessed at a temperature of, for example, about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., or about 0° C. to about 5° C., about 1° C. to about 6° C., about 2° C. to about 7° C., about 2° C. to about 8° C., about 3° C. to about 8° C., about 4° C. to about 9° C., about 5° C. to about 10° C., about 6° C. to about 11° C., about 7° C. to about 12° C., about 8° C. to about 13° C., about 9° C. to about 14° C., about 10° C. to about 15° C., about 11° C. to about 16° C., about 12° C. to about 17° C., about 13° C. to about 18° C., about 14° C. to about 19° C., about 15° C. to about 20° C., about 16° C. to about 21° C., about 17° C. to about 22° C., about 18° C. to about 23° C., about 19° C. to about 24° C., about 20° C. to about 25° C., about 21° C. to about 26° C., about 22° C. to about 27° C., about 23° C. to about 28° C., about 24° C. to about 29° C., about 25° C. to about 30° C., about 26° C. to about 31° C., about 27° C. to about 32° C., about 28° C. to about 33° C., about 29° C. to about 34° C., about 30° C. to about 35° C., about 31° C. to about 36° C., about 32° C. to about 37° C., about 33° C. to about 38° C., about 34° C. to about 39° C., about 35° C. to about 40° C., about 36° C. to about 41° C., about 37° C. to about 42° C., about 38° C. to about 43° C., about 39° C. to about 44° C., about 40° C. to about 45° C., about 41° C. to about 46° C., about 42° C. to about 47° C., about 43° C. to about 48° C., about 44° C. to about 49° C., about 45° C. to about 50° C.

In some embodiments, a vasopressin formulation of the invention comprises an excipient and the vasopressin has a level of decomposition at a specified temperature that is about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 250%, about 300%, about 350%, about 400%, about 450%, about 500%, about 600%, about 700%, about 800%, about 900%, or about 1000% less than the level of decomposition of a formulation of the invention in the absence of the excipient.

Pharmaceutical compositions of the invention can be used, stored, tested, analyzed or assayed at any suitable temperature. Non-limiting examples of temperatures include about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39°

C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., or about 75° C.

Pharmaceutical compositions of the invention can be used, stored, tested, analyzed or assayed at any suitable temperature. Non-limiting examples of temperatures include from about 0° C. to about 5° C., about 1° C. to about 6° C., about 2° C. to about 7° C., about 2° C. to about 8° C., about 3° C. to about 8° C., about 4° C. to about 9° C., about 5° C. to about 10° C., about 6° C. to about 11° C., about 7° C. to about 12° C., about 8° C. to about 13° C., about 9° C. to about 14° C., about 10° C. to about 15° C., about 11° C. to about 16° C., about 12° C. to about 17° C., about 13° C. to about 18+° C., about 14° C. to about 19° C., about 15° C. to about 20° C., about 16° C. to about 21° C., about 17° C. to about 22° C., about 18° C. to about 23° C., about 19° C. to about 24° C., about 20° C. to about 25° C., about 21° C. to about 26° C., about 22° C. to about 27° C., about 23° C. to about 28° C., about 24° C. to about 29° C., about 25° C. to about 30° C., about 26° C. to about 31° C., about 27° C. to about 32° C., about 28° C. to about 33° C., about 29° C. to about 34° C., about 30° C. to about 35° C., about 31° C. to about 36° C., about 32° C. to about 37° C., about 33° C. to about 38° C., about 34° C. to about 39° C., about 35° C. to about 40° C., about 36° C. to about 41° C., about 37° C. to about 42° C., about 38° C. to about 43° C., about 39° C. to about 44° C., about 40° C. to about 45° C., about 41° C. to about 46° C., about 42° C. to about 47° C., about 43° C. to about 48° C., about 44° C. to about 49° C., about 45° C. to about 50° C., about 46° C. to about 51° C., about 47° C. to about 52° C., about 48° C. to about 53° C., about 49° C. to about 54° C., about 50° C. to about 55° C., about 51° C. to about 56° C., about 52° C. to about 57° C., about 53° C. to about 58° C., about 54° C. to about 59° C., about 55° C. to about 60° C., about 56° C. to about 61° C., about 57° C. to about 62° C., about 58° C. to about 63° C., about 59° C. to about 64° C., about 60° C. to about 65° C., about 61° C. to about 66° C., about 62° C. to about 67° C., about 63° C. to about 68° C., about 64° C. to about 69° C., about 65° C. to about 70° C., about 66° C. to about 71° C., about 67° C. to about 72° C., about 68° C. to about 73° C., about 69° C. to about 74° C., about 70° C. to about 74° C., about 71° C. to about 76° C., about 72° C. to about 77° C., about 73° C. to about 78° C., about 74° C. to about 79° C., or about 75° C. to about 80° C.

Pharmaceutical compositions of the invention can be used, stored, tested, analyzed or assayed at room temperature. The room temperature can be, for example, about 20.0° C., about 20.1° C., about 20.2° C., about 20.3° C., about 20.4° C., about 20.5° C., about 20.6° C., about 20.7° C., about 20.8° C., about 20.9° C., about 21.0° C., about 21.1° C., about 21.2° C., about 21.3° C., about 21.4° C., about 21.5° C., about 21.6° C., about 21.7° C., about 21.8° C., about 21.9° C., about 22.0° C., about 22.1° C., about 22.2° C., about 22.3° C., about 22.4° C., about 22.5° C., about 22.6° C., about 22.7° C., about 22.8° C., about 22.9° C., about 23.0° C., about 23.1° C., about 23.2° C., about 23.3° C., about 23.4° C., about 23.5° C., about 23.6° C., about 23.7° C., about 23.8° C., about 23.9° C., about 24.0° C., about 24.1° C., about 24.2° C., about 24.3° C., about 24.4° C., about 24.5° C., about 24.6° C., about 24.7° C., about 24.8° C., about 24.9° C., or about 25.0° C.

A pharmaceutical composition of the disclosed can be supplied, stored, or delivered in a vial or tube that is, for example, about 0.5 mL, about 1 mL, about 2 mL, about 3 mL, about 4 mL, about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, or about 20 mL in volume.

A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts, for example, intravenous, subcutaneous, intramuscular, transdermal, or parenteral administration.

Pharmaceutical preparations can be formulated for intravenous administration. The pharmaceutical compositions can be in a form suitable for parenteral injection as a sterile suspension, solution, or emulsion in oily or aqueous vehicles, and can contain formulation agents such as suspending, stabilizing, and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, for example, sterile pyrogen-free water, before use.

Comparison Formulations.

A pharmaceutical composition described herein can be analyzed by comparison to a reference formulation. A reference formulation can be generated from any combination of compounds, peptides, excipients, diluents, carriers, and solvents disclosed herein. Any compound, peptide, excipient, diluent, carrier, or solvent used to generate the reference formulation can be present in any percentage, ratio, or amount, for example, those disclosed herein. The reference formulation can comprise, consist essentially of, or consist of any combination of any of the foregoing.

A non-limiting example of a comparison formulation comprises, consists essentially of, or consists of: an amount, such as about 20 Units or about 0.04 mg, of vasopressin or a pharmaceutically-acceptable salt thereof, an amount, such as about 5 mg, of chlorobutanol (for example, hydrous), an amount, such as about 0.22 mg, of acetic acid or a pharmaceutically-acceptable salt thereof or a quantity sufficient to bring pH to about 3.4 to about 3.6, and water as needed. Another non-limiting example of a comparison formulation comprises, consists essentially of, or consists of: vasopressin or a pharmaceutically-acceptable salt thereof, chlorobutanol, acetic acid, and a solvent such as water. Another non-limiting example of a comparison formulation comprises, consists essentially of, or consists of: vasopressin or a pharmaceutically-acceptable salt thereof, chlorobutanol, and a solvent such as water. Another non-limiting example of a comparison formulation comprises, consists essentially of, or consists of: vasopressin or a pharmaceutically-acceptable salt thereof, acetic acid, and a solvent such as water. Another non-limiting example of a comparison formulation comprises, consists essentially of, or consists of: vasopressin or a pharmaceutically-acceptable salt thereof and a solvent such as water. Another non-limiting example of a comparison formulation comprises, consists essentially of, or consists of: vasopressin or a pharmaceutically-acceptable salt thereof and a buffer having acidic pH, such as pH 3.5 or any buffer or pH described herein.

Methods.

Any formulation described herein can be diluted prior to administration to a subject. Diluents that can be used in a method of the invention include, for example, compound sodium lactate solution, 6% dextran, 10% dextran, 5% dextrose, 20% fructose, Ringer's solution, 5% saline, 1.39% sodium bicarbonate, 1.72% sodium lactate, or water. Upon dilution, any diluted formulation disclosed herein can be stored for, for example, about 24 hours, about 36 hours, about 72 hours, about 96 hours, about 1 week, about 2 weeks, about 3 weeks, about 4 weeks, about 5 weeks, about 6 weeks, about 2 months, about 3 months, about 4 months, about 5 months, about 6 months, about 8 months, about 10 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years of storage. Upon dilution, any diluted formulation disclosed herein can be stored at, for example, about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., or about 0° C. to about 5° C., about 1° C. to about 6° C., about 2° C. to about 7° C., about 2° C. to about 8° C., about 3° C. to about 8° C., about 4° C. to about 9° C., about 5° C. to about 10° C., about 6° C. to about 11° C., about 7° C. to about 12° C., about 8° C. to about 13° C., about 9° C. to about 14° C., about 10° C. to about 15° C., about 11° C. to about 16° C., about 12° C. to about 17° C., about 13° C. to about 18° C., about 14° C. to about 19° C., about 15° C. to about 20° C., about 16° C. to about 21° C., about 17° C. to about 22° C., about 18° C. to about 23° C., about 19° C. to about 24° C., about 20° C. to about 25° C., about 21° C. to about 26° C., about 22° C. to about 27° C., about 23° C. to about 28° C., about 24° C. to about 29° C., about 25° C. to about 30° C., about 26° C. to about 31° C., about 27° C. to about 32° C., about 28° C. to about 33° C., about 29° C. to about 34° C., about 30° C. to about 35° C., about 31° C. to about 36° C., about 32° C. to about 37° C., about 33° C. to about 38° C., about 34° C. to about 39° C., about 35° C. to about 40° C., about 36° C. to about 41° C., about 37° C. to about 42° C., about 38° C. to about 43° C., about 39° C. to about 44° C., about 40° C. to about 45° C., about 41° C. to about 46° C., about 42° C. to about 47° C., about 43° C. to about 48° C., about 44° C. to about 49° C., about 45° C. to about 50° C.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 48 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about two weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL (about 0.21 µg/mL to about 2.1 µg/mL) of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about three weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL (about 0.21 µg/mL to about 2.1 µg/mL) of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL (about 0.21 µg/mL to about 2.1 µg/mL) of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about six weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about three months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about six months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one year.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about two years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about three years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 24 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 48 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 96 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 1 week; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 6 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 months; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 6 months; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least one year; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least two years; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least three years; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 24 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 48 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 48 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 96 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least one week; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 months; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 6 months; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 6 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 1 year; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 1 year.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 years; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 years; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 24 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 48 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 96 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 1 week; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 months; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 6 months; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 1 year; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 years; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 years; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 48 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 1 week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 6 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 1 year.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 24 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 48 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 48 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 96 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least one week; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 1 week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 weeks; c) diluting the unit dosage form in 0.9% saline or 5% dextrose in water to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 weeks; c) diluting the unit dosage form in 0.9% saline or 5% dextrose in water to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 months; c) diluting the unit dosage form in 0.9% saline or 5% dextrose in water to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 6 months; c) diluting the unit dosage form in 0.9% saline or 5% dextrose in water to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 6 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least one year; c) diluting the unit dosage form in 0.9% saline or 5% dextrose in water to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one year.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 years; c) diluting the unit dosage form in 0.9% saline or 5% dextrose in water to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 years; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 years.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 24 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 48 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 96 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 1 week; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 2 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 1 week.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 months; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 6 months; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 1 year; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 2 years; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 years; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 48 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii)

water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 1 week.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about two weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about three weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 3 months.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 6 months.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 1 year.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 2 years.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 3 years.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 24 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 48 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C. for about, for example, 5° C., 48 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 96 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 1 week; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 1 week.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 2 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 2 weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 3 weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 months; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 3 months.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 6 months; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 6 months.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 1 year; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 1 year.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 2 years; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 2 years.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 years; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 3 years.

A formulation described herein can be used without initial vasopressin dilution for use in, for example, intravenous drip-bags. The formulation can be premixed, already-diluted, and ready for use as provided in, for example, a bottle or intravenous drip-bag. The formulation supplied in the bottle can then be transferred to an intravenous drip-bag for administration to a subject. The formulation can be stable for about 24 hours, about 36 hours, about 72 hours, about 96 hours, about 1 week, about 2 weeks, about 3 weeks, about 4 weeks, about 5 weeks, about 6 weeks, about 2 months, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years prior to discarding.

The premixed formulation described herein can be disposed in a container or vessel, which can be sealed. The container or vessel can maintain the sterility of, or reduce the likelihood of contamination of, the premixed formulation. The premixed formulation described herein can be disposed in a container or vessel and is formulated as, for example, a single use dosage or a multiple use dosage. The container or vessel can be, for example, a glass vial, an ampoule, or a plastic flexible container. The plastic flexible container can be made of, for example, PVC (polyvinyl chloride), or polypropylene.

A premixed vasopressin formulation described herein can be stored as a liquid in an aliquot having a total volume of between about 1 and about 500 mL, between about 1 and about 250 mL, between about 1 and about 200 mL, between about 1 and about 150 mL, between about 1 and about 125 mL, between about 1 and about 120 mL, between about 1 and about 110 mL, between about 1 and about 100 mL, between about 1 and about 90 mL, between about 1 and about 80 mL, between about 1 and about 70 mL, between about 1 and about 60 mL, between about 1 and about 50 mL, between about 1 and about 40 mL, between about 1 and about 30 mL, between about 1 and about 20 mL, between about 1 and about 10 mL, or between about 1 and about 5 mL.

A premixed vasopressin formulation described herein can be administered as, for example, a single continuous dose over a period of time. For example, the premixed vasopressin formulation can be administered for a period of time of between about 1 and about 10 minutes, between about 1 and about 20 minutes, between about 1 and about 30 minutes, between about 1 and about 2 hours, between about 1 and about 3 hours, between about 1 and about 4 hours, between about 1 and about 5 hours, between about 1 and about 6 hours, between about 1 and about 7 hours, between about 1 and about 8 hours, between about 1 and about 9 hours, between about 1 and about 10 hours, between about 1 and about 11 hours, between about 1 and about 12 hours, between about 1 and about 13 hours, between about 1 and about 14 hours, between about 1 and about 15 hours, between about 1 and about 16 hours, between about 1 and about 17 hours, between about 1 and about 18 hours, between about 1 and about 19 hours, between about 1 and about 20 hours, between about 1 and about 21 hours, between about 1 and about 22 hours, between about 1 and about 23 hours, between about 1 and about 1 day, between about 1 and about 32 hours, between about 1 and about 36 hours, between about 1 and about 42 hours, between about 1 and about 2 days, between about 1 and about 54 hours, between about 1 and about 60 hours, between about 1 and about 66 hours, between about 1 and about 3 days, between about 1 and about 78 hours, between about 1 and about 84 hours, between about 1 and about 90 hours, between about 1 and about 4 days, between about 1 and about 102 hours, between about 1 and about 108 hours, between about 1 and about 114 hours, between about 1 and about 5 days, between about 1 and about 126 hours, between about 1 and about 132 hours, between about 1 and about 138 hours, between about 1 and about 6 days, between about 1 and about 150 hours, between about 1 and about 156 hours, between about 1 and about 162 hours, or between about 1 and about 1 week.

A premixed vasopressin formulation described herein can be administered as a loading dose followed by a maintenance dose over a period of time. For example, the loading dose can comprise administration of the premixed vasopressin formulation at a first dosage amount for a first period of time, followed by administration of the maintenance dose at a second dosage amount for a second period of time. The loading dose can be administered for a period of time of between about 1 and about 5 minutes, between about 1 and about 10 minutes, between about 1 and about 15 minutes, between about 1 and about 20 minutes, between about 1 and about 25 minutes, between about 1 and about 30 minutes, between about 1 and about 45 minutes, between about 1 and about 60 minutes, between about 1 and about 90 minutes, between 1 minute and about 2 hours, between 1 minute and about 2.5 hours, between 1 minute and about 3 hours, between 1 minute and about 3.5 hours, between 1 minute and about 4 hours, between 1 minute and about 4.5 hours, between 1 minute and about 5 hours, between 1 minute and about 5.5 hours, between 1 minute and about 6 hours, between 1 minute and about 6.5 hours, between 1 minute and about 7 hours, between 1 minute and about 7.5 hours, between 1 minute and about 8 hours, between 1 minute and about 10 hours, between 1 minute and about 12 hours, between 1 minute about 14 hours, between 1 minute and about 16 hours, between 1 minute and about 18 hours, between 1 minute and about 20 hours, between 1 minute and about 22 hours, or between 1 minute and about 24 hours. Following the loading dose, the maintenance dose can be administered for a period of time as described above for a single continuous dose.

A premixed vasopressin formulation described herein, when administered as a single continuous, loading, or maintenance dose, can be administered for about 1 hour to about 7 days, about 1 hour to about 4 days, about 1 hour to about 48 hours, about 1 hour to about 36 hours, about 1 hour to about 24 hours, about 1 hour to about 12 hours, about 24 hours to about 120 hours, about 24 hours to about 108 hours, about 24 hours to about 96 hours, about 24 hours to about 72 hours, about 24 hours to about 48 hours, or about 24 hours to about 36 hours.

The volume of the premixed formulation can be, for example, about 25 mL, about 30 mL, about 35 mL, about 40 mL, about 45 mL, about 50 mL, about 55 mL, about 60 mL, about 65 mL, about 70 mL, about 75 mL, about 80 mL, about 85 mL, about 90 mL, about 95 mL, about 100 mL, about 110 mL, about 120 mL, about 130 mL, about 140 mL, about 150 mL, about 175 mL, about 200 mL, about 225 mL, about 250 mL, about 275 mL, about 300 mL, about 350 mL, about 400 mL, about 450 mL, about 500 mL, about 550 mL, about 600 mL, about 650 mL, about 700 mL, about 750 mL, about 800 mL, about 850 mL, about 900 mL, about 950 mL, or about 1 L. In some embodiments, the volume of the vasopressin formulation formulated for use without initial vasopressin dilution is 100 mL.

The concentration of vasopressin in the container or vessel in which the premixed vasopressin formulation is disposed can be, for example, about 0.1 units/mL, about 0.2 units/mL, about 0.3 units/mL, about 0.4 units/mL, about 0.5 units/mL, about 0.6 units/mL, about 0.7 units/mL, about 0.8 units/mL, about 0.9 units/mL, about 1 unit/mL, about 2 units/mL, about 3 units/mL, about 4 units/mL, about 5 units/mL, about 6 units/mL, about 7 units/mL, about 8 units/mL, about 9 units/mL, about 10 units/mL, about 11 units/mL, about 12 units/mL, about 13 units/mL, about 14 units/mL, about 15 units/mL, about 16 units/mL, about 17 units/mL, about 18 units/mL, about 19 units/mL, about 20 units/mL, about 21 units/mL, about 22 units/mL, about 23 units/mL, about 24 units/mL about 25 units/mL, about 30 units/mL, about 35 units/mL, about 40 units/mL, about 45 units/mL, or about 50 units/mL. In some embodiments, the concentration of vasopressin in the container or vessel is 0.4 units/mL. In some embodiments, the concentration of vasopressin in the container or vessel is 0.6 units/mL.

The concentration of vasopressin in the container or vessel in which the premixed vasopressin formulation is disposed can be, for example, about 0.01 µg/mL, about 0.05 µg/mL, about 0.1 µg/mL, about 0.15 µg/mL, about 0.2 µg/mL, about 0.25 µg/mL, about 0.3 µg/mL, about 0.35 µg/mL, about 0.4 µg/mL, about 0.5 µg/mL, about 0.6 µg/mL, about 0.7 µg/mL, about 0.8 µg/mL, about 0.9 µg/mL, about 1 µg/mL, about 2 µg/mL, about 3 µg/mL, about 4 µg/mL, about 5 µg/mL, about 10 µg/mL, about 15 µg/mL, about 20 µg/mL, about 25 µg/mL, about 30 µg/mL, about 35 µg/mL, about 40 µg/mL, about 45 µg/mL, about 50 µg/mL, about 60 µg/mL, about 70 µg/mL, about 80 µg/mL, about 90 µg/mL, about 100 µg/mL, about 125 µg/mL, about 150 µg/mL, about 175 µg/mL, about 200 µg/mL, about 250 µg/mL, about 300 µg/mL, about 350 µg/mL, about 400 µg/mL, about 450 µg/mL, about 500 µg/mL, about 600 µg/mL, about 700 µg/mL, about 800 µg/mL, about 900 µg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, or about 10 mg/mL.

A formulation formulated for use without initial vasopressin dilution can be administered as intravenous drip therapy for about 15 min, about 20 min, about 25 min, about 30 min, about 35 min, about 40 min, about 45 min, about 50 min, about 55 min, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 1 day, about 2 days, about 3 days, about 4 days, about 5 days, about 6 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, or about 1 year. A formulation for use in a drip-bag can be replaced up to, for example, one time, two times, three times, four times, five times, six times, seven times, eight times, nine times, ten times, 11 times, 12 times, 13 times, 14 times, 15 times, 16 times, 17 times, 18 times, 19 times, or 20 times during the course of the treatment period. The formulation can be used for continuous or intermittent intravenous infusion.

A formulation formulated for use without initial vasopressin dilution can be modified using an excipient, for example, any excipient disclosed herein, to improve the stability of vasopressin for long-term storage and use. Non-limiting examples of excipients that can be used in an intravenous drip-bag include dextrose, saline, half-strength saline, quarter-strength saline, Ringers Lactate solution, sodium chloride, and potassium chloride. In some embodiments, dextrose is used as an excipient for the vasopressin formulation formulated for use without initial vasopressin dilution.

A formulation formulated for use without initial vasopressin dilution can be modified using a buffer, for example, any buffer disclosed herein, to adjust the pH of the formulation. A non-limiting example of a buffer that can be used in the formulation includes acetate buffer. The concentration of buffer used in the formulation can be, for example, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, or about 30 mM. In some embodiments, the concentration of the acetate buffer is 1 mM. In some embodiments, the concentration of the acetate buffer is 10 mM.

In some embodiments, an additive that is used in a formulation described herein is dextrose. The concentration of dextrose used in the formulation can be, for example, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, or about 30 mM. In some embodiments, the concentration of dextrose is 1 mM. In some embodiments, the concentration of dextrose is 10 mM. The concentration of dextrose used in the formulation can be, for example, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%. In some embodiments, a formulation described herein contains 5% dextrose.

In some embodiments, an additive that is used in a formulation described herein is sodium chloride. The concentration of sodium chloride used in the formulation can be, for example, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, or about 30 mM. In some embodiments, the concentration of the sodium chloride is 1 mM. In some embodiments, the concentration of sodium chloride is 10 mM.

In some embodiments, a combination of dextrose and sodium chloride is used in a formulation described herein. When used in combination, the concentration of sodium chloride and dextrose can be the same or different. In some embodiments, the concentration of dextrose or sodium chloride is 1 mM, or any value above 1 mM, when dextrose and sodium chloride are used in a combination in a formulation described herein.

A formulation formulated for use without initial vasopressin dilution can be modified using a pH adjusting agent, for example, any pH adjusting agent disclosed herein, to adjust the pH of the formulation. Non-limiting examples of a pH adjusting agent that can be used in the formulation include acetic acid, sodium acetate, hydrochloric acid, and sodium hydroxide. The concentration of buffer used in the formulation can be, for example, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, or about 30 mM. In some embodiments, the concentration of the acetate buffer is 1 mM. In some embodiments, the concentration of the acetate buffer is 10 mM.

The formulation can be stable for and have a shelf-life of about 24 hours, about 36 hours, about 72 hours, about 96 hours, about 1 week, about 2 weeks, about 3 weeks, about 4 weeks, about 5 weeks, about 6 weeks, about 2 months, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years of storage at any temperature. In some embodiments, the shelf-life of the formulation is 2 years under refrigeration. In some embodiments, the shelf-life of the formulation is 6 months at room temperature. In some embodiments, the total shelf-life of the formulation is 30 months, where the formulation is stored for 2 years under refrigeration and 6 months at room temperature.

Dosage Amounts.

In practicing the methods of treatment or use provided herein, therapeutically-effective amounts of the compounds described herein are administered in pharmaceutical compositions to a subject having a disease or condition to be treated. A therapeutically-effective amount can vary widely depending on the severity of the disease, the age and relative health of the subject, the potency of the compounds used, and other factors. Subjects can be, for example, humans, elderly adults, adults, adolescents, pre-adolescents, children, toddlers, infants, or neonates. A subject can be a patient.

Pharmaceutical compositions of the invention can be formulated in any suitable volume. The formulation volume can be, for example, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.1 mL, about 1.2 mL, about 1.3 mL, about 1.4 mL, about 1.5 mL, about 1.6 mL, about 1.7 mL, about 1.8 mL, about 1.9 mL, about 2 mL, about 2.1 mL, about 2.2 mL, about 2.3 mL, about 2.4 mL, about 2.5 mL, about 2.6 mL, about 2.7 mL, about 2.8 mL, about 2.9 mL, about 3 mL, about 3.1 mL, about 3.2 mL, about 3.3 mL, about 3.4 mL, about 3.5 mL, about 3.6 mL, about 3.7 mL, about 3.8 mL, about 3.9 mL, about 4 mL, about 4.1 mL, about 4.2 mL, about 4.3 mL, about 4.4 mL, about 4.5 mL, about 4.6 mL, about 4.7 mL, about 4.8 mL, about 4.9 mL, about 5 mL, about 5.1 mL, about 5.2 mL, about 5.3 mL, about 5.4 mL, about 5.5 mL, about 5.6 mL, about 5.7 mL, about 5.8 mL, about 5.9 mL, about 6 mL, about 6.1 mL, about 6.2 mL, about 6.3 mL, about 6.4 mL, about 6.5 mL, about 6.6 mL, about 6.7 mL, about 6.8 mL, about 6.9 mL, about 7 mL, about 7.1 mL, about 7.2 mL, about 7.3 mL, about 7.4 mL, about 7.5 mL, about 7.6 mL, about 7.7 mL, about 7.8 mL, about 7.9 mL, about 8 mL, about 8.1 mL, about 8.2 mL, about 8.3 mL, about 8.4 mL, about 8.5 mL, about 8.6 mL, about 8.7 mL, about 8.8 mL, about 8.9 mL, about 9 mL, about 9.1 mL, about 9.2 mL, about 9.3 mL, about 9.4 mL, about 9.5 mL, about 9.6 mL, about 9.7 mL, about 9.8 mL, about 9.9 mL, about 10 mL, about 11 mL, about 12 mL, about 13 mL, about 14 mL, about 15 mL, about 16 mL, about 17 mL, about 18 mL, about 19 mL, or about 20 mL.

A therapeutically-effective amount of a compound described herein can be present in a composition at a concentration of, for example, about 0.1 units/mL, about 0.2 units/mL, about 0.3 units/mL, about 0.4 units/mL, about 0.5 units/mL, about 0.6 units/mL, about 0.7 units/mL, about 0.8 units/mL, about 0.9 units/mL, about 1 unit/mL, about 2 units/mL, about 3 units/mL, about 4 units/mL, about 5 units/mL, about 6 units/mL, about 7 units/mL, about 8 units/mL, about 9 units/mL, about 10 units/mL, about 11 units/mL, about 12 units/mL, about 13 units/mL, about 14 units/mL, about 15 units/mL, about 16 units/mL, about 17 units/mL, about 18 units/mL, about 19 units/mL, about 20 units/mL, about 21 units/mL, about 22 units/mL, about 23 units/mL, about 24 units/mL about 25 units/mL, about 30 units/mL, about 35 units/mL, about 40 units/mL, about 45 units/mL, or about 50 units/mL.

A therapeutically-effective amount of a compound described herein can be present in a composition of the invention at a mass of about, for example, about 0.01 µg, about 0.05 µg, about 0.1 µg, about 0.15 µg, about 0.2 µg, about 0.25 µg, about 0.3 µg, about 0.35 µg, about 0.4 µg, about 0.5 µg, about 0.6 µg, about 0.7 µg, about 0.8 µg, about 0.9 µg, about 1 µg, about 2 µg, about 3 µg, about 4 µg, about 5 µg, about 10 µg, about 15 µg, about 20 µg, about 25 µg, about 30 µg, about 35 µg, about 40 µg, about 45 µg, about 50 µg, about 60 µg, about 70 µg, about 80 µg, about 90 µg, about 100 µg, about 125 µg, about 150 µg, about 175 µg, about 200 µg, about 250 µg, about 300 µg, about 350 µg, about 400 µg, about 450 µg, about 500 µg, about 600 µg, about 700 µg, about 800 µg, about 900 µg, about 1 mg, about 2 mg, about 3 mg, about 4 mg, about 5 mg, about 6 mg, about 7 mg, about 8 mg, about 9 mg, or about 10 mg.

A therapeutically-effective amount of a compound described herein can be present in a composition of the invention at a concentration of, for example, about 0.001 mg/mL, about 0.002 mg/mL, about 0.003 mg/mL, about 0.004 mg/mL, about 0.005 mg/mL, about 0.006 mg/mL, about 0.007 mg/mL, about 0.008 mg/mL, about 0.009 mg/mL, about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 6 mg/mL, about 7 mg/mL, about 8 mg/mL, about 9 mg/mL, or about 10 mg/mL.

A therapeutically-effective amount of a compound described herein can be present in a composition of the invention at a unit of active agent/unit of active time. Non-limiting examples of therapeutically-effective amounts can be, for example, about 0.01 units/minute, about 0.02 units/minute, about 0.03 units/minute, about 0.04 units/minute, about 0.05 units/minute, about 0.06 units/minute, about 0.07 units/minute, about 0.08 units/minute, about 0.09 units/minute or about 0.1 units/minute.

Pharmaceutical compositions of the invention can be formulated at any suitable pH. The pH can be, for example, about 2, about 2.05, about 2.1, about 2.15, about 2.2, about 2.25, about 2.3, about 2.35, about 2.4, about 2.45, about 2.5, about 2.55, about 2.6, about 2.65, about 2.7, about 2.75, about 2.8, about 2.85, about 2.9, about 2.95, about 3, about 3.05, about 3.1, about 3.15, about 3.2, about 3.25, about 3.3, about 3.35, about 3.4, about 3.45, about 3.5, about 3.55, about 3.6, about 3.65, about 3.7, about 3.75, about 3.8, about 3.85, about 3.9, about 3.95, about 4, about 4.05, about 4.1, about 4.15, about 4.2, about 4.25, about 4.3, about 4.35, about 4.4, about 4.45, about 4.5, about 4.55, about 4.6, about 4.65, about 4.7, about 4.75, about 4.8, about 4.85, about 4.9, about 4.95, or about 5 pH units.

Pharmaceutical compositions of the invention can be formulated at any suitable pH. The pH can be, for example, from about 2 to about 2.2, about 2.05 to about 2.25, about 2.1 to about 2.3, about 2.15 to about 2.35, about 2.2 to about 2.4, about 2.25 to about 2.45, about 2.3 to about 2.5, about 2.35 to about 2.55, about 2.4 to about 2.6, about 2.45 to about 2.65, about 2.5 to about 2.7, about 2.55 to about 2.75, about 2.6 to about 2.8, about 2.65 to about 2.85, about 2.7 to about 2.9, about 2.75 to about 2.95, about 2.8 to about 3, about 2.85 to about 3.05, about 2.9 to about 3.1, about 2.95 to about 3.15, about 3 to about 3.2, about 3.05 to about 3.25, about 3.1 to about 3.3, about 3.15 to about 3.35, about 3.2 to about 3.4, about 3.25 to about 3.45, about 3.3 to about 3.5, about 3.35 to about 3.55, about 3.4 to about 3.6, about 3.45 to about 3.65, about 3.5 to about 3.7, about 3.55 to about 3.75, about 3.6 to about 3.8, about 3.65 to about 3.85, about 3.7 to about 3.9, about 3.7 to about 3.8, about 3.75 to about 3.95, about 3.75 to about 3.8, about 3.8 to about 3.85, about 3.75 to about 3.85, about 3.8 to about 4, about 3.85 to about 4.05, about 3.9 to about 4.1, about 3.95 to about 4.15, about 4 to about 4.2, about 4.05 to about 4.25, about 4.1 to about 4.3, about 4.15 to about 4.35, about 4.2 to about 4.4, about 4.25 to about 4.45, about 4.3 to about 4.5, about 4.35 to about 4.55, about 4.4 to about 4.6, about 4.45 to about 4.65, about 4.5 to about 4.7, about 4.55 to about 4.75, about 4.6 to about 4.8, about 4.65 to about 4.85, about 4.7 to about 4.9, about 4.75 to about 4.95, about 4.8 to about 5, about 4.85 to about 5.05, about 4.9 to about 5.1, about 4.95 to about 5.15, or about 5 to about 5.2 pH units.

In some embodiments, the addition of an excipient can change the viscosity of a pharmaceutical composition of the invention. In some embodiments the use of an excipient can increase or decrease the viscosity of a fluid by at least 0.001 Pascal-second (Pa·s), at least 0.001 Pa·s, at least 0.0009 Pa·s, at least 0.0008 Pa·s, at least 0.0007 Pa·s, at least 0.0006 Pa·s, at least 0.0005 Pa·s, at least 0.0004 Pa·s, at least 0.0003 Pa·s, at least 0.0002 Pa·s, at least 0.0001 Pa·s, at least 0.00005 Pa·s, or at least 0.00001 Pa·s.

In some embodiments, the addition of an excipient to a pharmaceutical composition of the invention can increase or decrease the viscosity of the composition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the addition of an excipient to a pharmaceutical composition of the invention can increase or decrease the viscosity of the composition by no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%.

Any compound herein can be purified. A compound can be at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Compositions of the invention can be packaged as a kit. In some embodiments, a kit includes written instructions on the administration or use of the composition. The written material can be, for example, a label. The written material can suggest conditions methods of administration. The instructions provide the subject and the supervising physician with the best guidance for achieving the optimal clinical outcome from the administration of the therapy. In some embodiments, the label can be approved by a regulatory agency, for example the U.S. Food and Drug Administration (FDA), the European Medicines Agency (EMA), or other regulatory agencies.

Pharmaceutically-Acceptable Excipients.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

In some embodiments, the pharmaceutical composition provided herein comprises a sugar as an excipient. Non-limiting examples of sugars include trehalose, sucrose, glucose, lactose, galactose, glyceraldehyde, fructose, dextrose, maltose, xylose, mannose, maltodextrin, starch, cellulose, lactulose, cellobiose, mannobiose, and combinations thereof.

In some embodiments, the pharmaceutical composition provided herein comprises a buffer as an excipient. Non-limiting examples of buffers include potassium phosphate, sodium phosphate, saline sodium citrate buffer (SSC), acetate, saline, physiological saline, phosphate buffer saline (PBS), 4-2-hydroxyethyl-1-piperazineethanesulfonic acid buffer (HEPES), 3-(N-morpholino)propanesulfonic acid buffer (MOPS), and piperazine-N,N'-bis(2-ethanesulfonic acid) buffer (PIPES), or combinations thereof.

In some embodiments, a pharmaceutical composition of the invention comprises a source of divalent metal ions as an excipient. A metal can be in elemental form, a metal atom, or a metal ion. Non-limiting examples of metals include transition metals, main group metals, and metals of Group 1, Group 2, Group 3, Group 4, Group 5, Group 6, Group 7, Group 8, Group 9, Group 10, Group 11, Group 12, Group 13, Group 14, and Group 15 of the Periodic Table. Non-limiting examples of metals include lithium, sodium, potassium, cesium, magnesium, calcium, strontium, scandium, titanium, vanadium, chromium, manganese, iron, cobalt, nickel, copper, zinc, yttrium, zirconium, niobium, molybdenum, palladium, silver, cadmium, tungsten, rhenium, osmium, iridium, platinum, gold, mercury, cerium, and samarium.

In some embodiments, the pharmaceutical composition provided herein comprises an alcohol as an excipient. Non-limiting examples of alcohols include ethanol, propylene glycol, glycerol, polyethylene glycol, chlorobutanol, isopropanol, xylitol, sorbitol, maltitol, erythritol, threitol, arabitol, ribitol, mannitol, galactilol, fucitol, lactitol, and combinations thereof.

Pharmaceutical preparations can be formulated with polyethylene glycol (PEG). PEGs with molecular weights ranging from about 300 g/mol to about 10,000,000 g/mol can be used. Non-limiting examples of PEGs include PEG 200, PEG 300, PEG 400, PEG 540, PEG 550, PEG 600, PEG 1000, PEG 1450, PEG 1500, PEG 2000, PEG 3000, PEG 3350, PEG 4000, PEG 4600, PEG 6000, PEG 8000, PEG 10,000, and PEG 20,000.

Further excipients that can be used in a composition of the invention include, for example, benzalkonium chloride, benzethonium chloride, benzyl alcohol, butylated hydroxyanisole, butylated hydroxytoluene, chlorobutanol, dehydroacetic acid, ethylenediamine, ethyl vanillin, glycerin, hypophosphorous acid, phenol, phenylethyl alcohol, phenylmercuric nitrate, potassium benzoate, potassium metabisulfite, potassium sorbate, sodium bisulfite, sodium metabisulfite, sorbic acid, thimerasol, acetic acid, aluminum monostearate, boric acid, calcium hydroxide, calcium stearate, calcium sulfate, calcium tetrachloride, cellulose acetate pthalate, microcrystalline celluose, chloroform, citric acid, edetic acid, and ethylcellulose.

In some embodiments, the pharmaceutical composition provided herein comprises an aprotic solvent as an excipient. Non-limiting examples of aprotic solvents include perfluorohexane, α,α,α-trifluorotoluene, pentane, hexane, cyclohexane, methylcyclohexane, decalin, dioxane, carbon tetrachloride, freon-11, benzene, toluene, carbon disulfide, diisopropyl ether, diethyl ether, t-butyl methyl ether, ethyl acetate, 1,2-dimethoxyethane, 2-methoxyethyl ether, tetrahydrofuran, methylene chloride, pyridine, 2-butanone, acetone, N-methylpyrrolidinone, nitromethane, dimethylformamide, acetonitrile, sulfolane, dimethyl sulfoxide, and propylene carbonate.

The amount of the excipient in a pharmaceutical composition of the invention can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 60%, about 70%, about 80%, about 90%, about 100%, about 200%, about 300%, about 400%, about 500%, about 600%, about 700%, about 800%, about 900%, or about 1000% by mass of the vasopressin in the pharmaceutical composition.

The amount of the excipient in a pharmaceutical composition of the invention can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 55% about 60%, about 65%, about 70%, about 75%, about 80%, about 85%, about 90%, about 95%, about 99%, or about 100% by mass or by volume of the unit dosage form.

The ratio of vasopressin to an excipient in a pharmaceutical composition of the invention can be about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1 about 30:about 1, about 25:about 1, about 20:about 1, about 15:about 1, about 10:about 1, about 9:about 1, about 8:about 1, about 7:about 1, about 6:about 1, about 5:about 1, about 4:about 1, about 3:about 1, about 2:about 1, about 1:about 1, about 1:about 2, about 1:about 3, about 1:about 4, about 1:about 5, about 1:about 6, about 1:about 7, about 1:about 8, about 1:about 9, or about 1:about 10.

Pharmaceutically-Acceptable Salts.

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Peptide Sequence.

As used herein, the abbreviations for the L-enantiomeric and D-enantiomeric amino acids are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). In some embodiments, the amino acid is a L-enantiomer. In some embodiments, the amino acid is a D-enantiomer.

A peptide of the disclosure can have about 5%, about 10%, about 15%, about 20%, about 25%, about 30%, about 35%, about 40%, about 45%, about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% amino acid sequence homology to SEQ ID NO. 1.

In some embodiments, a pharmaceutical composition of the invention comprises one or a plurality of peptides having about 80% to about 90% sequence homology to SEQ ID NO. 1, about 88% to about 90% sequence homology to SEQ ID NO. 1 or 88% to 90% sequence homology to SEQ ID NO. 1. In some embodiments, a pharmaceutical composition of the invention comprises vasopressin and one or more of a second, third, fourth, fifth, sixth, seventh, eighth, ninth, and tenth peptide.

The ratio of vasopressin to another peptide in a pharmaceutical composition of the invention can be, for example, about 1000:about 1, about 990:about 1, about 980:about 1, about 970:about 1, about 960:about 1, about 950:about 1, about 800:about 1, about 700:about 1, about 600:1, about 500:about 1, about 400:about 1, about 300:about 1, about 200:about 1, about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1, about 30:about 1, about 25:about 1, about 20:about 1, about 19:about 1, about 18:about 1, about 17:about 1, about 16:about 1, about 15:about 1, about 14:about 1, about 13:about 1, about 12:about 1, about 11:about 1, or about 10:about 1.

The amount of another peptide or impurity in a composition of the invention can be, for example, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% by mass of vasopressin.

Another peptide or impurity present in a composition described herein can be, for example, SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, a dimer of SEQ ID NO.: 1, an unidentified impurity, or any combination thereof.

Non-limiting examples of methods that can be used to identify peptides of the invention include high-performance liquid chromatography (HPLC), mass spectrometry (MS), Matrix Assisted Laser Desorption Ionization Time-of-Flight (MALDI-TOF), electrospray ionization Time-of-flight (ESI-TOF), gas chromatography-mass spectrometry (GC-MS), liquid chromatography-mass spectrometry (LC-MS), and two-dimensional gel electrophoresis.

HPLC can be used to identify peptides using high pressure to separate components of a mixture through a packed column of solid adsorbent material, denoted the stationary phase. The sample components can interact differently with the column based upon the pressure applied to the column, material used in stationary phase, size of particles used in the stationary phase, the composition of the solvent used in the column, and the temperature of the column. The interaction between the sample components and the stationary phase can affect the time required for a component of the sample to move through the column. The time required for component to travel through the column from injection point to elution is known as the retention time.

Upon elution from the column, the eluted component can be detected using a UV detector attached to the column. The wavelength of light at which the component is detected, in combination with the component's retention time, can be used to identify the component. Further, the peak displayed by the detector can be used to determine the quantity of the component present in the initial sample. Wavelengths of light that can be used to detect sample components include, for example, about 200 nM, about 225 nm, about 250 nm, about 275 nm, about 300 nm, about 325 nm, about 350 nm, about 375 nm, and about 400 nm.

Mass spectrometry (MS) can also be used to identify peptides of the invention. To prepare samples for MS analysis, the samples, containing the proteins of interest, are digested by proteolytic enzymes into smaller peptides. The enzymes used for cleavage can be, for example, trypsin, chymotrypsin, glutamyl endopeptidase, Lys-C, and pepsin. The samples can be injected into a mass spectrometer. Upon injection, all or most of the peptides can be ionized and detected as ions on a spectrum according to the mass to charge ratio created upon ionization. The mass to charge ratio can then be used to determine the amino acid residues present in the sample.

The present disclosure provides several embodiments of pharmaceutical formulations that provide advantages in stability, administration, efficacy, and modulation of formulation viscosity. Any embodiments disclosed herein can be used in conjunction or individually. For example, any pharmaceutically-acceptable excipient, method, technique, solvent, compound, or peptide disclosed herein can be used together with any other pharmaceutically-acceptable excipient, method, technique, solvent, compound, or peptide disclosed herein to achieve any therapeutic result. Compounds, excipients, and other formulation components can be present at any amount, ratio, or percentage disclosed herein in any such formulation, and any such combination can be used therapeutically for any purpose described herein and to provide any viscosity described herein.

EXAMPLES

Example 1: Impurities of Vasopressin as Detected by HPLC

To analyze degradation products of vasopressin that can be present in an illustrative formulation of vasopressin, gradient HPLC was performed to separate vasopressin from related peptides and formulation components. TABLE 2 below depicts the results of the experiment detailing the chemical formula, relative retention time (RRT), molar mass, and structure of vasopressin and detected impurities.

Vasopressin was detected in the eluent using UV absorbance. The concentration of vasopressin in the sample was determined by the external standard method, where the peak area of vasopressin in sample injections was compared to the peak area of vasopressin reference standards in a solution of known concentration. The concentrations of related peptide impurities in the sample were also determined using the external standard method, using the vasopressin reference standard peak area and a unit relative response factor. An impurities marker solution was used to determine the relative retention times of identified related peptides at the time of analysis.

Experimental conditions are summarized in TABLE 2 below.

TABLE 2

| Column | YMC-Pack ODS-AM, 3 µm, 120 Å pore, 4.6 × 100 mm |
|---|---|
| Column Temperature | 25° C. |
| Flow Rate | 1.0 mL/min |
| Detector | 215 nm |
| | Note: For Identification a Diode Array Detector (DAD) was used with the range of 200-400 nm. |
| Injection Volume | 100 µL |
| Run time | 55 minutes |
| Autosampler Vials | Polypropylene vials |

| Pump (gradient) | Time (min) | % A | % B | Flow |
|---|---|---|---|---|
| | 0 | 90 | 10 | 1.0 |
| | 40 | 50 | 50 | 1.0 |
| | 45 | 50 | 50 | 1.0 |
| | 46 | 90 | 10 | 1.0 |
| | 55 | 90 | 10 | 1.0 |

The diluent used for the present experiment was 0.25% v/v Acetic Acid, which was prepared by transferring 2.5 mL of glacial acetic acid into a 1-L volumetric flask containing 500 mL of water. The solution was diluted to the desired volume with water.

Phosphate buffer at pH 3.0 was used for mobile phase A. The buffer was prepared by weighing approximately 15.6 g of sodium phosphate monobasic monohydrate into a beaker. 1000 mL of water was added, and mixed well. The pH was adjusted to 3.0 with phosphoric acid. The buffer was filtered through a 0.45 µm membrane filter under vacuum, and the volume was adjusted as necessary.

An acetonitrile:water (50:50) solution was used for mobile phase B. To prepare mobile phase B, 500 mL of acetonitrile was mixed with 500 mL of water.

The working standard solution contained approximately 20 units/mL of vasopressin. The standard solution was prepared by quantitatively transferring the entire contents of 1 vial of USP Vasopressin RS with diluent to a 50-mL volumetric flask.

The intermediate standard solution was prepared by pipetting 0.5 mL of the working standard solution into a 50-mL volumetric flask.

The sensitivity solution was prepared by pipetting 5.0 mL of the intermediate standard solution into a 50-mL volumetric flask. The solution was diluted to the volume with Diluent and mixed well.

A second working standard solution was prepared as directed under the standard preparation.

A portion of the vasopressin control sample was transferred to an HPLC vial and injected. The control was stable for 120 hours when stored in autosampler vials at ambient laboratory conditions.

To prepare the impurities marker solution, a 0.05% v/v acetic acid solution was prepared by pipetting 200.0 mL of a 0.25% v/v acetic acid solution into a 1-L volumetric flask. The solution was diluted to the desired volume with water and mixed well.

To prepare the vasopressin impurity stock solutions, the a solution of each impurity was prepared in a 25 mL volumetric flask and diluted with 0.05% v/v acetic acid to a concentration suitable for HPLC injection.

To prepare the MAA/H-IBA (Methacrylic Acid/α-Hydroxy-isobutyric acid) stock solution, a stock solution containing approximately 0.3 mg/mL H-IBA and 0.01 mg/mL in 0.05% v/v acetic acid was made in a 50 mL volumetric flask.

To prepare the chlorobutanol diluent, about one gram of hydrous chlorobutanol was added to 500 mL of water. Subsequently, 0.25 mL of acetic acid was added and the solution was stirred to dissolve the chlorobutanol.

To prepare the impurity marker solution, vasopressin powder was mixed with the impurity stock solutions prepared above.

The solutions were diluted to volume with the chlorobutanol diluent. The solutions were aliquoted into individual crimp top vials and stored at 2-8° C. At time of use, the solutions were removed from refrigeration (2-8° C.) and allowed to reach room temperature.

The vasopressin impurity marker solution was stable for at least 120 hours when stored in auto-sampler vials at ambient laboratory conditions. The solution was suitable for use as long as the chromatographic peaks could be identified based on comparison to the reference chromatogram.

To begin the analysis, the HPLC system was allowed to equilibrate for at least 30 minutes using mobile phase B, followed by time 0 min gradient conditions until a stable baseline was achieved.

The diluent was injected at the beginning of the run, and had no peaks that interfered with Vasopressin at around 18 minutes as shown in FIG. 1.

Figure 2:
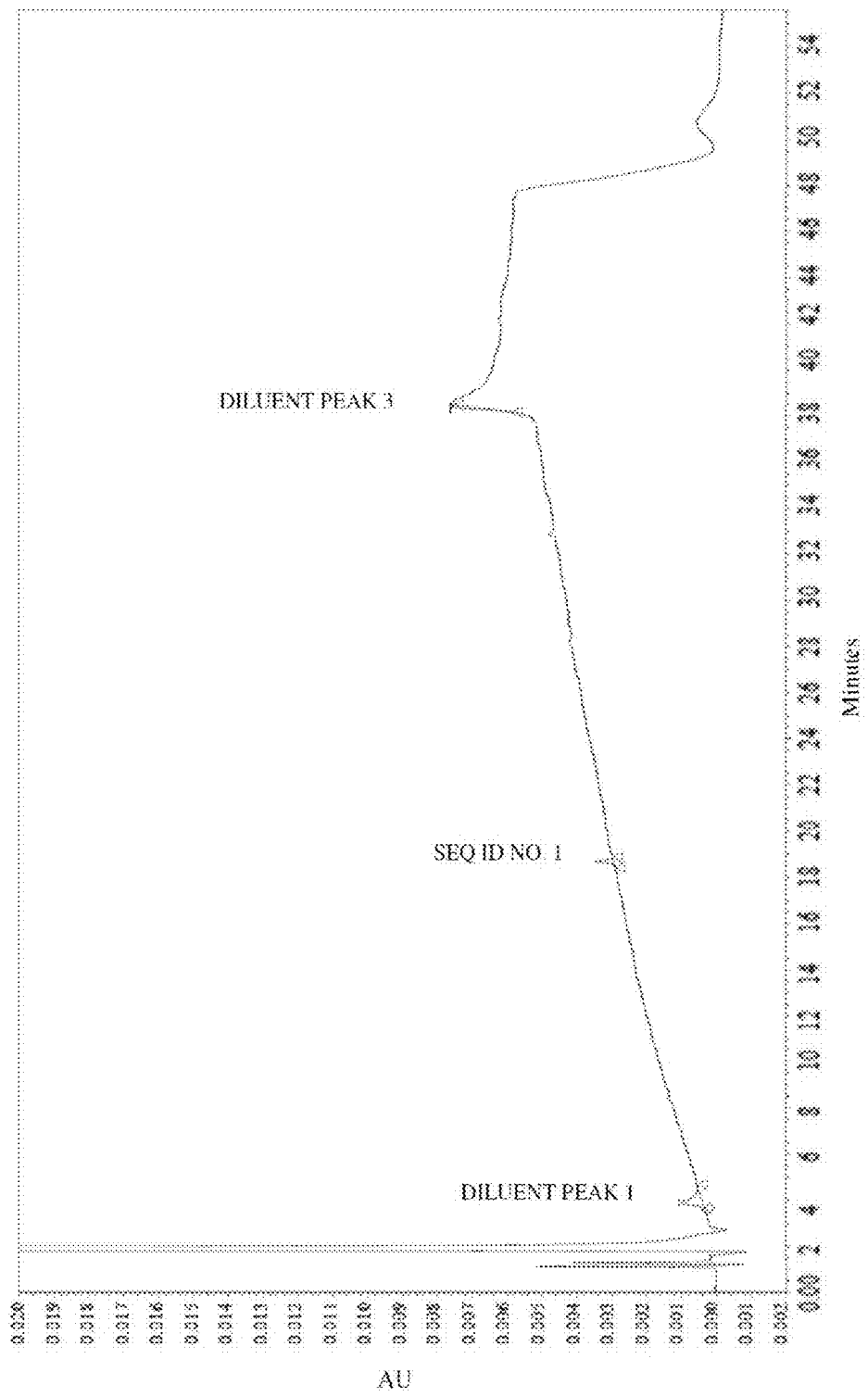
FIG. 2 is a chromatogram of a sensitivity solution used in a vasopressin assay.

A single injection of the sensitivity solution was performed, wherein the signal-to-noise ratio of the Vasopressin was greater than or equal to ten as shown in FIG. 2.

Figure 3:
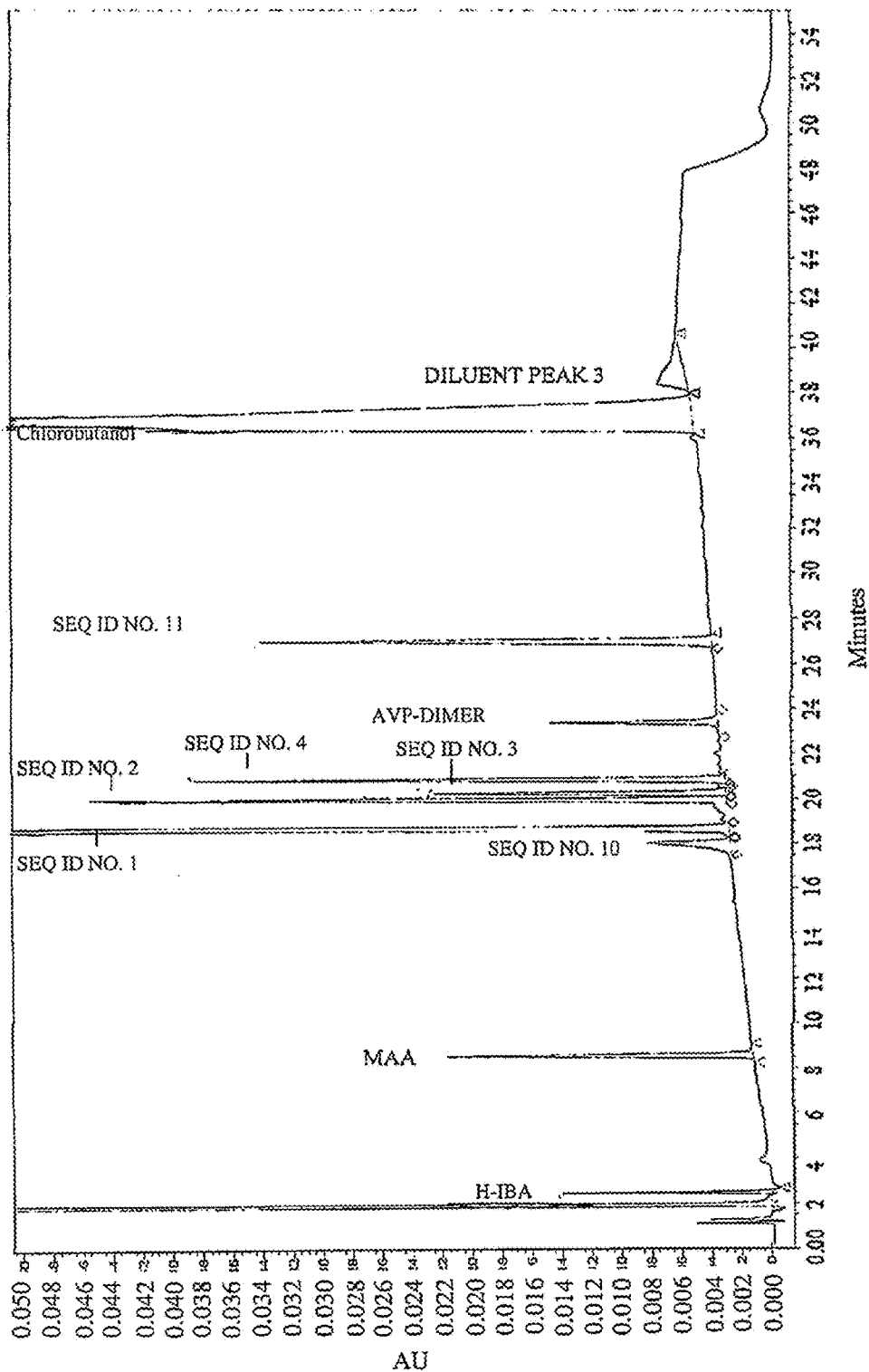
FIG. 3 is a chromatogram of an impurity marker solution used in a vasopressin assay.
Figure 4:
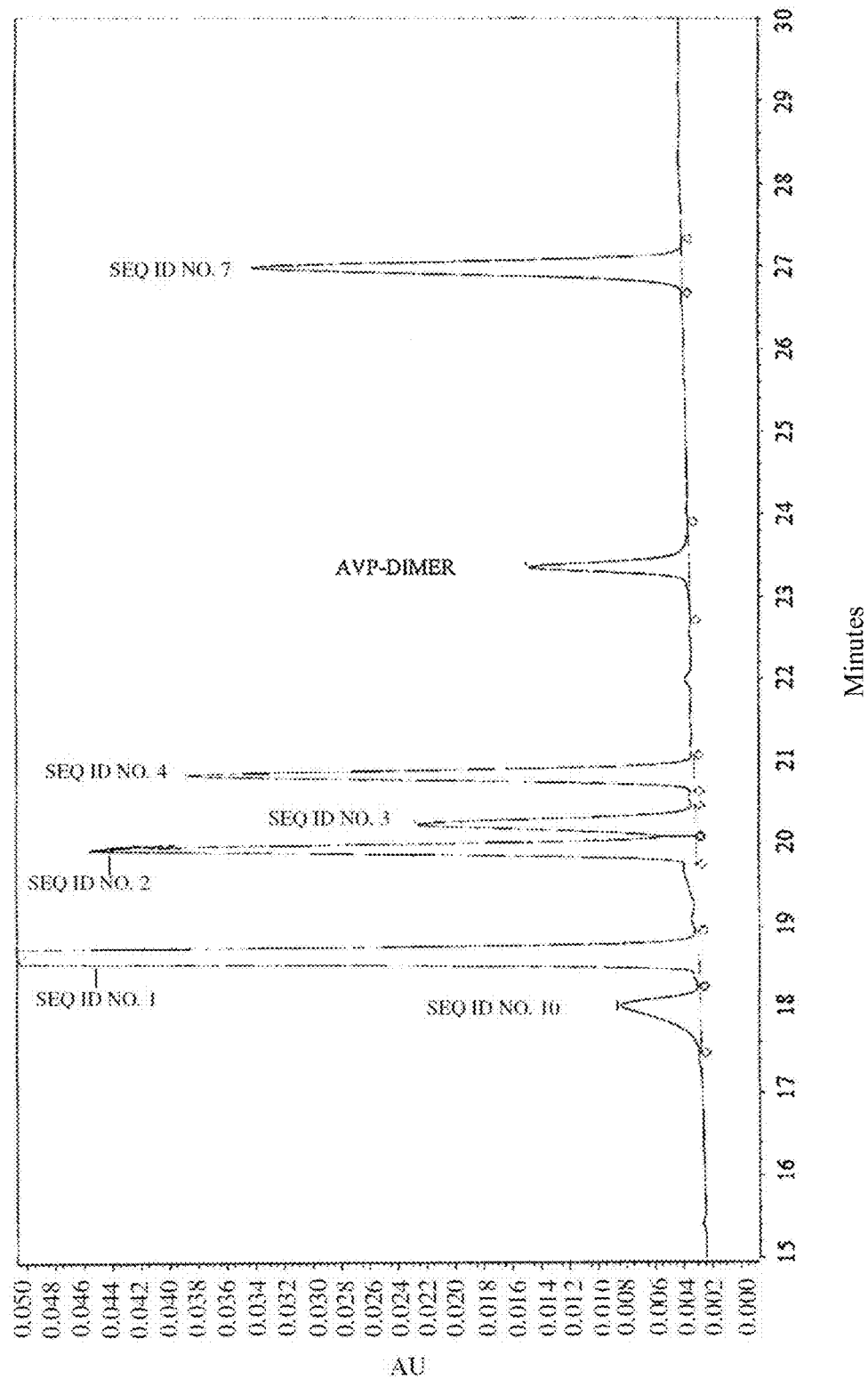
FIG. 4 is a zoomed-in depiction of the chromatogram in FIG. 3.

A single injection of the impurities marker solution was then made. The labeled impurities in the reference chromatogram were identified in the chromatogram of the marker solution based on their elution order and approximate retention times shown in FIG. 3 and FIG. 4. FIG. 4 is a zoomed in chromatograph of FIG. 3 showing the peaks that eluted between 15 and 30 minutes. The nomenclature, structure, and approximate retention times for individual identified impurities are detailed in TABLE 3.

Figure 5:
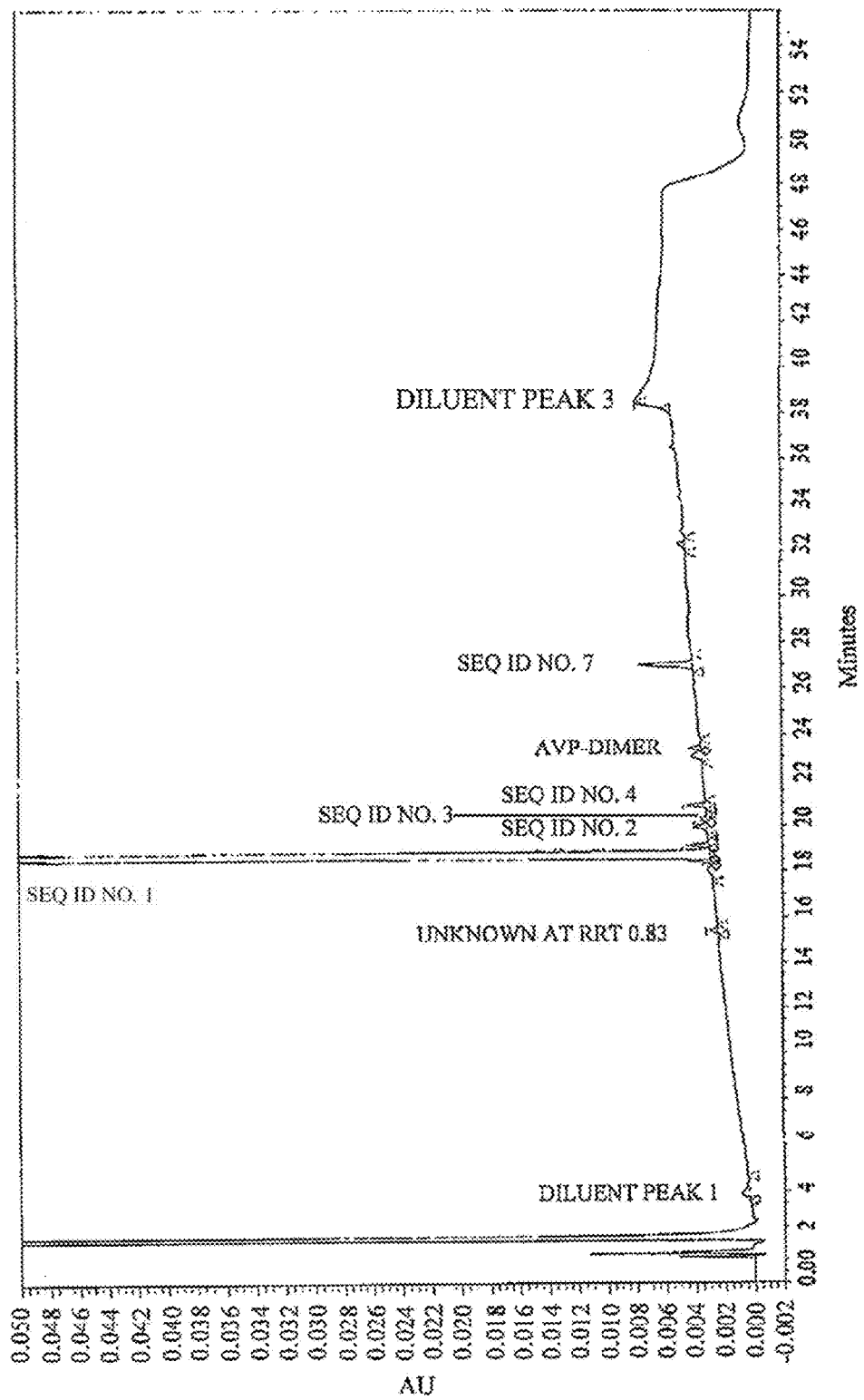
FIG. 5 is a chromatogram of a vasopressin standard solution.

A single injection of the working standard solution was made to ensure that the tailing factor of the vasopressin peak was less than or equal to about 2.0 as shown in FIG. 5.

A total of five replicate injections of the working standard solution were made to ensure that the relative standard deviation (% RSD) of the five replicate vasopressin peak areas was not more than 2.0%.

Two replicate injections of the check standard preparation were to confirm that the check standard conformity was 99.0%-101.0%. One injection of the control sample was made to confirm that the assay of the control sample met the control limits established for the sample.

Then, one injection of the working standard solution was made.

Figure 6:
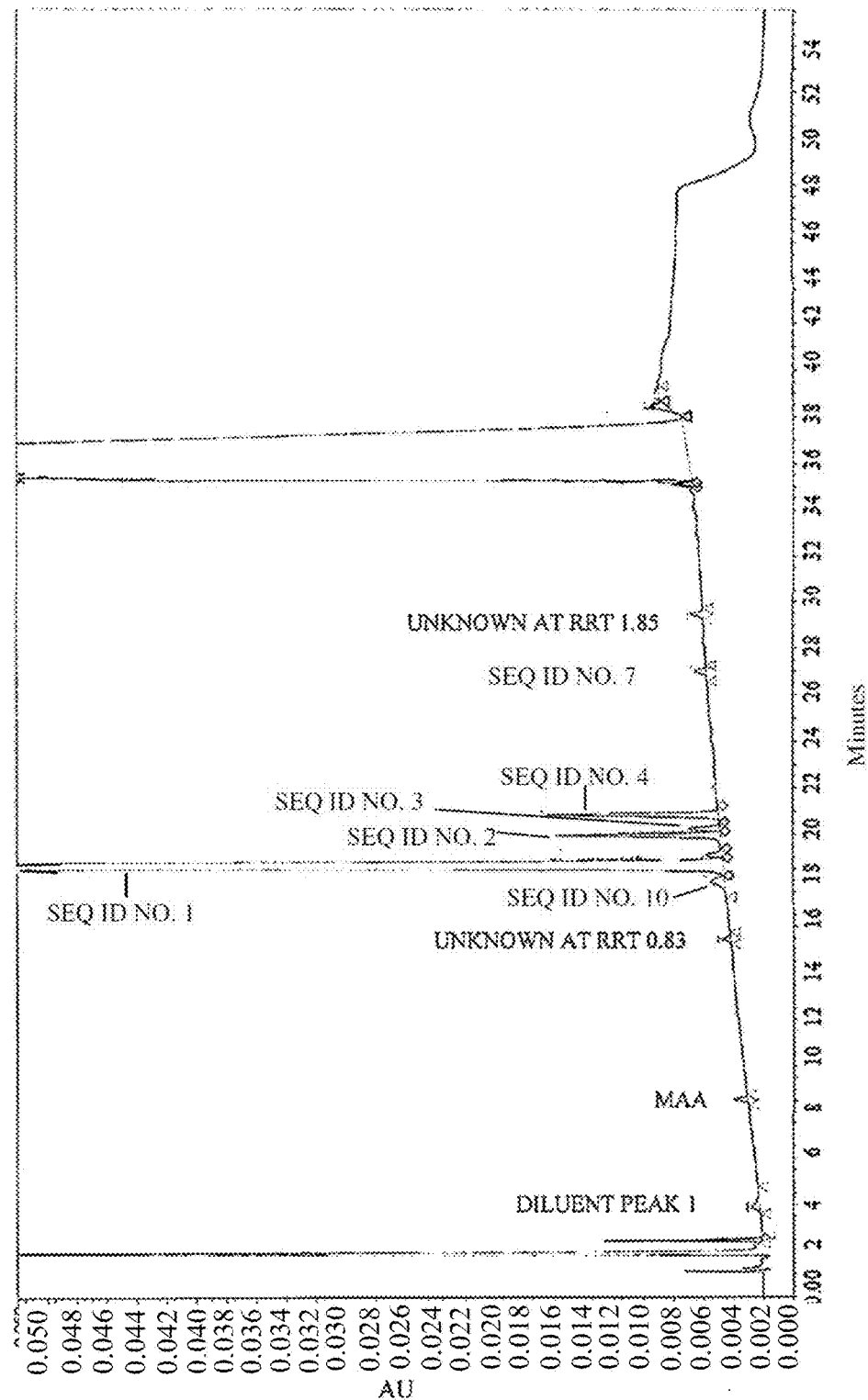
FIG. 6 is a chromatogram of a sample vasopressin preparation.

Following the steps above done to confirm system suitability, a single injection of each sample preparation was made. The chromatograms were analyzed to determine the vasopressin and impurity peak areas. The chromatogram is depicted in FIG. 6.

The working standard solution was injected after 1 to 4 sample injections, and the bracketing standard peak areas were averaged for use in the calculations to determine peak areas of vasopressin and associated impurities.

The relative standard deviation (% RSD) of vasopressin peak areas for the six injections of working standard solution was calculated by including the initial five injections from the system suitability steps above and each of the subsequent interspersed working standard solution injections. The calculations were done to ensure that each of the % RSD were not more than 2.0%.

The retention time of the major peak in the chromatogram of the sample preparation corresponded to that of the vasopressin peak in the working standard solution injection that preceded the sample preparation injection.

Figure 7:
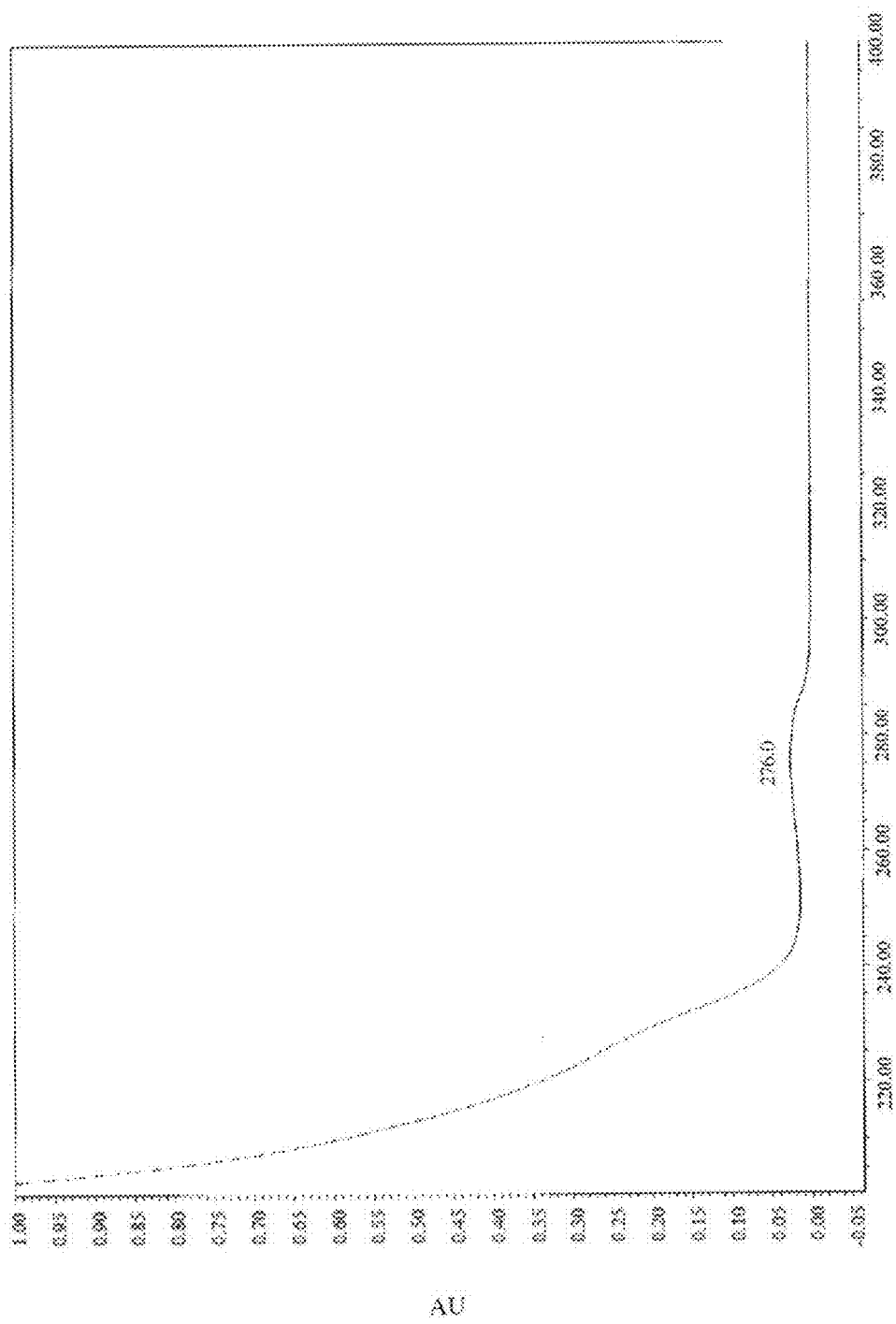
FIG. 7 is a UV spectrum of a vasopressin sample.
Figure 8:
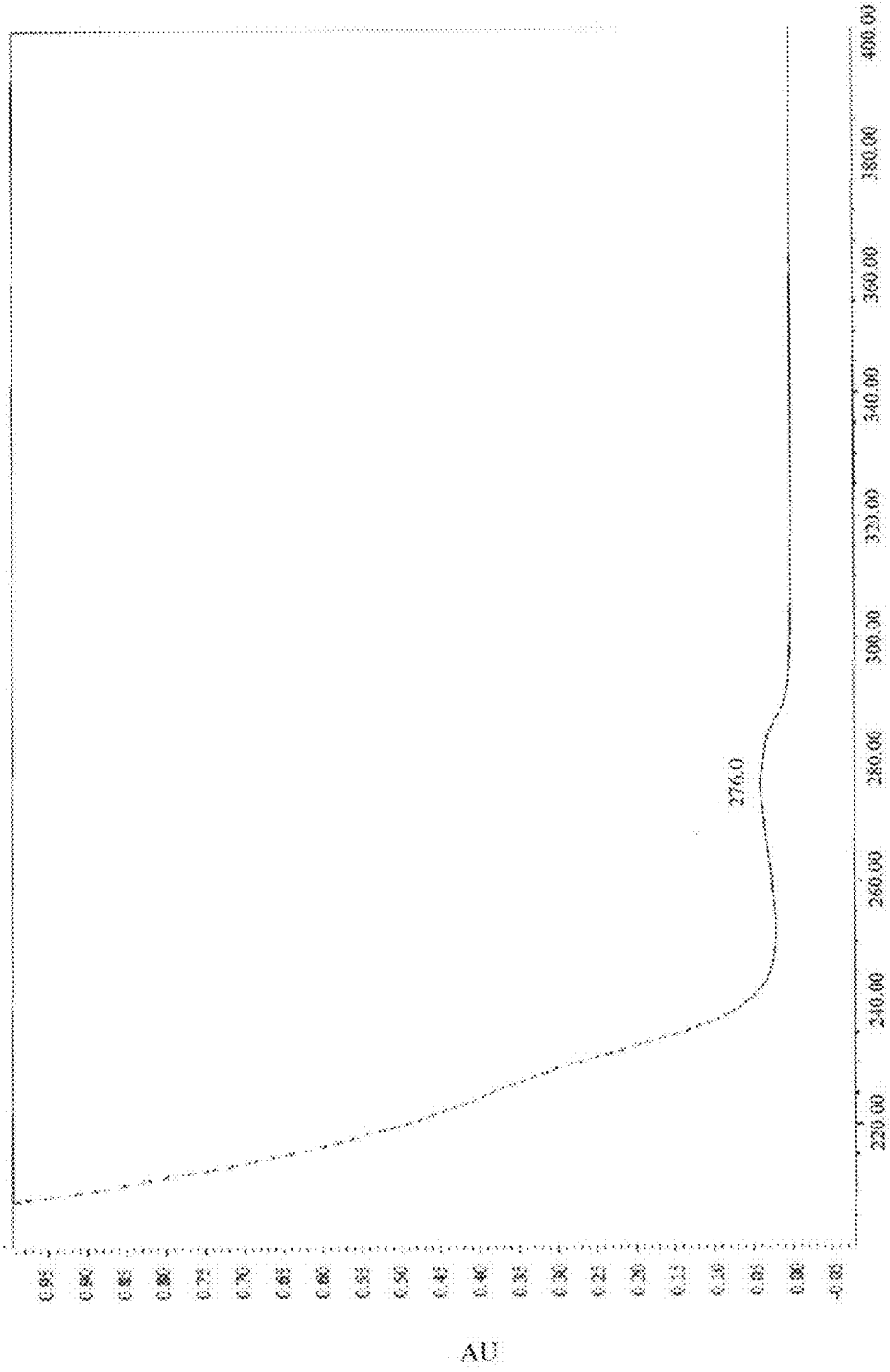
FIG. 8 is a UV spectrum of a vasopressin standard.

The UV spectrum (200-400 nm) of the main peak in the chromatogram of the sample preparation compared to the UV spectrum of vasopressin in the working standard preparation. FIG. 7 depicts a UV spectrum of a vasopressin sample and FIG. 8 depicts a UV spectrum of vasopressin standard.

To calculate the vasopressin units/mL, the following formula was used:

$$\text{Vasopressin units/mL} = \frac{R_U}{R_S} \times \text{Conc STD}$$

where:

$R_U$=Vasopressin peak area response of Sample preparation.

$R_S$=average vasopressin peak area response of bracketing standards.

Conc STD=concentration of the vasopressin standard in units/mL

To identify the impurities, the % Impurity and identity for identified impurities (TABLE 3) that are were greater than or equal to 0.10% were reported. Impurities were truncated to 3 decimal places and then rounded to 2 decimal places, unless otherwise specified.

The impurities were calculated using the formula below:

$$\%\ \text{impurity} = \frac{R_I}{R_S} \times \frac{\text{Conc STD}}{20\ \text{U/mL}} \times 100\%$$

where:

$R_I$=Peak area response for the impurity

20 U/mL=Label content of vasopressin

TABLE 3 below details the chemical formula, relative retention time (RRT in minutes), molar mass, and structure of vasopressin and detected impurities.

TABLE 3

| Name | Formula | Appr. RRT | Molar Mass (g) |
|---|---|---|---|
| Vasopressin (Arginine Vasopressin, AVP) | $C_{46}H_{65}N_{15}O_{12}S_2$ | 1.00 | 1084.23 |
| CYFQNCPRG-NH$_2$ SEQ ID NO.: 1 (disulfide bridge between cys residues) | | | |
| Gly9-vasopressin (Gly9-AVP) | $C_{46}H_{64}N_{14}O_{13}S_2$ | 1.07 | 1085.22 |
| CYFQNCPRG SEQ ID NO.: 2 (disulfide bridge between cys residues) | | | |
| Asp5-vasopressin (Asp5-AVP) | $C_{46}H_{64}N_{14}O_{13}S_2$ | 1.09 | 1085.22 |
| CYFQDCPRG-NH$_2$ SEQ ID NO.: 3 (disulfide bridge between cys residues) | | | |
| Glu4-vasopressin (Glu4-AVP) | $C_{46}H_{64}N_{14}O_{13}S_2$ | 1.12 | 1085.22 |
| CYFENCPRG-NH$_2$ SEQ ID NO.: 4 (disulfide bridge between cys residues) | | | |
| Acetyl-vasopressin (Acetyl-AVP) | $C_{48}H_{67}N_{15}O_{13}S_2$ | 1.45 | 1126.27 |
| Ac-CYFQNCPRG-NH$_2$ SEQ ID NO.: 7 (disulfide bridge between cys residues) | | | |
| D-Asn-vasopressin (DAsn-AVP) | $C_{46}H_{65}N_{15}O_{12}S_2$ | 0.97 | 1084.23 |
| CYFQ(D-Asn)CPRG-NH$_2$ SEQ ID NO.: 10 (disulfide bridge between cys residues) | | | |

TABLE 3-continued

| Name | Formula | Appr. RRT | Molar Mass (g) |
|---|---|---|---|
| Dimeric-vasopressin (Dimer-AVP) (monomers cross linked by disulfide bridges) | $C_{92}H_{130}N_{30}O_{24}S_4$ | 1.22 | 2168.46 |

Example 2: Investigation of pH

Figure 9:
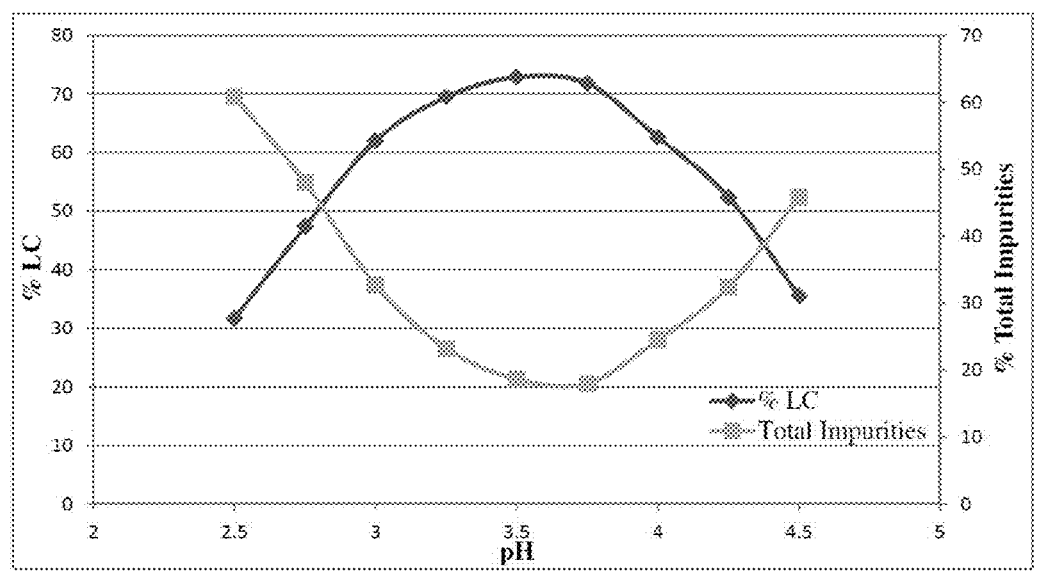
FIG. 9 plots vasopressin stability across a range of pH as determined experimentally.

To determine a possible pH for a vasopressin formulation with good shelf life, vasopressin formulations were prepared in 10 mM citrate buffer diluted in isotonic saline across a range of pH. Stability was assessed via HPLC as in EXAMPLE 1 after incubation of the formulations at 60° C. for one week. FIG. 9 illustrates the results of the experiment. The greatest level of stability was observed at pH 3.5. At pH 3.5, the percent label claim (% LC) of vasopressin was highest, and the proportion of total impurities was lowest.

Example 3: Effect of Peptide Stabilizers on Vasopressin Formulation

To observe the effect of stabilizers on the degradation of vasopressin, a series of peptide stabilizers were added to a vasopressin formulation as detailed in TABLE 4. Stability of vasopressin was assessed via HPLC after incubation of the formulations at 60° C. for one week.

TABLE 4

| Ethanol | PEG 400 | Glycerol | Poloxamer 188 | HPbCD[a] | n-Methylpyrrolidone (NMP) |
|---|---|---|---|---|---|
| 1% | 1% | 1% | 1% | 1% | 1% |
| 10% | 10% | 10% | 10% | 10% | 10% |

[a]Hydroxypropyl beta-Cyclodextrin

Figure 10:
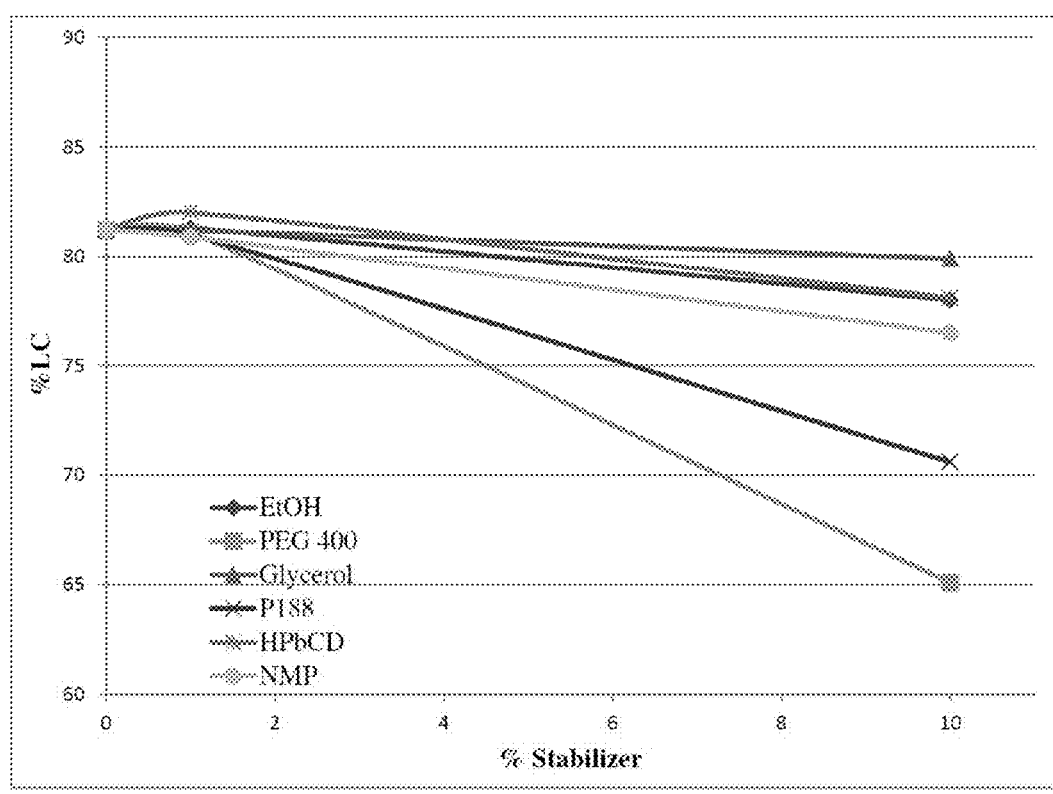
FIG. 10 illustrates the effects of various stabilizers on vasopressin stability.

FIG. 10 illustrates the stability of vasopressin in terms of % label claim at varying concentrations of stabilizer. The results indicate that the tested stabilizers provided a greater stabilizing effect at 1% concentration than at 10%. Also, in several cases the stabilization effect was about 5% to about 10% greater than that observed in the experiments of EXAMPLE 2.

Example 4: Effect of Buffer and Divalent Metals on Vasopressin Formulation

To determine whether different combinations of buffers and use of divalent metals affect vasopressin stability, vasopressin formulations with varying concentrations of citrate and acetate buffers and variable concentrations of calcium, magnesium, and zinc ions were prepared. Solutions of 0 mM, 10 mM, 20 mM, and 80 mM calcium, magnesium, and zinc were prepared and each was combined with 1 mM or 10 mM of citrate or acetate buffers to test vasopressin stability.

The tested combinations provided vasopressin stability comparable to that of a vasopressin formulation lacking buffers and divalent metals. However, that the addition of divalent metal ions was able to counteract the degradation of vasopressin caused by the use of a citrate buffer.

Example 5: Illustrative Formulations for Assessment of Vasopressin Stability An aqueous formulation of vasopressin is prepared using 10% trehalose, 1% sucrose, or 5% NaCl and incubated at 60° C. for one week, at which point stability of vasopressin is assessed using HPLC.

A formulation containing 50 units of vasopressin is lyophilized. The lyophilate is reconstituted with water and either 100 mg of sucrose or 100 mg of lactose, and the stability of vasopressin is tested via HPLC after incubation at 60° C. for one week.

Co-solvents are added to a vasopressin solution to assess vasopressin stability. 95% solvent/5% 20 mM acetate buffer solutions are prepared using propylene glycol, DMSO, PEG300, NMP, glycerol, and glycerol:NMP (1:1), and used to create formulations of vasopressin. The stability of vasopressin is tested after incubation at 60° C. for one week.

Amino acid and phosphate buffers are tested with vasopressin to assess vasopressin stability. Buffers of 10 mM glycine, aspartate, phosphate are prepared at pH 3.5 and 3.8 and used to create formulations of vasopressin. The stability of vasopressin is tested after incubation at 60° C. for one week.

A vasopressin formulation in 10% polyvinylpyrrolidone is prepared to assess vasopressin stability. The stability of vasopressin will be tested after incubation at 60° C. for one week.

A vasopressin formulation that contains 0.9% saline, 10 mM acetate buffer, 0.2 unit/mL API/mL in 100 mL of total volume is prepared. The pH of the solution is varied from pH 3.5-3.8 to test the stability of vasopressin.

A vasopressin formulation in about 50% to about 80% DMSO (for example, about 80%), about 20% to about 50% ethyl acetate (for example, about 20%), and about 5% to about 30% polyvinylpyrrolidone (PVP) (for example, about 10% by mass of the formulation) is prepared to assess vasopressin stability. PVP K12 and PVP K17 are each independently tested in the formulation. The stability of vasopressin is tested after incubation at 60° C. for one week.

A vasopressin formulation in about 70% to about 95% ethyl acetate, and about 5% to about 30% PVP is prepared to assess vasopressin stability. PVP K12 and PVP K17 are each independently tested in the formulation. The stability of vasopressin is tested after incubation at 60° C. for one week.

A vasopressin formulation in 90% DMSO and 10% PVP is prepared to test vasopressin stability. PVP K12 and PVP K17 are each independently tested in the formulation. The stability of vasopressin is tested after incubation at 60° C. for one week.

Example 6: Illustrative Vasopressin Formulation for Clinical Use

A formulation for vasopressin that can be used in the clinic is detailed in TABLE 5 below:

TABLE 5

| Ingredient | Function | Amount (per mL) |
|---|---|---|
| Vasopressin, USP | Active Ingredient | 20 Units (~0.04 mg) |
| Chlorobutanol, Hydrous NF | Preservative | 5.0 mg |
| Acetic Acid, NF | pH Adjustment | To pH 3.4-3.6 (~0.22 mg) |
| Water for injection, USP/EP | Diluent | QS |

Example 7: Illustrative Regimen for Therapeutic Use of a Vasopressin Formulation Vasopressin is indicated to increase blood pressure in adults with vasodilatory shock (for example, adults who are post-cardiotomy or septic) who remain hypotensive despite fluids and catecholamines.

Preparation and Use of Vasopressin.

Vasopressin is supplied in a carton of 25 multi-dose vials each containing 1 mL vasopressin at 20 units/mL.

Vasopressin is stored between 15° C. and 25° C. (59° F. and 77° F.), and is not frozen. Alternatively, a unit dosage form of vasopressin can be stored between 2° C. and 8° C. for about 1 week, 2 weeks, 3 weeks, 4 weeks, 5 weeks, 6 weeks, 7 weeks, or 8 weeks.

Vials of vasopressin are to be discarded 48 hours after first puncture.

Vasopressin is prepared according to TABLE 6 below:

TABLE 6

| Fluid Restriction? | Final Concentration | Mix Vasopressin | Diluent |
|---|---|---|---|
| No | 0.1 units/mL | 2.5 mL (50 units) | 500 mL |
| Yes | 1 unit/mL | 5 mL (100 units) | 100 mL |

Vasopressin is diluted in normal saline (0.9% sodium chloride) or 5% dextrose in water (D5W) prior to use to either 0.1 units/mL or 1 unit/mL for intravenous administration. Unused diluted solution is discarded after 18 hours at room temperature or after 24 hours under refrigeration.

Diluted vasopressin should be inspected for particulate matter and discoloration prior to use whenever solution and container permit.

The goal of treatment with vasopressin is optimization of perfusion to critical organs, but aggressive treatment can compromise perfusion of organs, like the gastrointestinal tract, for which function is difficult to monitor. Titration of vasopressin to the lowest dose compatible with a clinically-acceptable response is recommended.

For post-cardiotomy shock, a dose of 0.03 units/minute is used as a starting point. For septic shock, a dose of 0.01 units/minute is recommended. If the target blood pressure response is not achieved, titrate up by 0.005 units/minute at 10- to 15-minute intervals. The maximum dose for post-cardiotomy shock is 0.1 units/minute and for septic shock 0.07 units/minute. After target blood pressure has been maintained for 8 hours without the use of catecholamines, taper vasopressin by 0.005 units/minute every hour as tolerated to maintain target blood pressure.

Vasopressin is provided at 20 units per mL of diluent, which is packaged as 1 mL of vasopressin per vial, and is diluted prior to administration.

Contraindications, Adverse Reactions, and Drug-Drug Interactions.

Vasopressin is contraindicated in patients with known allergy or hypersensitivity to 8-L-arginine vasopressin or chlorobutanol. Additionally, use of vasopressin in patients with impaired cardiac response can worsen cardiac output.

Adverse reactions have been observed with the use of vasopressin, which adverse reactions include bleeding/lymphatic system disorders, specifically, hemorrhagic shock, decreased platelets, intractable bleeding; cardiac disorders, specifically, right heart failure, atrial fibrillation, bradycardia, myocardial ischemia; gastrointestinal disorders, specifically, mesenteric ischemia; hepatobiliary disorders, specifically, increased bilirubin levels; renal/urinary disorders, specifically, acute renal insufficiency; vascular disorders, specifically, distal limb ischemia; metabolic disorders, specifically, hyponatremia; and skin disorders, specifically, and ischemic lesions.

These reactions are reported voluntarily from a population of uncertain size. Thus, reliable estimation of frequency or establishment of a causal relationship to drug exposure is unlikely.

Vasopressin has been observed to interact with other drugs. For example, use of vasopressin with catecholamines is expected to result in an additive effect on mean arterial blood pressure and other hemodynamic parameters. Use of vasopressin with indomethacin can prolong the effect of vasopressin on cardiac index and systemic vascular resistance. Indomethacin more than doubles the time to offset for vasopressin's effect on peripheral vascular resistance and cardiac output in healthy subjects.

Further, use of vasopressin with ganglionic blocking agents can increase the effect of vasopressin on mean arterial blood pressure. The ganglionic blocking agent tetra-ethylammonium increases the pressor effect of vasopressin by 20% in healthy subjects.

Use of vasopressin with furosemide increases the effect of vasopressin on osmolar clearance and urine flow. Furosemide increases osmolar clearance 4-fold and urine flow 9-fold when co-administered with exogenous vasopressin in healthy subjects.

Use of vasopressin with drugs suspected of causing SIADH (Syndrome of inappropriate antidiuretic hormone secretion), for example, SSRIs, tricyclic antidepressants, haloperidol, chlorpropamide, enalapril, methyldopa, pentamidine, vincristine, cyclophosphamide, ifosfamide, and felbamate can increase the pressor effect in addition to the antidiuretic effect of vasopressin. Additionally, use of vasopressin with drugs suspected of causing diabetes insipidus for example, demeclocycline, lithium, foscarnet, and clozapine can decrease the pressor effect in addition to the antidiuretic effect of vasopressin.

Halothane, morphine, fentanyl, alfentanyl and sufentanyl do not impact exposure to endogenous vasopressin.

Use of Vasopressin in Specific Populations.

Vasopressin is a Category C drug for pregnancy.

Due to a spillover into the blood of placental vasopressinase, the clearance of exogenous and endogenous vasopressin increases gradually over the course of a pregnancy. During the first trimester of pregnancy the clearance is only slightly increased. However, by the third trimester the clearance of vasopressin is increased about 4-fold and at term up to 5-fold. Due to the increased clearance of vasopressin in the second and third trimester, the dose of vasopressin can be up-titrated to doses exceeding 0.1 units/minute in post-cardiotomy shock and 0.07 units/minute in septic shock. Vasopressin can produce tonic uterine contractions that could threaten the continuation of pregnancy. After delivery, the clearance of vasopressin returns to preconception levels.

Overdosage.

Overdosage with vasopressin can be expected to manifest as a consequence of vasoconstriction of various vascular beds, for example, the peripheral, mesenteric, and coronary vascular beds, and as hyponatremia. In addition, overdosage of vasopressin can lead less commonly to ventricular tachyarrhythmias, including Torsade de Pointes, rhabdomyolysis, and non-specific gastrointestinal symptoms. Direct effects of vasopressin overdose can resolve within minutes of withdrawal of treatment.

Pharmacology of Vasopressin.

Vasopressin is a polypeptide hormone that causes contraction of vascular and other smooth muscles and antidiuresis, which can be formulated as a sterile, aqueous solution of synthetic arginine vasopressin for intravenous administration. The 1 mL solution contains vasopressin 20 units/mL, chlorobutanol, NF 0.5% as a preservative, and water for injection, USP adjusted with acetic acid to pH 3.4-3.6.

The chemical name of vasopressin is Cyclo (1-6) L-Cysteinyl-L-Tyrosyl-L-Phenylalanyl-L-Glutaminyl-L-Asparaginyl-L-Cysteinyl-L-Prolyl-L-Arginyl-L-Glycinamide. Vasopressin is a white to off-white amorphous powder, freely soluble in water. The structural formula of vasopressin is:

SEQ ID NO.: 1

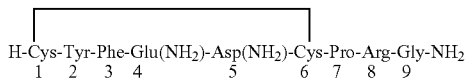

Molecular Formula: $C_{46}H_{65}N_{15}O_{12}S_2$; Molecular Weight: 1084.23

One mg of vasopressin is equivalent to 530 units. Alternatively, one mg of vasopressin is equivalent to 470 units.

The vasoconstrictive effects of vasopressin are mediated by vascular V1 receptors. Vascular V1 receptors are directly coupled to phopholipase C, resulting in release of calcium, leading to vasoconstriction. In addition, vasopressin stimulates antidiuresis via stimulation of V2 receptors which are coupled to adenyl cyclase.

At therapeutic doses, exogenous vasopressin elicits a vasoconstrictive effect in most vascular beds including the splanchnic, renal, and cutaneous circulation. In addition, vasopressin at pressor doses triggers contractions of smooth muscles in the gastrointestinal tract mediated by muscular V1-receptors and release of prolactin and ACTH via V3 receptors. At lower concentrations typical for the antidiuretic hormone, vasopressin inhibits water diuresis via renal V2 receptors. In patients with vasodilatory shock, vasopressin in therapeutic doses increases systemic vascular resistance and mean arterial blood pressure and reduces the dose requirements for norepinephrine.

Vasopressin tends to decrease heart rate and cardiac output. The pressor effect is proportional to the infusion rate of exogenous vasopressin. Onset of the pressor effect of vasopressin is rapid, and the peak effect occurs within 15 minutes. After stopping the infusion, the pressor effect fades within 20 minutes. There is no evidence for tachyphylaxis or tolerance to the pressor effect of vasopressin in patients.

At infusion rates used in vasodilatory shock (0.01-0.1 units/minute), the clearance of vasopressin is 9 to 25 mL/min/kg in patients with vasodilatory shock. The apparent half-life of vasopressin at these levels is ≤10 minutes. Vasopressin is predominantly metabolized and only about 6% of the dose is excreted unchanged in urine. Animal experiments suggest that the metabolism of vasopressin is primarily by liver and kidney. Serine protease, carboxipeptidase and disulfide oxido-reductase cleave vasopressin at sites relevant for the pharmacological activity of the hormone. Thus, the generated metabolites are not expected to retain important pharmacological activity.

Carcinogenesis, Mutagenesis, Impairment of Fertility.

Vasopressin was found to be negative in the in vitro bacterial mutagenicity (Ames) test and the in vitro Chinese hamster ovary (CHO) cell chromosome aberration test. In mice, vasopressin can have an effect on function and fertilizing ability of spermatozoa.

Clinical Studies.

Increases in systolic and mean blood pressure following administration of vasopressin were observed in seven studies in septic shock and eight studies in post-cardiotomy vasodilatory shock.

Example 8: Effect of Temperature on Vasopressin Formulations

To test the effect of temperature on the stability of vasopressin formulation, solutions containing 20 units/mL vasopressin and chlorobutanol, adjusted to pH 3.5 with acetic acid, were prepared. One mL of each vasopressin formulations was then filled into 3 cc vials. Each Vasopressin Formulation was stored either inverted or upright for at least three months, up to 24 months, at: (i) 5° C.; (ii) 25° C. and 60% relative humidity; or (iii) 40° C. and 75% humidity, and the amount of vasopressin (U/mL) and % total impurities were measured periodically. TABLES 7-12 below display the results of the experiments at 5° C. The results of the experiments at 25° C. are included in TABLES 13-18. All of the experiments were performed in triplicate. The results of the experiments at 40° C. are included in TABLES 19-24. For each temperature tested, three lots of the vasopressin formulation were stored for 24 months (5° C. and 25° C.) and 3 months (40° C.), and measurements were taken at regular intervals during the testing periods. "NMT" as used in the tables denotes "not more than."

The vasopressin and impurity amounts observed in the experiments conducted at 5° C. are shown in TABLES 7-12 below (AVP=Vasopressin).

TABLE 7

Samples stored inverted at 5° C.

| Test | Initial | Time in months | | | | | | | |
| --- | --- | --- | --- | --- | --- | --- | --- | --- | --- |
| | | 1 | 2 | 3 | 6 | 9 | 12 | 18 | 24 |
| AVP Assay | 19.4 | 19.4 | 19.4 | 19.3 | 19.5 | 19.4 | 19.5 | 19.4 | 19.3 |
| Total Impurities | 2.3% | 2.0% | 2.1% | 2.3% | 2.2% | 2.3% | 2.6% | 2.9% | 2.9% |

TABLE 8

| | | Samples stored inverted at 5° C. | | | | | | | | |
|---|---|---|---|---|---|---|---|---|---|---|
| | Acceptance | | | | Time in months | | | | | |
| Test | Criteria | Initial | 1 | 2 | 3 | 6 | 9 | 12 | 18 | 24 |
| AVP Assay | 16.0-21.0 U/mL | 19.7 | 19.7 | 19.7 | 19.7 | 19.9 | 19.7 | 19.8 | 19.7 | 19.5 |
| | Total Impurities: NMT 17.0% | 2.7% | 2.2% | 2.3% | 2.4% | 2.1% | 2.3% | 2.7% | 2.9% | 2.9% |

TABLE 9

| | | Samples stored inverted at 5° C. | | | | | | | | |
|---|---|---|---|---|---|---|---|---|---|---|
| | Acceptance | | | | Time in months | | | | | |
| Test | Criteria | Initial | 1 | 2 | 3 | 6 | 9 | 12 | 18 | 24 |
| AVP Assay | 16.0-21.0 U/mL | 19.7 | 19.7 | 19.6 | 19.7 | 19.8 | 19.7 | 19.9 | 19.8 | 19.5 |
| | Total Impurities: NMT 17.0% | 2.2% | 1.9% | 2.0% | 2.2% | 2.0% | 2.1% | 2.4% | 2.6% | 2.8% |

TABLE 10

| | | Samples stored upright at 5° C. | | | | | | | | |
|---|---|---|---|---|---|---|---|---|---|---|
| | Acceptance | | | | Time in months | | | | | |
| Test | Criteria | Initial | 1 | 2 | 3 | 6 | 9 | 12 | 18 | 24 |
| AVP Assay | 16.0-21.0 U/mL | 19.4 | 19.5 | 19.4 | 19.4 | 19.5 | 19.5 | 19.5 | 19.4 | 19.3 |
| | Total Impurities: NMT 17.0% | 2.3% | 2.1% | 2.1% | 2.3% | 2.1% | 2.3% | 2.5% | 2.9% | 2.9% |

TABLE 11

| | | Samples stored upright at 5° C. | | | | | | | | |
|---|---|---|---|---|---|---|---|---|---|---|
| | Acceptance | | | | Time in months | | | | | |
| Test | Criteria | Initial | 1 | 2 | 3 | 6 | 9 | 12 | 18 | 24 |
| AVP Assay | 16.0-21.0 U/mL | 19.7 | 19.7 | 19.6 | 19.7 | 19.8 | 19.7 | 19.8 | 19.7 | 19.5 |
| | Total Impurities: NMT 17.0% | 2.7% | 2.1% | 2.2% | 2.2% | 2.2% | 2.3% | 2.6% | 2.9% | 2.8% |

TABLE 12

| | | Samples stored upright at 5° C. | | | | | | | | |
|---|---|---|---|---|---|---|---|---|---|---|
| | Acceptance | | | | Time in months | | | | | |
| Test | Criteria | Initial | 1 | 2 | 3 | 6 | 9 | 12 | 18 | 24 |
| AVP Assay | 16.0-21.0 U/mL | 19.7 | 19.7 | 19.6 | 19.7 | 19.8 | 19.7 | 19.9 | 19.8 | 19.5 |
| | Total Impurities: NMT 17.0% | 2.2% | 1.8% | 2.0% | 2.2% | 2.2% | 2.1% | 2.4% | 2.8% | 2.7% |

The vasopressin and impurity amounts observed in the experiments conducted at 25° C. and 60% relative humidity are shown in TABLES 13-18 below.

TABLE 13

Samples stored inverted at 25° C. and 60% Relative Humidity

| Test | Acceptance Criteria | Initial | \multicolumn{6}{c}{Time in months} |||||| 
|---|---|---|---|---|---|---|---|---|
| | | | 3 | 6 | 9 | 12 | 18 | 24 |
| AVP Assay | 16.0-21.0 U/mL | 19.8 | 19.4 | 19.1 | 18.8 | 18.3 | 17.5 | 17.3 |
| | Total Impurities: NMT 17.0% | 1.1% | 2.4% | 3.7% | 4.7% | 5.9% | 9.0% | 13.6% |

TABLE 14

Samples stored inverted at 25° C. and 60% Relative Humidity

| Test | Acceptance Criteria | Initial | 3 | 6 | 9 | 12 | 18 | 24 |
|---|---|---|---|---|---|---|---|---|
| AVP Assay | 16.0-21.0 U/mL | 20.1 | 19.7 | 19.3 | 19 | 18.6 | 17.6 | 17.6 |
| | Total Impurities: NMT 17.0% | 1.3% | 2.5% | 3.4% | 4.6% | 5.6% | 9.0% | 13.4% |

TABLE 15

Samples stored inverted at 25° C. and 60% Relative Humidity

| Test | Acceptance Criteria | Initial | 3 | 6 | 9 | 12 | 18 | 24 |
|---|---|---|---|---|---|---|---|---|
| AVP Assay | 16.0-21.0 U/mL | 19.9 | 19.6 | 19.2 | 19 | 18.7 | 18 | 17.4 |
| | Total Impurities: NMT 17.0% | 1.5% | 2.6% | 3.3% | 4.6% | 5.9% | 9.0% | 12.9% |

TABLE 16

Samples stored upright at 25° C. and 60% Relative Humidity

| Test | Acceptance Criteria | Initial | 3 | 6 | 9 | 12 | 18 | 24 |
|---|---|---|---|---|---|---|---|---|
| AVP Assay | 16.0-21.0 U/mL | 19.8 | 19.4 | 19.1 | 18.8 | 18.3 | 17.5 | 17.4 |
| | Total Impurities: NMT 17.0% | 1.1% | 2.4% | 3.2% | 4.8% | 5.6% | 9.2% | 13.1% |

TABLE 17

Samples stored upright at 25° C. and 60% Relative Humidity

| Test | Acceptance Criteria | Initial | Time in months | | | | | |
|---|---|---|---|---|---|---|---|---|
| | | | 3 | 6 | 9 | 12 | 18 | 24 |
| AVP Assay | 16.0-21.0 U/mL | 20.1 | 19.7 | 19.4 | 18.9 | 18.6 | 17.8 | 17.7 |
| | Total Impurities: NMT 17.0% | 1.3% | 2.5% | 3.3% | 4.5% | 5.7% | 9.1% | 13.3% |

TABLE 18

Samples stored upright at 25° C. and 60% Relative Humidity

| Test | Acceptance Criteria | Initial | Time in months | | | | | |
|---|---|---|---|---|---|---|---|---|
| | | | 3 | 6 | 9 | 12 | 18 | 24 |
| AVP Assay | 16.0-21.0 U/mL | 19.9 | 19.6 | 19.2 | 19 | 18.5 | 18.1 | 17.4 |
| | Total Impurities: NMT 17.0% | 1.5% | 2.5% | 3.7% | 4.7% | 5.9% | 9.1% | 13.3% |

The vasopressin and impurity amounts observed in the experiments conducted at 40° C. and 75% relative humidity are shown in TABLES 19-24 below.

TABLE 19

Samples stored inverted at 40° C.

| Test | Acceptance Criteria | Initial | Time in months | | |
|---|---|---|---|---|---|
| | | | 1 | 2 | 3 |
| Vasopressin Assay | 18.0-21.0 U/mL | 19.8 | 19.1 | 18.6 | 17.3 |
| | Total Impurities: NMT 17.0% | 1.1% | 3.7% | 7.3% | 10.6% |

TABLE 20

Samples stored Upright at 40° C.

| Test | Acceptance Criteria | Initial | Time in months | | |
|---|---|---|---|---|---|
| | | | 1 | 2 | 3 |
| Vasopressin Assay | 18.0-21.0 U/mL | 19.8 | 18.9 | 18.5 | 17.2 |
| | Total Impurities: NMT 17.0% | 1.1% | 3.6% | 7.2% | 10.3% |

TABLE 21

Samples stored inverted at 40° C.

| Test | Acceptance Criteria | Initial | Time in months | | |
|---|---|---|---|---|---|
| | | | 1 | 2 | 3 |
| Vasopressin Assay | 18.0-21.0 U/mL | 20.1 | 19.3 | 18.7 | 17.6 |
| | Total Impurities: NMT 17.0% | 1.3% | 3.6% | 7.3% | 10.3% |

TABLE 22

Samples stored Upright at 40° C.

| Test | Acceptance Criteria | Initial | Time in months | | |
|---|---|---|---|---|---|
| | | | 1 | 2 | 3 |
| Vasopressin Assay | 18.0-21.0 U/mL | 20.1 | 18.9 | 18.7 | 17.4 |
| | Total Impurities: NMT 17.0% | 1.3% | 3.5% | 7.1% | 10.2% |

TABLE 23

Samples stored inverted at 40° C.

| Test | Acceptance Criteria | Initial | Time in months | | |
|---|---|---|---|---|---|
| | | | 1 | 2 | 3 |
| Vasopressin Assay | 18.0-21.0 U/mL | 19.9 | 19.2 | 18.3 | 17.4 |
| | Total Impurities: NMT 17.0% | 1.5% | 3.7% | 6.3% | 10.3% |

TABLE 24

Samples stored Upright at 40° C.

| Test | Acceptance Criteria | Initial | Time in months | | |
|---|---|---|---|---|---|
| | | | 1 | 2 | 3 |
| Vasopressin Assay | 18.0-21.0 U/mL | 19.9 | 19.2 | 18.3 | 17.5 |
| | Total Impurities: NMT 17.0% | 1.5% | 3.8% | 6.3% | 10.5% |

The results of the above experiments suggested that storage in either an upright or inverted position did not markedly affect the stability of vasopressin. The samples held at 5° C. exhibited little fluctuation in vasopressin amounts over 24 months, and the amount of total impurities did not increase above 3% during the testing period (TABLES 7-12). The samples held at 25° C. and 60% relative humidity exhibited a decrease in vasopressin amount of about 10-12% after 24 months (TABLES 13-18). The amount of impurities observed in the samples stored at 25° C. and 60% relative humidity after 24 months exceeded 13% in some samples, whereas the amount of impurities observed in the samples stored at 5° C. did not exceed 3% after 24 months. After about three months, the samples held at 40° C. exhibited a decrease in the amount of vasopressin of about 10-12%. The amount of impurities observed at 40° C. exceeded 10% after three months, whereas the amount of impurities observed in the samples stored at 5° C. was less than 3% after three months (TABLES 19-24).

Experiments were also conducted on the same samples above over the course of the experiments to measure the amount of individual impurities in the samples, pH of the samples, chlorobutanol content, particulate matter, antimicrobial effectiveness, and bacterial endotoxin levels (TABLES 25-42). (NR=no reading; ND=not determined; UI=unidentified impurity).

The anti-microbial effectiveness of the solution was established to determine the amount of antimicrobial agents in the formulation that protect against bacterial contamination. The bullets in the tables below indicate that the sample was not tested for anti-microbial effectiveness at that specific time point.

The bacterial endotoxin levels were also measured for some of the formulations. The bullets in the tables below indicate that the sample was not tested for bacterial endotoxin levels at that specific time point.

TABLE 25

Samples stored inverted at 5° C.

| Test | Acceptance Criteria | Initial | 1 | 2 | 3 | 6 | 9 | 12 | 18 | 24 |
|---|---|---|---|---|---|---|---|---|---|---|
| Vasopressin Assay | 16.0-21.0 U/mL | 19.4 | 19.4 | 19.4 | 19.3 | 19.5 | 19.4 | 19.5 | 19.4 | 19.3 |
| Related Substances | SEQ ID NO.: 2 NMT 6.0% | 0.5% | 0.5% | 0.6% | 0.6% | 0.6% | 0.6% | 0.7% | 0.8% | 0.9% |
| | SEQ ID NO.: 4: NMT 6.0% | 0.6% | 0.6% | 0.6% | 0.7% | 0.7% | 0.7% | 0.8% | 0.9% | 1.0% |
| | SEQ ID NO.: 10: NMT 1.0% | 0.3% | 0.3% | 0.3% | 0.4% | 0.3% | 0.3% | 0.4% | 0.4% | 0.3% |
| | Asp5-AVP: NMT 1.5% | 0.1% | 0.1% | 0.1% | 0.1% | 0.1% | 0.1% | 0.2% | 0.2% | 0.2% |
| | AVP-Dimer: NMT 1.0% | NR | NR | NR | NR | NR | NR | NR | NR | NR |
| | Acetyl-AVP: NMT 1.0% | 0.3% | 0.2% | 0.3% | 0.3% | 0.2% | 0.2% | 0.3% | 0.3% | 0.3% |
| | UI-0.84: NMT 1.0% | NR | NR | 0.1% | NR | NR | NR | NR | NR | NR |
| | UI-1.03: NMT 1.0% | 0.2% | 0.2% | 0.2% | 0.3% | 0.2% | 0.2% | 0.3% | 0.3% | 0.2% |
| | UI-1.67: NMT 1.0% | NR | NR | NR | NR | NR | NR | NR | NR | 0.2% |
| | UI-1.85: NMT 1.0% | 0.2% | NR | NR | NR | NR | NR | NR | NR | NR |
| | UI-2.05: NMT 1.0% | 0.1% | NR | 0.1% | NR | NR | NR | NR | NR | NR |
| | Total Impurities: NMT 17.0% | 2.3% | 2.0% | 2.1% | 2.3% | 2.2% | 2.3% | 2.6% | 2.9% | 2.9% |
| pH | 2.5-4.5 | 3.5 | 3.5 | 3.5 | 3.5 | 3.5 | 3.5 | 3.5 | 3.8 | 3.5 |
| Chlorobutanol | 0.25-0.60% w/v | 0.48% | 0.49% | 0.48% | 0.48% | 0.47% | 0.48% | 0.48% | 0.49% | 0.49% |
| Particulate Matter (USP) | NMT 6000 (≥10 μm) | 0 | 1 | 1 | 1 | 2 | 16 | 2 | 4 | 1 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 26

Samples stored inverted at 5° C.

| Test | Acceptance Criteria | Initial | 1 | 2 | 3 | 6 | 9 | 12 | 18 | 24 |
|---|---|---|---|---|---|---|---|---|---|---|
| Vasopressin Assay | 16.0-21.0 U/mL | 19.7 | 19.7 | 19.7 | 19.7 | 19.9 | 19.7 | 19.8 | 19.7 | 19.5 |
| Related Substances | SEQ ID NO.: 2: NMT 6.0% | 0.6% | 0.5% | 0.5% | 0.6% | 0.5% | 0.6% | 0.7% | 0.8% | 0.8% |
| | SEQ ID NO.: 4: NMT 6.0% | 0.6% | 0.6% | 0.6% | 0.6% | 0.6% | 0.7% | 0.7% | 0.8% | 0.9% |
| | SEQ ID NO.: 10: NMT 1.0% | 0.3% | 0.3% | 0.3% | 0.4% | 0.3% | 0.4% | 0.4% | 0.4% | 0.3% |
| | Asp5-AVP: NMT 1.5% | 0.1% | 0.1% | 0.1% | 0.1% | 0.1% | 0.1% | 0.2% | 0.2% | 0.2% |
| | AVP-Dimer: NMT 1.0% | NR | NR | NR | NR | NR | NR | NR | NR | NR |
| | Acetyl-AVP: NMT 1.0% | 0.3% | 0.3% | 0.3% | 0.3% | 0.3% | 0.3% | 0.3% | 0.3% | 0.3% |
| | UI-0.75-0.78: NMT 1.0% | 0.2% | 0.2% | 0.2% | 0.2% | NR | 0.1% | 0.2% | 0.2% | 0.2% |
| | UI-0.83-0.84: NMT 1.0% | 0.1% | 0.1% | 0.1% | NR | 0.1% | NR | NR | NR | NR |
| | UI-1.02-1.03: NMT 1.0% | 0.2% | 0.2% | 0.2% | 0.3% | 0.2% | 0.2% | 0.3% | 0.3% | 0.3% |
| | UI-1.67: NMT 1.0% | NR | NR | NR | NR | NR | NR | NR | NR | 0.2% |
| | UI-1.85: NMT 1.0% | 0.2% | NR | NR | NR | NR | NR | NR | NR | NR |
| | UI-2.05: NMT 1.0% | 0.2% | NR | NR | NR | NR | NR | NR | NR | NR |
| | Total Impurities: NMT 17.0% | 2.7% | 2.2% | 2.3% | 2.4% | 2.1% | 2.3% | 2.7% | 2.9% | 2.9% |
| pH | 2.5-4.5 | 3.6 | 3.6 | 3.6 | 3.6 | 3.6 | 3.6 | 3.6 | 3.6 | 3.6 |
| Chlorobutanol | 0.25-0.60% w/v | 0.48% | 0.48% | 0.48% | 0.47% | 0.48% | 0.48% | 0.49% | 0.48% | 0.49% |
| Particulate Matter (USP) | NMT 6000 (≥10 μm) | 1 | 1 | 1 | 1 | 1 | 15 | 2 | 3 | 2 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 27

Samples stored inverted at 5° C.

| Test | Acceptance Criteria | Initial | 1 | 2 | 3 | 6 | 9 | 12 | 18 | 24 |
|---|---|---|---|---|---|---|---|---|---|---|
| Vasopressin Assay | 16.0-21.0 U/mL | 19.7 | 19.7 | 19.6 | 19.7 | 19.8 | 19.7 | 19.9 | 19.8 | 19.5 |
| Related Substances | SEQ ID NO.: 2: NMT 6.0% | 0.5% | 0.5% | 0.5% | 0.5% | 0.5% | 0.6% | 0.6% | 0.8% | 0.8% |
| | SEQ ID NO.: 4: NMT 6.0% | 0.5% | 0.5% | 0.5% | 0.6% | 0.6% | 0.7% | 0.7% | 0.8% | 0.9% |
| | SEQ ID NO.: 10: NMT 1.0% | 0.3% | 0.3% | 0.3% | 0.4% | 0.3% | 0.3% | 0.4% | 0.4% | 0.3% |
| | Asp5-AVP: NMT 1.5% | 0.1% | 0.1% | 0.1% | 0.1% | 0.1% | 0.1% | 0.1% | 0.2% | 0.2% |

TABLE 27-continued

Samples stored inverted at 5° C.

| Test | Acceptance Criteria | Initial | 1 | 2 | 3 | 6 | 9 | 12 | 18 | 24 |
|---|---|---|---|---|---|---|---|---|---|---|
| | AVP-Dimer: NMT 1.0% | NR | NR | NR | NR | NR | NR | NR | NR | NR |
| | Acetyl-AVP: NMT 1.0% | 0.3% | 0.3% | 0.3% | 0.3% | 0.3% | 0.3% | 0.3% | 0.3% | 0.3% |
| | UI-0.75-0.78: NMT 1.0% | NR | NR | NR | NR | NR | NR | NR | NR | NR |
| | UI-0.83-0.84: NMT 1.0% | NR | NR | 0.1% | NR | NR | NR | NR | NR | 0.1% |
| | UI-1.02-1.03: NMT 1.0% | 0.2% | 0.2% | 0.2% | 0.3% | 0.2% | 0.2% | 0.3% | 0.3% | 0.2% |
| | UI-1.67: NMT 1.0% | NR | NR | NR | NR | NR | NR | NR | NR | 0.2% |
| | UI-1.76: NMT 1.0% | NR | NR | NR | 0.1% | NR | NR | NR | NR | NR |
| | UI-1.85: NMT 1.0% | 0.2% | NR | NR | NR | NR | NR | NR | NR | NR |
| | UI-2.05: NMT 1.0% | 0.1% | NR | NR | NR | NR | NR | NR | NR | NR |
| | Total Impurities: NMT 17.0% | 2.2% | 1.9% | 2.0% | 2.2% | 2.0% | 2.1% | 2.4% | 2.6% | 2.8% |
| pH | 2.5-4.5 | 3.6 | 3.5 | 3.6 | 3.5 | 3.5 | 3.5 | 3.6 | 3.5 | 3.5 |
| Chlorobutanol | 0.25-0.60% w/v | 0.47% | 0.48% | 0.47% | 0.47% | 0.47% | 0.47% | 0.48% | 0.48% | 0.48% |
| Particulate Matter (USP) | NMT 6000 (≥10 μm) | 1 | 2 | 1 | 2 | 1 | 4 | 2 | 1 | 3 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 28

Samples stored upright at 5° C.

| Test | Acceptance Criteria | Initial | 1 | 2 | 3 | 6 | 9 | 12 | 18 | 24 |
|---|---|---|---|---|---|---|---|---|---|---|
| Vasopressin Assay | 16.0-21.0 U/mL | 19.4 | 19.5 | 19.4 | 19.4 | 19.5 | 19.5 | 19.5 | 19.4 | 19.3 |
| Related Substances | SEQ ID NO.: 2: NMT 6.0% | 0.5% | 0.6% | 0.6% | 0.6% | 0.6% | 0.6% | 0.7% | 0.8% | 0.9% |
| | SEQ ID NO.: 4: NMT 6.0% | 0.6% | 0.6% | 0.6% | 0.7% | 0.7% | 0.7% | 0.7% | 0.9% | 1.0% |
| | SEQ ID NO.: 10: NMT 1.0% | 0.3% | 0.3% | 0.3% | 0.4% | 0.3% | 0.3% | 0.4% | 0.4% | 0.3% |
| | Asp5-AVP: NMT 1.5% | 0.1% | 0.1% | 0.1% | 0.1% | 0.1% | 0.1% | 0.2% | 0.2% | 0.2% |
| | AVP-Dimer: NMT 1.0% | NR | NR | NR | NR | NR | NR | NR | NR | NR |
| | Acetyl-AVP: NMT 1.0% | 0.3% | 0.3% | 0.3% | 0.2% | 0.2% | 0.3% | 0.3% | 0.3% | 0.3% |
| | UI-0.84: NMT 1.0% | NR | NR | 0.1% | NR | NR | NR | NR | NR | NR |
| | UI-1.03: | 0.2% | 0.2% | 0.2% | 0.3% | 0.2% | 0.2% | 0.3% | 0.3% | 0.2% |

TABLE 28-continued

Samples stored upright at 5° C.

| Test | Acceptance Criteria | Initial | \multicolumn{8}{c}{Time in months} |
|---|---|---|---|---|---|---|---|---|---|---|
| | | | 1 | 2 | 3 | 6 | 9 | 12 | 18 | 24 |
| | NMT 1.0% UI-1.67: NMT 1.0% | NR | NR | NR | NR | NR | NR | NR | NR | 0.2% |
| | UI-1.85: NMT 1.0% | 0.2% | NR | NR | NR | NR | NR | NR | NR | NR |
| | UI-2.05: NMT 1.0% | 0.1% | NR | NR | NR | NR | NR | NR | NR | NR |
| | Total Impurities: NMT 17.0% | 2.3% | 2.1% | 2.1% | 2.3% | 2.1% | 2.3% | 2.5% | 2.9% | 2.9% |
| pH | 2.5-4.5 | 3.5 | 3.5 | 3.5 | 3.5 | 3.5 | 3.5 | 3.5 | 3.8 | 3.5 |
| Chlorobutanol | 0.25-0.60% w/v | 0.48% | 0.48% | 0.48% | 0.48% | 0.48% | 0.48% | 0.48% | 0.49% | 0.49% |
| Particulate Matter (USP) | NMT 6000 (≥10 μm) | 0 | 2 | 2 | 2 | 1 | 2 | 2 | 4 | 1 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 29

Samples stored upright at 5° C.

| Test | Acceptance Criteria | Initial | \multicolumn{8}{c}{Time in months} |
|---|---|---|---|---|---|---|---|---|---|---|
| | | | 1 | 2 | 3 | 6 | 9 | 12 | 18 | 24 |
| Vasopressin Assay | 16.0-21.0 U/mL | 19.7 | 19.7 | 19.6 | 19.7 | 19.8 | 19.7 | 19.8 | 19.7 | 19.5 |
| Related Substances | SEQ ID NO.: 2: NMT 6.0% | 0.6% | 0.5% | 0.5% | 0.5% | 0.6% | 0.6% | 0.6% | 0.8% | 0.7% |
| | SEQ ID NO.: 4: NMT 6.0% | 0.6% | 0.6% | 0.6% | 0.6% | 0.6% | 0.7% | 0.7% | 0.8% | 0.8% |
| | SEQ ID NO.: 10: NMT 1.0% | 0.3% | 0.3% | 0.3% | 0.3% | 0.3% | 0.3% | 0.4% | 0.4% | 0.3% |
| | Asp5-AVP: NMT 1.5% | 0.1% | 0.1% | 0.1% | 0.1% | 0.1% | 0.1% | 0.2% | 0.2% | 0.2% |
| | AVP-Dimer: NMT 1.0% | NR | NR | NR | NR | NR | NR | NR | NR | NR |
| | Acetyl-AVP: NMT 1.0% | 0.3% | 0.3% | 0.3% | 0.3% | 0.2% | 0.3% | 0.3% | 0.3% | 0.3% |
| | UI-0.75-0.78: NMT 1.0% | 0.2% | 0.2% | NR | 0.2% | 0.2% | 0.2% | 0.2% | 0.2% | 0.2% |
| | UI-0.83-0.84: NMT 1.0% | 0.1% | NR | 0.1% | NR | NR | NR | NR | NR | NR |

TABLE 29-continued

Samples stored upright at 5° C.

| Test | Acceptance Criteria | Initial | 1 | 2 | 3 | 6 | 9 | 12 | 18 | 24 |
|---|---|---|---|---|---|---|---|---|---|---|
| | UI-1.02-1.03: NMT 1.0% | 0.2% | 0.2% | 0.2% | 0.2% | 0.2% | 0.2% | 0.3% | 0.3% | 0.2% |
| | UI-1.67: NMT 1.0% | NR | NR | NR | 0.2% | NR | NR | NR | NR | 0.2% |
| | UI-1.85: NMT 1.0% | 0.2% | NR | NR | NR | NR | NR | NR | NR | NR |
| | UI-2.05: NMT 1.0% | 0.2% | NR | NR | NR | NR | NR | NR | NR | NR |
| | Total Impurities: NMT 17.0% | 2.7% | 2.1% | 2.2% | 2.2% | 2.2% | 2.3% | 2.6% | 2.9% | 2.8% |
| pH | 2.5-4.5 | 3.6 | 3.6 | 3.6 | 3.6 | 3.6 | 3.6 | 3.6 | 3.6 | 3.6 |
| Chlorobutanol | 0.25-0.60% w/v | 0.48% | 0.48% | 0.48% | 0.48% | 0.48% | 0.48% | 0.49% | 0.49% | 0.49% |
| Particulate Matter (USP) | NMT 6000 (≥10 μm) | 1 | 1 | 1 | 2 | 2 | 6 | 4 | 4 | 1 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 30

Samples stored upright at 5° C.

| Test | Acceptance Criteria | Initial | 1 | 2 | 3 | 6 | 9 | 12 | 18 | 24 |
|---|---|---|---|---|---|---|---|---|---|---|
| Vasopressin Assay | 16.0-21.0 U/mL | 19.7 | 19.7 | 19.6 | 19.7 | 19.8 | 19.7 | 19.9 | 19.8 | 19.5 |
| Related Substances | SEQ ID NO.: 2: NMT 6.0% | 0.5% | 0.5% | 0.5% | 0.5% | 0.5% | 0.6% | 0.6% | 0.8% | 0.8% |
| | SEQ ID NO.: 4: NMT 6.0% | 0.5% | 0.5% | 0.5% | 0.6% | 0.6% | 0.7% | 0.7% | 0.8% | 0.9% |
| | SEQ ID NO.: 10: NMT 1.0% | 0.3% | 0.3% | 0.3% | 0.4% | 0.3% | 0.3% | 0.4% | 0.4% | 0.3% |
| | Asp5-AVP: NMT 1.5% | 0.1% | NR | 0.1% | 0.1% | 0.1% | 0.1% | 0.2% | 0.2% | 0.2% |
| | AVP-Dimer: NMT 1.0% | NR | NR | NR | NR | NR | NR | NR | NR | NR |
| | Acetyl-AVP: NMT 1.0% | 0.3% | 0.3% | 0.3% | 0.3% | 0.2% | 0.3% | 0.3% | 0.3% | 0.3% |
| | UI-0.75-0.78: NMT 1.0% | NR | NR | NR | NR | 0.2% | NR | NR | NR | NR |
| | UI-0.83-0.84: NMT 1.0% | NR | NR | 0.1% | NR | NR | NR | NR | 0.1% | NR |
| | UI-1.02-1.03: NMT 1.0% | 0.2% | 0.2% | 0.2% | 0.3% | 0.2% | 0.2% | 0.3% | 0.3% | 0.2% |
| | UI-1.67: NMT 1.0% | NR | NR | NR | NR | NR | NR | NR | NR | 0.2% |

TABLE 30-continued

Samples stored upright at 5° C.

| Test | Acceptance Criteria | Initial | 1 | 2 | 3 | 6 | 9 | 12 | 18 | 24 |
|---|---|---|---|---|---|---|---|---|---|---|
| | UI-1.76: NMT 1.0% | NR | NR | NR | 0.1% | NR | NR | NR | NR | NR |
| | UI-1.85: NMT 1.0% | 0.2% | NR | NR | NR | NR | NR | NR | NR | NR |
| | UI-2.05: NMT 1.0% | 0.1% | NR | NR | NR | NR | NR | NR | NR | NR |
| | Total Impurities: NMT 17.0% | 2.2% | 1.8% | 2.0% | 2.2% | 2.2% | 2.1% | 2.4% | 2.8% | 2.7% |
| pH | 2.5-4.5 | 3.6 | 3.5 | 3.6 | 3.5 | 3.5 | 3.5 | 3.6 | 3.5 | 3.5 |
| Chlorobutanol | 0.25-0.60% w/v | 0.47% | 0.48% | 0.47% | 0.47% | 0.48% | 0.47% | 0.48% | 0.48% | 0.48% |
| Particulate Matter (USP) | NMT 6000 (≥10 μm) | 1 | 1 | 1 | 1 | 1 | 3 | 2 | 1 | 3 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 31

Samples stored inverted at 25° C. and 60% Relative Humidity

| Test | Acceptance Criteria | Initial | 3 | 6 | 9 | 12 | 18 | 24 | 30 |
|---|---|---|---|---|---|---|---|---|---|
| Vasopressin Assay | 16.0-21.0 U/mL | 19.8 | 19.4 | 19.1 | 18.8 | 18.3 | 17.5 | 17.3 | — |
| Related Substances | SEQ ID NO.: 2: NMT 6.0% | 0.1% | 0.5% | 1.1% | 1.6% | 2.0% | 3.3% | 4.6% | — |
| | SEQ ID NO.: 4: NMT 6.0% | 0.1% | 0.6% | 1.2% | 1.8% | 2.2% | 3.7% | 5.2% | — |
| | SEQ ID NO.: 10: NMT 1.0% | 0.3% | 0.4% | 0.5% | 0.5% | 0.4% | 0.2% | 0.3% | — |
| | Asp5-AVP: NMT 1.5% | NR | 0.1% | 0.3% | 0.4% | 0.5% | 0.7% | 1.0% | — |
| | AVP-Dimer: NMT 1.0% | NR | NR | NR | NR | NR | NR | NR | — |
| | Acetyl-AVP: NMT 1.0% | 0.3% | 0.3% | 0.3% | 0.2% | 0.2% | 0.2% | 0.3% | — |
| | UI-0.83: NMT 1.0% | NR | NR | <0.10 | NR | NR | NR | 0.1% | — |
| | UI-0.99: NMT 1.0% | NR | NR | NR | NR | 0.1% | NR | NR | — |
| | UI-1.03: NMT 1.0% | 0.2% | 0.2% | 0.3% | 0.3% | 0.3% | 0.2% | 0.2% | — |
| | UI-1.14: NMT 1.0% | NR | NR | NR | NR | NR | NR | 0.1% | — |
| | UI-1.18: NMT 1.0% | NR | NR | NR | NR | NR | 0.1% | 0.3% | — |
| | UI-1.20: NMT 1.0% | NR | NR | NR | NR | NR | NR | 0.1% | — |
| | UI-1.22: NMT 1.0% | NR | NR | NR | NR | NR | NR | 0.1% | — |
| | UI-1.56-1.57: NMT 1.0% | NR | NR | <0.10 | 0.1% | 0.1% | 0.2% | 0.2% | — |
| | UI-1.60: NMT 1.0% | NR | NR | NR | 0.1% | 0.1% | 0.2% | NR | — |
| | UI-1.74: NMT 1.0% | NR | NR | NR | NR | NR | 0.2% | NR | — |
| | UI-1.85-1.88: NMT 1.0% | NR | 0.2% | NR | NR | NR | 0.1% | 0.1% | — |
| | UI-2.09-2.10: NMT 1.0% | NR | 0.2% | NR | NR | NR | NR | 0.4% | — |

TABLE 31-continued

Samples stored inverted at 25° C. and 60% Relative Humidity

| Test | Acceptance Criteria | Initial | Time in months | | | | | | |
|---|---|---|---|---|---|---|---|---|---|
| | | | 3 | 6 | 9 | 12 | 18 | 24 | 30 |
| | UI-2.15-2.16: NMT 1.0% | NR | NR | 0.1% | NR | NR | NR | 0.5% | — |
| | Total Impurities: NMT 17.0% | 1.1% | 2.4% | 3.7% | 4.7% | 5.9% | 9.0% | 13.6% | — |
| pH | 2.5-4.5 | 3.5 | 3.5 | 3.5 | 3.5 | 3.4 | 3.3 | 3.2 | — |
| Chlorobutanol | 0.25-0.60% w/v | 0.49% | 0.48% | 0.48% | 0.47% | 0.47% | 0.48% | 0.47 | — |
| Particulate Matter (USP) | NMT 6000 (≥10 µm) | 1 | 1 | 1 | 1 | 8 | 4 | 1 | — |
| | NMT 600 (≥25 µm) | 0 | 0 | 0 | 0 | 0 | 0 | 0 | — |
| AntiMicrobial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 32

Samples stored inverted at 25° C. and 60% Relative Humidity

| Test | Acceptance Criteria | Initial | Time in months | | | | | | |
|---|---|---|---|---|---|---|---|---|---|
| | | | 3 | 6 | 9 | 12 | 18 | 24 | 30 |
| Vasopressin Assay | 16.0-21.0 U/mL | 20.1 | 19.7 | 19.3 | 19 | 18.6 | 17.6 | 17.6 | — |
| Related Substances | SEQ ID NO.: 2: NMT 6.0% | 0.1% | 0.5% | 0.9% | 1.5% | 1.9% | 3.1% | 4.4% | — |
| | SEQ ID NO.: 4: NMT 6.0% | 0.1% | 0.5% | 1.1% | 1.6% | 2.2% | 3.4% | 4.9% | — |
| | SEQ ID NO.: 10: NMT 1.0% | 0.3% | 0.4% | 0.3% | 0.4% | 0.3% | 0.4% | 0.3% | — |
| | Asp5-AVP: NMT 1.5% | NR | 0.1% | 0.2% | 0.3% | 0.4% | 0.7% | 0.9% | — |
| | AVP-Dimer: NMT 1.0% | NR | NR | NR | NR | NR | NR | NR | — |
| | Acetyl-AVP: NMT 1.0% | 0.3% | 0.3% | 0.3% | 0.2% | 0.2% | 0.2% | 0.3% | — |
| | UI-0.75-0.76: NMT 1.0% | NR | 0.2% | 0.2% | 0.2% | 0.2% | 0.2% | 0.2% | — |
| | UI-0.83: NMT 1.0% | 0.2% | NR | 0.1% | NR | NR | 0.1% | 0.1% | — |
| | UI-0.99: NMT 1.0% | NR | NR | NR | NR | 0.1% | NR | NR | — |
| | UI-1.02-1.03: NMT 1.0% | 0.2% | 0.2% | 0.2% | 0.3% | 0.2% | 0.3% | 0.2% | — |
| | UI-1.14: NMT 1.0% | NR | NR | NR | NR | NR | NR | 0.1% | — |
| | UI-1.18: NMT 1.0% | NR | NR | NR | NR | NR | 0.1% | 0.3% | — |
| | UI-1.20: NMT 1.0% | NR | NR | NR | NR | NR | NR | 0.1% | — |
| | UI-1.22: NMT 1.0% | NR | NR | NR | NR | NR | NR | 0.1% | — |
| | UI-1.56-1.57: NMT 1.0% | NR | NR | 0.1% | 0.1% | 0.2% | 0.2% | 0.2% | — |
| | UI-1.60: NMT 1.0% | NR | NR | 0.1% | 0.1% | 0.2% | 0.2% | NR | — |
| | UI-1.74: NMT 1.0% | NR | NR | NR | NR | NR | 0.2% | NR | — |
| | UI-1.85-1.88: NMT 1.0% | NR | 0.2% | NR | NR | NR | 0.1% | 0.1% | — |

TABLE 32-continued

Samples stored inverted at 25° C. and 60% Relative Humidity

| Test | Acceptance Criteria | Initial | 3 | 6 | 9 | 12 | 18 | 24 | 30 |
|---|---|---|---|---|---|---|---|---|---|
| | UI-2.09-2.10: NMT 1.0% | NR | 0.2% | NR | NR | NR | NR | 0.4% | — |
| | UI-2.15-2.16: NMT 1.0% | NR | NR | NR | NR | NR | NR | 0.6% | — |
| | Total Impurities: NMT 17.0% | 1.3% | 2.5% | 3.4% | 4.6% | 5.6% | 9.0% | 13.4% | — |
| pH | 2.5-4.5 | 3.6 | 3.6 | 3.5 | 3.5 | 3.2 | 3.3 | 3.4 | — |
| Chlorobutanol | 0.25-0.60% w/v | 0.48% | 0.49% | 0.48% | 0.47% | 0.47% | 0.47% | 0.47 | — |
| Particulate Matter (USP) | NMT 6000 (≥10 μm) | 2 | 1 | 1 | 3 | 4 | 1 | 2 | — |
| | NMT 600 (≥25 μm) | 0 | 0 | 0 | 0 | 0 | 0 | 0 | — |
| AntiMicrobial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 33

Samples stored inverted at 25° C. and 60% Relative Humidity

| Test | Acceptance Criteria | Initial | 3 | 6 | 9 | 12 | 18 | 24 | 30 |
|---|---|---|---|---|---|---|---|---|---|
| Vasopressin Assay | 16.0-21.0 U/mL | 19.9 | 19.6 | 19.2 | 19 | 18.7 | 18 | 17.4 | — |
| Related Substances | SEQ ID NO.: 2: NMT 6.0% | 0.2% | 0.5% | 1.0% | 1.5% | 2.0% | 3.2% | 4.5% | — |
| | SEQ ID NO.: 4: NMT 6.0% | 0.1% | 0.6% | 1.1% | 1.8% | 2.2% | 3.7% | 5.0% | — |
| | SEQ ID NO.: 10: NMT 1.0% | 0.4% | 0.4% | 0.3% | 0.4% | 0.4% | 0.3% | 0.5% | — |
| | Asp5-AVP: NMT 1.5% | NR | 0.1% | 0.2% | 0.4% | 0.5% | 0.7% | 1.0% | — |
| | AVP-Dimer: NMT 1.0% | NR | NR | NR | NR | NR | NR | 0.1% | — |
| | Acetyl-AVP: NMT 1.0% | 0.3% | 0.3% | 0.3% | 0.3% | 0.3% | 0.3% | 0.3% | — |
| | UI-0.12: NMT 1.0% | NR | 0.1% | NR | NR | NR | NR | NR | |
| | UI-0.75-0.76: NMT 1.0% | NR | NR | NR | NR | NR | NR | NR | |
| | UI-0.83-0.84: NMT 1.0% | NR | 0.1% | 0.1% | | 0.1% | 0.1% | 0.1% | |
| | UI-0.93: NMT 1.0% | NR | NR | NR | NR | NR | NR | 0.1% | |
| | UI-0.99: NMT 1.0% | NR | NR | NR | NR | NR | NR | NR | |
| | UI-1.02-1.03: NMT 1.0% | 0.3% | 0.2% | 0.2% | 0.3% | 0.3% | 0.3% | 0.3% | — |
| | UI-1.15: NMT 1.0% | NR | NR | NR | NR | NR | NR | 0.1% | |
| | UI-1.18: NMT 1.0% | NR | NR | NR | NR | NR | 0.1% | 0.3% | |
| | UI-1.20: NMT 1.0% | NR | NR | NR | NR | NR | NR | NR | |
| | UI-1.22: NMT 1.0% | NR | NR | NR | NR | NR | NR | 0.1% | |
| | UI-1.26: NMT 1.0% | NR | NR | NR | NR | NR | NR | | |
| | UI-1.35: NMT 1.0% | 0.3% | NR | NR | NR | NR | NR | NR | |
| | UI-1.56-1.57: NMT 1.0% | NR | NR | 0.1% | NR | 0.1% | 0.2% | 0.3% | |
| | UI-1.60: NMT 1.0% | NR | NR | 0.1% | NR | 0.1% | NR | NR | — |
| | UI-1.74: | NR | NR | NR | NR | NR | NR | NR | |

TABLE 33-continued

Samples stored inverted at 25° C. and 60% Relative Humidity

| Test | Acceptance Criteria | Initial | Time in months | | | | | | |
|---|---|---|---|---|---|---|---|---|---|
| | | | 3 | 6 | 9 | 12 | 18 | 24 | 30 |
| | UI-1.84-1.89: NMT 1.0% | NR | 0.1% | NR | NR | NR | NR | 0.2% | |
| | UI-1.96: NMT 1.0% | 0.2% | NR | NR | NR | NR | NR | NR | |
| | UI-2.09-2.10: NMT 1.0% | NR | 20.0% | NR | NR | NR | <0.10 | 0.1% | |
| | UI-2.15-2.16: NMT 1.0% | NR | NR | 0.1% | NR | NR | 0.1% | NR | |
| | Total Impurities: NMT 17.0% | 1.5% | 2.6% | 3.3% | 4.6% | 5.9% | 9.0% | 12.9% | — |
| pH | 2.5-4.5 | 3.6 | 3.5 | 3.5 | 3.5 | 3.4 | 3.4 | 3.3 | — |
| Chlorobutanol | 0.25-0.60% w/v | 0.48% | 0.47% | 0.47% | 0.46% | 0.46% | 0.46% | 0.45% | — |
| Particulate Matter (USP) | NMT 6000 (≥10 μm) | 1 | 2 | 3 | 3 | 3 | 1 | 2 | — |
| | NMT 600 (≥25 μm) | 0 | 0 | 0 | 0 | 0 | 0 | 0 | — |
| Anti-Microbial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 34

Samples stored upright at 25° C. and 60% Relative Humidity

| Test | Acceptance Criteria | Initial | Time in months | | | | | | |
|---|---|---|---|---|---|---|---|---|---|
| | | | 3 | 6 | 9 | 12 | 18 | 24 | 30 |
| Vasopressin Assay | 16.0-21.0 U/mL | 19.8 | 19.4 | 19.1 | 18.8 | 18.3 | 17.5 | 17.4 | — |
| Related Substances | SEQ ID NO.: 2: NMT 6.0% | 0.1% | 0.5% | 1.1% | 1.6% | 2.0% | 3.2% | 4.5% | — |
| | SEQ ID NO.: 4: NMT 6.0% | 0.1% | 0.6% | 1.2% | 1.8% | 2.3% | 3.6% | 5.0% | — |
| | SEQ ID NO.: 10: NMT 1.0% | 0.3% | 0.4% | 0.3% | 0.4% | 0.3% | 0.2% | 0.3% | — |
| | Asp5-AVP: NMT 1.5% | NR | 0.1% | 0.2% | 0.4% | 0.4% | 0.7% | 0.9% | — |
| | AVP-Dimer: NMT 1.0% | NR | NR | NR | NR | NR | NR | NR | — |
| | Acetyl-AVP: NMT 1.0% | 0.3% | 0.3% | 0.3% | 0.2% | 0.2% | 0.2% | 0.3% | — |
| | UI-0.83: NMT 1.0% | NR | NR | <0.10 | NR | NR | 0.1% | 0.1% | — |
| | UI-0.99: NMT 1.0% | NR | NR | NR | NR | NR | NR | NR | — |
| | UI-1.03: NMT 1.0% | 0.2% | 0.2% | 0.2% | 0.3% | 0.2% | 0.2% | 0.2% | — |
| | UI-1.14: NMT 1.0% | NR | NR | NR | NR | NR | NR | 0.1% | — |
| | UI-1.18: NMT 1.0% | NR | NR | NR | NR | NR | 0.1% | 0.3% | — |
| | UI-1.20: NMT 1.0% | NR | NR | NR | NR | NR | NR | 0.1% | — |
| | UI-1.22: NMT 1.0% | NR | NR | NR | NR | NR | NR | NR | — |
| | UI-1.56-1.57: NMT 1.0% | NR | NR | NR | 0.1% | 0.1% | 0.2% | 0.2% | — |
| | UI-1.60: NMT 1.0% | NR | NR | NR | NR | NR | 0.1% | NR | — |
| | UI-1.74: NMT 1.0% | NR | NR | NR | NR | NR | 0.2% | NR | — |
| | UI-1.85-1.88: NMT 1.0% | NR | 0.2% | NR | NR | NR | 0.1% | 0.1% | — |
| | UI-2.09-2.10: | NR | 0.2% | NR | NR | NR | NR | 0.3% | — |

TABLE 34-continued

Samples stored upright at 25° C. and 60% Relative Humidity

| Test | Acceptance Criteria | Initial | 3 | 6 | 9 | 12 | 18 | 24 | 30 |
|---|---|---|---|---|---|---|---|---|---|
| | NMT 1.0% | | | | | | | | |
| | UI-2.15-2.16: NMT 1.0% | NR | NR | NR | NR | NR | NR | 0.5% | — |
| | Total Impurities: NMT 17.0% | 1.1% | 2.4% | 3.2% | 4.8% | 5.6% | 9.2% | 13.1% | — |
| pH | 2.5-4.5 | 3.5 | 3.5 | 3.5 | 3.5 | 3.4 | 3.3 | 3.3 | — |
| Chlorobutanol | 0.25-0.60% w/v | 0.49% | 0.48% | 0.48% | 0.48% | 0.47% | 0.48% | 0.47 | — |
| Particulate Matter (USP) | NMT 6000 (≥10 μm) | 1 | 2 | 2 | 2 | 2 | 4 | 2 | — |
| | NMT 600 (≥25 μm) | 0 | 0 | 0 | 0 | 0 | 0 | 0 | — |
| AntiMicrobial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 35

Samples stored upright at 25° C. and 60% Relative Humidity

| Test | Acceptance Criteria | Initial | 3 | 6 | 9 | 12 | 18 | 24 | 30 |
|---|---|---|---|---|---|---|---|---|---|
| Vasopressin Assay | 16.0-21.0 U/mL | 20.1 | 19.7 | 19.4 | 18.9 | 18.6 | 17.8 | 17.7 | — |
| Related Substances | SEQ ID NO.: 2: NMT 6.0% | 0.1% | 0.5% | 0.9% | 1.4% | 1.9% | 3.1% | 4.3% | — |
| | SEQ ID NO.: 4: NMT 6.0% | 0.1% | 0.5% | 1.1% | 1.6% | 2.2% | 3.4% | 4.9% | — |
| | D-Asn-AVP: NMT 1.0% | 0.3% | 0.4% | 0.3% | 0.3% | 0.3% | 0.4% | 0.3% | — |
| | Asp5-AVP: NMT 1.5% | NR | 0.1% | 0.2% | 0.3% | 0.4% | 0.7% | 0.9% | — |
| | AVP-Dimer: NMT 1.0% | NR | NR | NR | NR | NR | NR | NR | — |
| | Acetyl-AVP: NMT 1.0% | 0.30% | 0.30% | 0.30% | 0.20% | 0.20% | 0.20% | 0.3% | — |
| | UI-0.75-0.76: NMT 1.0% | NR | 0.2% | 0.2% | 0.2% | 0.2% | 0.2% | 0.2% | |
| | UI-0.83: NMT 1.0% | 0.2% | NR | <0.10 | NR | NR | 0.1% | 0.1% | |
| | UI-0.99: NMT 1.0% | NR | NR | NR | NR | 0.1% | NR | NR | |
| | UI-1.02-1.03: NMT 1.0% | 0.2% | 0.2% | 0.2% | 0.2% | 0.2% | 0.3% | 0.2% | — |
| | UI-1.14: NMT 1.0% | NR | NR | NR | NR | NR | NR | 0.1% | |
| | UI-1.18: NMT 1.0% | NR | NR | NR | NR | NR | 0.1% | 0.3% | |
| | UI-1.20: NMT 1.0% | NR | NR | NR | NR | NR | NR | 0.1% | |
| | UI-1.22: NMT 1.0% | NR | NR | NR | NR | NR | NR | 0.4% | |
| | UI-1.56-1.57: NMT 1.0% | NR | NR | 0.1% | 0.1% | 0.2% | 0.2% | 0.3% | |
| | UI-1.60: NMT 1.0% | NR | NR | 0.1% | 0.1% | 0.2% | 0.2% | NR | — |
| | UI-1.74: NMT 1.0% | NR | NR | NR | NR | NR | 0.2% | NR | |
| | UI-1.85-1.88: NMT 1.0% | NR | 0.2% | NR | NR | NR | 0.1% | 0.1 | |
| | UI-2.09-2.10: | NR | 0.2% | NR | NR | NR | 0.1% | 0.3 | |

TABLE 35-continued

Samples stored upright at 25° C. and 60% Relative Humidity

| Test | Acceptance Criteria | Initial | 3 | 6 | 9 | 12 | 18 | 24 | 30 |
|---|---|---|---|---|---|---|---|---|---|
| | NMT 1.0% UI-2.15-2.16: NMT 1.0% | NR | | NR | NR | NR | NR | 0.5 | |
| | Total Impurities: NMT 17.0% | 1.3% | 2.5% | 3.3% | 4.5% | 5.7% | 9.1% | 13.3% | — |
| pH | 2.5-4.5 | 3.6 | 3.6 | 3.5 | 3.5 | 3.4 | 3.3 | 3.3 | — |
| Chlorobutanol | 0.25-0.60% w/v | 0.48% | 0.49% | 0.48% | 0.47% | 0.47% | 0.48% | 0.46 | — |
| Particulate Matter (USP) | NMT 6000 (≥10 μm) | 2 | 1 | 1 | 2 | 5 | 1 | 4 | — |
| | NMT 600 (≥25 μm) | 0 | 0 | 0 | 0 | 0 | 0 | 0 | — |
| Anti-Microbial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 36

Samples stored upright at 25° C. and 60% Relative Humidity

| Test | Acceptance Criteria | Initial | 3 | 6 | 9 | 12 | 18 | 24 | 30 |
|---|---|---|---|---|---|---|---|---|---|
| Vasopressin Assay | 16.0-21.0 U/mL | 19.9 | 19.6 | 19.2 | 19 | 18.5 | 18.1 | 17.4 | — |
| Related Substances | SEQ ID NO.: 2: NMT 6.0% | 0.2% | 0.5% | 1.0% | 1.5% | 2.1% | 3.3% | 4.7% | — |
| | SEQ ID NO.: 4: NMT 6.0% | 0.1% | 0.6% | 1.1% | 1.7% | 2.3% | 3.7% | 5.3% | — |
| | D-Asn-AVP: NMT 1.0% | 0.4% | 0.4% | 0.3% | 0.4% | 0.4% | 0.3% | 0.5% | — |
| | Asp5-AVP: NMT 1.5% | NR | 0.1% | 0.2% | 0.3% | 0.5% | 0.7% | 1.0% | — |
| | AVP-Dimer: NMT 1.0% | NR | NR | NR | NR | NR | NR | NR | — |
| | Acetyl-AVP: NMT 1.0% | 0.3% | 0.3% | 0.3% | 0.3% | 0.3% | 0.3% | 0.3% | — |
| | UI-0.12: NMT 1.0% | NR | NR | NR | NR | NR | NR | NR | |
| | UI-0.75-0.76: NMT 1.0% | NR | NR | NR | NR | NR | NR | NR | |
| | UI-0.83-0.84: NMT 1.0% | NR | 0.1% | 0.1% | 0.1% | NR | 0.1% | 0.1% | |
| | UI-0.93: NMT 1.0% | NR | NR | NR | NR | NR | NR | 0.1% | |
| | UI-0.99: NMT 1.0% | NR | NR | NR | NR | NR | NR | NR | |
| | UI-1.02-1.03: NMT 1.0% | 0.3% | 0.2% | 0.2% | 0.3% | 0.3% | 0.3% | 0.3% | — |
| | UI-1.15: NMT 1.0% | NR | NR | NR | NR | NR | NR | 0.2% | |
| | UI-1.18: NMT 1.0% | NR | NR | NR | NR | NR | 0.1% | 0.3% | |
| | UI-1.20: NMT 1.0% | NR | NR | NR | NR | NR | NR | 0.1% | |
| | UI-1.22: NMT 1.0% | NR | NR | NR | NR | NR | NR | NR | |
| | UI-1.26: NMT 1.0% | NR | NR | 0.4% | NR | NR | NR | NR | |
| | UI-1.35: | 0.1% | NR | NR | NR | NR | NR | NR | |

TABLE 36-continued

Samples stored upright at 25° C. and 60% Relative Humidity

| Test | Acceptance Criteria | Initial | 3 | 6 | 9 | 12 | 18 | 24 | 30 |
|---|---|---|---|---|---|---|---|---|---|
| | UI-1.56-1.57: NMT 1.0% | NR | NR | 0.1% | 0.1% | NR | 0.2% | 0.3% | |
| | UI-1.60: NMT 1.0% | NR | NR | NR | NR | NR | NR | NR | — |
| | UI-1.74: NMT 1.0% | NR | NR | NR | NR | NR | NR | NR | |
| | UI-1.84-1.89: NMT 1.0% | NR | 0.1% | NR | NR | NR | NR | 0.2% | |
| | UI-1.96: NMT 1.0% | 0.2% | NR | NR | NR | NR | NR | NR | |
| | UI-2.09-2.10: NMT 1.0% | NR | NR | NR | NR | NR | <0.10 | NR | |
| | UI-2.15-2.16: NMT 1.0% | NR | NR | 0.1% | NR | NR | 0.2% | NR | |
| | Total Impurities: NMT 17.0% | 1.5% | 2.5% | 3.7% | 4.7% | 5.9% | 9.1% | 13.3% | — |
| pH | 2.5-4.5 | 3.6 | 3.5 | 3.5 | 3.5 | 3.4 | 3.4 | 3.3 | — |
| Chlorobutanol | 0.25-0.60% w/v | 0.48% | 0.48% | 0.47% | 0.47% | 0.46% | 0.45 | 0.46 | — |
| Particulate Matter (USP) | NMT 6000 (≥10 μm) | 1 | 0 | 1 | 3 | 7 | 0 | 3 | — |
| | NMT 600 (≥25 μm) | 0 | 0 | 0 | 0 | 0 | 0 | 0 | — |
| Anti-Microbial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 37

Samples stored inverted at 40° C.

| Test | Acceptance Criteria | Initial | 1 | 2 | 3 |
|---|---|---|---|---|---|
| Vasopressin Assay | 18.0-21.0 U/mL | 19.8 | 19.1 | 18.6 | 17.3 |
| Related Substances | SEQ ID NO.: 2: NMT 6.0% | 0.1% | 1.0% | 2.4% | 3.8% |
| | SEQ ID NO.: 4: NMT 6.0% | 0.1% | 1.1% | 2.7% | 4.3% |
| | D-Asn-AVP: NMT 1.0% | 0.3% | 0.4% | 0.3% | 0.3% |
| | Asp5-AVP: NMT 1.5% | ND | 0.2% | 0.5% | 0.8% |
| | AVP-Dimer: NMT 1.0% | ND | ND | ND | ND |
| | Acetyl-AVP: NMT 1.0% | 0.3% | 0.2% | 0.2% | 0.2% |
| | UI-0.13: NMT 1.0% | ND | 0.1% | ND | ND |
| | UI-0.75-0.78: NMT 1.0% | ND | ND | ND | ND |
| | UI-0.83-0.84: NMT 1.0% | ND | ND | ND | ND |
| | UI-1.02-1.03: NMT 1.0% | 0.2% | 0.3% | 0.2% | 0.3% |
| | UI-1.18: NMT 1.0% | ND | ND | ND | 0.2% |
| | UI-1.56-1.57: NMT 1.0% | ND | 0.2% | 0.4% | 0.4% |
| | UI-1.67: NMT 1.0% | ND | ND | ND | ND |
| | UI-1.76: NMT 1.0% | ND | ND | ND | ND |
| | UI-1.83-1.85: NMT 1.0% | ND | ND | 0.2% | 0.2% |
| | UI-1.87-1.88: NMT 1.0% | ND | ND | 0.2% | 0.2% |
| | UI-1.93: NMT 1.0% | ND | 0.1% | ND | ND |
| | UI-2.05-2.08: NMT 1.0% | ND | ND | 0.2% | ND |
| | Total Impurities: NMT 17.0% | 1.1% | 3.7% | 7.3% | 10.6% |
| pH | 2.5-4.5 | 3.5 | 3.3 | 3.2 | 3.1 |
| Chlorobutanol | 0.25-0.60% w/v | 0.49% | 0.48% | 0.50% | 0.47% |
| Particulate Matter (USP) | NMT 6000 (≥10 μm) | 1 | 1 | 1 | 1 |
| | NMT 600 (≥25 μm) | 0 | 0 | 0 | 0 |

TABLE 38

Samples stored inverted at 40° C.

| Test | Acceptance Criteria | Initial | 1 | 2 | 3 |
|---|---|---|---|---|---|
| Vasopressin Assay | 18.0-21.0 U/mL | 20.1 | 19.3 | 18.7 | 17.6 |
| Related Substances | SEQ ID NO.: 2: NMT 6.0% | 0.1% | 0.9% | 2.2% | 3.6% |
| | SEQ ID NO.: 4: NMT 6.0% | 0.1% | 1.0% | 2.5% | 3.9% |
| | D-Asn-AVP: NMT 1.0% | 0.3% | 0.4% | 0.3% | 0.3% |
| | Asp5-AVP: NMT 1.5% | ND | 0.2% | 0.5% | 0.8% |
| | AVP-Dimer: NMT 1.0% | ND | ND | ND | ND |
| | Acetyl-AVP: NMT 1.0% | 0.3% | 0.2% | 0.3% | 0.2% |
| | UI-0.13: NMT 1.0% | ND | 0.1% | ND | ND |
| | UI-0.75-0.78: NMT 1.0% | ND | ND | 0.2% | 0.2% |
| | UI-0.80-0.84: NMT 1.0% | 0.2% | 0.2% | ND | ND |
| | UI-1.02-1.03: NMT 1.0% | 0.2% | 0.3% | 0.2% | 0.3% |
| | UI-1.18: NMT 1.0% | ND | ND | 0.3% | 0.2% |
| | UI-1.56-1.57: NMT 1.0% | ND | 0.2% | ND | 0.4% |
| | UI-1.67: NMT 1.0% | ND | ND | ND | ND |
| | UI-1.76: NMT 1.0% | ND | ND | ND | ND |
| | UI-1.81-1.85: NMT 1.0% | ND | ND | 0.2% | 0.2% |
| | UI-1.87-1.88: NMT 1.0% | ND | ND | 0.2% | 0.2% |
| | UI-1.93: NMT 1.0% | ND | 0.1% | ND | ND |
| | UI-2.03-2.08: NMT 1.0% | ND | ND | 0.2% | 0.1% |
| | UI-2.14: NMT 1.0% | ND | ND | 0.2% | ND |
| | Total Impurities: NMT 17.0% | 1.3% | 3.6% | 7.3% | 10.3% |
| pH | 2.5-4.5 | 3.6 | 3.3 | 3.2 | 3.1 |
| Chlorobutanol | 0.25-0.60% w/v | 0.48% | 0.48% | 0.50% | 0.47% |
| Particulate Matter (USP) | NMT 6000 (≥10 μm) | 2 | 2 | 1 | 1 |
| | NMT 600 (≥25 μm) | 0 | 0 | 0 | 0 |

TABLE 39

Samples stored inverted at 40° C.

| Test | Acceptance Criteria | Initial | 1 | 2 | 3 |
|---|---|---|---|---|---|
| Vasopressin Assay | 18.0-21.0 U/mL | 19.9 | 19.2 | 18.3 | 17.4 |
| Related Substances | SEQ ID NO.: 2: NMT 6.0% | 0.2% | 0.9% | 2.2% | 3.8% |
| | SEQ ID NO.: 4: NMT 6.0% | 0.1% | 1.0% | 2.4% | 4.0% |
| | D-Asn-AVP: NMT 1.0% | 0.4% | 0.3% | 0.3% | 0.3% |
| | Asp5-AVP: NMT 1.5% | ND | 0.2% | 0.5% | 0.8% |
| | AVP-Dimer: NMT 1.0% | ND | ND | ND | ND |
| | Acetyl-AVP: NMT 1.0% | 0.3% | 0.3% | 0.3% | 0.2% |
| | UI-0.13: NMT 1.0% | ND | ND | ND | ND |
| | UI-0.75-0.78: NMT 1.0% | ND | ND | ND | ND |
| | UI-0.80-0.84: NMT 1.0% | ND | ND | ND | ND |
| | UI-1.02-1.03: NMT 1.0% | 0.3% | 0.2% | 0.2% | 0.3% |
| | UI-1.18: NMT 1.0% | ND | ND | ND | 0.2% |
| | UI-1.35: NMT 1.0% | 0.1% | ND | ND | ND |
| | UI-1.52-1.58: NMT 1.0% | ND | 0.2% | 0.3% | 0.4% |
| | UI-1.67: NMT 1.0% | ND | ND | ND | ND |
| | UI-1.76: NMT 1.0% | ND | ND | ND | ND |
| | UI-1.81-1.85: NMT 1.0% | ND | ND | ND | ND |
| | UI-1.86-1.88: NMT 1.0% | ND | 0.1% | 0.2% | ND |
| | UI-1.91-1.96: NMT 1.0% | 0.2% | 0.2% | ND | ND |
| | UI-2.02-2.08: NMT 1.0% | ND | ND | ND | 0.2% |
| | UI-2.11-2.14: NMT 1.0% | ND | 0.2% | ND | ND |
| | Total Impurities: NMT 17.0% | 1.5% | 3.7% | 6.3% | 10.3% |
| pH | 2.5-4.5 | 3.6 | 3.4 | 3.2 | 3.1 |
| Chlorobutanol | 0.25-0.60% w/v | 0.48% | 0.47% | 0.46% | 0.46% |
| Particulate Matter (USP) | NMT 6000 (≥10 μm) | 2 | 2 | 1 | 1 |
| | NMT 600 (≥25 μm) | 0 | 0 | 0 | 0 |

TABLE 40

Samples stored Upright at 40° C.

| Test | Acceptance Criteria | Initial | 1 | 2 | 3 |
|---|---|---|---|---|---|
| Vasopressin Assay | 18.0-21.0 U/mL | 19.8 | 18.9 | 18.5 | 17.2 |
| Related Substances | SEQ ID NO.: 2: NMT 6.0% | 0.1% | 1.0% | 2.4% | 3.8% |
| | SEQ ID NO.: 4: NMT 6.0% | 0.1% | 1.1% | 2.7% | 4.3% |
| | D-Asn-AVP: NMT 1.0% | 0.3% | 0.3% | 0.3% | 0.3% |
| | Asp5-AVP: NMT 1.5% | ND | 0.2% | 0.5% | 0.8% |
| | AVP-Dimer: NMT 1.0% | ND | ND | ND | ND |
| | UI-0.13: NMT 1.0% | ND | 0.1% | ND | ND |
| | UI-0.75-0.78: NMT 1.0% | ND | ND | ND | ND |
| | UI-0.83-0.84: NMT 1.0% | ND | ND | ND | ND |
| | UI-1.02-1.03: NMT 1.0% | 0.2% | 0.2% | 0.2% | 0.2% |
| | UI-1.18: NMT 1.0% | ND | ND | ND | 0.2% |

TABLE 40-continued

Samples stored Upright at 40° C.

| Test | Acceptance Criteria | Initial | 1 | 2 | 3 |
|---|---|---|---|---|---|
| | UI-1.56-1.57: NMT 1.0% | ND | 0.2% | 0.3% | 0.3% |
| | UI-1.67: NMT 1.0% | ND | ND | ND | ND |
| | UI-1.76: NMT 1.0% | ND | ND | ND | ND |
| | UI-1.83-1.85: NMT 1.0% | ND | ND | 0.2% | ND |
| | UI-1.87-1.88: NMT 1.0% | ND | ND | 0.2% | 0.2% |
| | UI-1.93: NMT 1.0% | ND | 0.1% | ND | ND |
| | UI-2.05-2.08: NMT 1.0% | ND | ND | 0.2% | ND |
| | Total Impurities: NMT 17.0% | 1.1% | 3.6% | 7.2% | 10.3% |
| | Total Impurities: NMT 17.0% | 1.1% | 3.6% | 7.2% | 10.3% |
| pH | 2.5-4.5 | 3.5 | 3.3 | 3.2 | 3.1 |
| Chlorobutanol | 0.25-0.60% w/v | 0.49% | 0.48% | 0.50% | 0.48% |
| Particulate Matter (USP) | NMT 6000 (≥10 μm) | 1 | 1 | 1 | 1 |
| | NMT 600 (≥25 μm) | 0 | 0 | 0 | 0 |

TABLE 41

Samples stored Upright at 40° C.

| Test | Acceptance Criteria | Initial | 1 | 2 | 3 |
|---|---|---|---|---|---|
| Vasopressin Assay | 18.0-21.0 U/mL | 20.1 | 18.9 | 18.7 | 17.4 |
| Related Substances | SEQ ID NO.: 2: NMT 6.0% | 0.1% | 0.9% | 2.3% | 3.7% |
| | SEQ ID NO.: 4: NMT 6.0% | 0.1% | 1.0% | 2.5% | 3.9% |
| | D-Asn-AVP: NMT 1.0% | 0.3% | 0.4% | 0.3% | 0.3% |
| | Asp5-AVP: NMT 1.5% | ND | 0.2% | 0.5% | 0.8% |
| | AVP-Dimer: NMT 1.0% | ND | ND | ND | ND |
| | Acetyl-AVP: NMT 1.0% | 0.3% | 0.2% | 0.3% | 0.2% |
| | UI-0.13: NMT 1.0% | ND | ND | ND | ND |
| | UI-0.75-0.78: NMT 1.0% | ND | ND | 0.2% | 0.2% |
| | UI-0.80-0.84: NMT 1.0% | 0.2% | 0.2% | ND | ND |
| | UI-1.02-1.03: NMT 1.0% | 2.0% | 0.3% | 0.2% | 0.3% |
| | UI-1.18: NMT 1.0% | ND | ND | ND | 0.2% |
| | UI-1.56-1.57: NMT 1.0% | ND | 0.2% | 0.4% | 0.4% |
| | UI-1.67: NMT 1.0% | ND | ND | ND | ND |
| | UI-1.76: NMT 1.0% | ND | ND | ND | ND |
| | UI-1.83-1.85: NMT 1.0% | ND | ND | 0.2% | 0.1% |
| | UI-1.87-1.88: NMT 1.0% | ND | ND | 0.2% | 0.2% |
| | UI-1.93: NMT 1.0% | ND | 0.1% | ND | ND |

TABLE 41-continued

Samples stored Upright at 40° C.

| Test | Acceptance Criteria | Initial | 1 | 2 | 3 |
|---|---|---|---|---|---|
| | UI-2.05-2.08: NMT 1.0% | ND | ND | 0.2% | ND |
| | UI-2.14: NMT 1.0% | ND | ND | ND | ND |
| | Total Impurities: NMT 17.0% | 1.3% | 3.5% | 7.1% | 10.2% |
| pH | 2.5-4.5 | 3.6 | 3.3 | 3.2 | 3.1 |
| Chlorobutanol | 0.25-0.60% w/v | 0.48% | 0.48% | 0.49% | 0.47% |
| Particulate Matter (USP) | NMT 6000 (≥10 μm) | 2 | 1 | 1 | 1 |
| | NMT 600 (≥25 μm) | 0 | 0 | 0 | 0 |

TABLE 42

Samples stored Upright at 40° C.

| Test | Acceptance Criteria | Initial | 1 | 2 | 3 |
|---|---|---|---|---|---|
| Vasopressin Assay | 18.0-21.0 U/mL | 19.9 | 19.2 | 18.3 | 17.5 |
| Related Substances | SEQ ID NO.: 2: NMT 6.0% | 0.2% | 1.0% | 2.2% | 3.9% |
| | SEQ ID NO.: 4: NMT 6.0% | 0.1% | 1.1% | 2.4% | 4.2% |
| | D-Asn-AVP: NMT 1.0% | 0.4% | 0.3% | 0.3% | 0.3% |
| | Asp5-AVP: NMT 1.5% | ND | 0.2% | 50.0% | 0.8% |
| | AVP-Dimer: NMT 1.0% | ND | ND | ND | ND |
| | Acetyl-AVP: NMT 1.0% | 0.3% | 0.3% | 0.3% | 0.2% |
| | UI-0.13: NMT 1.0% | ND | ND | ND | ND |
| | UI-0.75-0.78: NMT 1.0% | ND | ND | ND | ND |
| | UI-0.80-0.84: NMT 1.0% | ND | ND | ND | ND |
| | UI-1.02-1.03: NMT 1.0% | 0.3% | 0.2% | 0.2% | 0.3% |
| | UI-1.18: NMT 1.0% | ND | ND | ND | 0.2% |
| | UI-1.35: NMT 1.0% | 0.1% | ND | ND | ND |
| | UI-1.52-1.58: NMT 1.0% | ND | 0.2% | 0.3% | 0.4% |
| | UI-1.67: NMT 1.0% | ND | ND | ND | ND |
| | UI-1.76: NMT 1.0% | ND | ND | ND | ND |
| | UI-1.83-1.85: NMT 1.0% | ND | ND | ND | ND |
| | UI-1.86-1.88: NMT 1.0% | ND | 0.1% | 0.2% | ND |
| | UI-1.91-1.96: NMT 1.0% | 0.2% | 0.2% | ND | ND |
| | UI-2.02-2.08: | ND | ND | ND | 0.1% |

TABLE 42-continued

Samples stored Upright at 40° C.

| Test | Acceptance Criteria | Initial | Time in months | | |
|---|---|---|---|---|---|
| | | | 1 | 2 | 3 |
| | NMT 1.0% UI-2.11-2.14: NMT 1.0% | ND | 0.2% | ND | ND |
| | Total Impurities: NMT 17.0% | 1.5% | 3.8% | 6.3% | 10.5% |
| pH | 2.5-4.5 | 3.6 | 3.4 | 3.2 | 3.1 |
| Chlorobutanol | 0.25-0.60% w/v | 0.48% | 0.47% | 0.47% | 0.45% |
| Particulate Matter (USP) | NMT 6000 (≥10 μm) | 1 | 2 | 1 | 1 |
| | NMT 600 (≥25 μm) | 0 | 0 | 0 | 0 |

Example 9: Effect of pH 3.5-4.5 on Vasopressin Formulations

To test of effect of pH on vasopressin formulations, solutions containing 20 units/mL vasopressin, adjusted to pH 3.5, 3.6, 3.7, 3.8, 3.9, 4, 4.1, 4.2, 4.3, 4.4, or 4.5 with 10 mM acetate buffer, were prepared. One mL of each of the vasopressin formulations was then filled into 10 cc vials.

Figure 11:
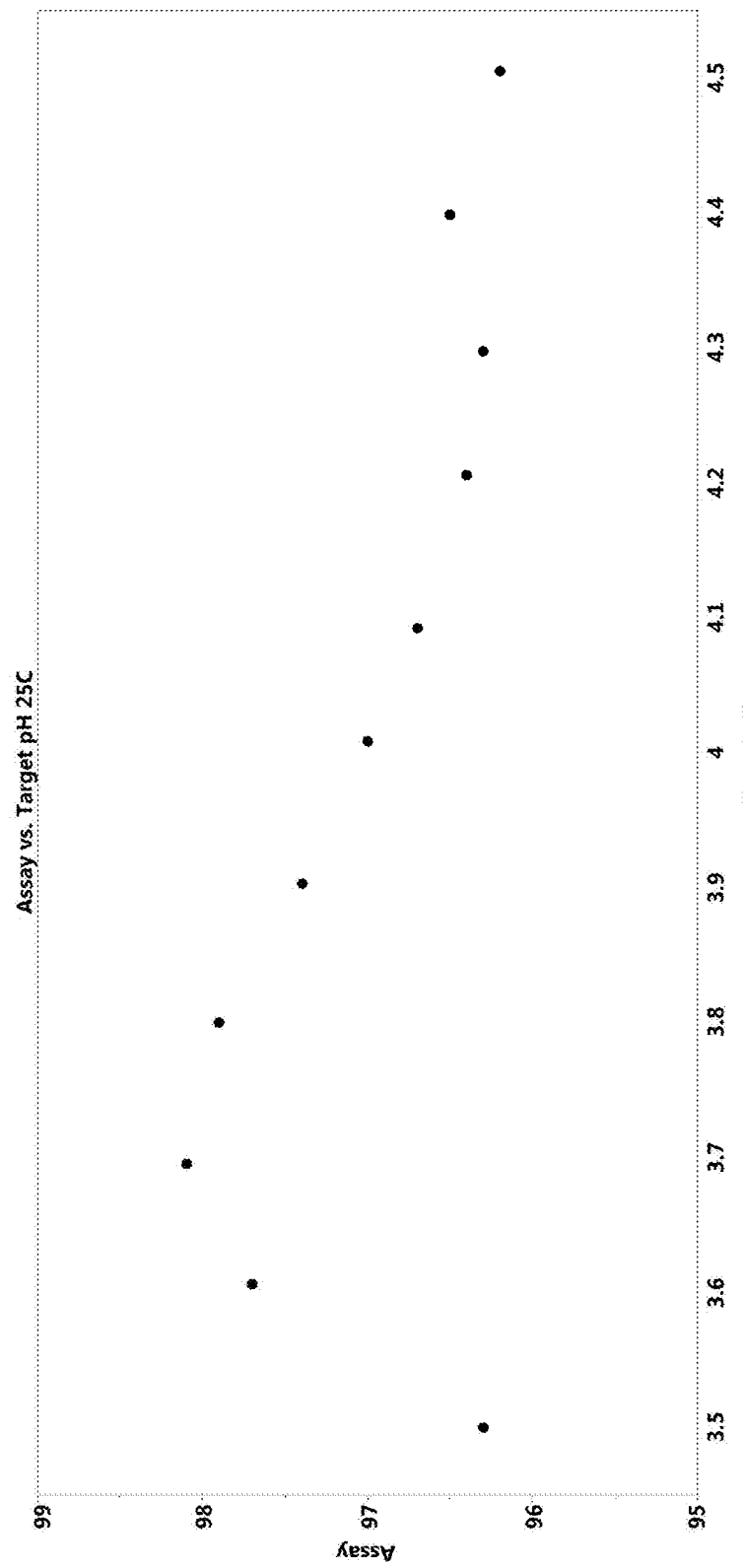
FIG. 11 plots vasopressin stability across a range of pH at 25° C.
Figure 12:
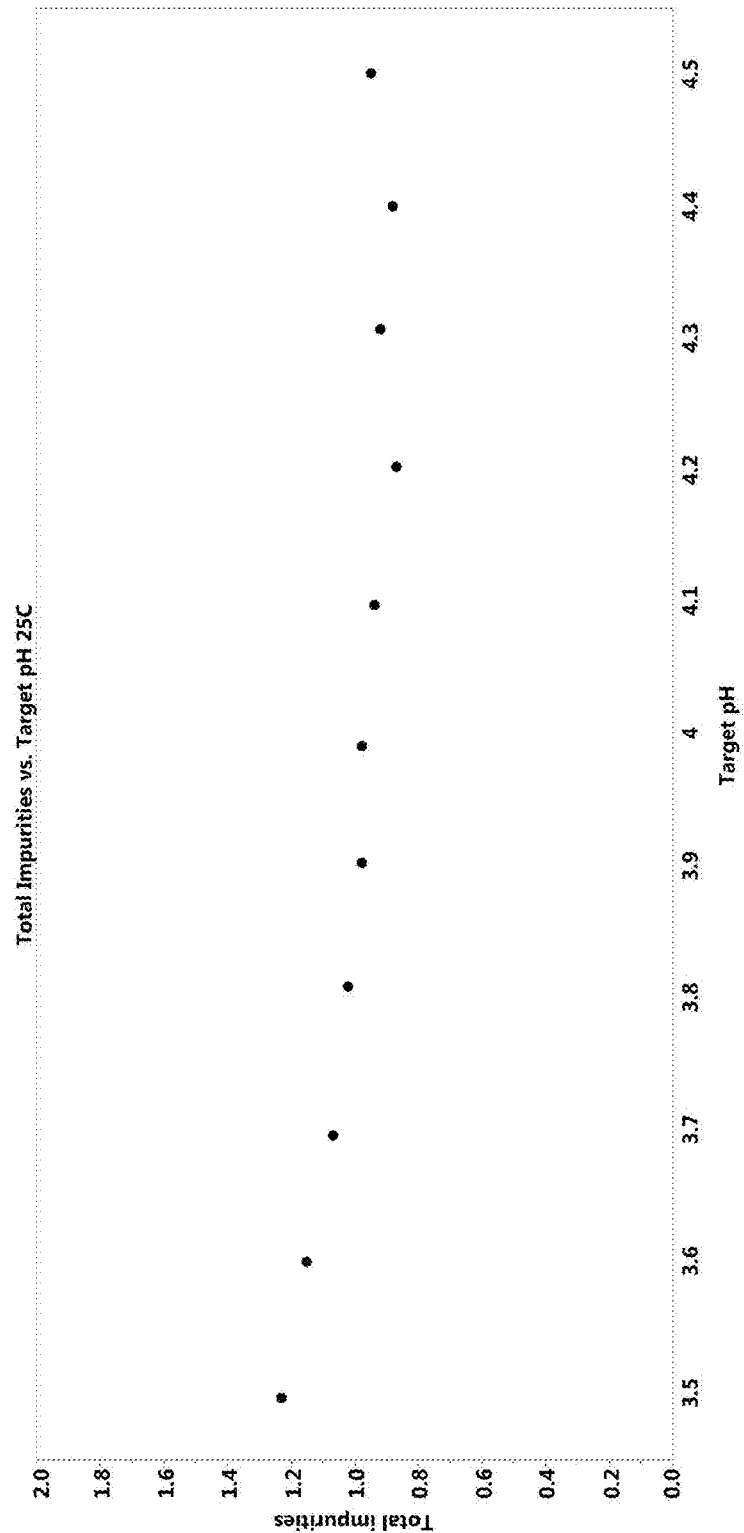
FIG. 12 plots vasopressin impurities across a range of pH at 25° C.

The vasopressin formulations were stored for four weeks at: (i) 25° C.; or (ii) 40° C., and the assay (% label claim; vasopressin remaining) and % total impurities after four weeks were measured using the methods described in EXAMPLE 1. FIGS. 11 and 12 below display the results of the experiments at 25° C. The results of the experiments at 40° C. are included in FIGS. 13 and 14.

The results of the experiments suggested that the stability of a vasopressin formulation was affected by pH. At 25° C., the remaining vasopressin after four weeks was highest between pH 3.6 and pH 3.8 (FIG. 11). Within the range of pH 3.6 to pH 3.8, the level of impurities was lowest at pH 3.8 (FIG. 12). At 25° C., pH 3.7 provided the highest stability for vasopressin (FIG. 11).

Figure 13:
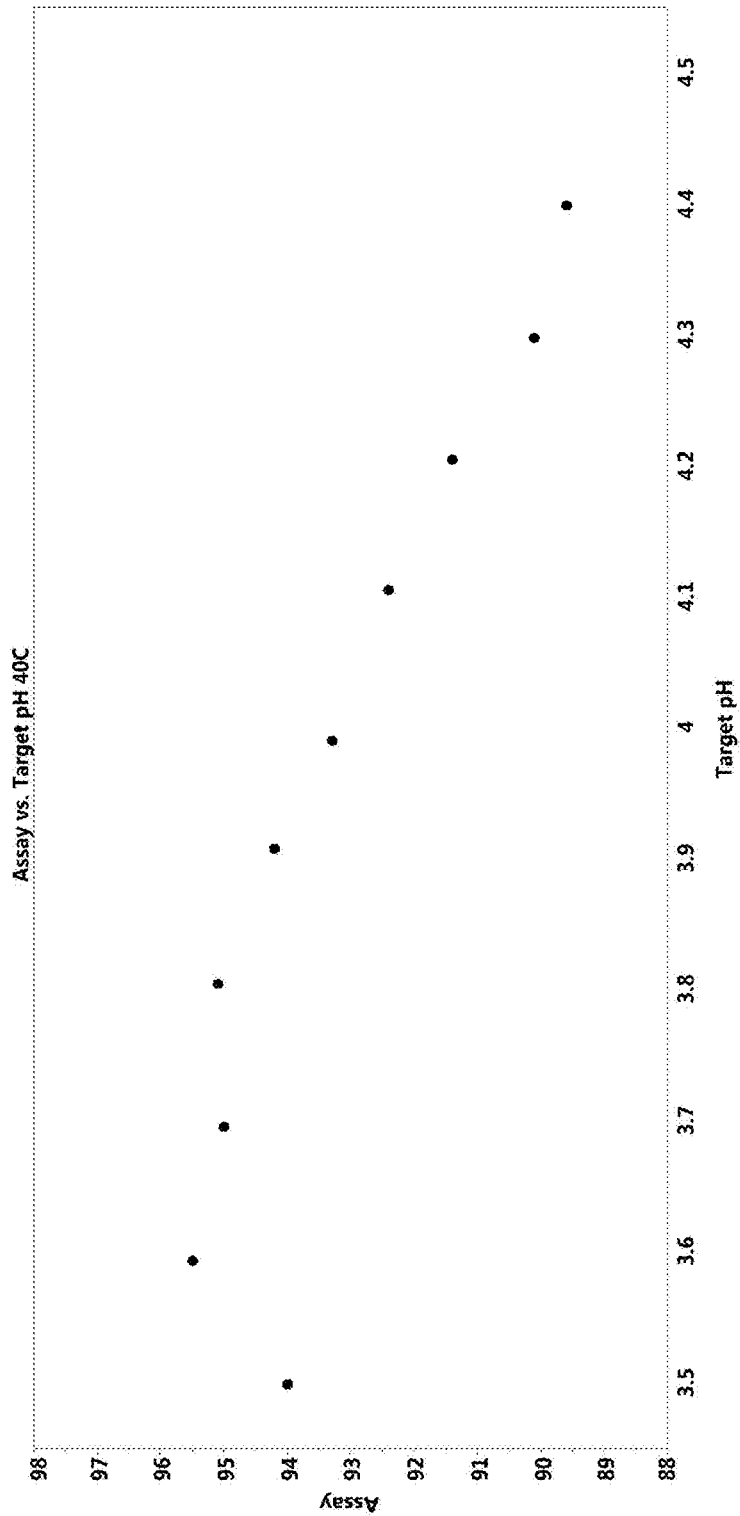
FIG. 13 plots vasopressin stability across a range of pH at 40° C.
Figure 14:
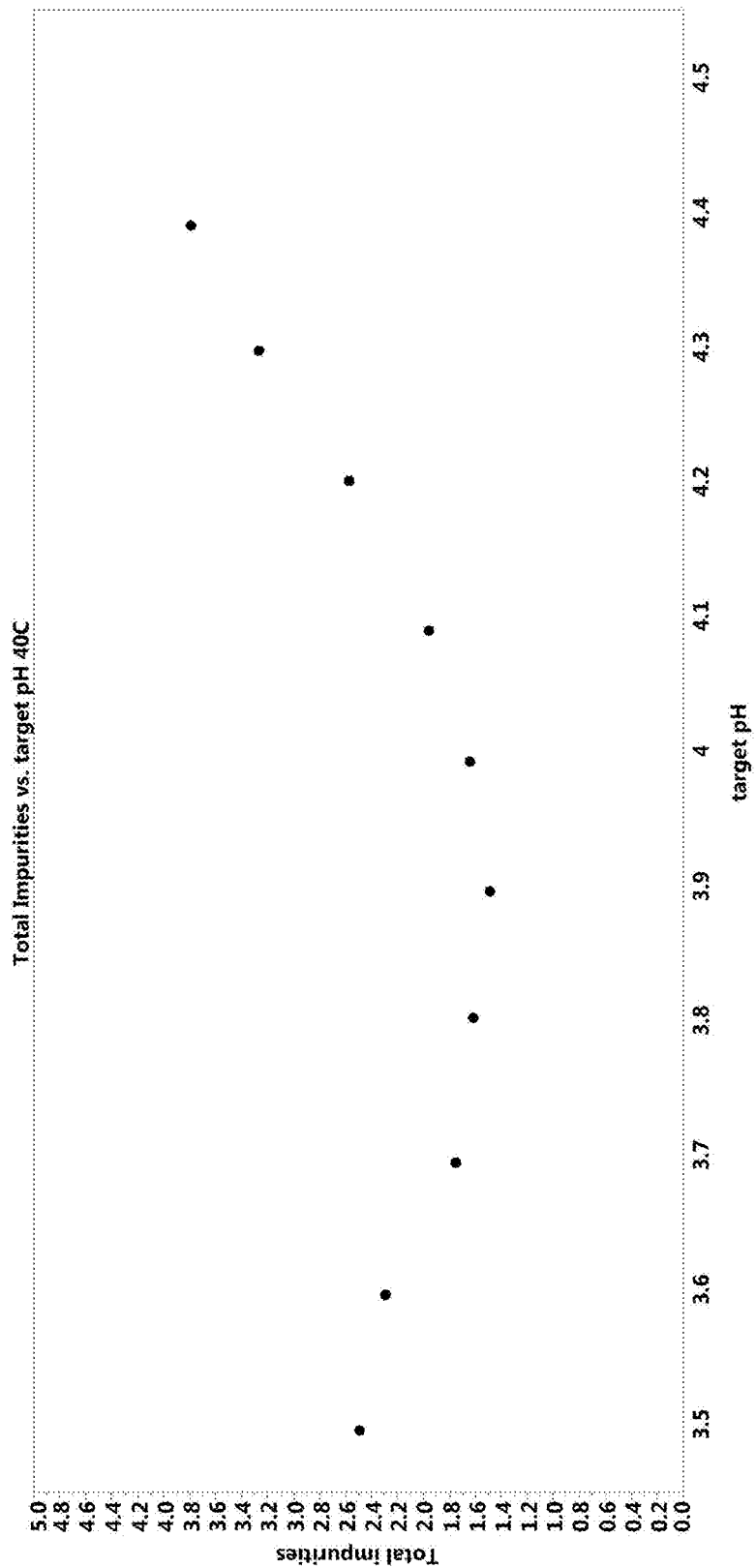
FIG. 14 plots vasopressin impurities across a range of pH at 40° C.

At 40° C., the remaining vasopressin after four weeks was highest between pH 3.6 and pH 3.8 (FIG. 13). Within the range of pH 3.6 to pH 3.8, the level of impurities was lowest at pH 3.8 (FIG. 14). At 40° C., pH 3.6 provided the highest stability for vasopressin (FIG. 13),

Example 10: Effect of pH 2.5-4.5 of Vasopressin Formulations

To test of effect of pH on vasopressin formulations, solutions containing 20 units/mL vasopressin, adjusted to pH 2.5, 2.6, 2.7, 2.8, 2.9, 3, 3.1, 3.2, 3.3, or 3.4 with 10 mM acetate buffer were also prepared. One mL of each of the vasopressin formulations was then filled into 10 cc vials.

The amount of vasopressin, impurities, and associated integration values were determined using the methods describes in EXAMPLE 1. The results from the stability tests on the vasopressin formulations from pH 2.5 to 3.4 were plotted against the results from the stability tests on vasopressin formulations from pH 3.5 to 4.5 as disclosed in EXAMPLE 9, and are displayed in FIGS. 15-18.

The assay (% label claim; vasopressin remaining) and % total impurities in the vasopressin pH 2.5 to 3.4 formulations after four weeks are reported in TABLE 43.

TABLE 43

| Batch | Target pH | Week | Condition | Vasopressin (% LC) | % Total Impurities |
|---|---|---|---|---|---|
| 1A | 2.5 | 0 | 25° C. | 100.57 | 2.48 |
| 1B | 2.6 | 0 | 25° C. | 101.25 | 2.24 |
| 1C | 2.7 | 0 | 25° C. | 101.29 | 2.26 |
| 1D | 2.8 | 0 | 25° C. | 101.53 | 2.00 |
| 1E | 2.9 | 0 | 25° C. | 102.33 | 1.95 |
| 1F | 3 | 0 | 25° C. | 102.32 | 1.89 |
| 1G | 3.1 | 0 | 25° C. | 102.59 | 2.06 |
| 1H | 3.2 | 0 | 25° C. | 102.60 | 1.85 |
| 1I | 3.3 | 0 | 25° C. | 102.73 | 1.81 |
| 1J | 3.4 | 0 | 25° C. | 101.93 | 1.75 |
| 1A | 2.5 | 0 | 40° C. | 100.57 | 2.48 |
| 1B | 2.6 | 0 | 40° C. | 101.25 | 2.24 |
| 1C | 2.7 | 0 | 40° C. | 101.29 | 2.26 |
| 1D | 2.8 | 0 | 40° C. | 101.53 | 2.00 |
| 1E | 2.9 | 0 | 40° C. | 102.33 | 1.95 |
| 1F | 3 | 0 | 40° C. | 102.32 | 1.89 |
| 1G | 3.1 | 0 | 40° C. | 102.59 | 2.06 |
| 1H | 3.2 | 0 | 40° C. | 102.60 | 1.85 |
| 1I | 3.3 | 0 | 40° C. | 102.73 | 1.81 |
| 1J | 3.4 | 0 | 40° C. | 101.93 | 1.75 |
| 1A | 2.5 | 4 | 25° C. | 95.70 | 6.66 |
| 1B | 2.6 | 4 | 25° C. | 98.58 | 5.29 |
| 1C | 2.7 | 4 | 25° C. | 98.94 | 4.26 |
| 1D | 2.8 | 4 | 25° C. | 99.14 | 3.51 |
| 1E | 2.9 | 4 | 25° C. | 100.08 | 3.41 |
| 1F | 3 | 4 | 25° C. | 100.29 | 2.92 |
| 1G | 3.1 | 4 | 25° C. | 100.78 | 2.55 |
| 1H | 3.2 | 4 | 25° C. | 100.74 | 2.16 |
| 1I | 3.3 | 4 | 25° C. | 100.46 | 2.14 |
| 1J | 3.4 | 4 | 25° C. | 100.25 | 2.03 |
| 1A | 2.5 | 4 | 40° C. | 81.89 | 19.41 |
| 1B | 2.6 | 4 | 40° C. | 90.10 | 15.60 |
| 1C | 2.7 | 4 | 40° C. | 92.19 | 13.46 |
| 1D | 2.8 | 4 | 40° C. | 94.89 | 10.98 |
| 1E | 2.9 | 4 | 40° C. | 96.03 | 9.78 |
| 1F | 3 | 4 | 40° C. | 97.26 | 8.09 |
| 1G | 3.1 | 4 | 40° C. | 99.61 | 6.39 |
| 1H | 3.2 | 4 | 40° C. | 98.58 | 5.25 |
| 1I | 3.3 | 4 | 40° C. | 97.81 | 4.41 |
| 1J | 3.4 | 4 | 40° C. | 97.35 | 3.85 |

Figure 15:
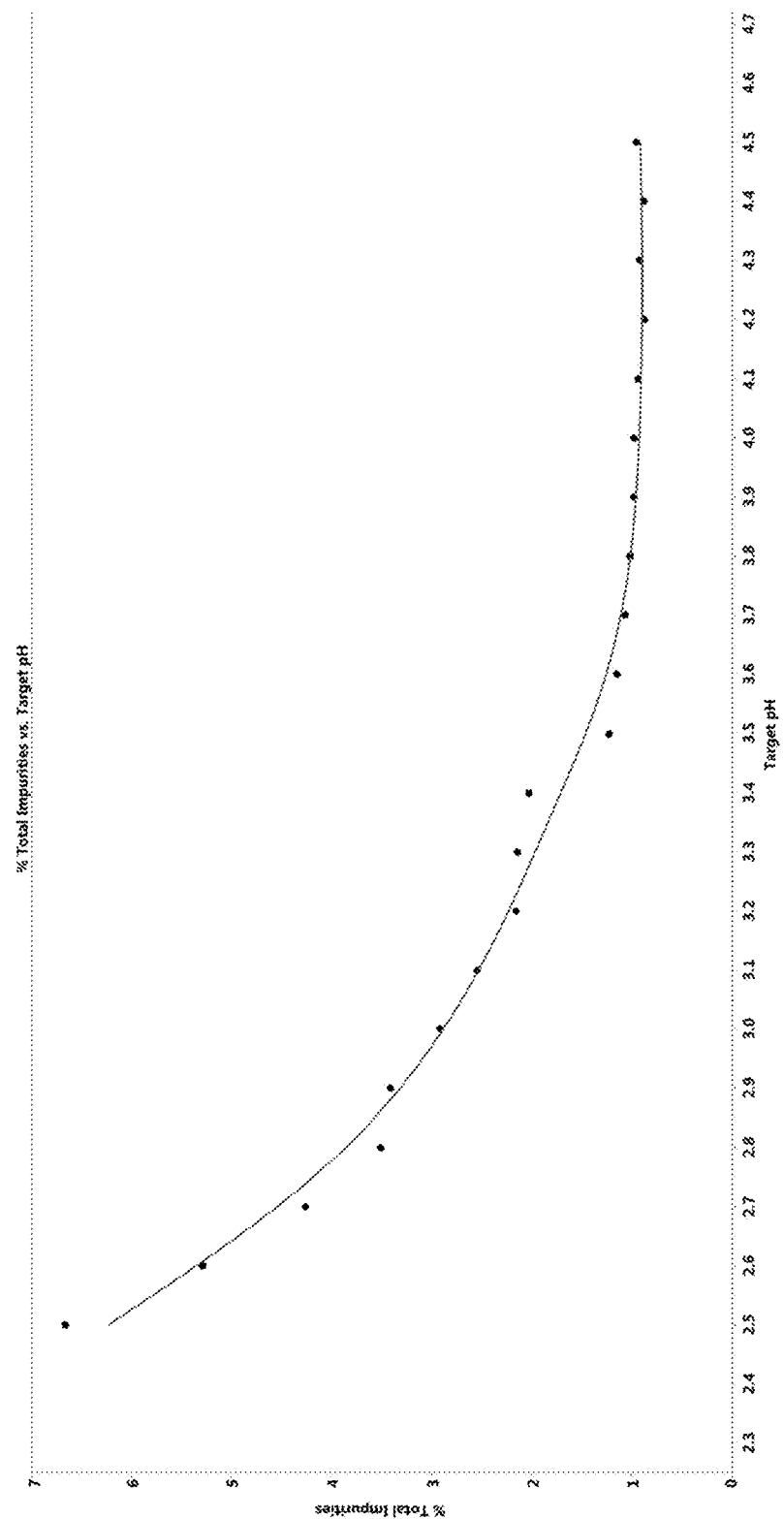
FIG. 15 illustrates vasopressin impurities across a range of pH at 25° C.

The % total impurities for the pH 2.5 to 3.4 formulations and the pH 3.5 to 4.5 formulations observed in the experiments conducted at 25° C. and 40° C. are shown in FIGS. 15 (25° C.) and 16 (40° C.).

Figure 17:
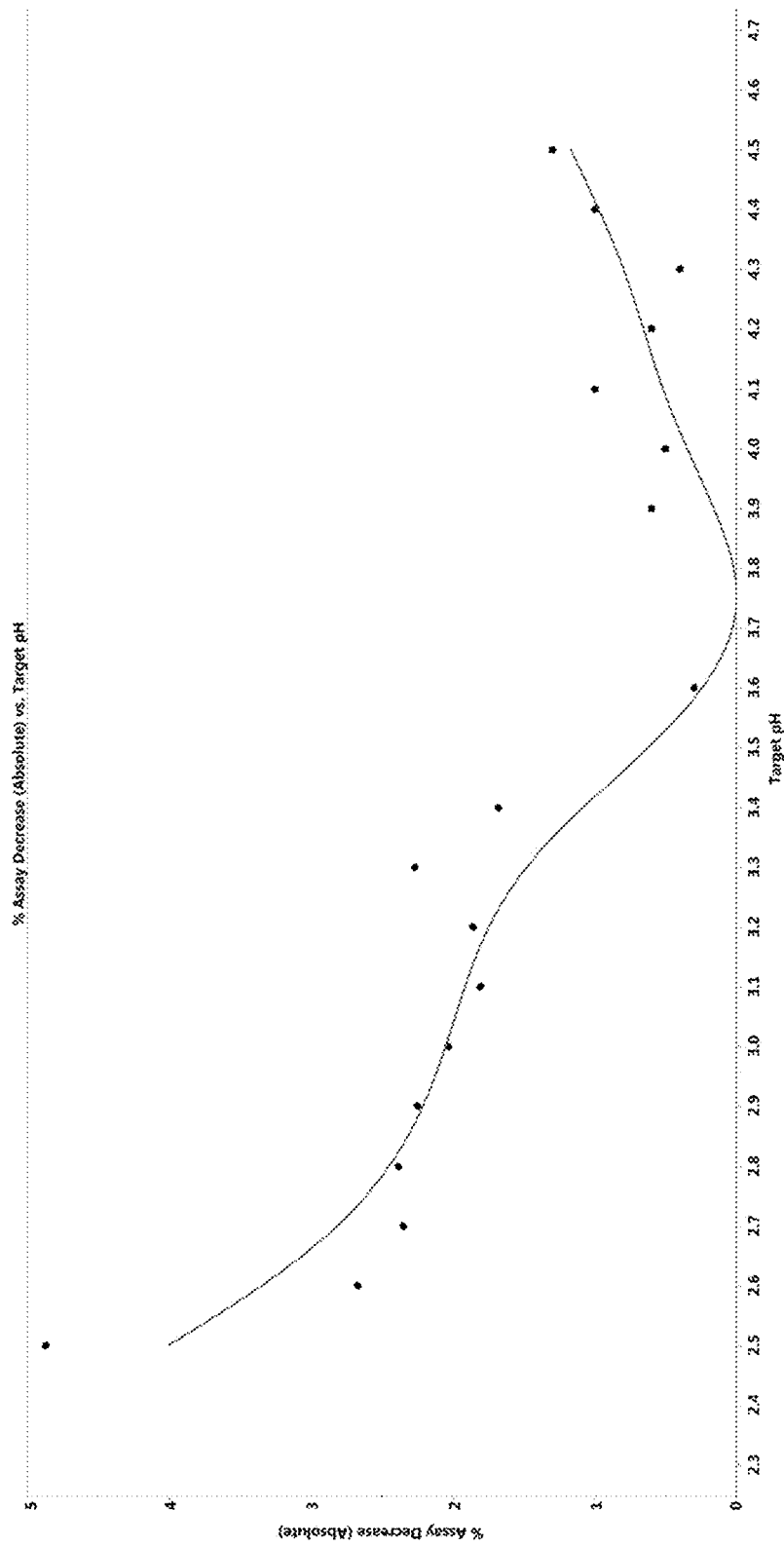
FIG. 17 illustrates the effect of pH on vasopressin at 25° C.

The vasopressin assay amount for the vasopressin pH 2.5 to 3.4 formulations and the vasopressin pH 3.5 to 4.5 formulations observed in the experiments conducted at 25° C. and 40° C. are shown in FIGS. 17 (25° C.) and 18 (40° C.). The vasopressin assay is presented as a % assay decrease of vasopressin over the four-week study period, rather than absolute assay, because the amount of starting vasopressin varied between the vasopressin pH 2.5 to 3.4 formulations and the vasopressin pH 3.5 to 4.5 formulations.

Figure 16:
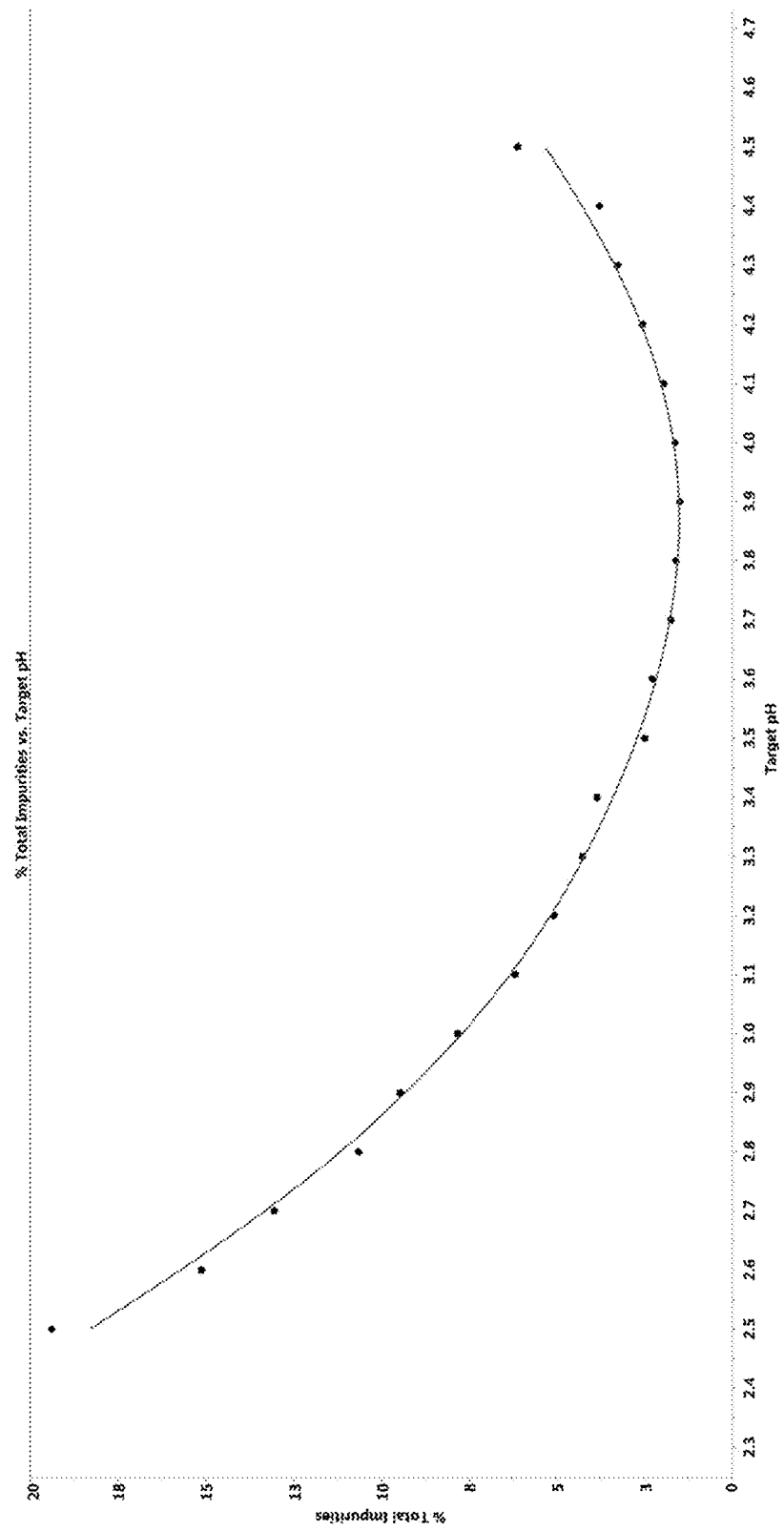
FIG. 16 illustrates vasopressin impurities across a range of pH at 40° C.
Figure 18:
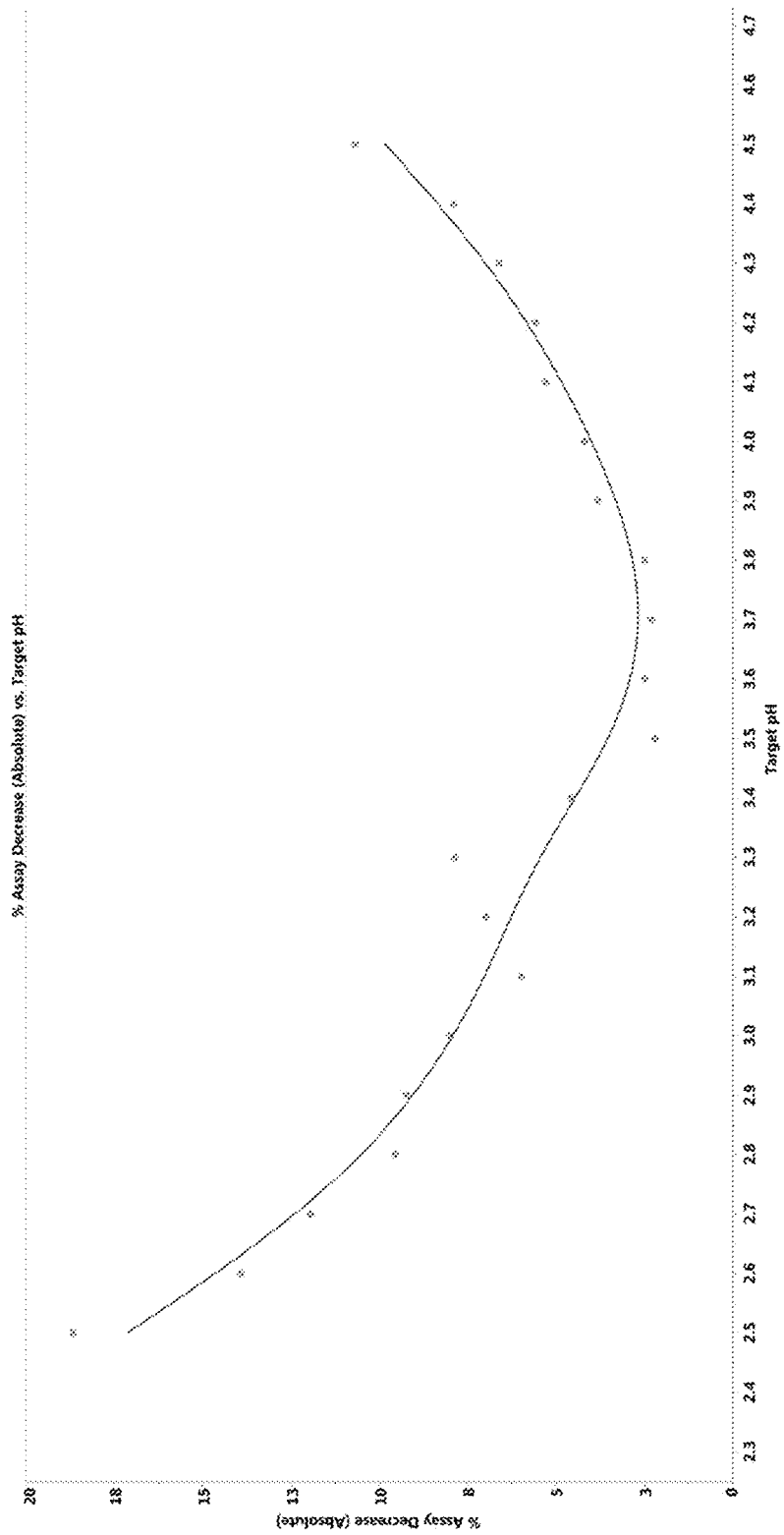
FIG. 18 illustrates the effect of pH on vasopressin at 40° C.

The results of the above experiments suggested that the stability of a vasopressin formulation was affected by pH. At 25° C., the percent decrease in vasopressin after four weeks was lowest between pH 3.7 and pH 3.8 (FIG. 17). Within the range of pH 3.7 to pH 3.8, the level of impurities was lowest at pH 3.8 (FIG. 15). At 40° C., the percent decrease in vasopressin after four weeks was lowest between pH 3.6 and pH 3.8 (FIG. 18). Within the range of pH 3.6 to pH 3.8, the level of impurities was lowest at pH 3.8 (FIG. 16).

Example 11: Intra-Assay and Inter-Analysis Precision of Vasopressin pH Experiments The methods used to determine the % assay decrease and amount of impurities in the vasopressin solutions over time in EXAMPLE 10 had both intra-assay and inter-analyst precision.

Intra-assay precision was demonstrated by performing single injections of aliquots of a vasopressin formulation (n=6; Chemist 1) from a common lot of drug product and determining the assay and repeatability (% RSD; relative standard deviation). Inter-analyst precision was demonstrated by two different chemists testing the same lot of drug product; however, the chemists used different instruments, reagents, standard preparations, columns, and worked in different laboratories. The procedure included a common pooling of 20 vials of vasopressin, which were assayed by the two chemists using different HPLC systems and different HPLC columns. The vasopressin assay results (units/mL) and repeatability (% RSD for n=6) were recorded and are reported in the TABLE 44 below.

TABLE 44

Precision of Vasopressin Results.

| Sample | Chemist 1 (units/mL) | Chemist 2 (units/mL) |
| --- | --- | --- |
| 1 | 19.74 | 19.65 |
| 2 | 19.76 | 19.66 |
| 3 | 19.77 | 19.66 |
| 4 | 19.75 | 19.72 |
| 5 | 19.97 | 19.73 |
| 6 | 19.65 | 19.73 |
| Mean | 19.8 | 19.7 |
| % RSD (≤2.0%) | 0.5% | 0.2% |

% Difference = 0.5% (acceptance criteria: ≤3.0%)

$$\% \text{ Difference} = \frac{(\text{Chemist } 1_{Mean} - \text{Chemist } 2_{mean})}{(\text{Chemist } 1_{Mean} + \text{Chemist } 2_{Mean})} \times 200$$

The intra-assay repeatability met the acceptance criteria (% RSD≤2.0%) with values of 0.5% and 0.2%. The inter-analyst repeatability also met the acceptance criteria (% difference≤3.0%) with a difference of 0.5%.

Example 12: Effect of Citrate Versus Acetate Buffer on Vasopressin Formulations

To test the effect of citrate and acetate buffer on vasopressin formulations, a total of twelve solutions of 20 Units/mL vasopressin were prepared in 1 mM citrate buffer, 10 mM citrate buffer, 1 mM acetate buffer, and 10 mM acetate buffer. All of the solutions were prepared in triplicate. Each solution was adjusted to pH 3.5 with hydrochloric acid.

The vasopressin formulations were stored at 60° C. for 7 days, and the assay (% label claim; vasopressin remaining) and % total impurities after 7 days were analyzed by HPLC using the procedure and experimental conditions described in EXAMPLE 1.

The assay (% label claim; vasopressin remaining) and % total impurities for each of the Vasopressin Buffered Formulations are reported in the TABLES 45 and 46 below.

TABLE 45

Assay (% label claim; vasopressin remaining) in the vasopressin formulations after storage at 60° C. for 7 days.

| Buffer | Sample 1 | 2 | 3 | Average |
| --- | --- | --- | --- | --- |
| 1 mM citrate buffer | 89.5% | 89.7% | 90.6% | 89.9% |
| 10 mM citrate buffer | 84.1% | 84.4% | 84.5% | 84.3% |
| 1 mM acetate buffer | 90.5% | 91.1% | 91.9% | 91.2% |
| 10 mM acetate buffer | 90.9% | 90.9% | 92.4% | 91.4% |

TABLE 46

% Total Impurities in the vasopressin formulations after storage at 60° C. for 7 days.

| Buffer | Sample 1 | 2 | 3 | Average |
| --- | --- | --- | --- | --- |
| 1 mM citrate buffer | 3.4% | 3.5% | 2.5% | 3.1% |
| 10 mM citrate buffer | 9.5% | 9.0% | 9.4% | 9.3% |
| 1 mM acetate buffer | 3.3% | 2.8% | 3.2% | 3.1% |
| 10 mM acetate buffer | 2.9% | 2.6% | 3.1% | 2.9% |

The data indicated that the vasopressin assay in the vasopressin formulations with citrate buffer was lower than in the vasopressin formulations with acetate buffer. For example, at 10 mM of either citrate or acetate buffer, the average vasopressin assay was 91.4% in acetate buffer, but was 84.3% in citrate buffer. The data also indicated that % total impurities in the vasopressin formulations with citrate buffer were higher than in the vasopressin formulations with acetate buffer. For example, at 10 mM of either citrate or acetate buffer, the average % total impurities was 2.9% in acetate buffer, but was 9.3% in citrate buffer.

Further, as the citrate buffer concentration increased, the vasopressin assay further decreased (from an average of 89.9% to 84.3%), and the % total impurities increased (from an average of 3.1% to 9.3%). This effect was not observed in the vasopressin formulations with acetate buffer, where the average and % total impurities stayed fairly constant.

Example 13: Multi-Dose Vasopressin Formulation

A multi-dose formulation (10 mL) for vasopressin that can be used in the clinic is detailed in TABLE 47 below:

TABLE 47

Drug Product Description

| Vasopressin, USP | Active Ingredient | 20 Units (~0.04 mg) |
| --- | --- | --- |
| Dosage Form | Injection | — |
| Route of Administration | Intravenous | — |
| Description | Clear colorless to practically colorless solution supplied in a 10 mL clear glass vial with flip-off cap | |

The composition of a 10 mL formulation of vasopressin is provided below.

TABLE 48

Drug Product Composition

| Ingredient | Grade | Function | Batch Quantity | Unit Formula |
|---|---|---|---|---|
| Vasopressin, USP | USP | Active | 3,000,000 Units | 20 Units |
| Sodium Acetate Trihydrate | USP | Buffer | 214.2 g | 1.36 mg |
| Sodium Hydroxide | NF | pH Adjustor | 40 g | QS to pH 3.8 |
| Hydrochloric Acid | NF/EP | pH Adjustor | 237.9 g | QS to pH 3.8 |
| Chlorobutanol | NF | Preservative | 0.8274 kg | 5 mg |
| Water for Injection | USP | Solvent | QS | QS to 1 mL |
| Nitrogen | NF | Processing Aid | — | — |

The 10 mL vasopressin formulation was compared to the guidelines for inactive ingredients provided by the Food and Drug Administration (FDA). The results are shown in TABLE 49 below.

TABLE 49

| Ingredient | Vasopressin 10 mL Formulation (mg/mL) | Concentration (% w/v) | Inactive Ingredients Guideline Acceptable Level |
|---|---|---|---|
| Sodium Acetate Trihydrate | 1.36 | 0.136% | IV (infusion); Injection 0.16% |
| Sodium Hydroxide | QS to pH 3.8 | QS to pH 3.8 | N/A |
| Hydrochloric Acid | QS to pH 3.8 | QS to pH 3.8 | N/A |
| Chlorobutanol | 5 mg | 0.5% | IV (Infusion); Injection 1% |
| Water for Injection | QS to 1 mL | QS to target volume | N/A |

Example 14: Alternative Vasopressin Formulation for Clinical Use

A 1 mL dosage of vasopressin was prepared. A description of the formulation is shown in TABLE 50 below.

TABLE 50

Drug Product Description

| Vasopressin, USP | Active Ingredient | 20 Units/mL (~0.04 mg) |
|---|---|---|
| Dosage Form | Injection | — |
| Route of Administration | Intravenous | — |
| Vasopressin, USP | Active Ingredient | 20 Units/mL (~0.04 mg) |
| Description | Clear colorless to practically colorless solution supplied in a 3 mL vial with flip-off cap | — |

The drug composition of the formulation is provided in TABLE 51.

TABLE 51

Drug Product Composition

| Ingredient | Function | Quantity (mg/mL) |
|---|---|---|
| Vasopressin, USP | Active | 20 Units |
| Sodium Acetate Trihydrate, USP | Buffer | 1.36 |
| Sodium Hydroxide NF/EP | pH Adjustor | QS for pH adjustment to pH 3.8 |
| Hydrochloric Acid, NF/EP | pH Adjustor | QS for pH adjustment to pH 3.8 |
| Water for Injection | Solvent | QS to 1 mL |

The 1 mL vasopressin formulation was compared to the guidelines for inactive ingredients provided by the Food and Drug Administration (FDA). The results are shown in TABLE 52 below.

TABLE 52

| Ingredient | Vasopressin 1 mL Formulation (mg/mL) | Concentration (% w/v) | Inactive Ingredients Guideline Acceptable Level |
|---|---|---|---|
| Sodium Acetate Trihydrate | 1.36 | 0.136% | 0.16% |
| Sodium Hydroxide | QS to pH 3.8 | QS to pH 3.8 | 8% |
| Hydrochloric Acid | QS to pH 3.8 | QS to pH 3.8 | 10% |
| Water for Injection | QS to 1 mL | QS to target volume | N/A |

Example 15: 15-Month Stability Data for Vasopressin Formulations

The drug product detailed in TABLE 51 was tested for stability over a 15-month period. Three different lots (X, Y, and Z) of the vasopressin drug formulation were stored at 25° C. for 15 months in an upright or inverted position. At 0, 1, 2, 3, 6, 9, 12, 13, 14, and 15 months, the amount of vasopressin (AVP), % label claim (LC), amount of various impurities, and pH was measured. The vasopressin and impurity amounts were determined using the HPLC method described above in EXAMPLE 1. The results of the stability experiment are shown in TABLES 53-54 below.

TABLE 53

Inverted Storage of Vasopressin Formulations at 25° C.

| Lot | Month | AVP (U/mL) | % LC | Gly9 (%) | Glu4 (%) | D-Asn (%) | Asp5 (%) | Dimer (%) | Acetyl (%) | UI-0.81-0.86 (%) |
|---|---|---|---|---|---|---|---|---|---|---|
| X | 0 | 19.6 | 97.9 | | | | | | 0.3 | 0.4 |
| Y | 0 | 19.7 | 98.6 | | | | | | 0.3 | 0.4 |
| Z | 0 | 19.9 | 99.3 | 0.1 | | | | | 0.5 | |
| X | 1 | 19.6 | 98.1 | 0.2 | 0.2 | 0.1 | | | 0.4 | 0.4 |
| Y | 1 | 19.6 | 97.9 | 0.2 | 0.2 | 0.1 | | | 0.4 | 0.4 |

TABLE 53-continued

Inverted Storage of Vasopressin Formulations at 25° C.

| Lot | Month | AVP (U/mL) | % LC | Gly9 (%) | Glu4 (%) | D-Asn (%) | Asp5 (%) | Dimer (%) | Acetyl (%) | UI-0.81-0.86 (%) |
|---|---|---|---|---|---|---|---|---|---|---|
| Z | 1 | 19.8 | 99 | 0.2 | 0.2 | | | | 0.6 | 0.1 |
| X | 2 | 19.6 | 98.1 | 0.3 | 0.3 | 0.1 | | | 0.3 | 0.4 |
| Y | 2 | 19.5 | 97.5 | 0.2 | 0.3 | 0.1 | | | 0.3 | 0.4 |
| Z | 2 | 19.8 | 99 | 0.3 | 0.4 | | | | 0.5 | |
| X | 3 | 19.6 | 97.8 | 0.4 | 0.5 | 0.1 | 0.1 | | 0.3 | 0.4 |
| Y | 3 | 19.5 | 97.4 | 0.4 | 0.4 | 0.1 | | | 0.3 | 0.4 |
| Z | 3 | 19.7 | 98.6 | 0.4 | 0.4 | | | | 0.5 | |
| X | 6 | 19.3 | 96.5 | 0.7 | 0.8 | 0.1 | 0.2 | | 0.3 | 0.4 |
| Y | 6 | 19.2 | 95.9 | 0.6 | 0.7 | 0.1 | 0.1 | 0.1 | 0.3 | 0.4 |
| Z | 6 | 19.6 | 98 | 0.6 | 0.7 | | 0.1 | | 0.5 | |
| X | 9 | 19 | 95 | 1.0 | 1.0 | | 0.2 | | 0.3 | 0.4 |
| Y | 9 | 18.9 | 94.5 | 0.8 | 1.0 | | 0.2 | | 0.3 | 0.4 |
| Z | 9 | 19.2 | 96 | 1.0 | 1.1 | | 0.2 | | 0.5 | |
| X | 12 | 18.7 | 93.5 | 1.4 | 1.5 | 0.1 | 0.3 | | 0.3 | 0.4 |
| Y | 12 | 18.6 | 93 | 1.1 | 1.2 | 0.2 | 0.2 | | 0.3 | 0.4 |
| Z | 12 | 18.9 | 94.5 | 1.2 | 1.3 | | 0.3 | | 0.5 | |
| X | 13 | 18.6 | 93 | 1.5 | 1.6 | 0.2 | 0.3 | | 0.4 | 0.4 |
| Y | 13 | 18.5 | 92.5 | 1.2 | 1.3 | 0.2 | 0.3 | | 0.3 | 0.4 |
| Z | 13 | 19 | 95 | 1.3 | 1.5 | 0.1 | 0.3 | | 0.5 | 0.1 |
| X | 14 | 18.6 | 93 | 1.5 | 1.7 | 0.1 | 0.3 | | 0.3 | 0.5 |
| Y | 14 | 18.5 | 92.5 | 1.2 | 1.4 | 0.1 | 0.3 | | 0.3 | 0.5 |
| Z | 14 | 18.9 | 94.5 | 1.3 | 1.6 | | 0.3 | | 0.5 | 0.2 |
| X | 15 | 18.5 | 92.5 | 1.6 | 1.8 | 0.1 | 0.4 | | 0.3 | 0.4 |
| Y | 15 | 18.4 | 92 | 1.3 | 1.5 | 0.1 | 0.3 | | 0.3 | 0.4 |
| Z | 15 | 18.8 | 94 | 1.5 | 1.6 | | 0.3 | | 0.5 | |

| Lot | Month | UI 0.97-0.99 (%) | UI-1.02-1.03 (%) | UI-1.72-1.76 (%) | UI-1.81-1.89 (%) | UI-1.90-1.96 (%) | UI-2.05-2.07 (%) | UI-2.09-2.10 (%) | Total Impurities | pH |
|---|---|---|---|---|---|---|---|---|---|---|
| X | 0 | | 0.3 | | | | | | 1.0 | 3.8 |
| Y | 0 | | 0.3 | | | | | | 1.1 | 3.8 |
| Z | 0 | | 0.2 | | | | | | 0.8 | 3.8 |
| X | 1 | | 0.3 | | | | | | 1.6 | 3.8 |
| Y | 1 | | 0.3 | | | | | | 1.6 | 3.9 |
| Z | 1 | | 0.2 | | | | | | 1.4 | 3.8 |
| X | 2 | | 0.3 | | | | | | 1.7 | 3.7 |
| Y | 2 | | 0.3 | | | | | | 1.6 | 3.8 |
| Z | 2 | | 0.2 | | | | | | 1.3 | 3.8 |
| X | 3 | | 0.4 | | | | | | 2.2 | |
| Y | 3 | | 0.4 | | | | | | 2.0 | 3.8 |
| Z | 3 | | 0.3 | | | | | | 1.6 | |
| X | 6 | | 0.4 | | | | | | 2.9 | 3.8 |
| Y | 6 | | 0.4 | | | | | | 2.5 | 3.9 |
| Z | 6 | | 0.2 | | | | | | 2.3 | 3.9 |
| X | 9 | | 0.4 | | 0.1 | | | | 3.6 | |
| Y | 9 | | 0.4 | | 0.1 | | | | 3.1 | 3.9 |
| Z | 9 | | 0.3 | | | | | | 3.1 | 3.8 |
| X | 12 | | 0.5 | | 0.2 | | | | 4.8 | 3.8 |
| Y | 12 | | 0.5 | | 0.3 | 0.2 | | | 4.4 | 3.8 |
| Z | 12 | | 0.3 | | 0.3 | 0.1 | | | 4.0 | 3.8 |
| X | 13 | 0.1 | 0.4 | | 0.2 | 0.1 | | | 5.2 | 3.8 |
| Y | 13 | 0.1 | 0.5 | 0.1 | 0.4 | 0.2 | 0.2 | | 5.2 | 3.9 |
| Z | 13 | | 0.3 | 0.1 | 0.3 | 0.2 | 0.2 | | 4.9 | 3.8 |
| X | 14 | 0.1 | 0.4 | | 0.4 | 0.1 | 0.1 | | 5.5 | 3.8 |
| Y | 14 | 0.1 | 0.4 | | 0.5 | 0.2 | 0.2 | | 5.3 | 3.9 |
| Z | 14 | | 0.3 | | 0.4 | 0.2 | 0.2 | | 5.0 | 3.8 |
| X | 15 | 0.1 | 0.4 | | 0.3 | 0.2 | 0.2 | | 5.9 | 3.8 |
| Y | 15 | 0.1 | 0.4 | | 0.5 | 0.3 | 0.1 | | 5.3 | 3.9 |
| Z | 15 | | 0.3 | | 0.4 | 0.2 | 0.1 | | 4.9 | 3.9 |

TABLE 54

Upright Storage of Vasopressin Formulations at 25° C.

| Lot | Month | AVP (U/mL) | % LC | Gly9 (%) | Glu4 (%) | D-Asn (%) | Asp5 (%) | Dimer (%) | Acetyl (%) | UI-0.81-0.86 (%) |
|---|---|---|---|---|---|---|---|---|---|---|
| X | 0 | 19.6 | 97.9 | | | | | | 0.3 | 0.4 |
| Y | 0 | 19.7 | 98.6 | | | | | | 0.3 | 0.4 |
| Z | 0 | 19.9 | 99.3 | 0.1 | | | | | 0.5 | |
| X | 1 | 19.6 | 98 | 0.2 | 0.2 | 0.1 | | | 0.3 | 0.4 |
| Y | 1 | 19.5 | 97.7 | 0.2 | 0.2 | | | | 0.3 | 0.4 |

TABLE 54-continued

Upright Storage of Vasopressin Formulations at 25° C.

| Lot | Month | | | | | | | | |
|---|---|---|---|---|---|---|---|---|---|
| Z | 1 | 19.7 | 98.3 | 0.2 | 0.2 | | | 0.6 | |
| X | 2 | 19.6 | 98.2 | 0.3 | 0.3 | | | 0.3 | 0.4 |
| Y | 2 | 19.5 | 97.4 | 0.2 | 0.3 | 0.1 | | 0.4 | 0.4 |
| Z | 2 | 19.8 | 99 | 0.3 | 0.3 | | | 0.5 | |
| X | 3 | 19.5 | 97.6 | 0.4 | 0.4 | 0.1 | | 0.3 | 0.4 |
| Y | 3 | 19.5 | 97.5 | 0.4 | 0.4 | 0.1 | | | 0.4 |
| Z | 3 | 19.7 | 98.7 | 0.4 | 0.4 | | 0.1 | 0.5 | |
| X | 6 | 19.3 | 96.5 | 0.7 | 0.8 | 0.1 | 0.2 | 0.3 | 0.4 |
| Y | 6 | 19.2 | 96 | 0.5 | 0.7 | 0.1 | 0.1 | 0.3 | 0.4 |
| Z | 6 | 19.5 | 97.5 | 0.7 | 0.7 | | 0.2 | 0.5 | |
| X | 9 | 18.9 | 94.5 | 1.0 | 1.1 | | 0.2 | 0.3 | 0.4 |
| Y | 9 | 18.9 | 94.5 | 0.8 | 0.9 | | 0.2 | | 0.4 |
| Z | 9 | 19.2 | 96 | 0.9 | 1.0 | | 0.2 | 0.5 | |
| X | 12 | 18.6 | 93 | 1.4 | 1.5 | 0.1 | 0.3 | 0.3 | 0.4 |
| Y | 12 | 18.7 | 93.5 | 1.1 | 1.2 | 0.1 | 0.3 | 0.3 | 0.4 |
| Z | 12 | 18.9 | 94.5 | 1.3 | 1.4 | | 0.3 | 0.5 | |
| X | 13 | 18.4 | 92 | 1.5 | 1.6 | 0.2 | 0.3 | 0.3 | 0.4 |
| Y | 13 | 18.6 | 93 | 1.1 | 1.3 | 0.2 | 0.3 | 0.3 | 0.4 |
| Z | 13 | 18.8 | 94 | 1.3 | 1.5 | | 0.3 | 0.5 | 0.1 |
| X | 14 | 18.6 | 93 | 1.5 | 1.7 | 0.1 | 0.4 | 0.3 | 0.4 |
| Y | 14 | 18.5 | 92.5 | 1.2 | 1.4 | 0.1 | 0.3 | 0.3 | 0.5 |
| Z | 14 | 18.8 | 94 | 1.3 | 1.5 | | 0.3 | 0.5 | 0.1 |
| X | 15 | 18.4 | 92 | 1.6 | 1.8 | 0.1 | 0.4 | 0.3 | 0.4 |
| Y | 15 | 18.4 | 92 | 1.3 | 1.5 | 0.2 | 0.3 | 0.3 | 0.4 |
| Z | 15 | 18.6 | 93 | 1.5 | 1.6 | | 0.3 | 0.5 | |

| Lot | Month | UI 0.97-0.99 (%) | UI-1.02-1.03 (%) | UI-1.72-1.76 (%) | UI-1.81-1.89 (%) | UI-1.90-1.96 (%) | UI-2.05-2.07 (%) | UI-2.09-2.10 (%) | Total Impurities | pH |
|---|---|---|---|---|---|---|---|---|---|---|
| X | 0 | | 0.3 | | | | | | 1.0 | 3.8 |
| Y | 0 | | 0.3 | | | | | | 1.1 | 3.8 |
| Z | 0 | | 0.2 | | | | | | 0.8 | 3.8 |
| X | 1 | | 0.3 | | | | | | 1.6 | 3.8 |
| Y | 1 | | 0.3 | | | | | | 1.4 | 3.9 |
| Z | 1 | | 0.2 | | | | | | 1.2 | 3.8 |
| X | 2 | | 0.3 | | | | | | 1.6 | 3.7 |
| Y | 2 | | 0.3 | | | | | | 1.6 | 3.8 |
| Z | 2 | | 0.2 | | | | | | 1.3 | 3.8 |
| X | 3 | | 0.4 | | | | | | 2.1 | 3.7 |
| Y | 3 | | 0.4 | | | | | | 1.9 | 3.8 |
| Z | 3 | | 0.3 | | | | | | 1.7 | |
| X | 6 | | 0.4 | | | | | | 2.9 | 3.8 |
| Y | 6 | | 0.4 | | | | | | 2.5 | 3.9 |
| Z | 6 | | 0.3 | | | | | | 2.3 | 3.9 |
| X | 9 | | | | 0.2 | 0.1 | | | 3.7 | 3.8 |
| Y | 9 | | 0.4 | | 0.2 | | | | 3.1 | 3.9 |
| Z | 9 | | 0.3 | | | | | | 2.9 | 3.8 |
| X | 12 | | 0.5 | | 0.2 | 0.1 | | | 4.8 | 3.7 |
| Y | 12 | | 0.5 | | | 0.2 | | 0.2 | 4.6 | 3.9 |
| Z | 12 | | 0.4 | | 0.3 | 0.2 | | | 4.2 | 3.8 |
| X | 13 | 0.1 | 0.4 | | 0.3 | 0.1 | 0.1 | | 5.4 | 3.8 |
| Y | 13 | 0.1 | 0.4 | | 0.3 | 0.2 | | | 4.6 | 3.9 |
| Z | 13 | | 0.3 | | 0.4 | 0.2 | 0.1 | | 4.7 | 3.8 |
| X | 14 | 0.1 | 0.4 | | 0.3 | 0.1 | | | 5.4 | 3.8 |
| Y | 14 | | 0.4 | | 0.5 | 0.3 | 0.3 | | 5.4 | 3.9 |
| Z | 14 | | 0.3 | | 0.5 | 0.2 | 0.2 | | 5.0 | 3.8 |
| X | 15 | 0.1 | 0.4 | | 0.3 | 0.2 | | | 5.7 | 3.8 |
| Y | 15 | 0.1 | 0.4 | | 0.5 | 0.3 | 0.3 | | 5.4 | 3.9 |
| Z | 15 | | 0.2 | | 0.4 | 0.2 | 0.3 | | 5.1 | 3.9 |

The results from TABLES 53-54 indicate that stability of the vasopressin formulations was not significantly affected by either inverted or upright storage. The impurities detected included Gly9 (SEQ ID NO.: 2), Glu4 (SEQ ID NO.: 4), D-Asn (SEQ ID NO.: 10), Asp5 (SEQ ID NO.: 3), Acetyl-AVP (SEQ ID NO.: 7), vasopressin dimer, and several unidentified impurities (UI). The unidentified impurities are labeled with a range of relative retention times at which the impurities eluted from the column.

The results indicate that the pH remained fairly constant over the 15-month period, fluctuating between 3.8 and 3.9 throughout the 15 months. The total impurities did not increase over 5.9%, and the % LC of vasopressin did not decrease below 92%.

Figure 19:
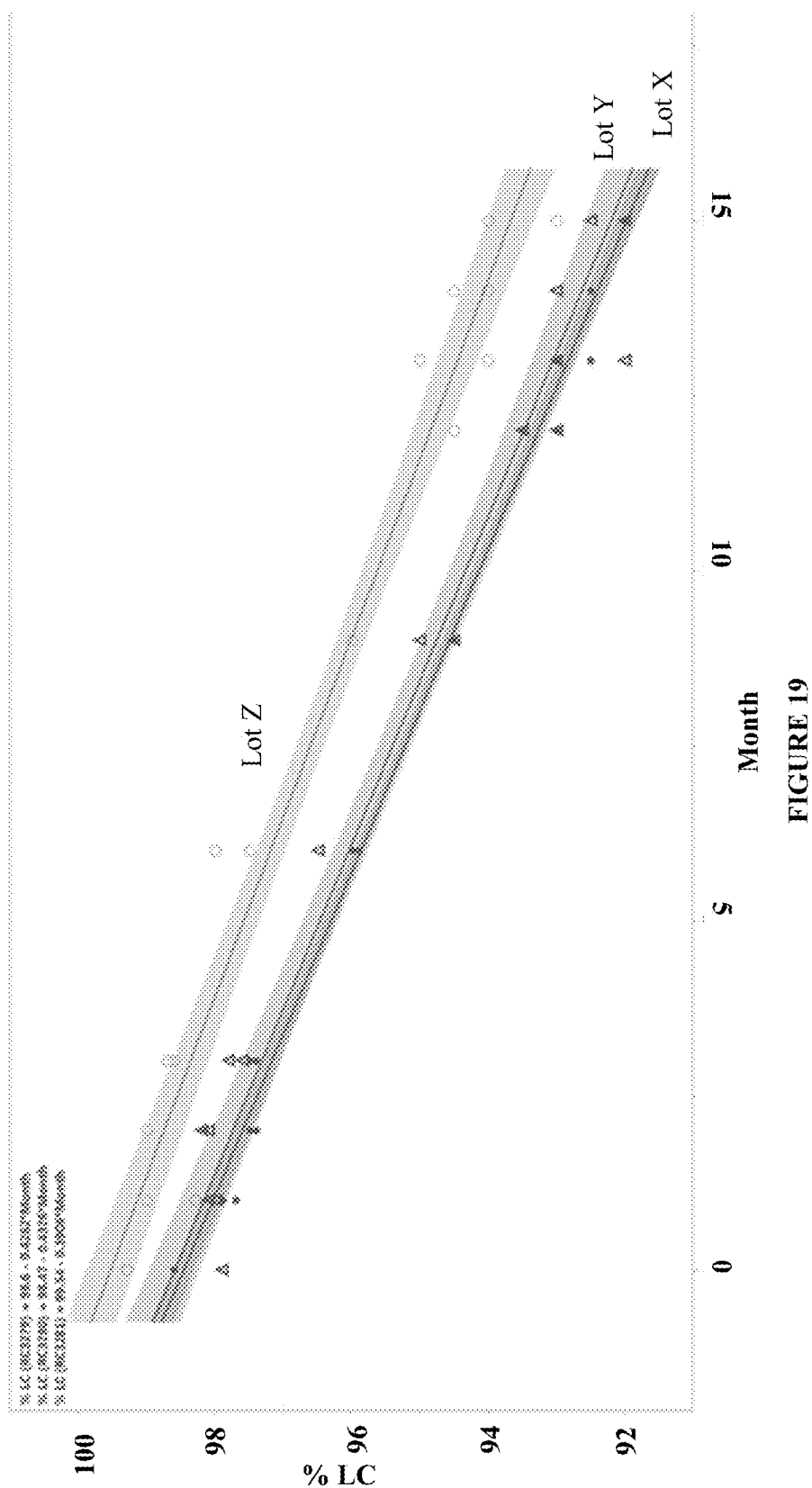
FIG. 19 depicts the % LC of vasopressin formulations stored for 15 months at 25° C.

FIG. 19 shows a graph depicting the % LC over the 15-month study period for the results provided in TABLES 53-54. The starting amounts of vasopressin were 97.9% LC for lot X, 98.6% LC for lot Y, and 99.3% LC for lot Z. The results indicate that the % LC of vasopressin decreased over the 15-month study period, but did not decrease below 92% LC.

The formula for the trend line of lot X was:

% $LC = 98.6 - 0.4262(\text{month})$

The formula for the trend line of lot Y was:

% $LC = 98.47 - 0.4326(\text{month})$

The formula for the trend line of lot Z was:

% $LC = 99.54 - 0.3906(\text{month})$

Example 16: Vasopressin Formulation for Bottle or Intravenous Drip-Bag

The following formulations can be used without initial vasopressin dilution in drip-bags for intravenous therapy.

TABLE 55

Formulation A (40 IU/100 mL) (10 mM Buffer)

| Ingredient | Concentration |
| --- | --- |
| Vasopressin (IU) | 0.4 |
| Sodium chloride (mg) | 8.7 |
| Acetic acid (mg) | 0.546 |
| Sodium Acetate Trihydrate (mg) | 0.12 |
| Hydrochloric acid QS for | pH adjustment |
| Sodium hydroxide QS for | pH adjustment |
| Water for injection QS to (mL) | 1 |

TABLE 56

Formulation B (60 IU/100 mL) (10 mM Buffer)

| Ingredient | Concentration |
| --- | --- |
| Vasopressin (IU) | 0.6 |
| Sodium chloride (mg) | 8.7 |
| Acetic acid (mg) | 0.546 |
| Sodium Acetate Trihydrate (mg) | 0.12 |
| Hydrochloric acid QS for | pH adjustment |
| Sodium hydroxide QS for | pH adjustment |
| Water for injection QS to (mL) | 1 |

TABLE 57

Formulation C (40 IU/100 mL) (10 mM Buffer)

| Ingredient | Concentration |
| --- | --- |
| Vasopressin (IU) | 0.4 |
| Dextrose Anhydrous (mg) | 50 |
| Acetic acid (mg) | 0.546 |
| Sodium Acetate Trihydrate (mg) | 0.12 |
| Hydrochloric acid QS for | pH adjustment |
| Sodium hydroxide QS for | pH adjustment |
| Water for injection QS to (mL) | 1 |

TABLE 58

Formulation D (60 IU/100 mL) (10 mM Buffer)

| Ingredient | Concentration |
| --- | --- |
| Vasopressin (IU) | 0.6 |
| Dextrose Anhydrous (mg) | 50 |
| Acetic acid (mg) | 0.546 |
| Sodium Acetate Trihydrate (mg) | 0.12 |
| Hydrochloric acid QS for | pH adjustment |
| Sodium hydroxide QS for | pH adjustment |
| Water for injection QS to (mL) | 1 |

TABLE 59

Formulation E (40 IU/100 mL) (1 mM Buffer)

| Ingredient | Concentration |
| --- | --- |
| Vasopressin (IU) | 0.4 |
| Sodium chloride (mg) | 8.7 |
| Acetic acid (mg) | 0.0546 |
| Sodium Acetate Trihydrate (mg) | 0.012 |
| Hydrochloric acid QS for | pH adjustment |
| Sodium hydroxide QS for | pH adjustment |
| Water for injection QS to (mL) | 1 |

TABLE 60

Formulation F (60 IU/100 mL) (1 mM Buffer)

| Ingredient | Concentration |
| --- | --- |
| Vasopressin (IU) | 0.6 |
| Sodium chloride (mg) | 8.7 |
| Acetic acid (mg) | 0.0546 |
| Sodium Acetate Trihydrate (mg) | 0.012 |
| Hydrochloric acid QS for | pH adjustment |
| Sodium hydroxide QS for | pH adjustment |
| Water for injection QS to (mL) | 1 |

TABLE 61

Formulation G (40 IU/100 mL) (1 mM Buffer)

| Ingredient | Concentration |
| --- | --- |
| Vasopressin (IU) | 0.4 |
| Dextrose Anhydrous (mg) | 50 |
| Acetic acid (mg) | 0.0546 |
| Sodium Acetate Trihydrate (mg) | 0.012 |
| Hydrochloric acid QS for | pH adjustment |
| Sodium hydroxide QS for | pH adjustment |
| Water for injection QS to (mL) | 1 |

TABLE 62

Formulation H (60 IU/100 mL) (1 mM Buffer)

| Ingredient | Concentration |
|---|---|
| Vasopressin (IU) | 0.6 |
| Dextrose Anhydrous (mg) | 50 |
| Acetic acid (mg) | 0.0546 |
| Sodium Acetate Trihydrate (mg) | 0.012 |
| Hydrochloric acid QS for | pH adjustment |
| Sodium hydroxide QS for | pH adjustment |
| Water for injection QS to (mL) | 1 |

TABLE 63

Formulation 9 (60 IU/100 mL) (1 mM Buffer)

| Ingredient | Concentration |
|---|---|
| Vasopressin (IU) | 0.4 |
| Dextrose Anhydrous (mg) | 45 |
| Sodium Chloride (mg) | 0.9 |
| Acetic acid (mg) | 0.0546 |
| Sodium Acetate Trihydrate (mg) | 0.012 |
| Hydrochloric acid QS for | pH adjustment |
| Sodium hydroxide QS for | pH adjustment |

Example 17: Impurity Measurement for Vasopressin Formulation for Bottle or Intravenous Drip-Bag Gradient HPLC was used to determine the concentration of vasopressin and associated impurities in vasopressin formulations similar to those outlined in TABLES 55-63 above. Vasopressin was detected in the eluent using UV absorbance at a short wavelength. The concentration of vasopressin in the sample was determined by the external standard method, where the peak area of vasopressin in sample injections was compared to the peak area of a vasopressin reference standard in a solution of known concentration. The concentrations of related peptide impurities in the sample were also determined using the external standard method, using the vasopressin reference standard peak area and a unit relative response factor. An impurities marker solution was used to determine the relative retention times of identified related peptides at the time of analysis.

The chromatographic conditions used for the analysis are shown in TABLE 64 below:

TABLE 64

| Column | Phenomenex Kinetex XB-C18, 2.6 µm, 100 Å pore, 4.6 × 150 mm, Part No. 00F-4496-E0 |
|---|---|
| Column Temperature | 35° C. |
| Flow Rate | 1.0 mL/min |
| Detector | VWD: Signal at 215 nm |
| Injection Volume | 500 µL |
| Run time | 55 minutes |
| Auto sampler Vials | Amber glass vial |
| Auto Sampler Temperature | 10° C. |

| Pump (gradient) | Time (min) | % A | % B | Flow |
|---|---|---|---|---|
| | 0 | 90 | 10 | 1.0 |
| | 40 | 50 | 50 | 1.0 |
| | 45 | 50 | 50 | 1.0 |
| | 46 | 90 | 10 | 1.0 |
| | 55 | 90 | 10 | 1.0 |

Diluent A was 0.25% v/v acetic acid, which was prepared by pipetting 2.5 mL of glacial acetic acid into a 1 L volumetric flask containing 500 mL of water. The volume was diluted with water and mixed well.

Diluent B was prepared by weighing and transferring about 3 g of sodium chloride into a 1 L volumetric flask and then adding 2.5 mL of glacial acetic acid. The solution was diluted to volume with water and mixed well.

Phosphate buffer at pH 3.0 was used for mobile phase A. The buffer was prepared by weighing approximately 15.6 g of sodium phosphate monobasic monohydrate into a beaker. 1000 mL of water was added, and mixed well. The pH was adjusted to 3.0 with phosphoric acid. The buffer was filtered through a 0.45 µm membrane filter under vacuum, and the volume was adjusted as necessary.

An acetonitrile:water (50:50) solution was used for mobile phase B. To prepare mobile phase B, 500 mL of acetonitrile was mixed with 500 mL of water.

The stock standard solution was prepared at 20 units/mL of vasopressin. A solution of vasopressin in diluent was prepared at a concentration of about 20 units/mL. The stock standard solution was prepared by quantitatively transferring the entire contents of 5 vials of USP Vasopressin RS with diluent A to the same 250-mL volumetric flask. The solution was diluted to volume with diluent A and mixed well. 10 mL aliquots of the standard solution was transferred into separate polypropylene tubes. The aliquots were stored at 2-8° C. The stock standard solution was stable for 6 months from the date of preparation when stored in individual polypropylene tubes at 2-8° C.

The working standard solution contained about 0.5 units/mL of vasopressin. Aliquots of the stock standard solution were allowed to warm to room temperature and then mixed well. 2.5 mL of the stock standard solution was transferred into a 100 mL volumetric flask and diluted to volume with Diluent B, and the resultant mixture was denoted as the Working Standard Solution.

The stock standard solution and working standard solution can also be prepared from a single vasopressin vial in the following manner.

One vial of vasopressin with diluent A can be quantitatively transferred to a 50-mL volumetric flask. The solution can be dissolved in and diluted to volume with diluent A and mixed well, and denoted as the stock standard solution. To prepare the working standard solution, 2.5 mL of the stock standard solution was diluted to 100 mL with diluent B and mixed well.

The working standard solution was stable for at least 72 hours when stored in refrigerator or in autosampler vial at 10° C.

The intermediate standard solution was prepared by pipetting 1 mL of the working standard solution into a 50 mL volumetric flask. The solution was diluted to volume with diluent B and mixed well.

The sensitivity solution (0.1% of 0.4 units/mL vasopressin formulation) was prepared by pipetting 2 mL of the intermediate standard solution into a 50 mL volumetric flask. The solution was diluted to the volume with diluent B and mixed well. The sensitivity solution was stable for at least 72 hours when stored in the refrigerator.

To prepare the impurities marker solution, a 0.05% v/v acetic acid solution was prepared by pipetting 200 mL of a 0.25% v/v acetic acid solution into a 1 L volumetric flask. The solution was diluted to the desired volume with water and mixed well.

To prepare the vasopressin impurity stock solutions, the a solution of each impurity as shown below was prepared in a 25 mL volumetric flask and diluted with 0.05% v/v acetic acid to a concentration suitable for HPLC injection.

Gly-9 AVP: 0.09 mg/mL
Glu-4 AVP: 0.08 mg/mL
Asp-5 AVP: 0.1 mg/mL
D-Asn AVP: 0.08 mg/mL
Dimer AVP: 0.07 mg/mL
Acetyl AVP: 0.08 mg/mL To prepare the MAA/H-IBA (Methacrylic Acid/α-Hydroxy-isobutyric acid) stock solution, a stock solution containing approximately 0.3 mg/mL H-IBA and 0.01 mg/mL in 0.05% v/v acetic acid was made in a 50 mL volumetric flask.

To prepare the chlorobutanol diluent, about one gram of hydrous chlorobutanol was added to 500 mL of water. Subsequently, 0.25 mL of acetic acid was added and the solution was stirred to dissolve the chlorobutanol.

To prepare the stock impurity marker solutions, 6.5 mg of vasopressin powder was added to a 500 mL volumetric flask. To the flask, the following quantities of the above stock solutions were added:

Gly-9 AVP: 20.0 mL
Glu-4 AVP: 20.0 mL
Asp-5 AVP: 10.0 mL
D-Asn AVP: 10.0 mL
Dimer AVP: 10.0 mL
Acetyl AVP: 20.0 mL
H-IBA/MAA: 30.0 mL The solutions were diluted to volume with the chlorobutanol diluent. The solutions were aliquoted into individual crimp top vials and stored at 2-8° C. The solutions, stored at 2-8° C., were suitable for use as long as the chromatographic peaks could be identified based on comparison to the reference chromatogram.

At time of use the solutions were removed from refrigerated (2-8° C.) storage and allowed to reach room temperature.

The vasopressin stock impurity marker solution was stable for at least 120 hours when stored in autosampler vials at room temperature.

The impurity marker solution were prepared by diluting 1 mL of the stock impurity marker solution to 50 mL with diluent B, and mixed well. The vasopressin impurity marker solution was stable for at least 72 hours when stored in the refrigerator.

To begin the analysis, the HPLC system was allowed to equilibrate for at least 30 minutes using mobile phase B, followed by time 0 min gradient conditions until a stable baseline was achieved.

Figure 20:
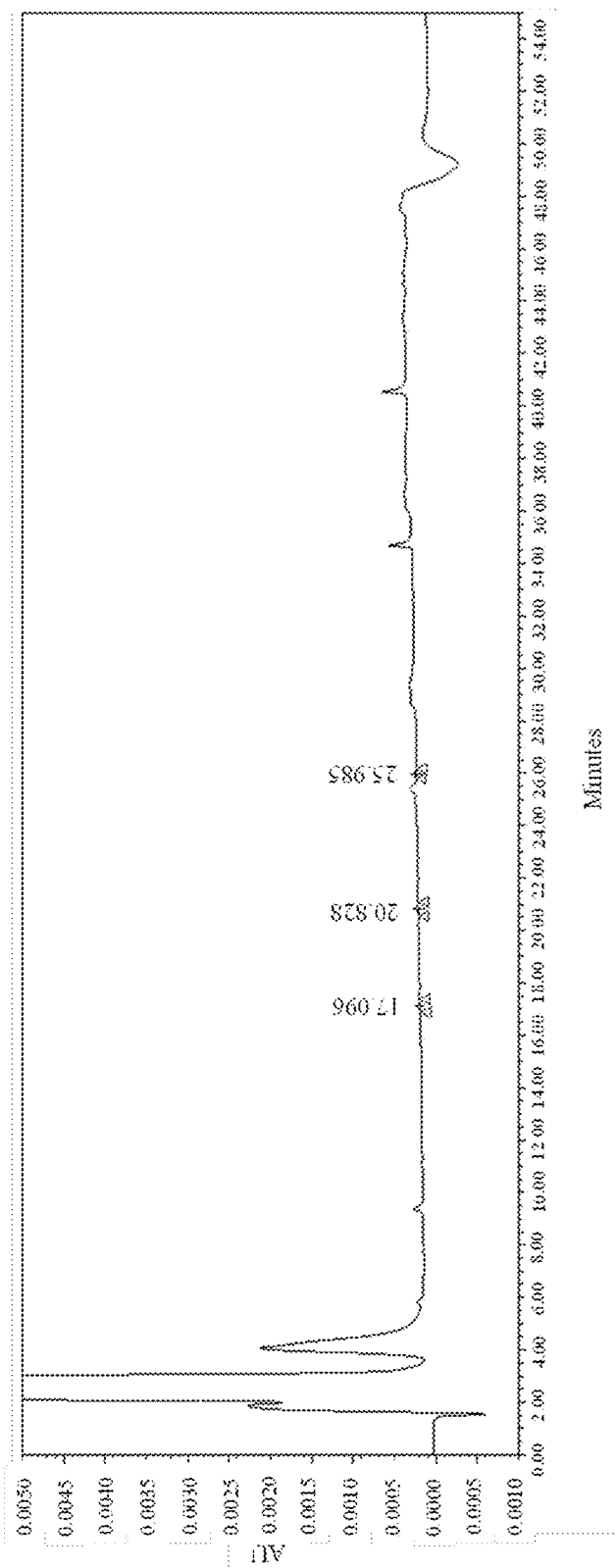
FIG. 20 is a chromatogram of a diluent used in a vasopressin assay.

Diluent B was injected at the beginning of the run, and had no peaks that interfered with vasopressin as shown in FIG. 20.

Figure 21:
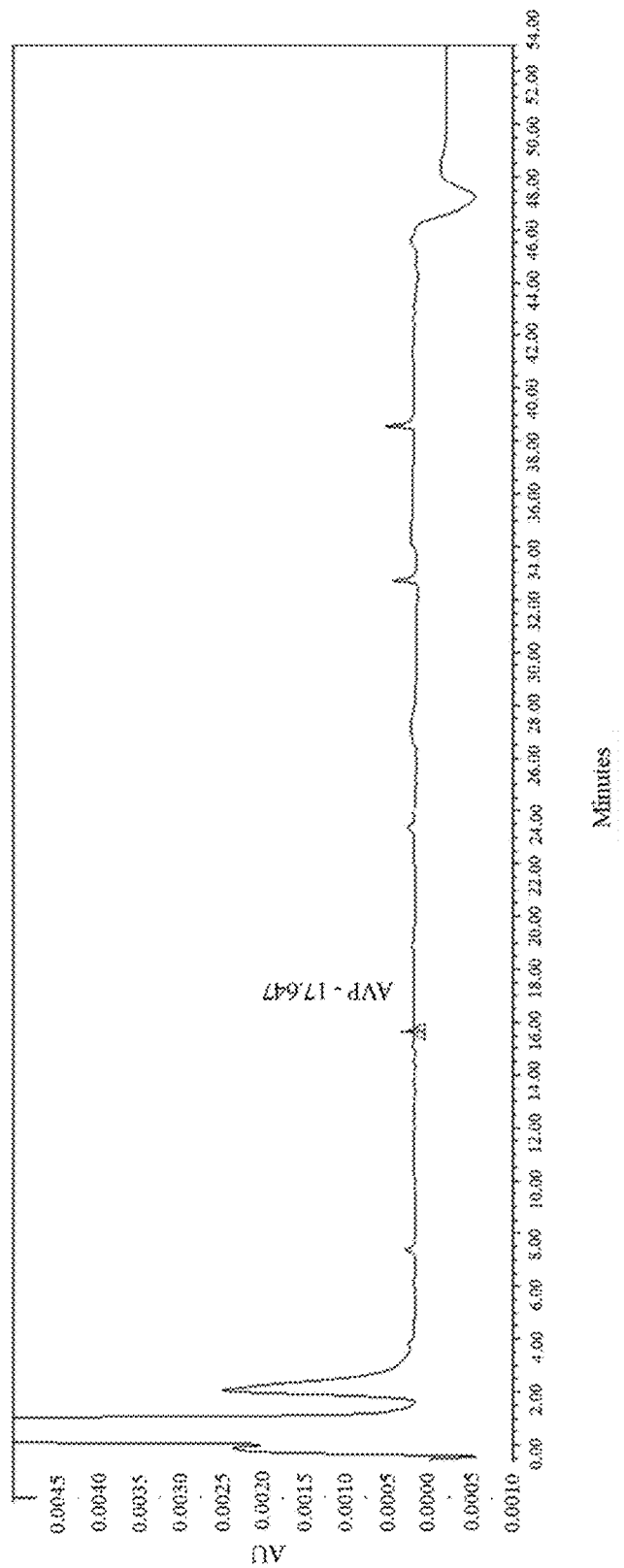
FIG. 21 is a chromatogram of a sensitivity solution used in a vasopressin assay.

A single injection of the sensitivity solution was performed, wherein the signal-to-noise ratio of the vasopressin was greater than or equal to ten as shown in FIG. 21.

Figure 22:
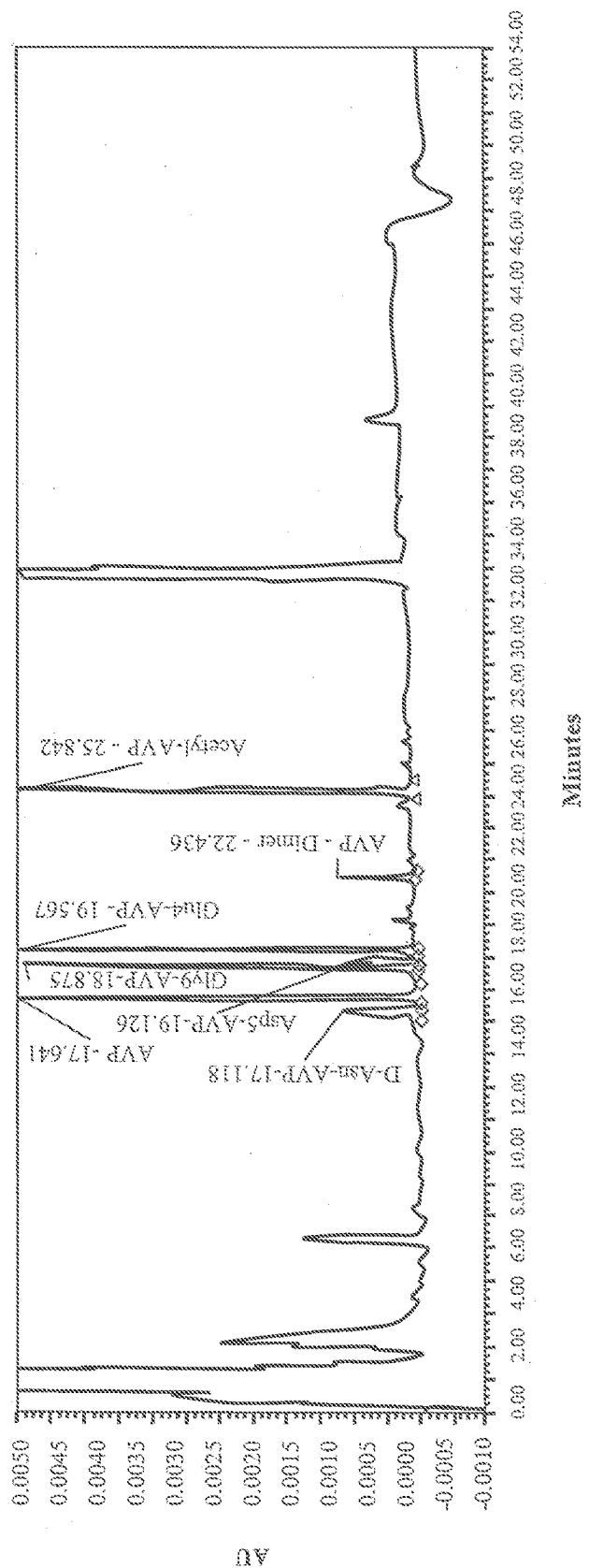
FIG. 22 is a chromatogram of an impurity marker solution used in a vasopressin assay.
Figure 23:
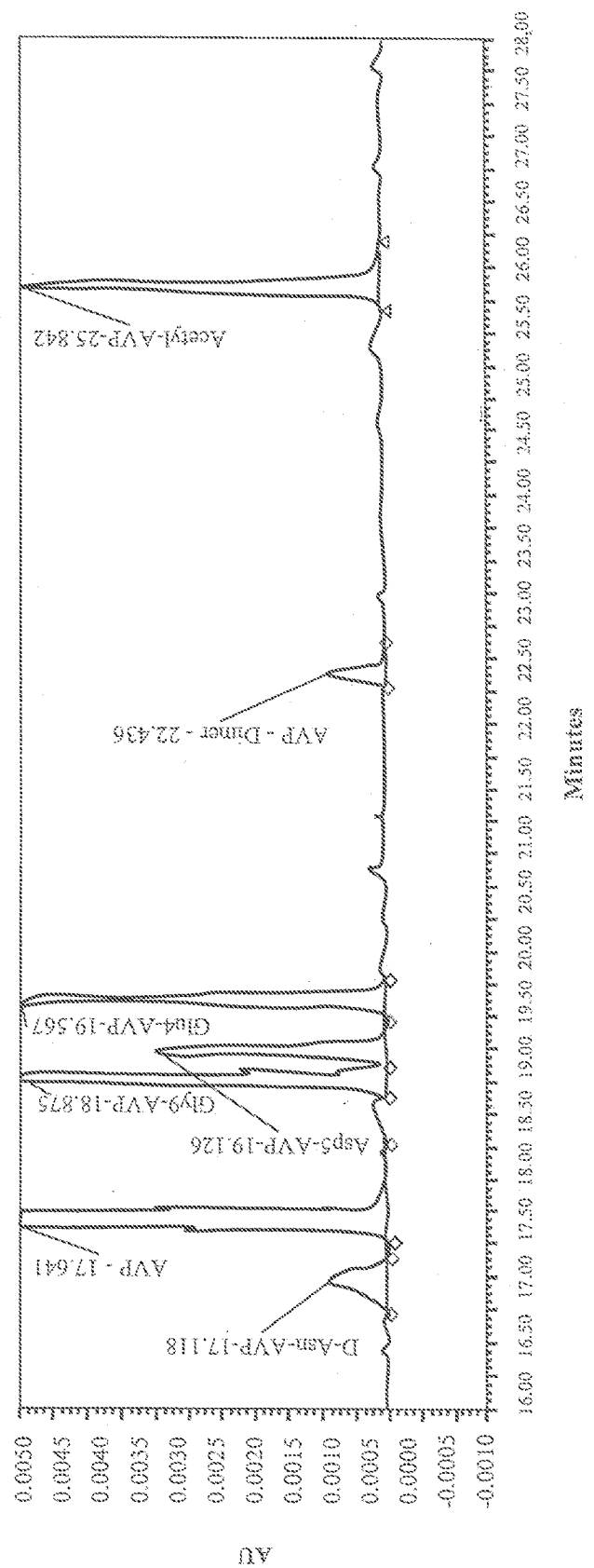
FIG. 23 is a zoomed-in depiction of the chromatogram in FIG. 22.

A single injection of the impurities marker solution was then made. The labeled impurities in the reference chromatogram were identified in the chromatogram of the marker solution based on their elution order and approximate retention times shown in FIG. 22 and FIG. 23. FIG. 23 is a zoomed-in chromatograph of FIG. 22 showing the peaks that eluted between 16 and 28 minutes. The nomenclature, structure, and approximate retention times for individual identified impurities are detailed in TABLE 3.

Figure 24:
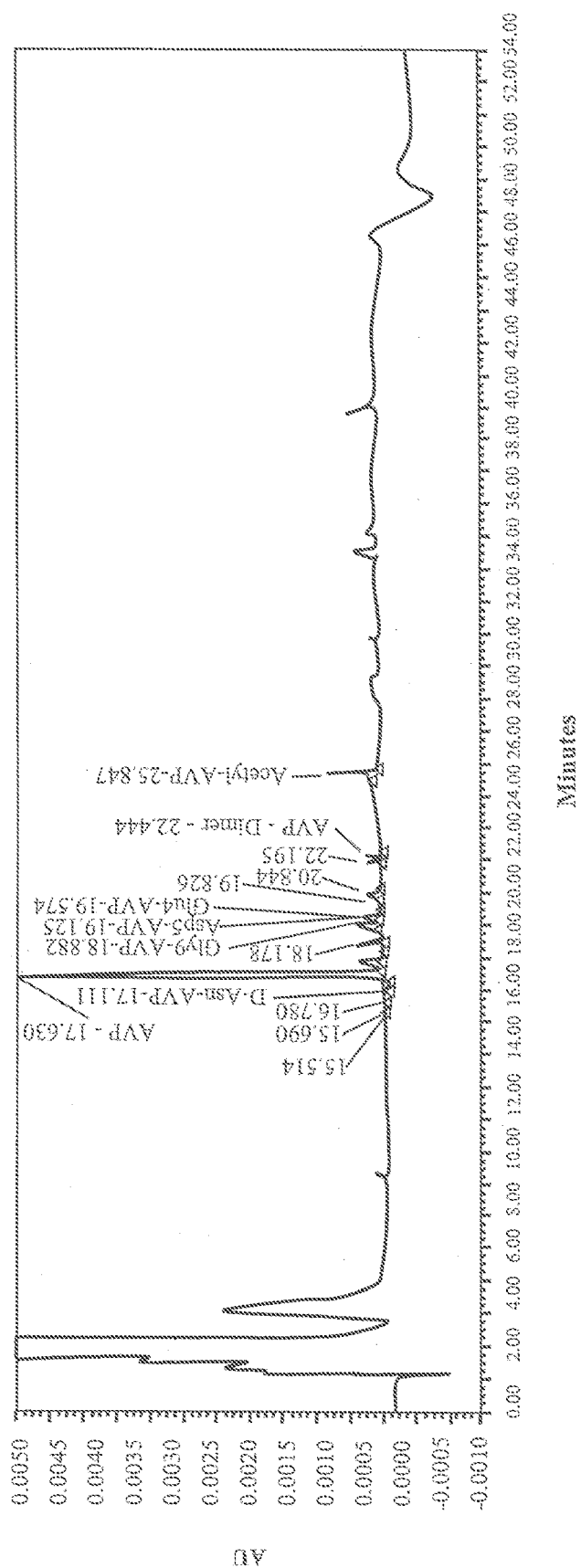
FIG. 24 is a chromatogram of a working solution.

A single injection of the working standard solution was made to ensure that the tailing factor of the vasopressin peak was less than or equal to about 2.0 as shown in FIG. 24.

A total of five replicate injections of the working standard solution were made to ensure that the relative standard deviation (% RSD) of the five replicate vasopressin peak areas was not more than 2.0%.

Figure 25:
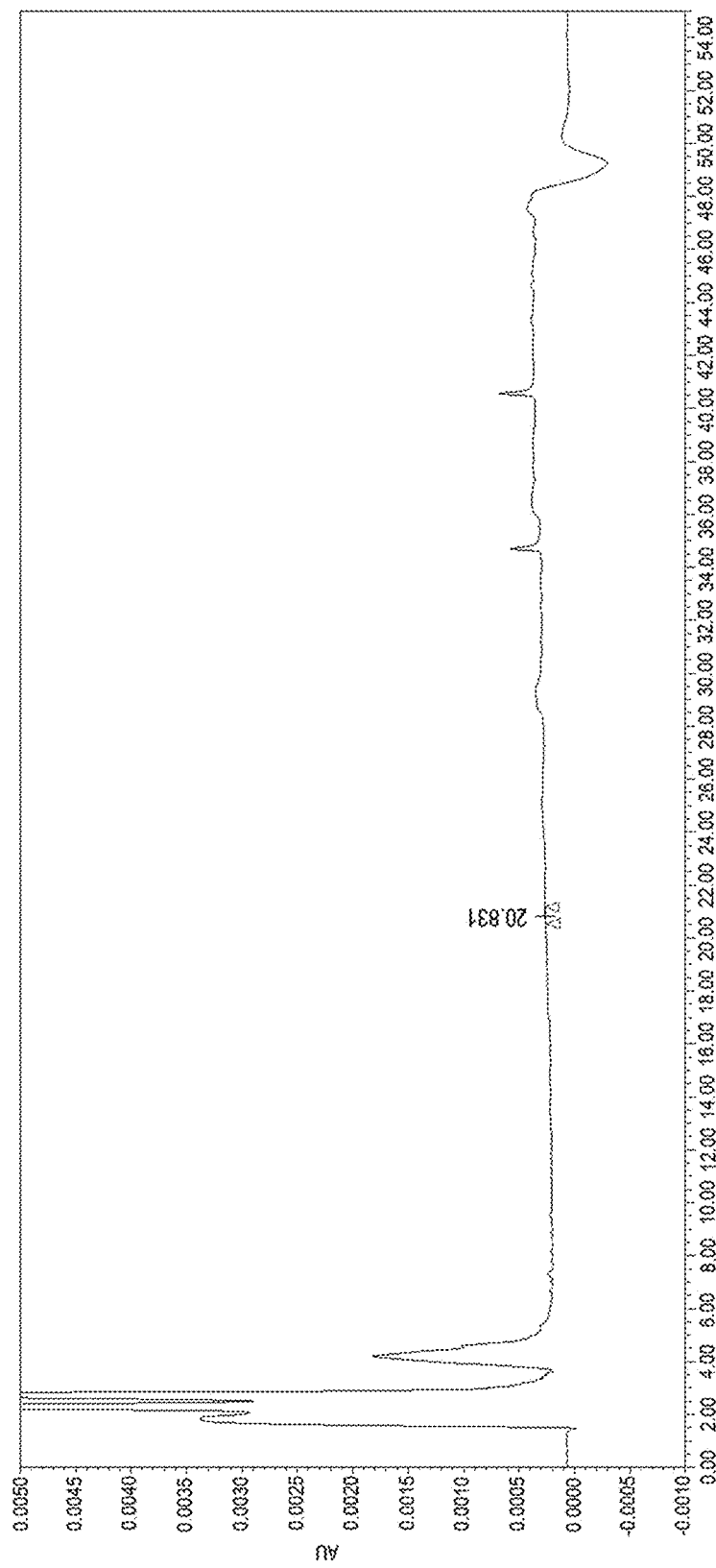
FIG. 25 is a chromatogram of a placebo sample.
Figure 26:
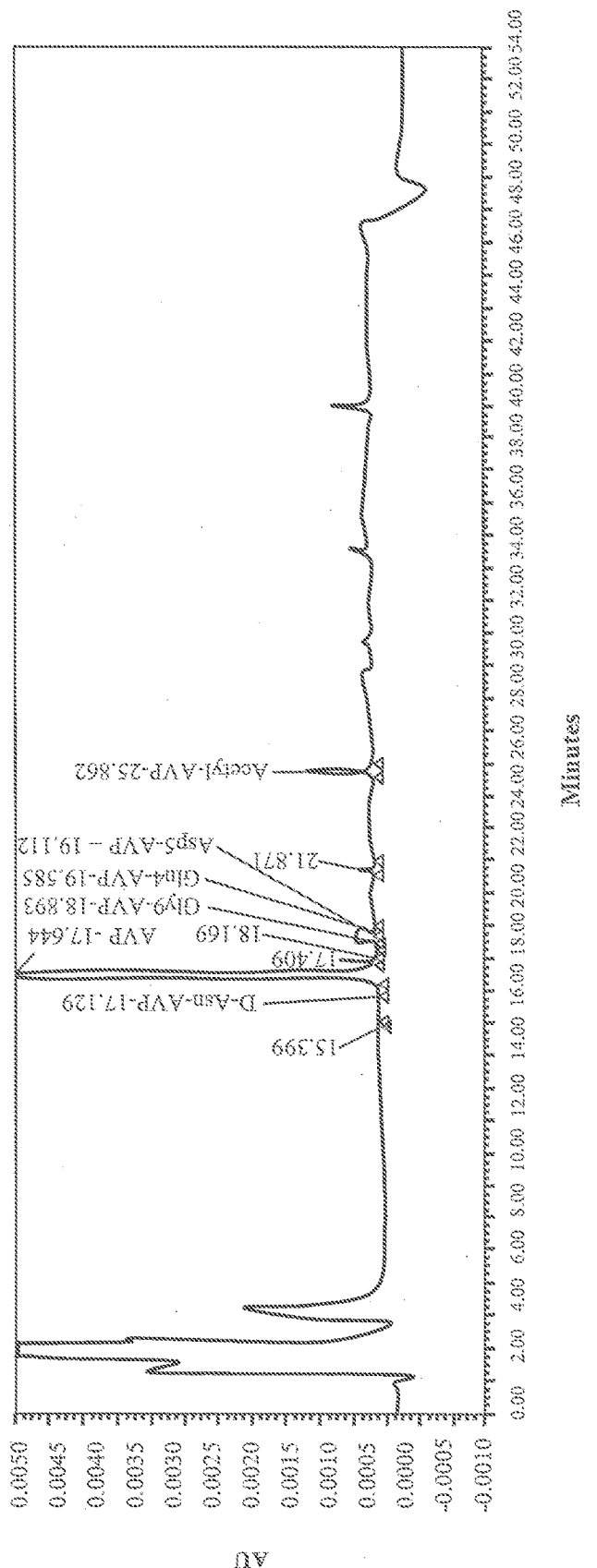
FIG. 26 is a chromatogram of a vasopressin sample.

Following the steps above done to confirm system suitability, a single injection of the placebo and sample preparations was made. The chromatograms were analyzed to determine the vasopressin and impurity peak areas. The chromatogram for the placebo is depicted in FIG. 25, and the chromatogram for the sample preparation is shown in FIG. 26. Then, the working standard solution was injected after 1 to 10 sample injections, and the average of the bracketing standard peak areas were used in the calculations for vasopressin and impurity amounts. Additional injections of the impurities marker solution could be made to help track any changes in retention time for long chromatographic sequences.

The relative standard deviation (% RSD) of vasopressin peak areas for the six injections of working standard solution was calculated by including the initial five injections from the system suitability steps above and each of the subsequent interspersed working standard solution injections. The calculations were done to ensure that each of the % RSD were not more than 2.0%.

The retention time of the major peak in the chromatogram of the sample preparation corresponded to that of the vasopressin peak in the working standard solution injection that preceded the sample preparation injection.

To calculate the vasopressin units/mL, the following formula was used:

$$\text{Vasopressin units/mL} = \frac{R_U}{R_S} \times Conc\ STD$$

where:

$R_U$=Vasopressin peak area response of Sample preparation.

$R_S$=average vasopressin peak area response of bracketing standards.

Conc STD=concentration of the vasopressin standard in units/mL

To identify the impurities, the % Impurity and identity for identified impurities (TABLE 3) that are were greater than or equal to 0.10% were reported. Impurities were truncated to 3 decimal places and then rounded to 2 decimal places, unless otherwise specified. The following formula was used:

$$\%\ \text{impurity} = \frac{R_1}{R_s} \times \frac{Conc\ STD}{LC} \times 100\%$$

where $R_1$=Peak area response for the impurity; LC=label content of vasopressin (units/mL).

The formulations used for the vasopressin and impurity studies are summarized in TABLE 65 below and correspond to several of the formulations detailed above in TABLES 55-63.

TABLE 65

| Lot | Vasopressin (units/100 mL) | Buffer Conc. (mM) | Vehicle |
|---|---|---|---|
| A | 40 | 10 | NaCl |
| B | 60 | 10 | NaCl |
| C | 40 | 10 | Dextrose |

TABLE 65-continued

| Lot | Vasopressin (units/100 mL) | Buffer Conc. (mM) | Vehicle |
|---|---|---|---|
| D | 60 | 10 | Dextrose |
| E | 40 | 1 | NaCl |
| F | 60 | 1 | NaCl |
| G | 40 | 1 | Dextrose |
| H | 60 | 1 | Dextrose |
| A1 | 40 | 1 | Dextrose |
| B1 | 60 | 1 | Dextrose |
| C1 | 40 | 1 | Dextrose/NaCl |

The drug products detailed in TABLE 65 were tested for stability over a six month period. The vasopressin drug formulations were stored at 5° C., 25° C., or 40° C. for up to six months. At 0, 1, 2, 3, 4, 5, and 6 months, the amount of vasopressin (AVP), % label claim (LC), amount of various impurities, pH, and % reference standard was measured. The vasopressin and impurity amounts were determined using the HPLC method described above. The results of the stability experiment are shown in TABLES 66-72 below.

TABLE 66

| Lot | Condition (° C.) | Time (m) | pH | Vasopressin (% LC) | RRT 0.30 (%) | RRT 0.33 (%) | RRT 0.34 (%) | RRT 0.35 (%) | RRT 0.362 (%) | RRT 0.37 (%) | RRT 0.38 (%) | RRT 0.39 (%) | RRT 0.40 (%) | RRT 0.42 (%) | RRT 0.44 (%) |
|---|---|---|---|---|---|---|---|---|---|---|---|---|---|---|---|
| A | 5 | 0 | 3.63 | 102.5 | 0.36 | | 0.14 | | | | | | | | 0.13 |
| A | 25 | 0 | 3.63 | 102.5 | 0.36 | | 0.14 | | | | | | | | 0.13 |
| A | 40 | 0 | 3.63 | 102.5 | 0.36 | | 0.14 | | | | | | | | 0.13 |
| B | 5 | 0 | 3.64 | 102.2 | 0.24 | | 0.09 | 0.08 | | | | | | | 0.10 |
| B | 25 | 0 | 3.64 | 102.2 | 0.24 | | 0.09 | 0.08 | | | | | | | 0.10 |
| B | 40 | 0 | 3.64 | 102.2 | 0.24 | | 0.09 | 0.08 | | | | | | | 0.10 |
| C | 5 | 0 | 3.64 | 98.2 | 0.34 | | 0.13 | | | | | | 0.56 | | 0.20 |
| C | 25 | 0 | 3.64 | 98.2 | 0.34 | | 0.13 | | | | | | 0.56 | | 0.20 |
| C | 40 | 0 | 3.64 | 98.2 | 0.34 | | 0.13 | | | | | | 0.56 | | 0.20 |
| D | 5 | 0 | 3.65 | 100.1 | 0.24 | | 0.08 | | | | | | 0.15 | | 0.06 |
| D | 25 | 0 | 3.65 | 100.1 | 0.24 | | 0.08 | | | | | | 0.15 | | 0.06 |
| D | 40 | 0 | 3.65 | 100.1 | 0.24 | | 0.08 | | | | | | 0.15 | | 0.06 |
| E | 5 | 0 | 3.67 | 100.5 | | | | | | | | | | | 0.13 |
| E | 25 | 0 | 3.67 | 100.5 | | | | | | | | | | | 0.13 |
| E | 40 | 0 | 3.67 | 100.5 | | | | | | | | | | | 0.13 |
| F | 5 | 0 | 3.71 | 101.5 | | | | | | | | | | | 0.09 |
| F | 25 | 0 | 3.71 | 101.5 | | | | | | | | | | | 0.09 |
| F | 40 | 0 | 3.71 | 101.5 | | | | | | | | | | | 0.09 |
| G | 5 | 0 | 3.75 | 99.5 | | | | | | | | | | | |
| G | 25 | 0 | 3.75 | 99.5 | | | | | | | | | | | |
| G | 40 | 0 | 3.75 | 99.5 | | | | | | | | | | | |
| H | 5 | 0 | 3.74 | 100.2 | | | | | | | | | | | |
| H | 25 | 0 | 3.74 | 100.2 | | | | | | | | | | | |
| H | 40 | 0 | 3.74 | 100.2 | | | | | | | | | | | |
| A1 | 5 | 0 | 3.86 | 97.5 | | | | | | | | | | | |
| A1 | 25 | 0 | 3.86 | 97.5 | | | | | | | | | | | |
| A1 | 40 | 0 | 3.86 | 97.5 | | | | | | | | | | | |
| B1 | 5 | 0 | 3.84 | 97.6 | | | | | | | | | | | |
| B1 | 25 | 0 | 3.84 | 97.6 | | | | | | | | | | | |
| B1 | 40 | 0 | 3.84 | 97.6 | | | | | | | | | | | |
| C1 | 5 | 0 | 3.78 | 99.3 | | | | | | | | | | | |
| C1 | 25 | 0 | 3.78 | 99.3 | | | | | | | | | | | |
| C1 | 40 | 0 | 3.78 | 99.3 | | | | | | | | | | | |
| A | 5 | 1 | 3.62 | 101.6 | 0.37 | | 0.15 | | | | | | | | 0.11 |
| A | 25 | 1 | 3.63 | 101.5 | | 0.34 | | | | | | 0.19 | | | |
| A | 40 | 1 | 3.61 | 98.2 | | 0.27 | | | | | | 0.18 | | | |
| B | 5 | 1 | 3.61 | 102.2 | 0.25 | | 0.12 | | | | | | 0.06 | | 0.13 |
| B | 25 | 1 | 3.63 | 101.0 | | 0.24 | | | | | | 0.11 | | | |
| B | 40 | 1 | 3.63 | 97.2 | | 0.19 | | | | | | 0.65 | | | |
| C | 5 | 1 | 3.66 | 99.7 | 0.37 | | 0.11 | | | | | | | | 0.79 |
| C | 25 | 1 | 3.65 | 98.7 | | 0.36 | | | | | | 0.17 | | | |
| C | 40 | 1 | 3.66 | 93.8 | | 0.60 | | | | | | 0.19 | | | |
| D | 5 | 1 | 3.66 | 101.1 | 0.24 | | 0.08 | | | | | | | | |
| D | 25 | 1 | 3.65 | 99.8 | | 0.24 | | | | | | 0.11 | | | |
| D | 40 | 1 | 3.66 | 92.4 | | 0.41 | | | | | | 0.11 | | | |
| E | 5 | 1 | 3.67 | 101.0 | | | | | | | | | | | |
| E | 25 | 1 | 3.67 | 99.2 | | | | | | | | | | | |
| E | 40 | 1 | 3.68 | 95.5 | | | | | | | | | | | 0.08 |
| F | 5 | 1 | 3.71 | 101.5 | | | | | | | | | | | |
| F | 25 | 1 | 3.72 | 100.1 | | | | | | | | | | | |
| F | 40 | 1 | 3.71 | 96.6 | | | | | | | | | 0.12 | | |
| G | 5 | 1 | 3.71 | 99.8 | | | | | | | | | | | |
| G | 25 | 1 | 3.76 | 99.0 | | | | | | | | | | | |
| G | 40 | 1 | 3.75 | 94.2 | | 0.34 | | | | | | | | 0.26 | |
| H | 5 | 1 | 3.76 | 99.8 | | | | | | | | | | | |
| H | 25 | 1 | 3.77 | 99.5 | | | | | | | | | | | |
| H | 40 | 1 | 3.77 | 97.0 | | 0.23 | | | | | | | | | |
| A1 | 5 | 1 | 3.81 | 97.0 | | | | | | | | | | | |
| A1 | 25 | 1 | 3.82 | 96.8 | | | | | | | | | | | |
| A1 | 40 | 1 | 3.83 | 91.8 | | | | | | | | | | | |

TABLE 66-continued

| Lot | Condition (° C.) | Time (m) | pH | Vasopressin (% LC) | RRT 0.30 (%) | RRT 0.33 (%) | RRT 0.34 (%) | RRT 0.35 (%) | RRT 0.362 (%) | RRT 0.37 (%) | RRT 0.38 (%) | RRT 0.39 (%) | RRT 0.40 (%) | RRT 0.42 (%) | RRT 0.44 (%) |
|---|---|---|---|---|---|---|---|---|---|---|---|---|---|---|---|
| B1 | 5 | 1 | 3.82 | 97.5 | | | | | | | | | | | |
| B1 | 25 | 1 | 3.82 | 97.1 | | | | | | | | | | | |
| B1 | 40 | 1 | 3.82 | 92.0 | | | | | | | | | | | |
| C1 | 5 | 1 | 3.80 | 99.2 | | | | | | | | | | | |
| C1 | 25 | 1 | | 98.5 | | | | | | | | | | | |
| C1 | 40 | 1 | 3.82 | 94.7 | | | | | | | | | | | |
| A | 5 | 2 | 3.59 | 101.7 | | | | | | | 0.11 | | | | |
| A | 25 | 2 | 3.59 | 99.5 | | | | | | | 0.14 | | | | |
| A | 40 | 2 | 3.60 | 92.9 | | | | | | | 0.15 | | | | |
| B | 5 | 2 | 3.60 | 101.1 | | | | | | | 0.12 | | | | |
| B | 25 | 2 | 3.60 | 98.8 | | | | | | | 0.10 | | | | |
| B | 40 | 2 | 3.60 | 92.1 | | | | | | | 0.11 | | | | |
| C | 5 | 2 | 3.59 | 99.3 | 0.18 | | | | | | | | | | |
| C | 25 | 2 | 3.62 | 97.3 | | | | | | | 0.14 | | | | |
| C | 40 | 2 | 3.64 | 89.2 | | | | | | | 0.15 | | | | |
| D | 5 | 2 | 3.67 | 100.0 | | | | | | | 0.10 | | | | |
| D | 25 | 2 | 3.66 | 97.3 | | | | | | | 0.09 | | | | |
| D | 40 | 2 | 3.62 | 89.9 | | | | | | | 0.09 | | | | |
| E | 5 | 2 | 3.65 | 99.5 | | | | | | | | | | | |
| E | 25 | 2 | 3.67 | 95.8 | | | | | | | | | | | |
| E | 40 | 2 | 3.67 | 90.6 | | | | | | | 0.07 | | | | |
| F | 5 | 2 | 3.67 | 100.6 | | | | | | | | | | | |
| F | 25 | 2 | 3.71 | 97.9 | | | | | | | 0.14 | | | | |
| F | 40 | 2 | 3.70 | 92.3 | | | | | | | 0.33 | | | | |
| G | 5 | 2 | 3.70 | 98.9 | | | | | | | | | | | |
| G | 25 | 2 | 3.73 | 97.0 | | | | | | | | | | | |
| G | 40 | 2 | 3.71 | 90.5 | | | | | | | | | | | |
| H | 5 | 2 | 3.72 | 99.7 | | | | | | | | | | | |
| H | 25 | 2 | 3.74 | 98.0 | | | | | | | | | | | |
| H | 40 | 2 | 3.74 | 91.9 | | | | | | | | | | | |
| A1 | 5 | 2 | 3.77 | 97.3 | | | | | | | | | | | |
| A1 | 25 | 2 | 3.77 | 95.9 | | | | | | | | | | | |
| A1 | 40 | 2 | 3.78 | 86.1 | | | | | | | | | | | |
| B1 | 5 | 2 | 3.79 | 97.3 | | | | | | | | | | | |
| B1 | 25 | 2 | 3.78 | 96.5 | | | | | | | | | | | |
| B1 | 40 | 2 | 3.79 | 87.4 | | | | | | | | | | | |
| C1 | 5 | 2 | 3.73 | 99.3 | | | | | | | | | | | |
| C1 | 25 | 2 | 3.73 | 98.1 | | | | | | | | | | | |
| C1 | 40 | 2 | 3.74 | 91.0 | | | | | | | | | | | |
| A | 5 | 3 | 3.59 | 102.0 | | | | | | | 0.31 | | | | |
| A | 25 | 3 | 3.61 | 99.5 | | | | | | | 0.30 | | | | |
| A | 40 | 3 | 3.60 | 90.8 | | | | | | | 0.30 | | | | |
| B | 5 | 3 | 3.59 | 101.8 | | | | | | | 0.24 | | | | |
| B | 25 | 3 | 3.60 | 98.8 | | | | | | | 0.22 | | | | |
| B | 40 | 3 | 3.60 | 90.3 | | | | | | | 0.22 | | | | |
| C | 5 | 3 | 3.62 | 99.8 | | | | | | | 0.16 | | | | |
| C | 25 | 3 | 3.62 | 95.5 | | | | | | | 0.15 | | | | |
| C | 40 | 3 | 3.62 | 87.0 | | | | | | | 0.16 | | | | |
| D | 5 | 3 | 3.62 | 91.4 | | | | | | | 0.10 | | | | |
| D | 25 | 3 | 3.63 | 97.7 | | | | | | | 0.20 | | | | |
| D | 40 | 3 | 3.63 | 87.6 | | | | | | | 0.18 | | | | |
| E | 5 | 3 | 3.63 | 96.9 | | | | | | | | | | | |
| E | 25 | 3 | 3.64 | 96.3 | | | | | | | | | | | |
| E | 40 | 3 | 3.65 | 88.8 | | | | | | | 0.23 | | | | |
| F | 5 | 3 | 3.67 | 100.8 | | | | | | | | | | | |
| F | 25 | 3 | 3.68 | 97.9 | | | | | | | 0.23 | | | | |
| F | 40 | 3 | 3.70 | 90.0 | | | | | | | 0.20 | | | | |
| G | 5 | 3 | 3.73 | 98.8 | | | | | | | 0.16 | | | | |
| G | 25 | 3 | 3.72 | 97.5 | | | | | | | 0.07 | | | | |
| G | 40 | 3 | 3.74 | 88.6 | | | | | | | | | | | |
| H | 5 | 3 | 3.71 | 99.8 | | | | | | | 0.04 | | | | |
| H | 25 | 3 | 3.74 | 98.5 | | | | | | | | | | | |
| H | 40 | 3 | 3.75 | 89.1 | | | | | | | | | | | |
| A | 5 | 4 | 3.59 | 99.9 | | | | | | | 0.22 | | | | |
| A | 25 | 4 | 3.56 | 96.8 | | | | | | | 0.20 | | | | |
| A | 40 | 4 | 3.70 | 84.5 | | | | | | | 0.31 | | | | |
| B | 5 | 4 | 3.58 | 99.4 | | | | | | | 0.11 | | | | |
| B | 25 | 4 | 3.56 | 95.4 | | | | | | | 0.17 | | | | |
| B | 40 | 4 | 3.67 | 83.0 | | | | | | | 1.37 | | | | |
| C | 5 | 4 | 3.61 | 98.5 | | | | | | | 0.18 | | | | |
| C | 25 | 4 | 3.63 | 94.9 | | | | | | | 0.18 | | | | |
| C | 40 | 4 | 3.64 | 81.3 | | | | | | | 0.18 | | | | |
| D | 5 | 4 | 3.62 | 98.9 | | | | | | | 0.12 | | | | |
| D | 25 | 4 | 3.62 | 94.5 | | | | | | 0.07 | 0.09 | | | | |
| D | 40 | 4 | 3.61 | 82.1 | | | | | | | 0.13 | | | | |
| E | 5 | 4 | 3.63 | 97.6 | | | | | | | | | | | |

TABLE 66-continued

| Lot | Condition (°C.) | Time (m) | pH | Vasopressin (% LC) | RRT 0.30 (%) | RRT 0.33 (%) | RRT 0.34 (%) | RRT 0.35 (%) | RRT 0.362 (%) | RRT 0.37 (%) | RRT 0.38 (%) | RRT 0.39 (%) | RRT 0.40 (%) | RRT 0.42 (%) | RRT 0.44 (%) |
|---|---|---|---|---|---|---|---|---|---|---|---|---|---|---|---|
| E | 25 | 4 | 3.69 | 94.0 | | | | | | | | | | | |
| E | 40 | 4 | 3.63 | 83.2 | | | | | | | 0.26 | | | | |
| F | 5 | 4 | 3.68 | 98.9 | | | | | | | 0.08 | | | | |
| F | 25 | 4 | 3.69 | 95.3 | | | | | | | 0.19 | | | | |
| F | 40 | 4 | 3.70 | 84.6 | | | | | | | 0.24 | | | | |
| G | 5 | 4 | 3.68 | 98.1 | | | | | | | | | | | |
| G | 25 | 4 | 3.69 | 95.8 | | | | | | | | | | | |
| G | 40 | 4 | 3.84 | 83.2 | | | | | | | | | | | |
| H | 5 | 4 | 3.67 | 98.6 | | | | | | | | | | | |
| H | 25 | 4 | 3.62 | 93.1 | | | | 0.13 | | | | | | | 0.12 |
| H | 40 | 4 | 3.76 | 83.6 | | | | | | | | | | | |
| A | 5 | 5 | 3.63 | 99.7 | | | | | | | | | 0.10 | | |
| A | 25 | 5 | 3.63 | 95.8 | | | | | | | | | | | |
| B | 5 | 5 | 3.63 | 99.0 | | | | | | | | | 0.25 | | |
| B | 25 | 5 | 3.64 | 95.1 | | | | | | | | | | | |
| C | 5 | 5 | 3.68 | 98.2 | | | | | | | | | | | |
| C | 25 | 5 | 3.67 | 93.7 | | | | | | | | | | | |
| D | 5 | 5 | 3.67 | 98.7 | | | | | | | | | | | |
| D | 25 | 5 | 3.69 | 94.6 | | | | | | | | | | | |
| E | 5 | 5 | 3.69 | 97.5 | | | | | | | | | | | |
| E | 25 | 5 | 3.69 | 93.1 | | | | | | 0.09 | | | | | |
| F | 5 | 5 | 3.71 | 98.4 | | | | | | 0.05 | | | 0.14 | | |
| F | 25 | 5 | 3.74 | 94.4 | | | | | | 0.15 | | | | | |
| G | 5 | 5 | 3.74 | 97.2 | | | | | | | | | | | |
| G | 25 | 5 | 3.78 | 93.1 | | | | | | | | | 1.73 | | |
| H | 5 | 5 | 3.76 | 97.7 | | | | | | | | | | | |
| H | 25 | 5 | 3.76 | 95.7 | | | | | | | | | | | |
| A | 5 | 6 | 3.57 | 101.0 | | | | | | | | | | | |
| A | 25 | 6 | 3.49 | 95.4 | | | | | | | | | | | |
| A | 5 | 6 | 3.57 | 100.0 | | | | | | | | | | | |
| A | 25 | 6 | 3.49 | 94.5 | | | | | | | | | | | |
| B | 5 | 6 | 3.54 | 100.2 | | | | | | | | | | | |
| B | 25 | 6 | 3.49 | 95.7 | | | | | | | | | | | |
| B | 5 | 6 | 3.54 | 99.3 | | | 0.12 | | | 0.13 | | | | | |
| B | 25 | 6 | 3.49 | 94.6 | | | | | | | | | | | |
| C | 5 | 6 | 3.59 | 98.1 | | | | | | | | | | | |
| C | 25 | 6 | 3.56 | 95.1 | | | | | | | | | | | |
| C | 5 | 6 | 3.59 | 98.0 | | | | | | | | | | | |
| C | 25 | 6 | 3.56 | 93.5 | | | | | | | | | | | |
| D | 5 | 6 | 3.55 | 100.0 | | | | | | | | | | | |
| D | 25 | 6 | 3.56 | 95.8 | | | | | | | | | | | |
| D | 5 | 6 | 3.55 | 98.6 | | | | | | | | 0.10 | | | |
| D | 25 | 6 | 3.56 | 94.2 | | | | | | | | | | | |
| E | 5 | 6 | 3.54 | 98.1 | | | | | | | | | | | |
| E | 25 | 6 | 3.56 | 94.1 | | | | | | | | | | | |
| E | 5 | 6 | 3.54 | 97.0 | | | | | | | | | | | |
| E | 25 | 6 | 3.56 | 92.3 | | | | | | | | | | | |
| F | 5 | 6 | 3.60 | 99.0 | | | | | | | | | | | |
| F | 25 | 6 | 3.61 | 95.0 | | | | | | | | | | | |
| F | 5 | 6 | 3.60 | 98.2 | | | | | | 0.10 | | 0.14 | | | |
| F | 25 | 6 | 3.61 | 93.8 | | | | | | 0.21 | | | | | |
| G | 5 | 6 | 3.61 | 98.2 | | | | | | | | | | | |
| G | 25 | 6 | 3.66 | 96.1 | | | | | | | | | | | |
| G | 5 | 6 | 3.61 | 96.5 | | | | | | | | | | | |
| G | 25 | 6 | 3.66 | 94.4 | | | | | | | | | | | |
| H | 5 | 6 | 3.64 | 98.6 | | | | | | | | | | | |
| H | 25 | 6 | 3.65 | 97.0 | | | | | | | | | | | |
| H | 5 | 6 | 3.64 | 96.9 | | | | | | | | | | | |
| H | 25 | 6 | 3.65 | 95.3 | | | | | | | | | | | |
| Min | | | 3.49 | 81.258 | 0 | 0 | | 0 | | 0.053 | 0.042 | 0 | 0.104 | 0 | 0.116 |
| Max | | | 3.84 | 102.047 | 0 | 0 | | 0 | | 0.153 | 1.371 | 0 | 1.731 | 0 | 0.116 |

TABLE 67

| Lot | RRT 0.47 (%) | RRT 0.48 (%) | RRT 0.49 (%) | RRT 0.50 (%) | RRT 0.510 (%) | RRT 0.52 (%) | RRT 0.56 (%) | RRT 0.57 (%) | RRT 0.58 (%) | RRT 0.61 (%) | RRT 0.63 (%) | RRT 0.64 (%) | RRT 0.646 (%) | RRT 0.67 (%) | RRT 0.68 (%) | RRT 0.70 (%) |
|---|---|---|---|---|---|---|---|---|---|---|---|---|---|---|---|---|
| A | | | | | | | | | | | 0.63 | | | | | |
| A | | | | | | | | | | | 0.63 | | | | | |
| A | | | | | | | | | | | 0.63 | | | | | |
| B | | | | | | | | | | | 0.20 | | | | | |
| B | | | | | | | | | | | 0.20 | | | | | |

TABLE 67-continued

| Lot | RRT 0.47 (%) | RRT 0.48 (%) | RRT 0.49 (%) | RRT 0.50 (%) | RRT 0.510 (%) | RRT 0.52 (%) | RRT 0.56 (%) | RRT 0.57 (%) | RRT 0.58 (%) | RRT 0.61 (%) | RRT 0.63 (%) | RRT 0.64 (%) | RRT 0.646 (%) | RRT 0.67 (%) | RRT 0.68 (%) | RRT 0.70 (%) |
|---|---|---|---|---|---|---|---|---|---|---|---|---|---|---|---|---|
| B | | | | | | | | | | | 0.20 | | | | | |
| C | | | | 0.18 | | | | | | | 8.74 | | | | | |
| C | | | | 0.18 | | | | | | | 8.74 | | | | | |
| C | | | | 0.18 | | | | | | | 8.74 | | | | | |
| D | | | | 0.10 | | | | | | | 9.43 | | | | | |
| D | | | | 0.10 | | | | | | | 9.43 | | | | | |
| D | | | | 0.10 | | | | | | | 9.43 | | | | | |
| E | | | | | | | | | | | 1.55 | | | | | |
| E | | | | | | | | | | | 1.55 | | | | | |
| E | | | | | | | | | | | 1.55 | | | | | |
| F | | | | | | | | 0.23 | | | 0.22 | | | | | |
| F | | | | | | | | 0.23 | | | 0.22 | | | | | |
| F | | | | | | | | 0.23 | | | 0.22 | | | | | |
| G | | | | 0.12 | | | | | | | 0.44 | | | | | |
| G | | | | 0.12 | | | | | | | 0.44 | | | | | |
| G | | | | 0.12 | | | | | | | 0.44 | | | | | |
| H | | | | 0.08 | | | | | | | 0.27 | | | | | |
| H | | | | 0.08 | | | | | | | 0.27 | | | | | |
| H | | | | 0.08 | | | | | | | 0.27 | | | | | |
| A1 | | | | | | | | | | | | 0.06 | | | | |
| A1 | | | | | | | | | | | | 0.06 | | | | |
| A1 | | | | | | | | | | | | 0.06 | | | | |
| B1 | | | | | | | | | | | | | | | | |
| B1 | | | | | | | | | | | | | | | | |
| B1 | | | | | | | | | | | | | | | | |
| C1 | | | | | | | | | | | | | | | | |
| C1 | | | | | | | | | | | | | | | | |
| C1 | | | | | | | | | | | | | | | | |
| A | | | | | | | | | | | 0.67 | | | | | |
| A | | | | | | | 0.82 | | | | | 0.56 | | | | |
| A | | | | | | | 0.81 | | | | | 0.40 | | | | |
| B | | | | | | | | | | | 0.53 | | | | | |
| B | | | | | | | 0.46 | | | | | 0.21 | | | | |
| B | | | | | | | 0.47 | | | | | 0.34 | | | | |
| C | | | | | | 0.13 | | | | | 0.31 | | | | | |
| C | | | 0.18 | | | | | | | | | 0.25 | | | | |
| C | | | 0.23 | | | | | | | | | 0.29 | | | | |
| D | | | | | | 0.09 | | | | | 0.34 | | | | | |
| D | | | | | | | | 0.13 | | | | 0.35 | | | | |
| D | | | | | | 0.12 | 0.11 | | | | | 0.20 | | | | |
| E | | | | | | | | | | | 0.53 | | | | | |
| E | | | | | | | 0.30 | | | | | 0.50 | | | | |
| E | | | | | | | 0.32 | | | | | 0.49 | | | | |
| F | | | | | | | | | | | 0.22 | | | | | |
| F | | | | | | | 0.17 | | | | | 0.23 | | | | |
| F | | | | | | | 0.18 | | | | | 0.24 | | | | |
| G | | | | | | 0.12 | | | | | 0.35 | | | | | |
| G | | | | | | | 0.46 | | | | | 0.37 | | | | |
| G | | | | | | | 0.45 | | | | | 0.35 | | | | |
| H | | | | | | 0.08 | | | | | 0.28 | | | | | |
| H | | | | | | | 0.16 | | | | | 0.24 | | | | |
| H | | | | | | | 0.15 | | | | | 0.25 | | | | |
| A1 | | | | | | | | | | | | | | | | |
| A1 | | | | | | | | | | | | | | | | |
| A1 | | | | | | | | | | | | 0.06 | | | | |
| B1 | | | | | | | | | | | | | | | | |
| B1 | | | | | | | | | | | | | | | | |
| B1 | | | | | | | | | | | | | | | | |
| C1 | | | | | | | | | | | | | | | | |
| C1 | | | | | | | | | | | | | | | | |
| C1 | | | | | | | | | | | | | | | | |
| A | | 0.24 | | 0.76 | | | | | | | | | | | | |
| A | | 0.06 | | 0.73 | | | | | | | | | | | | |
| A | | 0.05 | | 0.83 | | | | | | | | | | | | |
| B | | 0.04 | | 0.40 | | | | | | | | | | | | |
| B | | 0.04 | | 0.42 | | | | | | | | | | | | |
| B | | 0.12 | | 0.45 | | | | | | | | | | | 0.05 | |
| C | | 0.17 | | 0.13 | | | | | | | | | | | | |
| C | | 0.15 | | 0.16 | | | | | | | | | | | | |
| C | | 0.10 | | | | | | | | | | | | | 0.07 | |
| D | | | | 0.14 | | | | | | | | | | | | |
| D | | 0.05 | | 0.13 | | | | | | | | | | | | |
| D | | 0.04 | | | | | | | | | | | | | 0.05 | |
| E | | | | 0.26 | | | | | | | | | | | | |
| E | | | | 0.27 | | | | | | | | | | | | |
| E | 0.09 | | | | | | | | | | | | | | | |

TABLE 67-continued

| Lot | RRT 0.47 (%) | RRT 0.48 (%) | RRT 0.49 (%) | RRT 0.50 (%) | RRT 0.510 (%) | RRT 0.52 (%) | RRT 0.56 (%) | RRT 0.57 (%) | RRT 0.58 (%) | RRT 0.61 (%) | RRT 0.63 (%) | RRT 0.64 (%) | RRT 0.646 (%) | RRT 0.67 (%) | RRT 0.68 (%) | RRT 0.70 (%) |
|---|---|---|---|---|---|---|---|---|---|---|---|---|---|---|---|---|
| F |  |  |  | 0.15 |  |  |  |  |  |  |  |  |  |  |  |  |
| F |  | 0.07 |  | 0.18 |  |  |  |  |  |  |  |  |  |  |  |  |
| F |  | 0.29 |  |  |  |  |  |  |  |  |  |  |  |  |  |  |
| G |  |  |  | 0.56 |  |  |  |  |  |  |  |  |  |  |  |  |
| G |  | 0.06 |  | 0.54 |  |  |  |  | 0.08 |  |  |  |  |  |  |  |
| G |  |  |  |  |  |  |  |  |  |  |  |  |  |  |  |  |
| H |  |  |  | 0.20 |  |  |  |  |  |  |  |  |  |  |  |  |
| H |  |  |  | 0.21 |  |  |  |  |  |  |  |  |  |  |  |  |
| H |  | 0.04 |  |  |  |  |  |  |  |  |  |  |  |  |  |  |
| A1 |  |  |  |  |  |  |  |  |  |  |  |  |  |  |  |  |
| A1 |  |  |  |  |  |  |  |  |  |  |  | 0.14 |  |  |  |  |
| A1 |  |  |  |  |  |  |  |  |  |  |  |  |  |  |  |  |
| B1 |  |  |  |  |  |  |  |  |  |  |  |  |  |  |  |  |
| B1 |  |  |  |  |  |  |  |  |  |  |  |  |  |  |  |  |
| B1 |  |  |  |  |  |  |  |  |  |  |  |  |  |  |  |  |
| C1 |  |  |  |  |  |  |  |  |  |  |  |  |  |  |  |  |
| C1 |  |  |  |  |  |  |  |  |  |  |  |  |  |  |  |  |
| C1 |  |  |  |  |  |  |  |  |  |  |  |  |  |  |  |  |
| A |  | 0.09 |  |  |  |  |  |  |  |  |  | 0.72 |  |  |  |  |
| A |  | 0.14 |  |  |  |  |  |  |  |  |  | 0.49 |  |  |  |  |
| A |  | 0.12 |  |  |  |  |  |  |  |  |  | 0.47 |  |  |  |  |
| B |  | 0.07 |  |  |  |  |  |  |  |  |  | 0.36 |  |  |  |  |
| B |  | 0.06 |  |  |  |  |  |  |  |  |  | 0.47 |  |  |  |  |
| B |  | 0.05 |  |  |  |  |  |  |  |  |  | 0.44 |  | 0.05 |  |  |
| C |  | 0.14 |  |  |  |  |  |  |  |  |  | 0.41 |  |  |  |  |
| C |  | 0.13 |  |  |  |  |  |  |  |  |  | 0.57 |  |  |  |  |
| C |  | 0.09 |  |  |  |  |  |  |  |  |  | 0.39 |  |  |  |  |
| D |  | 0.99 |  |  |  |  |  |  |  |  |  | 0.28 |  |  |  |  |
| D |  | 0.05 |  |  |  |  |  |  |  |  |  | 0.42 |  |  |  |  |
| D |  |  |  |  |  |  |  |  |  |  |  | 0.27 |  | 0.05 |  |  |
| E |  |  |  |  |  |  |  |  |  | 0.06 |  | 0.60 |  |  |  |  |
| E |  |  |  |  |  |  |  |  |  |  |  | 0.57 |  |  |  |  |
| E |  |  |  |  |  |  |  |  |  |  |  | 1.03 |  |  |  |  |
| F |  |  |  |  |  |  |  | 0.42 |  |  |  | 0.31 |  |  |  |  |
| F |  | 0.10 |  |  |  |  |  |  |  |  |  | 0.33 |  |  |  |  |
| F |  | 0.10 |  |  |  |  |  |  |  |  |  | 0.35 |  |  |  |  |
| G |  |  |  |  |  |  |  |  |  |  |  | 0.39 |  |  |  |  |
| G |  | 0.09 |  |  |  |  |  |  |  |  |  | 0.51 |  |  |  |  |
| G |  |  |  |  |  |  |  |  |  |  |  | 0.50 |  |  |  |  |
| H |  |  |  |  |  |  |  |  |  |  |  | 0.32 |  |  |  |  |
| H |  |  |  |  |  |  |  |  |  |  |  | 0.37 |  |  |  |  |
| H |  |  |  |  |  |  |  |  |  |  |  | 0.25 |  |  |  |  |
| A |  |  |  |  | 0.84 |  |  |  |  |  |  |  | 0.59 |  |  |  |
| A |  |  |  |  | 0.82 |  |  |  |  |  |  |  | 0.29 |  |  |  |
| A |  |  |  |  | 0.87 |  |  |  |  |  |  |  | 0.39 |  |  |  |
| B |  |  |  |  | 0.47 |  |  |  |  |  |  |  | 0.23 |  |  |  |
| B |  |  |  |  | 0.50 |  |  |  |  |  |  |  | 0.43 |  |  |  |
| B |  |  |  |  | 0.55 |  |  |  |  |  |  |  | 0.45 |  | 0.08 |  |
| C |  |  |  |  | 0.21 |  |  |  |  |  |  |  | 0.15 |  |  |  |
| C |  |  |  |  | 0.23 |  |  |  |  |  |  |  | 0.25 |  |  |  |
| C |  |  |  |  | 0.25 |  |  |  |  |  |  |  | 0.34 |  |  |  |
| D |  |  |  |  | 0.18 |  |  |  |  |  |  |  | 0.27 |  |  |  |
| D |  |  |  |  | 0.24 |  |  |  |  |  |  |  | 0.39 |  |  |  |
| D |  |  |  |  | 0.19 |  |  |  |  |  |  |  | 0.25 |  | 0.08 |  |
| E |  |  |  |  | 0.31 |  |  |  |  |  |  |  | 0.58 |  |  |  |
| E |  |  |  |  | 0.33 |  |  |  |  |  |  |  | 0.51 |  |  |  |
| E |  |  |  |  | 0.36 |  |  |  |  |  |  |  | 0.67 |  |  |  |
| F |  |  |  |  | 0.18 |  |  |  |  |  |  |  | 0.21 |  |  |  |
| F |  |  |  |  | 0.19 |  |  |  |  |  |  |  | 0.27 |  |  |  |
| F |  |  |  |  | 0.20 |  |  |  |  |  |  |  | 0.26 |  |  |  |
| G |  |  |  |  | 0.59 |  |  |  |  |  |  |  | 0.40 |  |  |  |
| G |  |  |  |  | 0.59 |  |  |  |  |  |  |  | 0.36 |  |  |  |
| G |  |  |  |  | 0.62 |  |  |  |  |  |  | 0.40 |  |  |  |  |
| H |  |  |  |  | 0.20 |  |  |  |  |  |  |  | 0.22 |  |  |  |
| H |  |  |  |  | 0.25 |  |  |  |  | 0.20 |  |  | 0.31 |  | 0.11 |  |
| H |  |  |  | 0.25 |  |  |  |  |  |  |  |  | 0.26 |  | 0.09 |  |
| A |  |  |  |  |  |  |  |  |  |  | 0.61 |  |  |  |  |  |
| A |  |  |  |  |  |  |  |  |  |  | 0.48 |  |  |  |  |  |
| B |  |  |  |  |  |  |  |  |  |  | 0.27 |  |  |  |  |  |
| B |  |  |  |  |  |  |  |  |  |  | 0.43 |  |  |  |  |  |
| C |  |  |  |  |  |  |  |  |  |  | 0.29 |  |  |  |  |  |
| C |  |  |  |  | 0.15 |  |  |  |  |  | 0.30 |  |  |  |  |  |
| D |  |  |  |  | 0.14 |  |  |  |  |  | 0.28 |  |  |  |  |  |
| D |  |  |  |  | 0.08 |  |  |  |  |  | 0.40 |  |  |  |  |  |
| E |  |  |  |  |  |  |  |  |  |  | 0.53 |  |  |  |  |  |
| E |  |  |  |  |  |  |  |  |  |  | 0.49 |  |  |  |  |  |

TABLE 67-continued

| Lot | RRT 0.47 (%) | RRT 0.48 (%) | RRT 0.49 (%) | RRT 0.50 (%) | RRT 0.510 (%) | RRT 0.52 (%) | RRT 0.56 (%) | RRT 0.57 (%) | RRT 0.58 (%) | RRT 0.61 (%) | RRT 0.63 (%) | RRT 0.64 (%) | RRT 0.646 (%) | RRT 0.67 (%) | RRT 0.68 (%) | RRT 0.70 (%) |
|---|---|---|---|---|---|---|---|---|---|---|---|---|---|---|---|---|
| F | | | | | | | | | | | 0.24 | | | | | |
| F | | | | | | | | | | | 0.24 | | | | | |
| G | | | | 0.14 | | | | | | | 0.39 | | | | | |
| G | | | | 0.17 | | | | | | | 0.44 | | | | | |
| H | | | | 0.10 | | | | | | | 0.23 | | | | | |
| H | | | | 0.13 | | | | | | | 0.28 | | | | | |
| A | | | | | | | | | | | | 0.62 | | | | |
| A | | | | | | | | | | | | 0.30 | | | | |
| A | 0.65 | | | | | | | | | | 0.62 | | | | | |
| A | 0.70 | | | | | | | | | | 0.30 | | | | | 0.19 |
| B | | | | | | | | | | | | 0.61 | | | | |
| B | | | | | | | | | | | | 0.26 | | | | |
| B | 0.38 | | | | | | | | | | 0.62 | | | | | |
| B | 0.38 | | | | | | | | | | 0.26 | | | | | 0.11 |
| C | | | | | | | | | | | | 0.49 | | | | |
| C | | | 0.17 | | | | | | | | | 0.30 | | | | |
| C | 0.14 | | | | | | | | | | | | | | | |
| C | | | 0.25 | | | | | | | | 0.31 | | | | | 0.21 |
| D | | | | 0.10 | | | | | | | | 0.26 | | | | |
| D | | | | 0.10 | | | | | | | | 0.31 | | | | |
| D | | | 0.11 | | | | | | | | 0.26 | | | | | 0.09 |
| D | 0.09 | | 0.13 | | | | | | | | 0.32 | | | | | 0.12 |
| E | | | | | | | | | | | | 1.04 | | | | |
| E | | | | | | | | | | | | 0.64 | | | | |
| E | 0.21 | | | | | | | | | | 1.07 | | | | | |
| E | 0.22 | | | | | | | | | | 0.60 | | | | | |
| F | | | | | | | | 0.08 | | | | 0.21 | | | | |
| F | | | | | | | | | | | | 0.22 | | | | |
| F | 0.11 | | | | | | | 0.08 | | | 0.19 | | | | | |
| F | 0.12 | | | | | | | | | | 0.19 | | | | | |
| G | | | | 0.14 | | | | | | | | 0.38 | | | | |
| G | | | | 0.14 | | | | 0.18 | | | | 0.36 | | | | |
| G | 0.45 | | 0.16 | | | | | | | | 0.42 | | | | | 0.22 |
| G | 0.45 | | 0.18 | | | | | 0.19 | | | 0.35 | | | | | 0.35 |
| H | | | | 0.10 | | | | | | | | 0.20 | | | | |
| H | | | | 0.10 | | | | | | | | 0.28 | | | | |
| H | 0.15 | | 0.11 | | | | | | | | | 0.20 | | | | 0.12 |
| H | 0.15 | | 0.12 | | | | | | | | | 0.28 | | | | 0.22 |
| Min | | 0.035 | 0 | | 0.125 | 0 | | 0.42 | 0.077 | 0.064 | 0.23 | 0.14 | | 0.051 | 0.048 | |
| Max | | 0.986 | 0 | | 0.555 | 0 | | 0.42 | 0.203 | 0.064 | 0.624 | 1.03 | | 0.052 | 0.109 | |

TABLE 68

| Lot | RRT 0.71 (%) | RRT 0.72 (%) | RRT 0.74 (%) | RRT 0.76 (%) | RRT 0.77 (%) | RRT 0.78 (%) | RRT 0.79 (%) | RRT 0.80 (%) | RRT 0.82 (%) | RRT 0.84 (%) | RRT 0.86 (%) | RRT 0.87 (%) | RRT 0.88 (%) | RRT 0.91 (%) | RRT 0.94 (%) | RRT 0.95 (%) |
|---|---|---|---|---|---|---|---|---|---|---|---|---|---|---|---|---|
| A | | 0.15 | | | | | | | 0.29 | | | | | | | |
| A | | 0.15 | | | | | | | 0.29 | | | | | | | |
| A | | 0.15 | | | | | | | 0.29 | | | | | | | |
| B | | 0.08 | | | | | | | 0.32 | | | | | | | |
| B | | 0.08 | | | | | | | 0.32 | | | | | | | |
| B | | 0.08 | | | | | | | 0.32 | | | | | | | |
| C | | 0.15 | | | | | | | 0.29 | | | | | | | |
| C | | 0.15 | | | | | | | 0.29 | | | | | | | |
| C | | 0.15 | | | | | | | 0.29 | | | | | | | |
| D | | 0.10 | | | | | | | 0.30 | | | | | | | |
| D | | 0.10 | | | | | | | 0.30 | | | | | | | |
| D | | 0.10 | | | | | | | 0.30 | | | | | | | |
| E | | | | | | | | | 0.28 | | | | | | | |
| E | | | | | | | | | 0.28 | | | | | | | |
| E | | | | | | | | | 0.28 | | | | | | | |
| F | | | | | | | | | 0.32 | | | | | | | |
| F | | | | | | | | | 0.32 | | | | | | | |
| F | | | | | | | | | 0.32 | | | | | | | |
| G | | 0.20 | | | | | | | 0.31 | | | | | | | |
| G | | 0.20 | | | | | | | 0.31 | | | | | | | |
| G | | 0.20 | | | | | | | 0.31 | | | | | | | |
| H | | 0.12 | | | | | | | 0.30 | | | | | | | |
| H | | 0.12 | | | | | | | 0.30 | | | | | | | |
| H | | 0.12 | | | | | | | 0.30 | | | | | | | |
| A1 | | | | | | | | | | | | 0.32 | | | | |
| A1 | | | | | | | | | | | | 0.32 | | | | |

TABLE 68-continued

| Lot | RRT 0.71 (%) | RRT 0.72 (%) | RRT 0.74 (%) | RRT 0.76 (%) | RRT 0.77 (%) | RRT 0.78 (%) | RRT 0.79 (%) | RRT 0.80 (%) | RRT 0.82 (%) | RRT 0.84 (%) | RRT 0.86 (%) | RRT 0.87 (%) | RRT 0.88 (%) | RRT 0.91 (%) | RRT 0.94 (%) | RRT 0.95 (%) |
|---|---|---|---|---|---|---|---|---|---|---|---|---|---|---|---|---|
| A1 | | | | | | | | | | | | 0.32 | | | | |
| B1 | | | | | | | | | | | | 0.30 | | | | |
| B1 | | | | | | | | | | | | 0.30 | | | | |
| B1 | | | | | | | | | | | | 0.30 | | | | |
| C1 | | | | | | | | | | | | 0.31 | | | | |
| C1 | | | | | | | | | | | | 0.31 | | | | |
| C1 | | | | | | | | | | | | 0.31 | | | | |
| A | 0.10 | | | | | | | | 0.31 | | | | | | | |
| A | | | | | | | | | | 0.36 | | | | | | |
| A | | | | | | 0.17 | | | | 0.39 | | | | | | |
| B | | | | | | | | | 0.30 | | | | | | | |
| B | | | | | | | | | | 0.35 | | | | | | |
| B | | | | | | | | | | 0.36 | | | | | | |
| C | 0.32 | | | | | | | | 0.31 | | | | | | | |
| C | | | | | | | | | | 0.40 | | | | | | |
| C | | | | | | | 0.16 | | | 0.40 | | | | | | |
| D | 0.10 | | | | | | | | 0.31 | | | | | | | |
| D | | | | | | | | | | 0.34 | | | | | | |
| D | | | | | | | | | | 0.36 | | | | | | |
| E | | | | | | | | | 0.32 | | | | | | | |
| E | | | | | | | | | | 0.34 | | | | | | |
| E | | | | | | | | | | 0.37 | | | | | | |
| F | | | | | | | | | 0.30 | | | | | | | |
| F | | | | | | | | | | 0.34 | | | | | | |
| F | | | | | | | | | | 0.33 | | | | | | |
| G | 0.18 | | | | | | 0.29 | | 0.31 | | | | | | | |
| G | | | | | | | 0.20 | | | 0.38 | | | | | | |
| G | | | | | | | 0.27 | | | 0.42 | | | | | | |
| H | 0.09 | | | | | | | | 0.31 | | | | | | | |
| H | | | | | | | 0.13 | | | 0.35 | | | | | | |
| H | | | | | | | 0.14 | | | 0.36 | | | | | | |
| A1 | | | | | | | | | | | 0.10 | 0.29 | | | | |
| A1 | | | | | | | | | | | | 0.30 | | | | |
| A1 | | | | | | | | | | | | 0.29 | | | | |
| B1 | | | | | | | | | | | | 0.30 | | | | |
| B1 | | | | | | | | | | | | 0.30 | | | | |
| B1 | | | | | | | | | | | | 0.33 | | | | |
| C1 | | | | | | | | | | | | 0.31 | | | | |
| C1 | | | | | | | | | | | | 0.30 | | | | |
| C1 | | | | | | | | | | | | 0.30 | | | | |
| A | | | | | 0.12 | | | | | 0.33 | | | | | | |
| A | | | | | 0.12 | | | | | 0.36 | | | | | | |
| A | | | | | 0.15 | | | | | 0.42 | | | | | | |
| B | | | | | | | | | | 0.34 | | | | | | |
| B | | | | | 0.07 | | | | | 0.36 | | | | | | |
| B | | | | | 0.10 | | | | | 0.41 | | | | | | |
| C | | | | | 0.12 | | | | | 0.41 | | | | | | |
| C | | | | | 0.15 | | | | | 0.36 | | | | | | |
| C | | | | | 0.17 | | | | | 0.40 | | | | | | |
| D | | | | | 0.09 | | | | | 0.36 | | | | | | |
| D | | | | | 0.11 | | | | | 0.35 | | | | | | |
| D | | | | | 0.10 | | | | | 0.37 | | | | | | |
| E | | | | | | | | | | 0.33 | | | | | | |
| E | | | | | | | | | 0.21 | 0.31 | | | | | 0.05 | |
| E | | | | | 0.10 | | | | | 0.36 | | | | | | |
| F | | | | | | | | | | 0.36 | | | | | | |
| F | | | | | | | | | | 0.34 | | | | | | |
| F | | | | | | | | | | 0.37 | | | | | | |
| G | | | | | 0.20 | | | | | 0.33 | | | | | | |
| G | | | | | 0.22 | | | | | 0.34 | | | | | | |
| G | | | | | 0.33 | | | | | 0.41 | | | | | | |
| H | | | | | 0.11 | | | | | 0.35 | | | | | | |
| H | | | | | 0.13 | | | | | 0.34 | | | | | | |
| H | | | | | 0.19 | | | | | 0.36 | | | | | | |
| A1 | | | | | | | | | | | | 0.30 | | | | |
| A1 | | | | | | | | | | | | 0.31 | | | | |
| A1 | | | | | | | | | | | | 0.31 | | | | 0.18 |
| B1 | | | | | | | | | | | | 0.30 | | | | |
| B1 | | | | | | | | | | | | 0.31 | | | | |
| B1 | | | | | | | | | | | | 0.29 | | | | 0.15 |
| C1 | | | | | | | | | | | | 0.31 | | | | |
| C1 | | | | | | | | | | | | 0.31 | | | | |
| C1 | | | | | | | | | | | | 0.30 | | | | |
| A | | | | | | | | | | | | | | | | |
| A | | | | | | | | | | | | | | | | |
| A | | | | | | | | | | | | | | | | |

TABLE 68-continued

| Lot | RRT 0.71 (%) | RRT 0.72 (%) | RRT 0.74 (%) | RRT 0.76 (%) | RRT 0.77 (%) | RRT 0.78 (%) | RRT 0.79 (%) | RRT 0.80 (%) | RRT 0.82 (%) | RRT 0.84 (%) | RRT 0.86 (%) | RRT 0.87 (%) | RRT 0.88 (%) | RRT 0.91 (%) | RRT 0.94 (%) | RRT 0.95 (%) |
|---|---|---|---|---|---|---|---|---|---|---|---|---|---|---|---|---|
| B | | | | | | | | | | | | | | | | |
| B | | | | | | | | | | | | | | | | |
| B | | | | | | | | | | | | | | | | |
| C | | | | | | | | | | | | | | | | |
| C | | | | | | | | | | | | | | | | |
| C | | | | | | | | | | | | | | | | |
| D | | | | | | | | | | | | | | | 0.49 | |
| D | | | | | | | | | | | | | | | | |
| D | | | | | | | | | | | | | | | | |
| E | | 0.25 | | | | | | | | | | | 0.16 | 0.38 | | |
| E | | | | | | | | | | | | | | | | |
| E | | | | | | | | | | | | | | | | |
| F | | | | | | | | | | | | | | | | |
| F | | | | | | | | | | | | | | | | |
| F | | | | | | | | | | | | | | | | |
| G | | | | | | | | | | | | | | | | |
| G | | | | | | | | | | | | | | | | |
| G | | | | | | | | | | | | | | | | |
| H | | | | | | | | | | | | | | | | |
| H | | | | | | | | | | | | | | | | |
| H | | | | | | | | | | | | | | | | |
| A | | | | | | 0.16 | | | | 0.33 | | | | | | |
| A | | | | | | 0.18 | | | | 0.33 | | | | | | |
| A | | | | | | 0.25 | | | | 0.40 | | | | | | |
| B | | | | | | | | | | 0.32 | | | | | | |
| B | | | | | | 0.09 | | | | 0.32 | | | | | | |
| B | | | | | | 0.17 | | | | 0.38 | | | | | | |
| C | | | | | | | | | | 0.34 | | | | | | |
| C | | | | | | 0.19 | | | | 0.35 | | | | | | |
| C | | | | | | 0.25 | | | | 0.42 | | | | | | |
| D | | | | | | 0.10 | | | | 0.32 | | | | | | |
| D | | | | | | 0.12 | | | | 0.36 | | | | | | |
| D | | | | | | 0.16 | | | | 0.45 | | | | | | |
| E | | | | | | | | | | 0.30 | | | | | | |
| E | | | | | | | | | | 0.32 | | | | | | |
| E | | | | | | 0.19 | | | | 0.40 | | | | | | |
| F | | | | | | | | | | 0.31 | | | | | | |
| F | | | | | | | | | | 0.33 | | | | | | |
| F | | | | | | 0.11 | | | | 0.37 | | | | | | |
| G | | | | | | 0.19 | | | | 0.35 | | | | | | |
| G | | | | | | 0.29 | | | | 0.37 | | | | | | |
| G | | | | | | 0.46 | | | | 0.45 | | | | | | |
| H | | | | | | 0.11 | | | | 0.34 | | | | | | |
| H | | | | | | 0.19 | | | | 0.36 | | | 0.08 | | | |
| H | | | | | | 0.26 | | | | 0.45 | | | | | | |
| A | 0.16 | | | | | | | 0.28 | | | | | | | | |
| A | 0.17 | | | | | | 0.28 | | | | | | | | | |
| B | | | | | | | | 0.29 | | | | | | | | |
| B | | | | | | | 0.29 | | | | | | | | | |
| C | 0.18 | | | | | | 0.27 | | | | | | | | | |
| C | 0.18 | | | | | | 0.29 | | | | | | | | | |
| D | | | | | | | 0.29 | | | | | | | | | |
| D | 0.11 | | | | | | 0.29 | | | | | | | | | |
| E | | | | | | | 0.27 | | | | | | | | | |
| E | | | | | | | 0.30 | | | | | | | | | |
| F | | | | | | | 0.31 | | | | | | | | | |
| F | | | | | | | 0.30 | | | | | | | | | |
| G | 0.23 | | | | | | 0.28 | | | | | | | | | |
| G | 0.29 | | | | | | 0.29 | | | | | | | | | |
| H | 0.12 | | | | | | | 0.29 | | | | | | | | |
| H | 0.18 | | | | | | 0.29 | | | | | | | | | |
| A | | | | | | | | | | | | 0.33 | | | | |
| A | | | | | 0.14 | | | | | | | 0.32 | | | | |
| A | | | | | | | | | 0.32 | | | | | | | |
| A | | | | | | | | | 0.28 | | | | | | | |
| B | | | | | | | | | | | | 0.32 | | | | |
| B | | | | | | | | | | | | 0.30 | | | | |
| B | | | | | | | | | 0.33 | | | | | | | |
| B | | | | | | | | | 0.28 | | | | | | | |
| C | | | | 0.17 | | | | | | | | 0.31 | | | | |
| C | | | | | 0.14 | | | | | | | 0.32 | | | | |
| C | 0.14 | | | | | | | | 0.26 | | | | | | | |
| C | | | | | | | | | 0.24 | | | | | | | |
| D | | | | | | | | | | | | 0.30 | | | | |
| D | | | | | | | | | | | | 0.32 | | | | |
| D | | | | | | | | | 0.32 | | | | | | | |

TABLE 68-continued

| Lot | RRT 0.71 (%) | RRT 0.72 (%) | RRT 0.74 (%) | RRT 0.76 (%) | RRT 0.77 (%) | RRT 0.78 (%) | RRT 0.79 (%) | RRT 0.80 (%) | RRT 0.82 (%) | RRT 0.84 (%) | RRT 0.86 (%) | RRT 0.87 (%) | RRT 0.88 (%) | RRT 0.91 (%) | RRT 0.94 (%) | RRT 0.95 (%) |
|---|---|---|---|---|---|---|---|---|---|---|---|---|---|---|---|---|
| D | | | | | | | | | 0.33 | | | | | | | |
| E | | | | | | | | | | | | 0.34 | | | | |
| E | | | | 0.12 | | | | | | | | 0.31 | | | | |
| E | | | | | | | | | 0.30 | | | | | | | |
| E | | | | | | | | | 0.28 | | | | | | | |
| F | | | | 0.07 | | | | | | | | 0.33 | | | | |
| F | | | | | | | | | | | | 0.32 | | | | |
| F | | | | | | | | | 0.30 | | | | | | | |
| F | | | | | | | | | 0.28 | | | | | | | |
| G | | | | | | | | | | | | 0.32 | | | | |
| G | | | | 0.18 | | | | | | | | 0.32 | | | | |
| G | | | | | | | | | 0.30 | | | | | | | |
| G | | | | | | | | | 0.24 | | | | | | | |
| H | | | | | | | | | | | | 0.30 | | | | |
| H | | | | 0.09 | | | | | | | | 0.31 | | | | |
| H | | | | | | | | | 0.32 | | | | | | | |
| H | | | | | | | | | 0.26 | | | | | | | |
| Min | 0.112 | 0.252 | | | 0.087 | 0.092 | | | 0.213 | 0.301 | | 0.161 | | | 0.053 | |
| Max | 0.287 | 0.252 | | | 0.33 | 0.456 | | | 0.328 | 0.453 | | 0.161 | | | 0.487 | |

TABLE 69

| Lot | D-Asn-AVP (%) | RRT 0.99 (%) | RRT 1.02 (%) | RRT 1.03 (%) | RRT 1.04 (%) | RRT 1.05 (%) | RRT 1.06 (%) | Gly9-AVP (%) | Asp5-AVP (%) | Glu4-AVP (%) | RRT 1.09 (%) | RRT 1.10 (%) | RRT 1.095 (%) | RRT 1.12 (%) | RRT 1.13 (%) | RRT 1.14 (%) |
|---|---|---|---|---|---|---|---|---|---|---|---|---|---|---|---|---|
| A | | | 0.35 | | 0.21 | | | 0.17 | 0.58 | 0.41 | | | | | | |
| A | | | 0.35 | | 0.21 | | | 0.17 | 0.58 | 0.41 | | | | | | |
| A | | | 0.35 | | 0.21 | | | 0.17 | 0.58 | 0.41 | | | | | | |
| B | 0.20 | | 0.43 | | 0.15 | | | 0.20 | 0.19 | 0.25 | | | | | | |
| B | 0.20 | | 0.43 | | 0.15 | | | 0.20 | 0.19 | 0.25 | | | | | | |
| B | 0.20 | | 0.43 | | 0.15 | | | 0.20 | 0.19 | 0.25 | | | | | | |
| C | | | 0.42 | | 0.30 | | | | 0.48 | 0.17 | | | | | | |
| C | | | 0.42 | | 0.30 | | | | 0.48 | 0.17 | | | | | | |
| C | | | 0.42 | | 0.30 | | | | 0.48 | 0.17 | | | | | | |
| D | 0.15 | | 0.41 | | 0.11 | | | 0.11 | 0.18 | 0.19 | | | | | | |
| D | 0.15 | | 0.41 | | 0.11 | | | 0.11 | 0.18 | 0.19 | | | | | | |
| D | 0.15 | | 0.41 | | 0.11 | | | 0.11 | 0.18 | 0.19 | | | | | | |
| E | 0.22 | | 0.34 | | 0.19 | | | 0.14 | 0.93 | 0.24 | | | | | | |
| E | 0.22 | | 0.34 | | 0.19 | | | 0.14 | 0.93 | 0.24 | | | | | | |
| E | 0.22 | | 0.34 | | 0.19 | | | 0.14 | 0.93 | 0.24 | | | | | | |
| F | 0.15 | | 0.33 | | 0.07 | | | 0.13 | 0.12 | 0.19 | | | | | | |
| F | 0.15 | | 0.33 | | 0.07 | | | 0.13 | 0.12 | 0.19 | | | | | | |
| F | 0.15 | | 0.33 | | 0.07 | | | 0.13 | 0.12 | 0.19 | | | | | | |
| G | | | 0.38 | | | | | | 0.19 | 0.24 | | | | | | |
| G | | | 0.38 | | | | | | 0.19 | 0.24 | | | | | | |
| G | | | 0.38 | | | | | | 0.19 | 0.24 | | | | | | |
| H | 0.16 | | 0.42 | | | | | 0.08 | 0.12 | 0.14 | | | | | | |
| H | 0.16 | | 0.42 | | | | | 0.08 | 0.12 | 0.14 | | | | | | |
| H | 0.16 | | 0.42 | | | | | 0.08 | 0.12 | 0.14 | | | | | | |
| A1 | 0.12 | 0.12 | | 0.24 | | | | 0.08 | | 0.10 | | | | 0.09 | | |
| A1 | 0.12 | 0.12 | | 0.24 | | | | 0.08 | | 0.10 | | | | 0.09 | | |
| A1 | 0.12 | 0.12 | | 0.24 | | | | 0.08 | | 0.10 | | | | 0.09 | | |
| B1 | 0.11 | 0.12 | | 0.24 | | | | 0.07 | | 0.07 | | | | 0.07 | | |
| B1 | 0.11 | 0.12 | | 0.24 | | | | 0.07 | | 0.07 | | | | 0.07 | | |
| B1 | 0.11 | 0.12 | | 0.24 | | | | 0.07 | | 0.07 | | | | 0.07 | | |
| C1 | 0.12 | 0.12 | | 0.25 | | | | 0.09 | | 0.10 | | | | 0.08 | | |
| C1 | 0.12 | 0.12 | | 0.25 | | | | 0.09 | | 0.10 | | | | 0.08 | | |
| C1 | 0.12 | 0.12 | | 0.25 | | | | 0.09 | | 0.10 | | | | 0.08 | | |
| A | | | 0.47 | | 0.63 | | | 0.39 | 0.70 | 0.51 | | | | | | |
| A | | | 0.33 | | | | | 0.41 | 0.46 | 0.61 | | | | | 0.44 | |
| A | | | 0.31 | | | | | 1.28 | 0.65 | 1.52 | | | | | 0.18 | |
| B | 0.19 | | 0.43 | | 0.26 | | | 0.25 | 0.58 | 0.27 | | | | | | |
| B | 0.12 | | 0.31 | | | | | 0.39 | 0.20 | 0.52 | | | | | | |
| B | 0.11 | | 0.31 | | | | | 0.29 | 0.44 | 1.47 | | | | | 0.23 | |
| C | | | 0.42 | | 0.21 | | | | 0.20 | 0.15 | | | | | | |
| C | | | 0.66 | | | | | 0.19 | 0.24 | 0.40 | | | | | 0.16 | |
| C | 0.16 | | 1.71 | | 0.58 | | | 0.55 | 0.43 | 0.86 | | | | | 0.17 | |
| D | | | 0.43 | | | | | 0.09 | 0.18 | 0.17 | | | | | | |
| D | 0.13 | | 0.75 | | | | | 0.23 | 0.13 | 0.38 | | | | | 0.17 | |
| D | 0.18 | | 1.71 | | | | | 0.57 | 1.43 | 0.82 | | | | | 0.14 | |
| E | | | 0.34 | | | | | 0.17 | 0.25 | 0.23 | | | | | | |
| E | | | 0.32 | | | | | 0.32 | 0.25 | 0.41 | | | | | 0.23 | |

TABLE 69-continued

| Lot | D-Asn-AVP (%) | RRT 0.99 (%) | RRT 1.02 (%) | RRT 1.03 (%) | RRT 1.04 (%) | RRT 1.05 (%) | RRT 1.06 (%) | Gly9-AVP (%) | Asp5-AVP (%) | Glu4-AVP (%) | RRT 1.09 (%) | RRT 1.10 (%) | RRT 1.095 (%) | RRT 1.12 (%) | RRT 1.13 (%) | RRT 1.14 (%) |
|---|---|---|---|---|---|---|---|---|---|---|---|---|---|---|---|---|
| E |  |  | 0.28 |  |  |  |  | 1.06 | 0.39 | 1.21 |  |  |  |  | 0.29 |  |
| F | 0.17 |  | 0.36 |  | 0.12 |  |  | 0.17 | 0.14 | 0.20 |  |  |  |  |  |  |
| F | 0.17 |  | 0.35 |  |  |  |  | 0.36 | 0.18 | 0.41 |  |  |  |  | 0.11 |  |
| F | 0.14 |  | 0.29 |  |  |  |  | 1.06 | 0.34 | 1.13 |  |  |  |  |  |  |
| G |  |  | 0.36 |  |  |  |  |  | 0.17 | 0.26 |  |  |  |  |  |  |
| G |  |  | 0.45 |  |  |  |  |  | 0.18 | 0.25 |  |  |  |  | 0.20 |  |
| G |  |  | 0.68 |  |  |  |  | 0.38 | 0.33 | 0.52 |  |  |  |  |  |  |
| H |  |  | 0.37 |  |  |  |  | 0.07 | 0.11 | 0.16 |  |  |  |  |  |  |
| H | 0.15 |  | 0.45 |  |  |  |  | 0.15 |  | 0.24 |  |  |  |  | 0.13 |  |
| H | 0.17 |  | 0.82 |  |  |  |  | 0.45 | 0.18 | 0.60 |  |  |  |  |  |  |
| A1 | 0.12 | 0.12 |  | 0.25 |  |  |  | 0.08 |  | 0.07 |  |  |  | 0.08 |  |  |
| A1 | 0.11 | 0.12 |  | 0.24 |  |  |  | 0.14 |  | 0.13 |  |  |  | 0.10 |  |  |
| A1 | 0.09 | 0.11 |  | 0.21 |  |  | 0.31 | 0.34 | 0.09 | 0.45 |  |  |  | 0.33 |  |  |
| B1 | 0.11 | 0.12 |  | 0.25 |  |  |  | 0.07 |  | 0.07 |  |  |  | 0.07 |  |  |
| B1 | 0.11 | 0.12 |  | 0.24 |  | 0.07 |  | 0.13 |  | 0.16 |  |  |  | 0.18 |  |  |
| B1 | 0.10 | 0.11 |  | 0.21 |  | 0.33 |  | 0.33 | 0.09 | 0.41 |  |  |  | 0.72 |  |  |
| C1 | 0.12 | 0.13 |  | 0.26 |  |  |  | 0.08 |  | 0.10 |  |  |  | 0.08 |  |  |
| C1 | 0.11 | 0.13 |  | 0.25 |  |  |  | 0.18 |  | 0.18 |  |  |  | 0.10 |  |  |
| C1 | 0.11 | 0.12 |  | 0.23 |  |  | 0.27 | 0.52 | 0.13 | 0.64 |  |  |  | 0.10 |  |  |
| A | 0.10 |  | 0.55 |  |  |  |  | 0.43 | 0.66 | 0.26 |  |  |  | 0.54 |  |  |
| A | 0.06 |  | 0.38 |  |  |  |  | 0.81 | 0.66 | 0.90 |  |  |  | 0.05 |  |  |
| A |  |  | 0.26 |  |  |  |  | 2.40 | 0.87 |  |  |  |  | 0.19 |  |  |
| B | 0.14 |  | 0.36 |  |  |  |  | 0.20 | 0.18 | 0.27 |  |  |  | 0.13 |  |  |
| B | 0.12 |  | 0.30 |  |  |  |  | 0.68 | 0.31 | 0.77 |  |  |  | 0.07 |  |  |
| B | 0.20 |  | 0.32 |  |  |  |  | 2.42 | 0.74 | 2.51 |  |  |  |  |  |  |
| C |  |  | 0.37 |  |  |  |  | 0.15 | 0.21 | 0.21 | 0.05 |  |  | 0.22 |  |  |
| C | 0.10 |  | 0.88 |  |  |  |  | 0.29 | 0.17 | 0.49 |  |  |  | 0.15 |  |  |
| C | 0.14 |  | 2.08 |  |  |  |  | 1.00 | 0.46 | 1.42 |  |  |  |  |  |  |
| D | 0.14 |  | 0.52 |  |  |  |  | 0.19 | 0.11 | 0.21 |  |  |  | 0.11 |  |  |
| D | 0.13 |  | 1.04 |  |  |  |  | 0.38 | 0.21 | 0.50 |  |  |  | 0.16 |  |  |
| D | 0.13 |  | 2.15 |  |  |  |  | 1.03 | 0.50 | 1.41 |  |  |  |  |  |  |
| E |  |  | 0.44 |  |  |  |  | 0.25 | 0.27 | 0.24 |  |  |  | 0.30 |  |  |
| E |  |  | 0.41 |  |  |  |  | 0.71 | 0.33 | 0.73 |  |  |  | 0.24 |  |  |
| E |  |  | 0.23 |  |  |  |  | 2.09 | 0.58 | 2.38 |  |  |  |  |  |  |
| F | 0.11 |  | 0.34 |  |  |  |  | 0.17 | 0.11 | 0.19 |  |  |  | 0.09 |  |  |
| F | 0.19 |  | 0.33 |  |  |  |  | 0.58 | 0.25 | 0.60 |  |  |  | 0.07 |  |  |
| F | 0.14 |  | 0.24 |  |  |  |  | 2.08 | 0.63 | 2.06 |  |  |  |  |  |  |
| G | 0.06 |  | 0.38 |  |  |  |  | 0.16 | 0.22 | 0.20 |  |  |  | 0.17 |  |  |
| G |  |  | 0.54 |  |  |  |  | 0.28 | 0.20 | 0.34 |  |  |  | 0.11 |  |  |
| G | 0.12 |  | 0.90 |  |  |  |  | 0.83 | 0.57 | 1.18 |  |  |  |  |  |  |
| H | 0.21 |  | 0.54 |  |  |  |  | 0.21 | 0.10 | 0.19 |  |  |  | 0.12 |  |  |
| H | 0.22 |  | 0.69 |  |  |  |  | 0.30 | 0.10 | 0.32 |  |  |  | 0.14 |  |  |
| H | 0.16 |  | 0.91 |  |  |  |  | 0.74 | 0.29 | 1.05 |  |  |  |  |  |  |
| A1 | 0.11 | 0.14 |  | 0.24 |  |  |  | 0.08 |  | 0.08 |  |  |  |  |  |  |
| A1 | 0.13 | 0.14 |  | 0.23 |  | 0.18 |  | 0.20 |  | 0.20 |  |  |  |  |  |  |
| A1 | 0.10 | 0.12 |  | 0.21 | 0.50 |  |  | 0.56 | 0.14 | 0.67 |  |  |  | 0.10 |  |  |
| B1 | 0.12 | 0.12 |  | 0.24 |  |  |  | 0.08 |  | 0.08 |  |  |  |  |  |  |
| B1 | 0.12 | 0.13 |  | 0.23 | 0.18 |  |  | 0.20 | 0.04 | 0.21 |  |  |  |  |  |  |
| B1 | 0.10 | 0.11 |  | 0.20 |  | 0.52 |  | 0.55 | 0.15 | 0.73 |  |  |  | 0.06 |  |  |
| C1 | 0.12 | 0.13 |  | 0.25 |  |  |  | 0.10 | 0.09 |  |  |  |  |  |  |  |
| C1 | 0.14 | 0.13 |  | 0.24 |  |  |  | 0.28 |  | 0.29 |  |  |  |  |  |  |
| C1 | 0.10 | 0.13 |  | 0.21 |  | 0.43 |  | 0.89 | 0.22 | 1.14 |  |  |  | 0.07 |  |  |
| A | 0.10 |  | 0.29 |  |  |  |  | 0.31 | 0.52 | 0.36 |  |  |  | 0.62 |  |  |
| A | 0.10 |  |  |  |  |  |  | 0.97 | 0.62 | 1.17 |  |  |  | 0.19 |  |  |
| A | 0.09 |  |  |  |  |  |  | 3.45 | 1.20 | 3.64 |  |  |  | 0.20 |  |  |
| B | 0.11 |  |  |  |  |  |  | 0.25 | 0.21 | 0.31 |  |  |  | 0.11 | 0.06 |  |
| B | 0.12 |  |  |  |  |  |  | 0.94 | 0.37 | 1.13 |  |  |  | 0.22 |  |  |
| B | 0.09 |  |  |  |  |  |  | 3.37 | 0.88 | 0.36 |  |  |  | 0.22 |  |  |
| C | 0.09 |  |  |  |  |  |  | 0.15 | 0.10 | 0.20 |  |  |  | 0.15 |  |  |
| C | 0.10 |  | 0.93 |  |  |  |  | 0.45 | 0.24 | 0.61 |  |  |  | 0.19 |  |  |
| C | 0.08 |  | 2.15 |  |  |  |  | 1.29 | 0.66 | 2.00 |  |  |  |  |  |  |
| D |  |  |  |  |  |  |  |  | 5.25 | 0.31 |  |  |  | 0.16 |  |  |
| D | 0.10 |  | 1.05 |  |  |  |  | 0.46 | 0.23 | 0.66 |  |  |  | 0.11 |  |  |
| D | 0.09 |  | 2.18 |  |  |  |  | 1.29 | 0.56 | 1.77 |  |  |  |  |  |  |
| E |  |  | 0.82 |  |  |  |  | 0.30 | 0.22 | 0.27 |  |  |  | 0.28 |  |  |
| E | 0.09 |  |  |  |  |  |  | 0.87 | 0.47 | 0.99 |  |  |  | 0.21 |  |  |
| E | 0.09 |  |  |  |  |  |  | 2.93 | 0.77 | 3.30 |  |  |  |  |  |  |
| F | 0.11 |  |  |  |  |  |  | 0.22 | 0.12 | 0.25 |  |  |  | 0.08 |  |  |
| F | 0.11 |  |  |  |  |  |  | 0.81 | 0.36 | 0.84 |  |  |  | 0.09 |  |  |
| F | 0.09 |  |  |  |  |  |  | 2.79 | 0.73 | 2.91 |  |  |  |  |  |  |
| G | 0.10 |  |  |  |  |  |  | 0.14 | 0.15 | 0.15 |  |  |  | 0.13 |  |  |
| G | 0.10 |  |  |  |  |  |  | 0.37 | 0.34 | 0.53 |  |  |  | 0.12 |  |  |
| G |  |  | 0.73 |  |  |  |  | 0.89 | 0.64 | 1.22 |  |  |  | 0.07 |  |  |
| H | 0.11 |  |  |  |  |  |  | 0.11 | 0.06 | 0.16 |  |  |  | 0.08 |  |  |
| H | 0.09 |  |  |  |  |  |  | 0.31 | 0.08 | 0.43 |  |  |  | 0.08 |  |  |
| H |  |  | 0.69 |  |  |  |  | 0.86 | 0.34 | 1.26 |  |  |  |  |  |  |

TABLE 69-continued

| Lot | D-Asn-AVP (%) | RRT 0.99 (%) | RRT 1.02 (%) | RRT 1.03 (%) | RRT 1.04 (%) | RRT 1.05 (%) | RRT 1.06 (%) | Gly9-AVP (%) | Asp5-AVP (%) | Glu4-AVP (%) | RRT 1.09 (%) | RRT 1.10 (%) | RRT 1.095 (%) | RRT 1.12 (%) | RRT 1.13 (%) | RRT 1.14 (%) |
|---|---|---|---|---|---|---|---|---|---|---|---|---|---|---|---|---|
| A |  |  | 0.33 |  |  |  |  | 0.18 | 0.22 | 0.07 | 0.18 |  |  | 0.25 |  |  |
| A |  |  | 0.29 |  |  |  |  | 1.14 | 0.31 | 1.24 |  |  | 0.17 |  |  |  |
| A |  |  | 0.27 |  |  |  |  | 4.38 | 1.21 | 4.48 |  |  |  |  |  |  |
| B | 0.12 |  | 0.32 |  |  |  |  | 0.19 | 0.14 | 0.15 |  |  |  |  |  |  |
| B | 0.14 |  | 0.30 |  |  |  |  | 1.16 | 0.34 | 0.95 |  |  |  |  | 0.05 |  |
| B | 0.14 |  | 0.27 |  |  |  |  | 4.31 | 1.01 | 4.71 |  |  |  |  |  | 0.06 |
| C |  |  | 0.38 |  |  |  |  | 0.10 | 0.12 | 0.08 |  |  |  |  | 0.09 |  |
| C |  |  | 0.38 | 0.95 |  |  |  | 0.51 | 0.26 | 0.48 |  |  |  |  |  |  |
| C |  |  |  | 2.09 |  |  |  | 1.48 | 0.68 | 2.32 |  |  |  |  |  |  |
| D | 0.14 |  | 0.42 |  |  |  |  | 0.13 | 0.07 | 0.09 |  |  |  |  |  |  |
| D | 0.16 |  | 0.41 | 0.94 |  |  |  | 0.53 | 0.34 | 0.52 |  |  |  |  |  |  |
| D |  |  |  | 2.10 |  |  |  | 1.47 | 0.54 | 2.29 |  |  |  |  |  |  |
| E |  |  | 0.32 |  |  |  |  | 0.17 | 0.21 | 0.09 |  |  |  | 0.17 |  |  |
| E |  |  | 0.29 |  |  |  |  | 1.02 | 0.34 | 1.29 |  |  |  |  |  |  |
| E |  |  | 0.24 |  |  |  |  | 3.78 | 0.89 | 4.08 |  |  |  |  |  |  |
| F | 0.14 |  | 0.32 |  |  |  |  | 0.19 | 0.06 | 0.15 |  |  |  |  |  |  |
| F | 0.12 |  | 0.29 |  |  |  |  | 0.95 | 0.26 | 1.08 |  |  |  |  |  |  |
| F | 0.14 |  | 0.27 |  |  |  |  | 3.55 | 0.84 | 3.64 |  |  |  |  |  |  |
| G |  |  | 0.36 |  |  |  |  | 0.11 |  | 0.07 |  |  |  | 0.10 |  |  |
| G |  |  | 0.48 | 0.18 |  |  |  | 0.39 | 0.17 | 0.37 |  |  |  |  |  |  |
| G |  |  | 0.43 | 0.47 |  |  |  | 1.06 | 0.42 | 1.66 |  |  | 0.17 |  |  |  |
| H | 0.16 |  | 0.39 |  |  |  |  | 0.11 |  | 0.09 |  |  |  |  |  |  |
| H | 0.23 |  | 0.46 | 0.21 |  |  |  | 0.45 | 0.39 | 0.61 |  |  |  |  |  |  |
| H | 0.18 |  | 0.45 | 0.52 |  |  |  | 1.08 | 0.48 | 1.72 |  |  |  |  |  |  |
| A | 0.15 |  | 0.51 |  |  |  |  | 0.26 | 0.62 | 0.27 |  | 0.24 |  |  |  |  |
| A | 0.14 |  | 0.52 |  |  |  |  | 1.41 | 0.40 | 1.71 |  | 0.28 |  |  |  |  |
| B | 0.19 |  | 0.49 |  | 0.06 |  |  | 0.27 | 0.24 | 0.28 |  |  |  |  |  |  |
| B | 0.20 |  | 0.55 |  |  |  |  | 1.53 | 0.38 | 1.54 |  | 0.37 |  |  |  |  |
| C |  |  | 0.64 |  |  |  |  | 0.13 | 0.20 | 0.16 |  |  |  |  |  |  |
| C | 0.16 |  | 1.86 |  |  |  |  | 0.69 | 0.20 | 0.75 |  | 0.24 |  |  |  |  |
| D | 0.14 |  | 0.66 |  |  |  |  | 0.18 | 0.20 | 0.18 |  |  |  |  |  |  |
| D | 0.15 |  | 1.76 |  |  |  |  | 0.72 | 0.25 | 0.80 |  | 0.16 |  |  |  |  |
| E | 0.19 |  | 0.43 |  |  |  |  | 0.25 | 0.40 | 0.27 |  |  |  |  |  |  |
| E |  |  | 0.35 |  |  |  |  | 1.24 | 0.55 | 1.37 |  |  |  |  |  |  |
| F | 0.16 |  | 0.41 |  |  |  |  | 0.26 | 0.18 | 0.29 |  |  |  |  |  |  |
| F | 0.12 |  | 0.38 |  |  |  |  | 1.15 | 0.39 | 1.23 |  |  |  |  |  |  |
| G | 0.10 |  | 0.41 |  |  |  |  | 0.12 | 0.21 | 0.17 |  |  |  |  |  |  |
| G |  |  | 0.74 |  |  |  |  | 0.52 | 0.11 | 0.68 |  | 0.24 |  |  |  |  |
| H | 0.11 |  | 0.44 |  |  |  |  | 0.12 | 0.14 | 0.17 |  |  |  |  |  |  |
| H | 0.13 |  | 0.77 |  |  |  |  | 0.51 | 0.16 | 0.60 |  | 0.16 |  |  |  |  |
| A | 0.12 | 0.13 |  |  | 0.27 |  | 0.09 | 0.84 |  | 0.22 |  |  |  |  |  |  |
| A | 0.10 | 0.13 |  |  | 0.24 |  |  | 1.84 | 0.31 | 1.57 |  |  |  | 0.15 |  |  |
| A |  |  | 0.30 |  |  |  |  | 0.21 | 0.48 | 0.13 |  |  |  |  |  |  |
| A |  |  | 0.75 |  |  |  |  | 1.62 | 0.45 | 1.38 |  |  |  |  |  |  |
| B | 0.13 | 0.13 |  |  | 0.25 |  | 0.07 | 0.77 |  | 0.22 |  |  |  |  |  |  |
| B | 0.12 | 0.13 |  |  | 0.23 |  |  | 1.67 | 0.33 | 1.61 |  |  |  |  |  |  |
| B | 0.19 |  | 0.33 |  |  |  |  | 0.24 | 0.56 | 0.20 |  |  |  |  |  |  |
| B | 0.12 |  | 0.37 |  |  |  |  | 1.64 | 0.42 | 1.73 |  |  |  |  |  |  |
| C | 0.12 | 0.13 | 0.24 |  |  |  |  | 0.21 | 0.22 | 0.14 |  |  |  | 0.10 |  |  |
| C | 0.12 | 0.13 |  |  | 0.20 |  |  | 0.90 | 0.12 | 0.77 |  |  |  |  |  |  |
| C | 0.16 |  | 0.90 |  |  | 1.31 |  | 0.25 | 0.34 | 0.31 |  |  |  |  |  |  |
| C |  |  | 1.70 |  |  |  |  | 0.71 | 0.40 | 0.79 |  |  |  |  |  |  |
| D | 0.13 | 0.13 |  |  | 0.23 |  | 0.12 | 0.28 |  | 0.13 |  |  |  | 0.06 |  |  |
| D | 0.11 | 0.13 |  |  | 0.21 | 1.32 |  | 0.81 | 0.13 | 0.79 |  |  |  | 0.05 |  |  |
| D | 0.15 |  | 0.46 |  |  |  |  | 0.19 | 0.16 | 0.14 |  |  |  |  |  |  |
| D | 0.15 |  | 1.72 |  |  |  |  | 0.75 | 0.33 | 0.83 |  |  |  |  |  |  |
| E | 0.11 | 0.13 |  |  | 0.25 |  | 0.12 | 0.86 |  | 0.20 |  |  |  | 0.06 |  |  |
| E | 0.12 |  |  |  | 0.24 |  |  | 1.65 | 0.25 | 1.41 |  |  |  |  |  |  |
| E |  |  | 0.30 |  | 0.09 |  |  | 0.21 | 0.66 | 0.20 |  |  |  |  |  |  |
| E |  |  | 0.34 |  |  |  |  | 1.44 | 0.59 | 1.51 |  |  |  |  |  |  |
| F | 0.15 | 0.14 |  |  | 0.25 |  | 0.06 | 0.30 |  | 0.20 |  |  |  | 0.06 |  |  |
| F | 0.12 | 0.12 |  |  | 0.25 |  |  | 1.36 | 0.26 | 1.30 |  |  |  | 0.05 |  |  |
| F | 0.17 |  | 0.35 |  |  |  |  | 0.25 | 0.13 | 0.21 |  |  |  |  |  |  |
| F | 0.19 |  | 0.36 |  |  |  |  | 0.39 | 1.30 | 1.40 |  |  |  |  |  |  |
| G | 0.13 | 0.14 |  |  | 0.24 |  |  | 0.39 |  | 0.11 |  |  |  | 0.13 |  |  |
| G | 0.12 | 0.14 |  |  | 0.22 | 0.33 |  | 0.72 | 0.09 | 0.64 |  |  |  |  |  |  |
| G |  |  | 0.36 |  |  |  |  | 0.17 | 0.19 | 0.12 |  |  |  |  |  |  |
| G | 0.27 |  | 0.76 |  |  |  |  | 0.33 | 0.58 | 0.54 |  |  |  |  |  |  |
| H | 0.12 | 0.13 |  |  | 0.24 |  |  | 0.24 |  | 0.12 |  |  |  | 0.05 |  |  |
| H | 0.13 | 0.13 |  |  | 0.22 | 0.39 |  | 0.59 | 0.09 | 0.56 |  |  |  | 0.06 |  |  |
| H | 0.18 |  | 0.43 |  |  |  |  | 0.21 | 0.15 | 0.16 |  |  |  |  |  |  |
| H | 0.15 |  | 0.81 |  |  |  |  | 0.30 | 0.56 | 0.61 |  |  |  |  |  |  |
| Min | 0.057 |  | 0.234 |  |  | 0.055 |  | 0.079 | 0.042 | 0.071 | 0.182 |  |  | 0.051 | 0.059 |  |
| Max | 0.231 |  | 2.177 |  |  | 0.501 |  | 4.376 | 5.246 | 4.713 | 0.182 |  |  | 0.622 | 0.1 |  |

TABLE 70

| Lot | RRT 1.16 (%) | RRT 1.168 (%) | RRT 1.19 (%) | RRT 1.20 (%) | RRT 1.206 (%) | RRT 1.23 (%) | RRT 1.24 (%) | RRT 1.25 (%) | RRT 1.26 (%) | RRT 1.27 (%) | AVP Dimer (%) | Acetyl-AVP (%) | RRT 1.32 (%) | RRT 1.33 (%) | RRT 1.34 (%) | RRT 1.35 (%) |
|---|---|---|---|---|---|---|---|---|---|---|---|---|---|---|---|---|
| A | | | 0.33 | | | | | | | | | 0.35 | | | | |
| A | | | 0.33 | | | | | | | | | 0.35 | | | | |
| A | | | 0.33 | | | | | | | | | 0.35 | | | | |
| B | | | 0.07 | | | | | | | | | 0.33 | | | | |
| B | | | 0.07 | | | | | | | | | 0.33 | | | | |
| B | | | 0.07 | | | | | | | | | 0.33 | | | | |
| C | | | 0.22 | | | | | | | | | 0.22 | | | | |
| C | | | 0.22 | | | | | | | | | 0.22 | | | | |
| C | | | 0.22 | | | | | | | | | 0.22 | | | | |
| D | | | 0.08 | | | | | | | | | 0.23 | | | | |
| D | | | 0.08 | | | | | | | | | 0.23 | | | | |
| D | | | 0.08 | | | | | | | | | 0.23 | | | | |
| E | | | 0.55 | | | | | | | | | 0.53 | | | | |
| E | | | 0.55 | | | | | | | | | 0.53 | | | | |
| E | | | 0.55 | | | | | | | | | 0.53 | | | | |
| F | | | | | | | | | | | | 0.34 | | | | |
| F | | | | | | | | | | | | 0.34 | | | | |
| F | | | | | | | | | | | | 0.34 | | | | |
| G | | | | | | | | | | | | 0.23 | | | | |
| G | | | | | | | | | | | | 0.23 | | | | |
| G | | | | | | | | | | | | 0.23 | | | | |
| H | | | | | | | | | | | | 0.23 | | | | |
| H | | | | | | | | | | | | 0.23 | | | | |
| H | | | | | | | | | | | | 0.23 | | | | |
| A1 | | | | | | | 0.21 | | | | | 0.28 | | | | |
| A1 | | | | | | | 0.21 | | | | | 0.28 | | | | |
| A1 | | | | | | | 0.21 | | | | | 0.28 | | | | |
| B1 | | | | | | | 0.21 | | | | | 0.29 | | | | |
| B1 | | | | | | | 0.21 | | | | | 0.29 | | | | |
| B1 | | | | | | | 0.21 | | | | | 0.29 | | | | |
| C1 | | | | | | | 0.14 | | | | | 0.29 | | | | |
| C1 | | | | | | | 0.14 | | | | | 0.29 | | | | |
| C1 | | | | | | | 0.14 | | | | | 0.29 | | | | |
| A | | | | 0.37 | | | | | | | | 0.22 | | | 0.13 | |
| A | | | | | | | | | | | 0.20 | 0.60 | | | | |
| A | | | | | | | | | | | | 0.59 | | | | |
| B | | | | 0.26 | | | | | | | | 0.35 | | | | |
| B | | | | | | | | | | | | 0.49 | | | | |
| B | | | | | | | | | | | | 0.48 | | | | |
| C | | | | | | | | | | | | 0.24 | | | | |
| C | | | | | 0.46 | | | | | | | 0.26 | | | | |
| C | | | | | 0.44 | | | | 0.73 | | | 0.25 | | | | |
| D | | | | 0.07 | | | | | | | | 0.22 | | | | |
| D | | | | | 0.35 | | | | | | | 0.25 | | | | |
| D | | | | | 0.41 | | | | | | | 0.27 | | | | |
| E | | | | 0.12 | | | | | | | | 0.43 | | | | |
| E | | | | | | | | | | | | 0.72 | | | | |
| E | | | | | | | | | | | | 0.68 | | | | |
| F | | | | 0.07 | | | | | | | | 0.35 | | | | |
| F | | | | | | | | | | | | 0.55 | | | | |
| F | | | | | | | | | | | | 0.53 | | | | |
| G | | | | | | | | | | | | 0.29 | | | | |
| G | | | | | 0.54 | | | | | | | 0.27 | | | | |
| G | | | | | 0.54 | | | | | | | 0.40 | | | | |
| H | | | | | | | | | | | | 0.21 | | | 0.12 | |
| H | | | | | 0.56 | | | | | | | 0.17 | | | | |
| H | | | | | 0.55 | | | | | | | 0.17 | | | | |
| A1 | | | | | | | 0.23 | | | | | 0.28 | | | | |
| A1 | | | | | | | 0.21 | | | | | 0.27 | | | | |
| A1 | | | | | | | 0.25 | | | | | 0.27 | | | | |
| B1 | | | | | | | 0.22 | | | | | 0.28 | | | | |
| B1 | | | | | | 0.21 | | | | | | 0.28 | | | | |
| B1 | | | | | | | 0.13 | | | | | 0.27 | | | | |
| C1 | | | | | | | 0.14 | | | | | 0.27 | | | | |
| C1 | | | | | | | 0.15 | | | | | 0.28 | | | | |
| C1 | | | | | | | 0.15 | | | | | 0.28 | | | | |
| A | | | | | | | | | | | 0.58 | 0.47 | | | | |
| A | | | | | | | | | | | | 0.76 | | | | |
| A | 0.06 | | | | | | | | | 0.08 | 0.32 | 0.51 | | | | |
| B | | | | | | | | | | | | 0.34 | | | | |
| B | | | | | | | | | | 0.07 | | 0.51 | | | | |
| B | 0.06 | | | | | | | | | 0.07 | 0.25 | 0.52 | | | | |
| C | | | | | 0.54 | | | | | | 0.25 | 0.26 | | | | |
| C | | | | | 0.58 | | | | | | 0.19 | 0.20 | | | | |
| C | | | | | 0.41 | | | | | | | 0.26 | | | | |
| D | | | | | 0.49 | | | | | | 0.15 | 0.23 | | | | |

TABLE 70-continued

| Lot | RRT 1.16 (%) | RRT 1.168 (%) | RRT 1.19 (%) | RRT 1.20 (%) | RRT 1.206 (%) | RRT 1.23 (%) | RRT 1.24 (%) | RRT 1.25 (%) | RRT 1.26 (%) | RRT 1.27 (%) | AVP Dimer (%) | Acetyl-AVP (%) | RRT 1.32 (%) | RRT 1.33 (%) | RRT 1.34 (%) | RRT 1.35 (%) |
|---|---|---|---|---|---|---|---|---|---|---|---|---|---|---|---|---|
| D |  |  |  | 0.47 |  |  |  |  |  |  | 0.25 | 0.24 |  |  |  |  |
| D |  |  |  | 0.32 |  |  |  |  |  | 0.03 |  | 0.25 |  |  |  |  |
| E |  |  |  |  |  |  |  |  |  |  | 0.34 | 0.40 |  |  |  |  |
| E |  |  |  |  |  |  |  |  |  |  | 0.20 | 0.51 |  |  |  |  |
| E |  |  |  |  |  |  |  |  |  | 0.06 |  | 0.76 |  |  |  |  |
| F |  |  |  |  |  |  |  |  |  |  | 0.12 | 0.33 |  |  |  |  |
| F |  |  |  |  |  |  |  |  |  |  | 0.10 | 0.77 |  |  |  |  |
| F |  |  |  |  |  |  |  |  |  | 0.04 |  | 0.58 |  |  |  |  |
| G |  |  |  | 0.62 |  |  |  |  |  |  | 0.25 | 0.23 |  |  |  |  |
| G |  |  |  | 0.62 |  |  |  |  |  |  | 0.18 |  |  |  |  |  |
| G |  |  |  | 0.52 |  |  |  |  |  |  |  | 0.25 |  |  |  |  |
| H |  |  |  | 0.56 |  |  |  |  |  |  | 0.09 | 0.42 |  |  |  |  |
| H |  |  |  | 0.59 |  |  |  |  |  |  | 0.16 | 0.38 |  |  |  |  |
| H |  |  |  | 0.56 |  |  |  |  |  |  |  | 0.46 |  |  |  |  |
| A1 |  |  |  |  |  |  | 0.20 |  |  |  |  | 0.30 |  |  |  |  |
| A1 |  |  |  |  |  |  | 0.20 |  |  |  |  | 0.29 |  |  |  |  |
| A1 |  |  |  |  |  |  | 0.28 |  |  |  |  | 0.29 |  |  |  |  |
| B1 |  |  |  |  |  |  | 0.23 |  |  |  |  | 0.32 |  |  |  |  |
| B1 |  |  |  |  |  |  | 0.23 |  |  |  |  | 0.28 |  |  |  |  |
| B1 |  |  |  |  |  |  | 0.12 |  |  |  |  | 0.28 |  |  |  |  |
| C1 |  |  |  |  |  |  | 0.13 |  |  |  |  | 0.28 |  |  |  |  |
| C1 |  |  |  |  |  |  | 0.13 |  |  |  |  | 0.32 |  |  |  |  |
| C1 |  |  |  |  |  |  | 0.16 |  |  |  |  | 0.28 |  |  |  |  |
| A |  |  |  | 0.08 |  |  |  |  |  |  | 0.62 | 0.55 |  |  |  |  |
| A |  |  |  |  |  |  |  |  |  |  | 0.32 | 0.80 |  |  |  |  |
| A | 0.14 |  |  |  |  |  |  |  |  |  | 0.21 | 0.51 |  |  |  |  |
| B |  |  |  |  |  |  |  |  |  |  | 0.18 | 0.42 |  |  |  |  |
| B |  |  |  |  |  |  |  |  |  |  | 0.45 | 0.64 |  |  |  |  |
| B | 0.13 |  |  |  |  |  |  |  |  |  | 0.22 | 0.49 |  | 0.05 |  |  |
| C |  |  |  | 0.42 |  |  |  |  |  |  |  | 0.27 |  |  |  |  |
| C |  |  |  | 0.39 |  |  |  |  |  |  | 0.31 | 0.28 |  |  |  |  |
| C |  |  |  | 0.38 |  |  |  |  |  |  | 0.19 | 0.29 |  |  |  |  |
| D |  |  |  | 0.37 |  |  |  |  |  |  |  | 0.21 |  |  |  |  |
| D |  |  |  | 0.40 |  |  |  |  |  |  | 0.15 | 0.23 |  |  |  |  |
| D |  |  |  | 0.39 |  |  |  |  |  |  | 0.09 | 0.24 |  |  |  |  |
| E |  |  |  |  |  |  |  |  |  |  | 0.19 | 0.31 |  |  |  |  |
| E |  |  |  |  |  |  |  |  |  |  | 0.25 | 0.93 |  |  |  |  |
| E | 0.10 |  |  |  |  |  |  |  |  |  | 0.22 | 0.77 |  |  |  |  |
| F |  |  |  |  |  |  |  |  |  |  | 0.23 | 0.51 |  |  |  |  |
| F |  |  |  |  |  |  |  |  |  |  |  | 0.69 |  |  |  |  |
| F | 0.09 |  |  |  |  |  |  |  |  |  | 0.07 | 0.51 |  |  |  |  |
| G |  |  |  | 0.52 |  |  |  |  |  |  | 0.22 | 0.24 |  |  |  |  |
| G |  |  |  | 0.52 |  |  |  |  |  |  | 0.32 | 0.24 |  |  |  |  |
| G |  |  |  | 0.51 |  |  |  |  |  |  | 0.06 | 0.46 |  |  |  |  |
| H |  |  |  | 0.53 |  |  |  |  |  |  | 0.04 | 0.46 |  |  |  |  |
| H |  |  |  | 0.53 |  |  |  |  |  |  |  | 0.42 |  |  |  |  |
| H |  |  |  | 0.55 |  |  |  |  |  |  |  | 0.50 |  |  |  |  |
| A |  |  |  |  |  |  |  |  |  |  | 0.29 | 0.43 |  |  |  |  |
| A |  |  |  |  |  |  |  |  |  |  |  | 0.55 |  |  |  |  |
| A |  | 0.23 |  |  |  |  |  |  |  |  | 0.11 | 0.58 |  |  |  |  |
| B |  |  |  |  |  |  |  |  |  |  | 0.10 | 0.39 |  |  |  |  |
| B |  |  |  |  |  |  |  |  |  |  | 0.24 | 0.31 |  |  |  |  |
| B |  | 0.24 |  |  |  |  |  | 0.13 |  |  | 0.14 | 0.50 |  |  |  |  |
| C |  |  |  |  |  | 0.35 |  |  |  |  | 0.44 | 0.21 |  |  |  |  |
| C |  |  |  |  |  | 0.42 |  | 0.95 |  |  |  | 0.22 |  |  |  |  |
| C |  |  |  |  |  | 0.39 |  |  |  |  | 0.49 | 0.24 |  |  |  |  |
| D |  |  |  |  |  | 0.39 |  |  |  |  | 0.11 | 0.22 |  |  |  |  |
| D |  |  |  |  |  | 0.39 |  | 0.82 |  |  |  | 0.24 |  |  |  |  |
| D |  |  |  |  |  | 0.38 |  | 0.70 |  |  |  | 0.25 |  |  |  |  |
| E |  |  |  |  |  |  |  |  |  |  | 0.23 | 0.50 |  |  |  |  |
| E |  |  |  |  |  |  |  |  |  |  | 0.57 | 0.88 |  |  |  |  |
| E |  | 0.18 |  |  |  |  |  |  |  |  | 0.17 | 0.73 |  |  |  |  |
| F |  |  |  |  |  |  |  |  |  |  | 0.26 | 0.32 |  |  |  |  |
| F |  |  |  |  |  |  |  |  |  | 0.08 | 0.07 | 0.74 |  |  |  |  |
| F |  |  | 0.15 |  |  |  |  |  |  |  | 0.09 | 0.59 |  |  |  |  |
| G |  |  |  | 0.49 |  |  |  |  |  |  | 0.21 | 0.21 |  |  |  |  |
| G |  |  |  | 0.51 |  |  |  |  |  |  | 0.48 | 0.23 |  |  |  |  |
| G |  |  |  | 0.49 |  |  |  | 0.14 |  |  |  | 0.19 |  |  |  |  |
| H |  |  |  | 0.51 |  |  |  |  |  |  | 0.12 | 0.38 |  |  |  |  |
| H |  |  |  | 0.54 |  |  |  | 0.80 |  |  |  | 0.45 |  |  |  |  |
| H |  |  |  | 0.53 |  |  |  |  |  |  | 0.30 | 0.49 |  |  |  |  |
| A |  |  |  | 0.22 |  |  |  |  |  |  |  | 0.56 |  |  |  |  |
| A |  |  |  | 0.14 |  | 0.21 |  |  |  |  |  | 0.70 |  |  |  |  |
| B |  |  |  | 0.08 |  |  |  |  |  |  |  | 0.41 |  |  |  |  |
| B |  |  |  | 0.21 |  | 0.12 |  |  |  |  |  | 0.53 |  |  |  |  |
| C |  |  |  | 0.65 |  |  |  |  |  |  |  | 0.21 |  |  |  |  |

TABLE 70-continued

| Lot | RRT 1.16 (%) | RRT 1.168 (%) | RRT 1.19 (%) | RRT 1.20 (%) | RRT 1.206 (%) | RRT 1.23 (%) | RRT 1.24 (%) | RRT 1.25 (%) | RRT 1.26 (%) | RRT 1.27 (%) | AVP Dimer (%) | Acetyl-AVP (%) | RRT 1.32 (%) | RRT 1.33 (%) | RRT 1.34 (%) | RRT 1.35 (%) |
|---|---|---|---|---|---|---|---|---|---|---|---|---|---|---|---|---|
| C | | | | 0.17 | | | | | | | | 0.21 | | | | |
| D | | | | 0.38 | | | | | | | | 0.22 | | | | |
| D | | | | 0.53 | | | | | | | | 0.23 | | | | |
| E | | | | 0.16 | | 0.14 | | | | | | 0.46 | | | | |
| E | | | | 0.11 | | 0.19 | | | | | | 0.99 | | | | 0.10 |
| F | | | | 0.06 | | 0.13 | | | | | | 0.45 | | | | |
| F | | | | 0.07 | | 0.12 | | | | | | 0.65 | | | | 0.07 |
| G | | | | 0.80 | | | | | | | | 0.21 | | | | |
| G | | | | 0.42 | | | | | | | | 0.23 | | | | 0.15 |
| H | | | | 0.48 | | | | | | | | 0.20 | | | 0.15 | |
| H | | | | 0.67 | | | | | | | | 0.21 | | | | 0.12 |
| A | | 0.22 | | | | 0.37 | | | | | | 0.25 | | | | |
| A | | 0.29 | | | | | | | | | | 0.23 | | | | |
| A | 0.30 | | | | | | | | | | | 0.54 | | | | |
| A | | | | | | | | | | | | 0.69 | | | | |
| B | | 0.17 | | | | 0.41 | | | | | | 0.23 | | | | |
| B | | 0.14 | | | | | | | | | | 0.22 | | | | |
| B | 0.34 | | | | | | | | | | | 0.28 | | | | |
| B | | | | | | | | | | | | 0.52 | | | | |
| C | | | | | | | | | | | 0.24 | 0.34 | | | | |
| C | | 0.29 | | | | 0.37 | | | | | | 0.25 | | | | |
| C | | 0.19 | | | | | | | | | | 0.25 | | | | |
| C | | | | | 0.42 | | | | | | | 0.21 | | | | |
| D | | | | | | 0.24 | | | | | | 0.22 | | | | |
| D | | 0.20 | | | | 0.26 | | | | | | 0.23 | | | | |
| D | | | | | 0.30 | | | | | | | 0.20 | | | | |
| D | | | | | 0.37 | | | | | | | 0.23 | | | | |
| E | | 0.32 | | | | 0.57 | | | | | | 0.22 | | | | |
| E | | 0.23 | | | | 0.18 | | | | | | 0.20 | | | | |
| E | 0.43 | | | | | | | | | | | 0.65 | | | | |
| E | 0.16 | | | | | | | | | | | 0.91 | | | | |
| F | | 0.14 | | | | 0.14 | | | | | | 0.21 | | | | |
| F | | 0.14 | | | | 0.09 | | | | | | 0.21 | | | | |
| F | | | | | | | | | | | | 0.44 | | | | |
| F | | | | | | | | | | | | 0.70 | 0.08 | | | |
| G | | 0.33 | | | | 0.39 | | | | | | 0.22 | | | | |
| G | | 0.26 | | | | 0.35 | | | | | | 0.23 | | | | |
| G | | | | | 0.37 | | | | | | | 0.24 | | | | |
| G | 0.37 | | | | | | | | | | | 0.20 | | | | |
| H | | 0.14 | | | | 0.32 | | | | | | 0.22 | | | 0.16 | |
| H | | 0.14 | | | | 0.33 | | | | | | 0.21 | | | 0.23 | |
| H | | | | | | 0.40 | | | | | | 0.19 | 0.18 | | | |
| H | 0.42 | | | | | | | | | | | 0.21 | 0.20 | | | |
| Min | 0.086 | | 0 | 0.057 | | | | 0 | 0.034 | 0.042 | | 0.193 | | | 0.047 | 0.147 |
| Max | 0.341 | | 0 | 0.796 | | | | 0 | 0.061 | 0.623 | | 0.986 | | | 0.047 | 0.147 |

TABLE 71

| Lot | RRT 1.37 (%) | RRT 1.44 (%) | RRT 1.45 (%) | RRT 1.46 (%) | RRT 1.47 (%) | RRT 1.48 (%) | RRT 1.55 (%) | RRT 1.57 (%) | RRT 1.59 (%) | RRT 1.62 (%) | RRT 1.68 (%) | RRT 1.70 (%) | RRT 1.71 (%) | RRT 1.72 (%) | RRT 1.80 (%) | RRT 1.82 (%) |
|---|---|---|---|---|---|---|---|---|---|---|---|---|---|---|---|---|
| A | | | | 0.32 | | | | | | | | | | | | |
| A | | | | 0.32 | | | | | | | | | | | | |
| A | | | | 0.32 | | | | | | | | | | | | |
| B | | | | 0.18 | | | | | | | | | | | | |
| B | | | | 0.18 | | | | | | | | | | | | |
| B | | | | 0.18 | | | | | | | | | | | | |
| C | | | | | | | | | | | | | | 0.15 | | |
| C | | | | | | | | | | | | | | 0.15 | | |
| C | | | | | | | | | | | | | | 0.15 | | |
| D | | | | | | | | | | | | | | 0.16 | | |
| D | | | | | | | | | | | | | | 0.16 | | |
| D | | | | | | | | | | | | | | 0.16 | | |
| E | | | | | | | | | | | | | | 0.61 | | |
| E | | | | | | | | | | | | | | 0.61 | | |
| E | | | | | | | | | | | | | | 0.61 | | |
| F | | | | | | | | | | | | | | 0.58 | | |
| F | | | | | | | | | | | | | | 0.58 | | |
| F | | | | | | | | | | | | | | 0.58 | | |
| G | | | | | | | | | | | | | | 1.34 | | |
| G | | | | | | | | | | | | | | 1.34 | | |
| G | | | | | | | | | | | | | | 1.34 | | |

TABLE 71-continued

| Lot | RRT 1.37 (%) | RRT 1.44 (%) | RRT 1.45 (%) | RRT 1.46 (%) | RRT 1.47 (%) | RRT 1.48 (%) | RRT 1.55 (%) | RRT 1.57 (%) | RRT 1.59 (%) | RRT 1.62 (%) | RRT 1.68 (%) | RRT 1.70 (%) | RRT 1.71 (%) | RRT 1.72 (%) | RRT 1.80 (%) | RRT 1.82 (%) |
|---|---|---|---|---|---|---|---|---|---|---|---|---|---|---|---|---|
| H | | | | | | | | | | | | | | 1.05 | | |
| H | | | | | | | | | | | | | | 1.05 | | |
| H | | | | | | | | | | | | | | 1.05 | | |
| A1 | | | | | | | | | | | | | | | | |
| A1 | | | | | | | | | | | | | | | | |
| A1 | | | | | | | | | | | | | | | | |
| B1 | | | | | | | | | | | | | | | | |
| B1 | | | | | | | | | | | | | | | | |
| B1 | | | | | | | | | | | | | | | | |
| C1 | | | | | | | | | | | | | | | | |
| C1 | | | | | | | | | | | | | | | | |
| C1 | | | | | | | | | | | | | | | | |
| A | | | | 0.21 | | | | | | | | | | 2.16 | | |
| A | | | | | | | | | | | | | | | | |
| A | | | | | | | | | | | | | | | | |
| B | | | | | | | | | | | | | | 1.67 | | |
| B | | | | | | | | | | | | | | | | |
| B | | | | | | | | | | | | | | | | |
| C | | | | | | | | | | | | | | 3.37 | | |
| C | | | | | | | | | | | | | | | | |
| C | | | | | | | | | | | | | | | | |
| D | | | | | | | | | | | | | | 2.40 | | |
| D | | | | | | | | | | | | | | | | |
| D | | | | | | | | | | | | | | | | |
| E | | | | 0.16 | | | | | | | | | | 3.70 | | |
| E | | | | | | | | | | | | | | | | |
| E | | | | | | | | | | | | | | | | |
| F | | | | | | | | | | | | | | 2.61 | | |
| F | | | | | | | | | | | | | | | | |
| F | | | | | | | | | | | | | | | | |
| G | | | | | | | | | | | | | | 4.10 | | |
| G | | | | | | | | | | | | | | | | |
| G | | | | | | | | | | | | | | | | |
| H | | | | | | | | | | | | | | 2.79 | | |
| H | | | | | | | | | | | | | | | | |
| H | | | | | | | | | | | | | | | | |
| A1 | | | | | | | | | | | | | | | | |
| A1 | | | | | | | | | | | | | | | | |
| A1 | | | | | | | | | | | | | | | | |
| B1 | | | | | | | | | | | | | | | | |
| B1 | | | | | | | | | | | | | | | | |
| B1 | | | | | | | | | 0.06 | | | | | | | |
| C1 | | | | | | | | | | | | | | | | |
| C1 | | | | | | | | | | | | | | | | |
| C1 | | | | | | | | | | | | | | | | |
| A | 0.10 | | | | | | | | | | | | | | | |
| A | | | | | | | | | | | | | | | | |
| A | | | | | | | | | | | | | | | | |
| B | | | | | | | | | | | | | | | | |
| B | | | | | | | | | | | | | | | | |
| B | | | | | | | | | | | | | | | | |
| C | | | | | | | | | | | | | | | | |
| C | | | | | | | | | | | | | | | | |
| C | | | | | | | | | | | | | | | | |
| D | | | | | | | | | | | | | | | | |
| D | | | | | | | | | | | | | | | | |
| D | | | | | | | | | | | | | | | | |
| E | | | | | | | | | | | | | | | | |
| E | | | | | | | | | | | | | | | | |
| E | | | | 0.14 | | | | | | | | | | | | |
| F | | | | | | | | | | | | | | | | |
| F | | | | | | | | | | | | | | | | |
| F | | | | 0.10 | | | | | | | | | | | | |
| G | | | | | | | | | | | | | | | | |
| G | | | | | | | | | | | | | | | | |
| G | | | | | | | | | | | | | | | | |
| H | | | | | | | | | | | | | | | | |
| H | | | | | | | | | | | | | | | | |
| H | | | | | | | | | | | | | | | | |
| A1 | | | | | | | | | | | | | 0.09 | | | |
| A1 | | | | | | | | | | | | | 0.09 | | | |
| A1 | | | | | | | | | | | | | 0.10 | | | |
| B1 | | | | | | | | | | | | | 0.06 | | | |
| B1 | | | | | | | | | | | | | 0.07 | | | |
| B1 | | | | | | | | | | | | | 0.05 | | | |
| C1 | | | | | | | | | | | | | 0.14 | | | |

TABLE 71-continued

| Lot | RRT 1.37 (%) | RRT 1.44 (%) | RRT 1.45 (%) | RRT 1.46 (%) | RRT 1.47 (%) | RRT 1.48 (%) | RRT 1.55 (%) | RRT 1.57 (%) | RRT 1.59 (%) | RRT 1.62 (%) | RRT 1.68 (%) | RRT 1.70 (%) | RRT 1.71 (%) | RRT 1.72 (%) | RRT 1.80 (%) | RRT 1.82 (%) |
|---|---|---|---|---|---|---|---|---|---|---|---|---|---|---|---|---|
| C1 | | | | | | | | | | | | | 0.13 | | | |
| C1 | | | | | | | | | | | | | 0.12 | | | |
| A | | | | 0.25 | | | | | | | | | | | | |
| A | | | | 0.32 | | | | | | | | | | | | |
| A | | | | 0.35 | | | | | | | | | | | | |
| B | | | | 0.16 | | | | | | | | | | | | |
| B | | | | 0.14 | | | | | | | | | | | | |
| B | | | | 0.14 | | | | | | | | | | | | |
| C | | | | | | | | | | | | | | | | |
| C | | | | | | | | | | | | | | | | |
| C | | | | | | | | | | | | | | | | |
| D | | | | | | | | | | | | | | | 0.14 | |
| D | | | | | | | | | | | | | | | | |
| D | | | | | | | | | | | | | | | | |
| E | | | | 0.09 | | | | | | | | | | | | |
| E | | | | 0.12 | | | | | | | | | | | | |
| E | | | | 0.20 | | | | | | | | | | | | |
| F | | | | 0.06 | | | | | 0.08 | | | | | | | |
| F | | | | 0.10 | | | | | | | | | | | | |
| F | | | | 0.14 | | | | | | | | | | | | |
| G | | | | | | | | | | | | | | | | |
| G | | | | | | | | | | | | | | | | |
| G | | | | | | | | | | | | | | | | |
| H | | | | | | | | | | | | | | | | |
| H | | | | | | | | | | | | | | | | |
| H | | | | | | | | | | | | | | 0.07 | 0.13 | |
| A | | | | 0.19 | | | | | | | 0.16 | | | | | |
| A | | | | 0.29 | | | | | | | 0.16 | | | | | |
| A | | | | 0.24 | | | | | | | | | | | | |
| B | | | | 0.07 | | | | | | | | | | | | |
| B | | | | 0.07 | | | | | | | 0.11 | | | | | |
| B | | | | 0.21 | | | | | | | | | | | | 0.12 |
| C | | | | | | | | | | | | | | | | |
| C | | | | | | | | | | | 0.14 | | | | | |
| C | | | | | | | | | | | | | | | | |
| D | | | | | | | | | | | 0.11 | | | | | |
| D | | | | | | | | | | | 0.10 | | | | | 0.07 |
| D | | | | | | | | | | 0.08 | | | | | | 0.16 |
| E | | | | | | | | | | | | | | | | |
| E | | | | 0.13 | | | | | | | | | | | | |
| E | | | | 0.13 | | | | | | | | | | | | |
| F | | | | | | | | | | | 0.12 | | | | | |
| F | | | | 0.08 | | | | | | | | | | | | |
| F | | | | 0.08 | | | | | | 0.06 | | | | | | 0.23 |
| G | | | | | | | | | | | 0.16 | | | | | |
| G | | | | | | | | | | | | | | | | |
| G | | | | | | | | | | | | | | | | 0.17 |
| H | | | | | | | | | | | | | | | | |
| H | | | | | | | | | | | 0.20 | | | | | 0.14 |
| H | | | | | | | | | | | 0.11 | | | | | 0.21 |
| A | | | | | 0.23 | | | | | | | | | | | |
| A | | | | | 0.33 | | | | | | | | | | | |
| B | | | | | 0.12 | | | | | | | | | | | |
| B | | | | | 0.11 | | | | | | | | | | | |
| C | | | | | | | | | | | | | | | | |
| C | | | | | | | | | | | | | | | | |
| C | | | | | | | | | | | | | | | | |
| D | | | | | | | | | | | | | | | | |
| D | | | | | | | | | | | | | | | | |
| E | | | | | 0.11 | | | | | | | | | | | |
| E | | | | | 0.13 | | | | | | | | | | | |
| F | | | | | | | | | | | | | | | | |
| F | | | | | 0.09 | | | | | | | | | | | |
| G | | | | | | | | | | | | | | | | |
| G | | | | | | | 0.36 | | | | | | | | | |
| H | | | | | | | | | | | | | | | | |
| H | | | | | | | | | | | | | | | | |
| A | | 0.44 | | | | 0.32 | | | | 0.16 | | | | | | |
| A | | 0.48 | | | | 0.23 | | | 0.21 | 0.12 | | | | | | |
| A | | | 0.26 | | | | | | | | | | | | | |
| A | | | 0.27 | | | | | | | | | | | | | |
| B | | 0.12 | | | | 0.16 | | | | | | | | | | |
| B | | 0.33 | | | | 0.15 | | 0.10 | 0.07 | | | | | | | |
| B | | | | | | | | | | | | | | | | |
| B | | | 0.16 | | | | | | | | | | | | | |
| C | | | | 0.21 | | | | | | | | | | | | |
| C | | | | | | | | | | 0.20 | | | | | | |

TABLE 71-continued

| Lot | RRT 1.37 (%) | RRT 1.44 (%) | RRT 1.45 (%) | RRT 1.46 (%) | RRT 1.47 (%) | RRT 1.48 (%) | RRT 1.55 (%) | RRT 1.57 (%) | RRT 1.59 (%) | RRT 1.62 (%) | RRT 1.68 (%) | RRT 1.70 (%) | RRT 1.71 (%) | RRT 1.72 (%) | RRT 1.80 (%) | RRT 1.82 (%) |
|---|---|---|---|---|---|---|---|---|---|---|---|---|---|---|---|---|
| C | | | | | | | | | | | | | | | | |
| C | | | | | | | | | | | | 2.69 | | | | |
| D | | | | | | | | | | 0.08 | | | | | | |
| D | | | | | | | | | 0.30 | 0.08 | | | | | | |
| D | | | | | | | | | | | | | | | | |
| D | | | | | | | | | | | | 1.83 | | | | |
| E | | 0.51 | | | | 0.13 | | | 0.16 | 0.10 | | | | | | |
| E | | 0.73 | | | | 0.14 | | | 0.72 | | | | | | | |
| E | | | 0.11 | | | | | | | | | | | | | |
| E | | | 0.16 | | | | | | | | | 2.74 | | | | |
| F | | 0.34 | | | | 0.10 | | | | 0.07 | | | | | | |
| F | | 0.53 | | | | 0.09 | | | | 0.06 | | | | | | |
| F | | | | | | | | | | | | | | | | |
| F | | | 0.10 | | | | | | | | | 1.80 | | | | |
| G | | | | | | | | | 0.36 | | | | | | | |
| G | | | | | | | | | 0.15 | | | | | | | |
| G | | | | | | | | | | | | | | | | |
| G | | | | | | | | | | | | 2.69 | | | | |
| H | | | | | | | | | | | | | | | | |
| H | | | | | | | | | 0.17 | | | | | | | |
| H | | | | | | | | | | | | | | | | |
| H | | | | | | | | | | | | 1.81 | | | | |
| Min | 0 | | | 0.059 | | | | | 0.077 | | | | | 0.07 | 0.128 | |
| Max | 0 | | | 0.347 | | | | | 0.213 | | | | | 0.07 | 0.138 | |

TABLE 72

| Lot | RRT 1.85 (%) | RRT 1.89 (%) | RRT 1.93 (%) | RRT 1.96 (%) | RRT 2.00 (%) | RRT 2.01 (%) | RRT 2.04 (%) | RRT 2.08 (%) | RRT 2.11 (%) | RRT 2.12 (%) | RRT 2.13 (%) | RRT 2.15 (%) | RRT 2.16 (%) | RRT 2.17 (%) | RRT 2.304 (%) | Total Imp (%) |
|---|---|---|---|---|---|---|---|---|---|---|---|---|---|---|---|---|
| A | | | | | | | | | | | | | | | | 4.44 |
| A | | | | | | | | | | | | | | | | 4.44 |
| A | | | | | | | | | | | | | | | | 4.44 |
| B | | | | | | | | | | | | | | | | 3.10 |
| B | | | | | | | | | | | | | | | | 3.10 |
| B | | | | | | | | | | | | | | | | 3.10 |
| C | | | | | | | | | | | | | | | | 12.55 |
| C | | | | | | | | | | | | | | | | 12.55 |
| C | | | | | | | | | | | | | | | | 12.55 |
| D | | | | | | | 0.07 | 0.09 | | 0.55 | | 0.15 | | | | 12.92 |
| D | | | | | | | 0.07 | 0.09 | | 0.55 | | 0.15 | | | | 12.92 |
| D | | | | | | | 0.07 | 0.09 | | 0.55 | | 0.15 | | | | 12.92 |
| E | | | | | | | | 0.18 | | | | | | | | 5.89 |
| E | | | | | | | | 0.18 | | | | | | | | 5.89 |
| E | | | | | | | | 0.18 | | | | | | | | 5.89 |
| F | | | | | | | | | | | | | | | | 2.77 |
| F | | | | | | | | | | | | | | | | 2.77 |
| F | | | | | | | | | | | | | | | | 2.77 |
| G | | | | | | | | | | | | | | | | 3.45 |
| G | | | | | | | | | | | | | | | | 3.45 |
| G | | | | | | | | | | | | | | | | 3.45 |
| H | | | | | | | | | | | | 0.69 | | | | 3.66 |
| H | | | | | | | | | | | | 0.69 | | | | 3.66 |
| H | | | | | | | | | | | | 0.69 | | | | 3.66 |
| A1 | | | | | | | | | | | | | | | | 1.61 |
| A1 | | | | | | | | | | | | | | | | 1.61 |
| A1 | | | | | | | | | | | | | | | | 1.61 |
| B1 | | | | | | | | | | | | | | | | 1.48 |
| B1 | | | | | | | | | | | | | | | | 1.48 |
| B1 | | | | | | | | | | | | | | | | 1.48 |
| C1 | | | | | | | | | | | | | | | | 1.50 |
| C1 | | | | | | | | | | | | | | | | 1.50 |
| C1 | | | | | | | | | | | | | | | | 1.50 |
| A | | | | | | | | 0.66 | | | | | | | | 8.15 |
| A | | | | | | | | | | | | | | | | 5.34 |
| A | | | | | | | | | | | | | | | | 6.74 |
| B | | | | | | | | | | | | | | | | 5.67 |
| B | | | | | | | | | | | | | | | | 3.40 |
| B | | | | | | | | | | | | | | | | 5.33 |
| C | | | | | | | | | | | | | | | | 6.91 |
| C | | | | | | | | | | | | | | | | 3.72 |
| C | | | | | | | | | | | | | | | | 7.74 |

TABLE 72-continued

| Lot | RRT 1.85 (%) | RRT 1.89 (%) | RRT 1.93 (%) | RRT 1.96 (%) | RRT 2.00 (%) | RRT 2.01 (%) | RRT 2.04 (%) | RRT 2.08 (%) | RRT 2.11 (%) | RRT 2.12 (%) | RRT 2.13 (%) | RRT 2.15 (%) | RRT 2.16 (%) | RRT 2.17 (%) | RRT 2.304 (%) | Total Imp (%) |
|---|---|---|---|---|---|---|---|---|---|---|---|---|---|---|---|---|
| D | | | | | | | | | | | | | | | | 4.71 |
| D | | | | | | | | | | | | | | | | 3.55 |
| D | | | | | | | | | | | | | | | | 6.86 |
| E | | | | | | | | | | | | | | | | 6.24 |
| E | | | | | | | | | | | | | | | | 3.38 |
| E | | | | | | | | | | | | | | | | 5.09 |
| F | | | | | | | | | | | | | | | | 4.78 |
| F | | | | | | | | | | | | | | | | 2.86 |
| F | | | | | | | | | | | | | | | | 4.35 |
| G | | | | | | | | | | | | | | | | 6.42 |
| G | | | | | | | | | | | | | | 1.08 | | 4.39 |
| G | | | | | | | | | | | | | | | | 4.93 |
| H | | | | | | | | | | | | | | | | 4.60 |
| H | | | | | | | | | | | | | | | | 2.73 |
| H | | | | | | | | | | | | | | | | 4.07 |
| A1 | | | | | | | | | | | | | | | | 1.60 |
| A1 | | | | | | | | | | | | | | | | 1.63 |
| A1 | | | | | | | | | | | | | | | | 2.80 |
| B1 | | | | | | | | | | | | | | | | 1.50 |
| B1 | | | | | | | | | | | | | | | | 1.80 |
| B1 | 0.44 | | | | | | | | | | | | | | | 3.53 |
| C1 | | | | | | | | | | | | | | | | 1.49 |
| C1 | | | | | | | | | | | | | | | | 1.66 |
| C1 | | | | | | | | | | | | | | | | 2.85 |
| A | | | | | | | | | | | | | | | | 5.25 |
| A | | | | | | | | | | | | | | | | 5.03 |
| A | | | | | | | | | | | | | | | | 6.29 |
| B | | | | | | | | | | | | | | | | 2.52 |
| B | | | | | | | | | | | | | | | | 3.83 |
| B | | | | | | | | | | | | | | | | 8.35 |
| C | | | | | | | | | | | | | | | | 3.27 |
| C | | | | | | | | | | | | | 0.85 | | | | 4.84 |
| C | | | | | | | | | | | | | | | | 6.65 |
| D | | | | | | | | | | | | | | | | 2.80 |
| D | | | | | | | | | | | | | | | | 4.10 |
| D | | | | | | | | | | | | | | | | 6.47 |
| E | | | | | | | | | | | | | | 0.23 | | 2.82 |
| E | | | | | | | | | | | | | | | | 3.98 |
| E | | | | | | | | | | | | | | | | 6.87 |
| F | | | | | | | | | | | | | | | | 1.96 |
| F | | | | | | | | | | | | | | | | 3.61 |
| F | | | | | | | | | | | | | | | | 6.85 |
| G | | | | | | | | | | | | | | | | 3.37 |
| G | | | | | | | | | | | | | | | | 3.51 |
| G | | | | | | | | | | | | | | | | 5.10 |
| H | | | | | | | | | | | | | | | | 3.10 |
| H | | | | | | | | | | | | | | | | 3.57 |
| H | | | | | | | | | | | | | | | | 4.76 |
| A1 | | | | | | | | | | | | | | | | 1.53 |
| A1 | | | | | | | | | | | | | | | | 2.10 |
| A1 | | | | | | | | | | | | | | | | 3.55 |
| B1 | | | | | | | | | | | | | | | | 1.56 |
| B1 | | | | | | | | | | | | | | | | 1.98 |
| B1 | | | | | | | | | | | | | | | | 3.31 |
| C1 | | | | | | | | | | | | | | | | 1.57 |
| C1 | | | | | | | | | | | | | | | | 1.97 |
| C1 | | | | | | | | | | | | | | | | 4.05 |
| A | | | | | | | | | | | | | | | | 4.82 |
| A | | | | | | | | | | | | | | | | 5.39 |
| A | | | | | | | | | | | | | | | | 10.68 |
| B | | | | | | | | | | | | | | | | 2.48 |
| B | | | | | | | | | | | | | | | | 4.73 |
| B | | | | | | | | | | | | | | | | 6.71 |
| C | | | | | | | | | | | | | | | | 2.09 |
| C | | | | | | | | | | | | | | | | 4.34 |
| C | | | | | | | | | | | | | | | | 7.69 |
| D | | | | | | | | | | | | | | | | 8.29 |
| D | | | | | | | | | | | | | | | | 4.06 |
| D | | | | | | | | | | | | | | | | 7.10 |
| E | | | | | | | | | | | | 3.57 | | | | 7.50 |
| E | | | | | | | | | | | | | | | | 4.50 |
| E | | | | | | | | | | | | | | | | 9.64 |
| F | | | | | | | | | | | | | | | | 2.39 |
| F | | | | | | | | | | | | | | | | 3.65 |
| F | | | | | | | | | | | | | | | | 7.97 |
| G | | | | | | | | | | | | | | | | 2.19 |

TABLE 72-continued

| Lot | RRT 1.85 (%) | RRT 1.89 (%) | RRT 1.93 (%) | RRT 1.96 (%) | RRT 2.00 (%) | RRT 2.01 (%) | RRT 2.04 (%) | RRT 2.08 (%) | RRT 2.11 (%) | RRT 2.12 (%) | RRT 2.13 (%) | RRT 2.15 (%) | RRT 2.16 (%) | RRT 2.17 (%) | RRT 2.304 (%) | Total Imp (%) |
|---|---|---|---|---|---|---|---|---|---|---|---|---|---|---|---|---|
| G | | | | | | | | | | | | | | | | 3.21 |
| G | | | | | | | | | | | | | | | | 5.08 |
| H | | | | | | | | | | | | | | | | 1.91 |
| H | | | | | | | | | | | | | | | | 2.31 |
| H | | | | | | | | | | | | | | | | 4.64 |
| A | | | | | 0.17 | 0.14 | | | | | 0.06 | | | | | 4.79 |
| A | | | | | | | | | | | | | | | | 5.96 |
| A | | | | | | | | | | | | | | | | 13.72 |
| B | | | | | | | | | | | | | | | | 2.60 |
| B | | | | | | | | | | | 0.65 | | | | | 5.84 |
| B | | | | | | | | | | | | | | | | 14.85 |
| C | | | | | | | | | | | | | | | | 2.66 |
| C | | | | | | | | | | | | | | | | 5.50 |
| C | | | | | | | | | | | | | | | | 9.14 |
| D | | | | | | | | | | | | | | | | 2.67 |
| D | | 0.08 | | | | | | | 1.22 | | | | | | | 7.08 |
| D | | | | | | | | | | | | | | | | 9.22 |
| E | | | | | | | | | | | | | | | | 2.87 |
| E | | | | | | | | | | | | | | | | 5.66 |
| E | | | | | | | | | | | | | | | | 12.07 |
| F | | | | | | | | | | | | | | | | 2.35 |
| F | | | | | | | | | | | | | | | | 4.64 |
| F | | | | | | | | | | | | | | | | 10.81 |
| G | | | | | | | | | | | | | | | | 3.23 |
| G | | | | | | | | | | | | | | | | 4.42 |
| G | | | | | | | | | | | | | | | | 7.12 |
| H | | | | | | | | | | | | | | | | 2.63 |
| H | | 0.31 | 0.11 | 0.08 | | | | | | | | | | | | 6.71 |
| H | | | | 0.08 | | | | | | | | | | | | 7.46 |
| A | | | | | | | | | | | | | | | | 4.23 |
| A | | | | | | | | | | | | | | | | 6.75 |
| B | | | | | | | | | | | | | | | | 2.94 |
| B | | | | | | | | | | 0.09 | | | | | | 6.36 |
| C | | | | | | | | | | | | | | | | 2.72 |
| C | | | | | | | | | | 0.13 | | | | | | 5.32 |
| D | | | | | | | | | | | | | | | | 2.67 |
| D | | | | | | | | | | | | | | | | 5.46 |
| E | | | | | | | | | | | | | | | | 3.19 |
| E | | | | | | | | | | | | | | | | 5.90 |
| F | | | | | | | | | | | | | | | | 2.66 |
| F | | | | | | | | | | | | | | | | 4.95 |
| G | | | | | | | | | | | | | | | | 3.05 |
| G | | | | | | | | | | | | | | | | 6.37 |
| H | | | | | | | | | | | | | | | | 2.55 |
| H | | | | | | | | | | | | | | | | 4.20 |
| A | | | | | | | | | | | | | | | | 4.36 |
| A | | | | | | | | | | | | | | | | 6.67 |
| A | | | | | | | | | | | | | | | | 3.81 |
| A | | | | | | | | | | | | | | | | 6.62 |
| B | | | | | | | | | | | | | | | | 3.60 |
| B | | | | | | | | | | | | | | | | 5.66 |
| B | | | | | | | | | | | | | | | | 3.71 |
| B | | | | | | | | | | | | | | | | 5.98 |
| C | | | | | | | | | | 0.14 | | | | | | 3.05 |
| C | | | | | | | | | | | | | | | | 5.58 |
| C | | | | | | | | | | | | | | | | 2.93 |
| C | | | | | | | | | | 0.18 | | | | | | 8.12 |
| D | | | | | | | | | | | | | | | | 2.28 |
| D | | | | | | | | | | | | | | | | 5.34 |
| D | | | | | | | | | | | | | | | | 2.48 |
| D | | | | | | | | | | | | | | | | 7.20 |
| E | | | | | | | | | | | | | | | | 5.11 |
| E | | | | | | | | | | | | | | | | 6.93 |
| E | | | | | | | | | | | | | | | | 4.22 |
| E | | | | | | | | | | | | | | | | 8.94 |
| F | | | | | | | | | | | | | | | | 2.83 |
| F | | | | | | | | | | | | | | | | 5.10 |
| F | | | | | | | | | | | | | | | | 2.47 |
| F | | | | | | | | | | | | | | | | 7.12 |
| G | | | | | | | | | | | | | | | | 3:26 |
| G | | | | | | | | | | | | | | | | 4.42 |
| G | | | | | | | | | | | | | | | | 2.98 |
| G | | | | | | | | | | | | | | | | 7.49 |
| H | | | | | | | | | | | | | | | | 2.35 |
| H | | | | | | | | | | | | | | | | 4.04 |
| H | | | | | | | | | | | | | | | | 2.80 |

TABLE 72-continued

| Lot | RRT 1.85 (%) | RRT 1.89 (%) | RRT 1.93 (%) | RRT 1.96 (%) | RRT 2.00 (%) | RRT 2.01 (%) | RRT 2.04 (%) | RRT 2.08 (%) | RRT 2.11 (%) | RRT 2.12 (%) | RRT 2.13 (%) | RRT 2.15 (%) | RRT 2.16 (%) | RRT 2.17 (%) | RRT 2.304 (%) | Total Imp (%) |
|---|---|---|---|---|---|---|---|---|---|---|---|---|---|---|---|---|
| H | | | | | | | | | | | | | | | | 6.09 |
| Min | | | | | | | 0 | 0 | | | 0 | 3.565 | 0 | 0 | | 1.533 |
| Max | | | | | | | 0 | 0 | | | 0 | 3.565 | 0 | 0 | | 14.845 |

TABLE 73

| Lot | Condition (° C.) | Time (m) | pH | AVP (% LC) | RRT 0.64 (%) | RRT 0.86 (%) | RRT 0.87 (%) | RRT 0.95 (%) | D-ASN-AVP (%) | RRT 0.99 (%) | RRT 1.03 (%) | RRT 1.04 (%) | RRT 1.05 (%) |
|---|---|---|---|---|---|---|---|---|---|---|---|---|---|
| A1 | 5 | 0 | 3.86 | 97.5 | 0.06 | | 0.32 | | | 0.12 | 0.12 | 0.24 | |
| A1 | 25 | 0 | 3.86 | 97.5 | 0.06 | | 0.32 | | | 0.12 | 0.12 | 0.24 | |
| A1 | 40 | 0 | 3.86 | 97.5 | 0.06 | | 0.32 | | | 0.12 | 0.12 | 0.24 | |
| B1 | 5 | 0 | 3.84 | 97.6 | | | 0.30 | | | 0.11 | 0.12 | 0.24 | |
| B1 | 25 | 0 | 3.84 | 97.6 | | | 0.30 | | | 0.11 | 0.12 | 0.24 | |
| B1 | 40 | 0 | 3.84 | 97.6 | | | 0.30 | | | 0.11 | 0.12 | 0.24 | |
| C1 | 5 | 0 | 3.78 | 99.3 | | | 0.31 | | | 0.12 | 0.12 | 0.25 | |
| C1 | 25 | 0 | 3.78 | 99.3 | | | 0.31 | | | 0.12 | 0.12 | 0.25 | |
| C1 | 40 | 0 | 3.78 | 99.3 | | | 0.31 | | | 0.12 | 0.12 | 0.25 | |
| A1 | 5 | 1 | 3.81 | 97.0 | | 0.10 | 0.29 | | | 0.12 | 0.12 | 0.25 | |
| A1 | 25 | 1 | 3.82 | 96.8 | | | 0.30 | | | 0.11 | 0.12 | 0.24 | |
| A1 | 40 | 1 | 3.83 | 91.8 | 0.06 | | 0.29 | | | 0.09 | 0.11 | 0.21 | |
| B1 | 5 | 1 | 3.82 | 97.5 | | | 0.30 | | | 0.11 | 0.12 | 0.25 | |
| B1 | 25 | 1 | 3.82 | 97.1 | | | 0.30 | | | 0.11 | 0.12 | 0.24 | |
| B1 | 40 | 1 | 3.82 | 92.0 | | | 0.33 | | | 0.10 | 0.11 | 0.21 | |
| C1 | 5 | 1 | 3.80 | 99.2 | | | 0.31 | | | 0.12 | 0.13 | 0.26 | |
| C1 | 25 | 1 | | 98.5 | | | 0.30 | | | 0.11 | 0.13 | 0.25 | |
| C1 | 40 | 1 | 3.82 | 94.7 | | | 0.30 | | | 0.11 | 0.12 | 0.23 | |
| A1 | 5 | 2 | 3.77 | 97.3 | | | 0.30 | | | 0.11 | 0.14 | 0.24 | |
| A1 | 25 | 2 | 3.77 | 95.9 | 0.14 | | 0.31 | | | 0.13 | 0.14 | 0.23 | 0.18 |
| A1 | 40 | 2 | 3.78 | 86.1 | | | 0.31 | 0.18 | | 0.10 | 0.12 | 0.21 | 0.50 |
| B1 | 5 | 2 | 3.79 | 97.3 | | | 0.30 | | | 0.12 | 0.12 | 0.24 | |
| B1 | 25 | 2 | 3.78 | 96.5 | | | 0.31 | | | 0.12 | 0.13 | 0.23 | 0.18 |
| B1 | 40 | 2 | 3.79 | 87.4 | | | 0.29 | 0.15 | | 0.10 | 0.11 | 0.20 | 0.52 |
| C1 | 5 | 2 | 3.73 | 99.3 | | | 0.31 | | | 0.12 | 0.13 | 0.25 | |
| C1 | 25 | 2 | 3.73 | 98.1 | | | 0.31 | | | 0.14 | 0.13 | 0.24 | |
| C1 | 40 | 2 | 3.74 | 91.0 | | | 0.30 | | | 0.10 | 0.13 | 0.21 | 0.43 |
| A1 | 5 | 3 | 3.80 | 95.8 | | | 0.28 | | | | 0.12 | 0.22 | |
| A1 | 25 | 3 | 3.78 | 94.0 | | | 0.28 | | | | 0.13 | 0.21 | 0.11 |
| A1 | 40 | 3 | 3.81 | 82.2 | | | 0.28 | 0.16 | | 0.11 | 0.15 | 0.29 | |
| B1 | 5 | 3 | 3.82 | 96.5 | | | 0.28 | | | 0.11 | 0.13 | 0.23 | |
| B1 | 25 | 3 | 3.82 | 94.8 | | | 0.29 | | | 0.12 | 0.13 | 0.21 | 0.11 |
| B1 | 40 | 3 | 3.83 | 82.0 | | | 0.27 | 0.06 | | 0.11 | 0.14 | 0.33 | |
| C1 | 5 | 3 | 3.75 | 97.5 | | | 0.29 | | | 0.12 | 0.13 | 0.24 | |
| C1 | 25 | 3 | 3.75 | 96.8 | | | 0.29 | | | 0.13 | 0.14 | 0.22 | |
| C1 | 40 | 3 | 3.75 | 85.5 | | | 0.27 | | | 0.11 | 0.16 | 0.26 | |
| Min | | | 3.78 | 91.842 | 0.061 | | | | 0.093 | | | 0 | |
| Max | | | 3.86 | 99.282 | 0.063 | | | | 0.124 | | | 0 | |

TABLE 74

| Lot | RRT 1.06 (%) | GLY9-AVP (%) | ASP5-AVP (%) | GLU4-AVP (%) | RRT 1.12 (%) | RRT 1.13 (%) | RRT 1.23 (%) | RRT 1.24 (%) | RRT 1.25 (%) | ACETYL-AVP (%) | RRT 1.57 (%) | RRT 1.71 (%) | RRT 1.77 (%) |
|---|---|---|---|---|---|---|---|---|---|---|---|---|---|
| A1 | | 0.08 | | 0.10 | 0.09 | | | | 0.21 | 0.28 | | | |
| A1 | | 0.08 | | 0.10 | 0.09 | | | | 0.21 | 0.28 | | | |
| A1 | | 0.08 | | 0.10 | 0.09 | | | | 0.21 | 0.28 | | | |
| B1 | | 0.07 | | 0.07 | 0.07 | | | | 0.21 | 0.29 | | | |
| B1 | | 0.07 | | 0.07 | 0.07 | | | | 0.21 | 0.29 | | | |
| B1 | | 0.07 | | 0.07 | 0.07 | | | | 0.21 | 0.29 | | | |
| C1 | | 0.09 | | 0.10 | 0.08 | | | | 0.14 | 0.29 | | | |
| C1 | | 0.09 | | 0.10 | 0.08 | | | | 0.14 | 0.29 | | | |
| C1 | | 0.09 | | 0.10 | 0.08 | | | | 0.14 | 0.29 | | | |
| A1 | | 0.08 | | 0.07 | 0.08 | | | | 0.23 | 0.28 | | | |
| A1 | | 0.14 | | 0.13 | 0.10 | | | | 0.21 | 0.27 | | | |
| A1 | 0.31 | 0.34 | 0.09 | 0.45 | 0.33 | | | | 0.25 | 0.27 | | | |
| B1 | | 0.07 | | 0.07 | 0.07 | | | | 0.22 | 0.28 | | | |
| B1 | 0.07 | 0.13 | | 0.16 | 0.18 | | 0.21 | | | 0.28 | | | |
| B1 | 0.33 | 0.33 | 0.09 | 0.41 | 0.72 | | | | 0.13 | 0.27 | 0.06 | | |
| C1 | | 0.08 | | 0.10 | 0.08 | | | | 0.14 | 0.27 | | | |

TABLE 74-continued

| Lot | RRT 1.06 (%) | GLY9-AVP (%) | ASP5-AVP (%) | GLU4-AVP (%) | RRT 1.12 (%) | RRT 1.13 (%) | RRT 1.23 (%) | RRT 1.24 (%) | RRT 1.25 (%) | ACETYL-AVP (%) | RRT 1.57 (%) | RRT 1.71 (%) | RRT 1.77 (%) |
|---|---|---|---|---|---|---|---|---|---|---|---|---|---|
| C1 |  | 0.18 |  | 0.18 | 0.10 |  |  | 0.15 |  | 0.28 |  |  |  |
| C1 | 0.27 | 0.52 | 0.13 | 0.64 | 0.10 |  |  | 0.15 |  | 0.28 |  |  |  |
| A1 |  | 0.08 |  | 0.08 |  |  |  | 0.20 |  | 0.30 |  | 0.09 |  |
| A1 |  | 0.20 |  | 0.20 |  |  |  | 0.20 |  | 0.29 |  | 0.09 |  |
| A1 |  | 0.56 | 0.14 | 0.67 |  | 0.10 |  | 0.28 |  | 0.29 |  | 0.10 |  |
| B1 |  | 0.08 |  | 0.08 |  |  |  | 0.23 |  | 0.32 |  | 0.06 |  |
| B1 |  | 0.20 | 0.04 | 0.21 |  |  |  | 0.23 |  | 0.28 |  | 0.07 |  |
| B1 |  | 0.55 | 0.15 | 0.73 |  | 0.06 |  | 0.12 |  | 0.28 |  | 0.05 |  |
| C1 |  | 0.10 | 0.09 |  |  |  |  | 0.13 |  | 0.28 |  | 0.14 |  |
| C1 |  | 0.28 |  | 0.29 |  |  |  | 0.13 |  | 0.32 |  | 0.13 |  |
| C1 |  | 0.89 | 0.22 | 1.14 |  | 0.07 |  | 0.16 |  | 0.28 |  | 0.12 |  |
| A1 |  | 0.09 |  | 0.09 |  |  |  | 0.18 |  | 0.29 |  |  |  |
| A1 |  | 0.26 |  | 0.29 |  |  |  | 0.21 |  | 0.28 |  |  |  |
| A1 |  | 0.73 | 0.18 | 0.82 |  | 0.19 |  | 0.11 |  | 0.27 |  |  |  |
| B1 |  | 0.09 |  | 0.09 |  |  |  | 0.19 |  | 0.28 |  |  |  |
| B1 |  | 0.25 |  | 0.25 |  |  |  | 0.20 |  | 0.28 |  |  |  |
| B1 |  | 0.73 | 0.19 | 0.82 |  | 0.09 |  | 0.09 | 0.07 | 0.28 |  |  | 0.06 |
| C1 |  | 0.10 |  | 0.10 |  |  |  | 0.13 |  | 0.28 |  |  |  |
| C1 |  | 0.35 |  | 0.38 |  |  |  | 0.11 |  | 0.28 |  |  |  |
| C1 |  | 1.22 | 0.30 | 1.56 |  | 0.12 |  | 0.15 |  | 0.27 |  |  |  |
| Min |  | 0.07 | 0.089 | 0.067 | 0.073 | 0 |  |  |  | 0.27 |  |  |  |
| Max |  | 0.344 | 0.089 | 0.448 | 0.326 | 0 |  |  |  | 0.288 |  |  |  |

TABLE 75

| Lot | RRT 1.85 (%) | RRT 1.91 (%) | RRRT 2.02 (%) | RRT 2.37 (%) | Total RS (%) |
|---|---|---|---|---|---|
| A1 |  |  |  |  | 1.61 |
| A1 |  |  |  |  | 1.61 |
| A1 |  |  |  |  | 1.61 |
| B1 |  |  |  |  | 1.48 |
| B1 |  |  |  |  | 1.48 |
| B1 |  |  |  |  | 1.48 |
| C1 |  |  |  |  | 1.50 |
| C1 |  |  |  |  | 1.50 |
| C1 |  |  |  |  | 1.50 |
| A1 |  |  |  |  | 1.60 |
| A1 |  |  |  |  | 1.63 |
| A1 |  |  |  |  | 2.80 |
| B1 |  |  |  |  | 1.50 |
| B1 |  |  |  |  | 1.80 |
| B1 | 0.44 |  |  |  | 3.53 |
| C1 |  |  |  |  | 1.49 |
| C1 |  |  |  |  | 1.66 |
| C1 |  |  |  |  | 2.85 |
| A1 |  |  |  |  | 1.53 |
| A1 |  |  |  |  | 2.10 |
| A1 |  |  |  |  | 3.55 |
| B1 |  |  |  |  | 1.56 |
| B1 |  |  |  |  | 1.98 |
| B1 |  |  |  |  | 3.31 |
| C1 |  |  |  |  | 1.57 |
| C1 |  |  |  |  | 1.97 |
| C1 |  |  |  |  | 4.05 |
| A1 |  |  |  |  | 1.26 |
| A1 |  |  |  |  | 1.76 |
| A1 |  |  |  |  | 3.29 |
| B1 |  |  |  |  | 1.40 |
| B1 |  |  |  |  | 1.82 |
| B1 | 0.10 | 0.10 | 0.17 |  | 3.68 |
| C1 |  |  |  |  | 1.38 |
| C1 |  |  |  |  | 1.89 |
| C1 |  |  |  |  | 4.41 |
| Min |  |  |  |  | 1.483 |
| Max |  |  |  |  | 2.799 |

Figure 27:
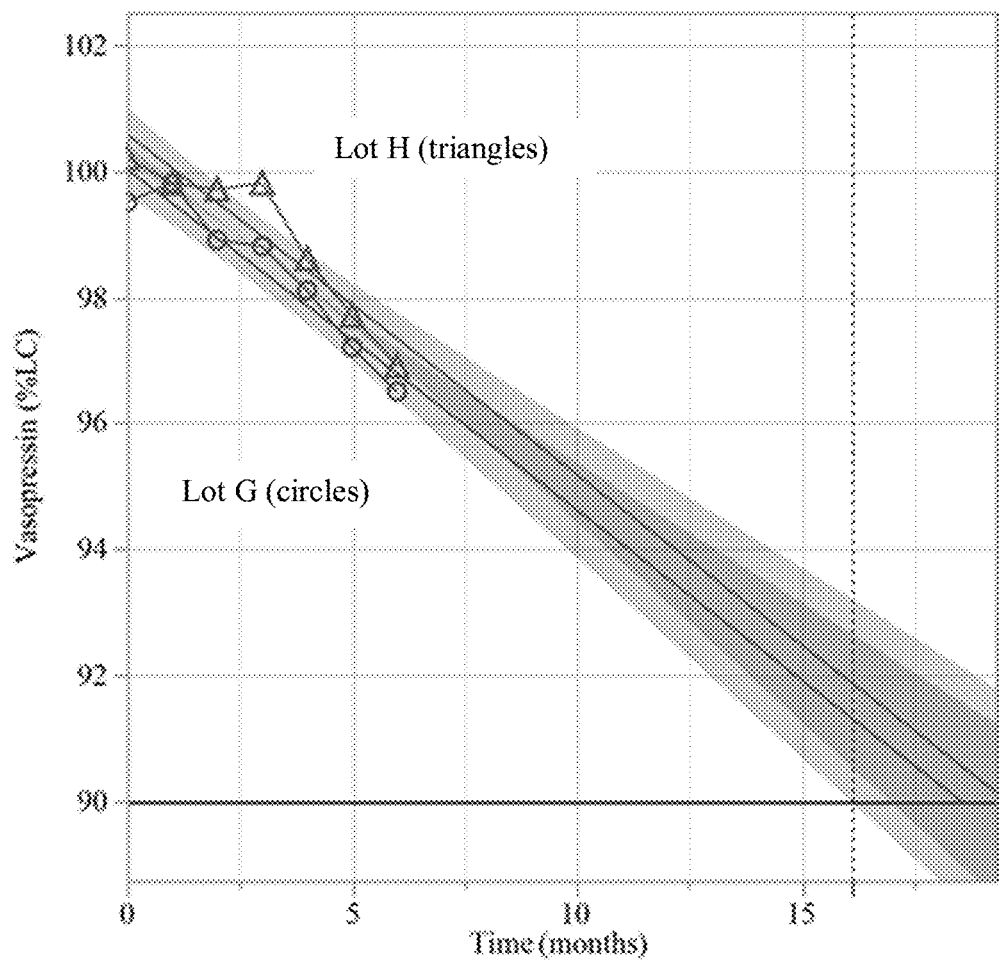
FIG. 27 depicts the estimated shelf-life of a vasopressin sample described herein at 5° C.
Figure 28:
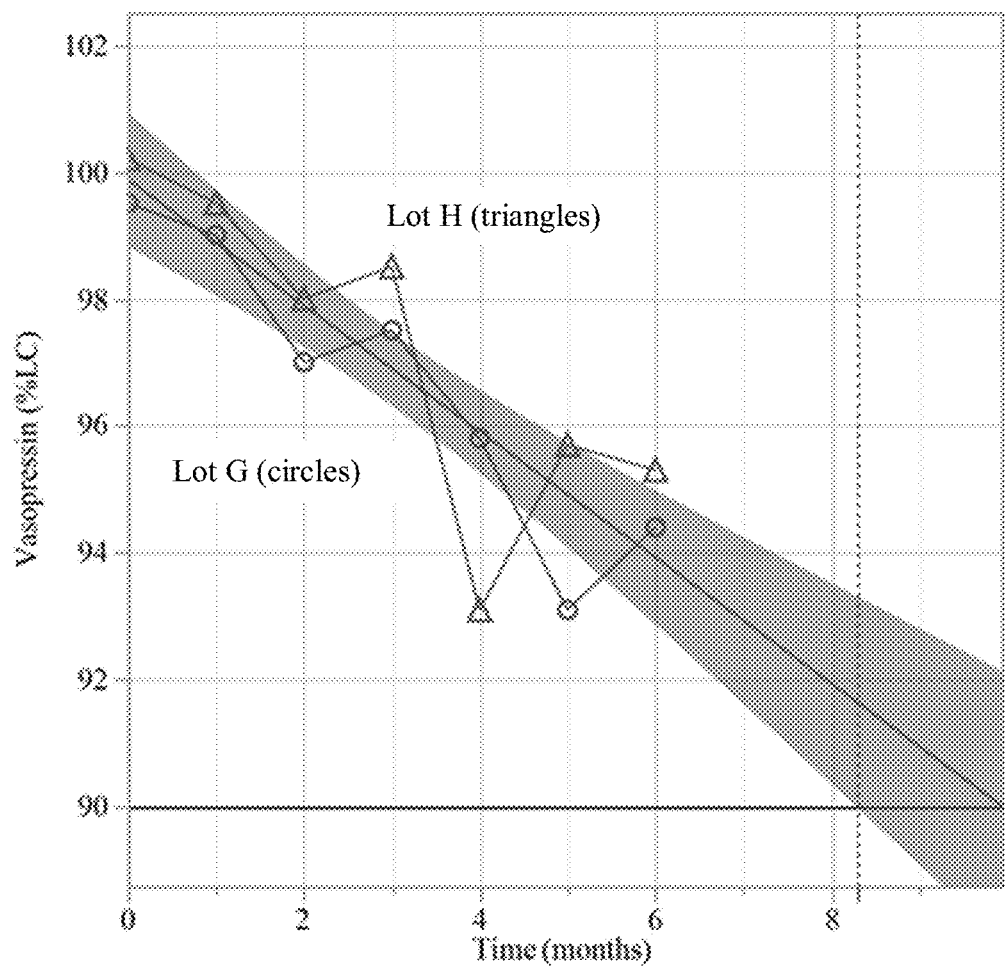
FIG. 28 depicts the estimated shelf-life of a vasopressin sample described herein at 25° C.
Figure 29:
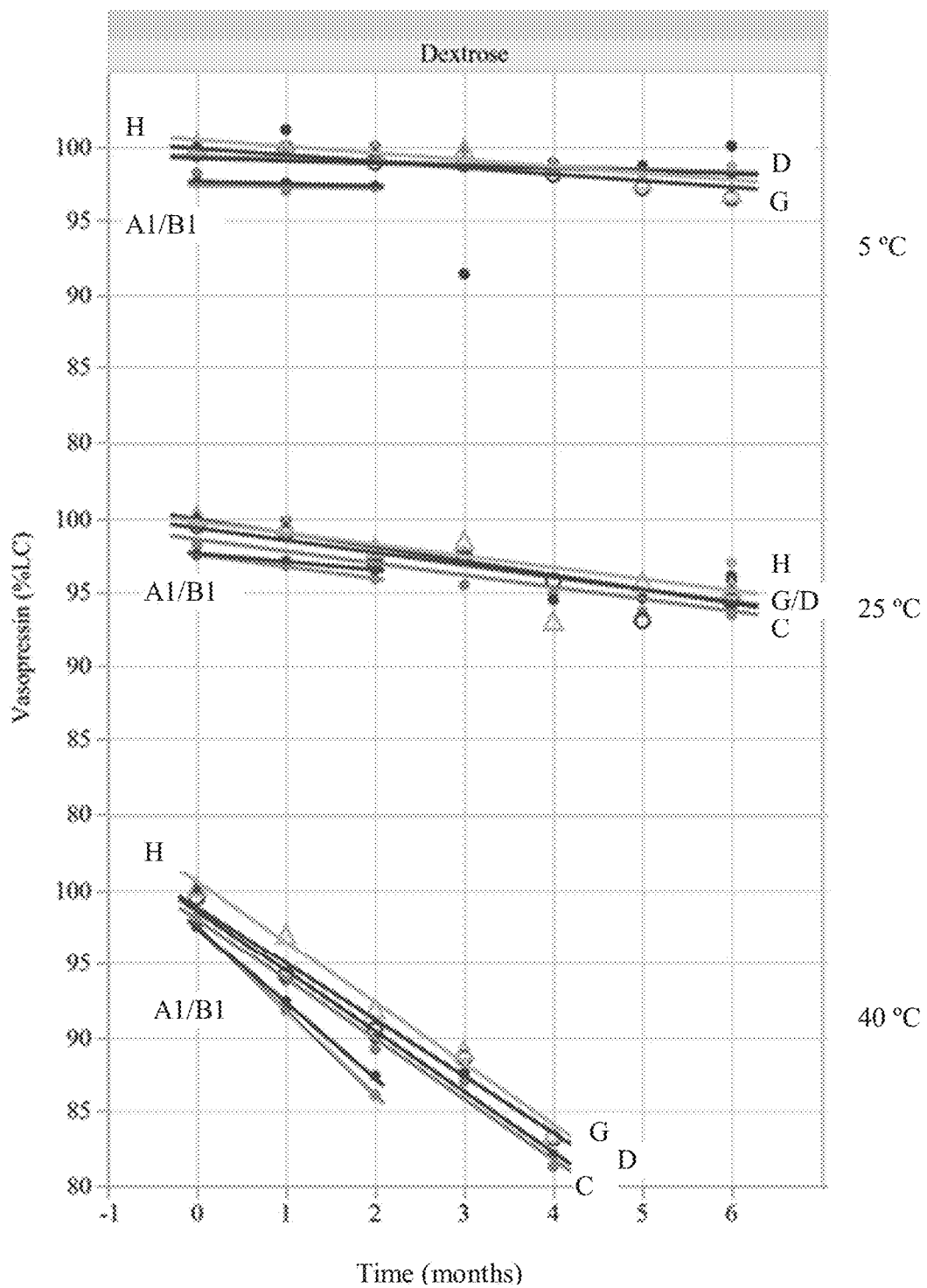
FIG. 29 shows the % LC of vasopressin after storage at 5° C., 25° C., and 40° C. of vasopressin formulations prepared in dextrose.
Figure 30:
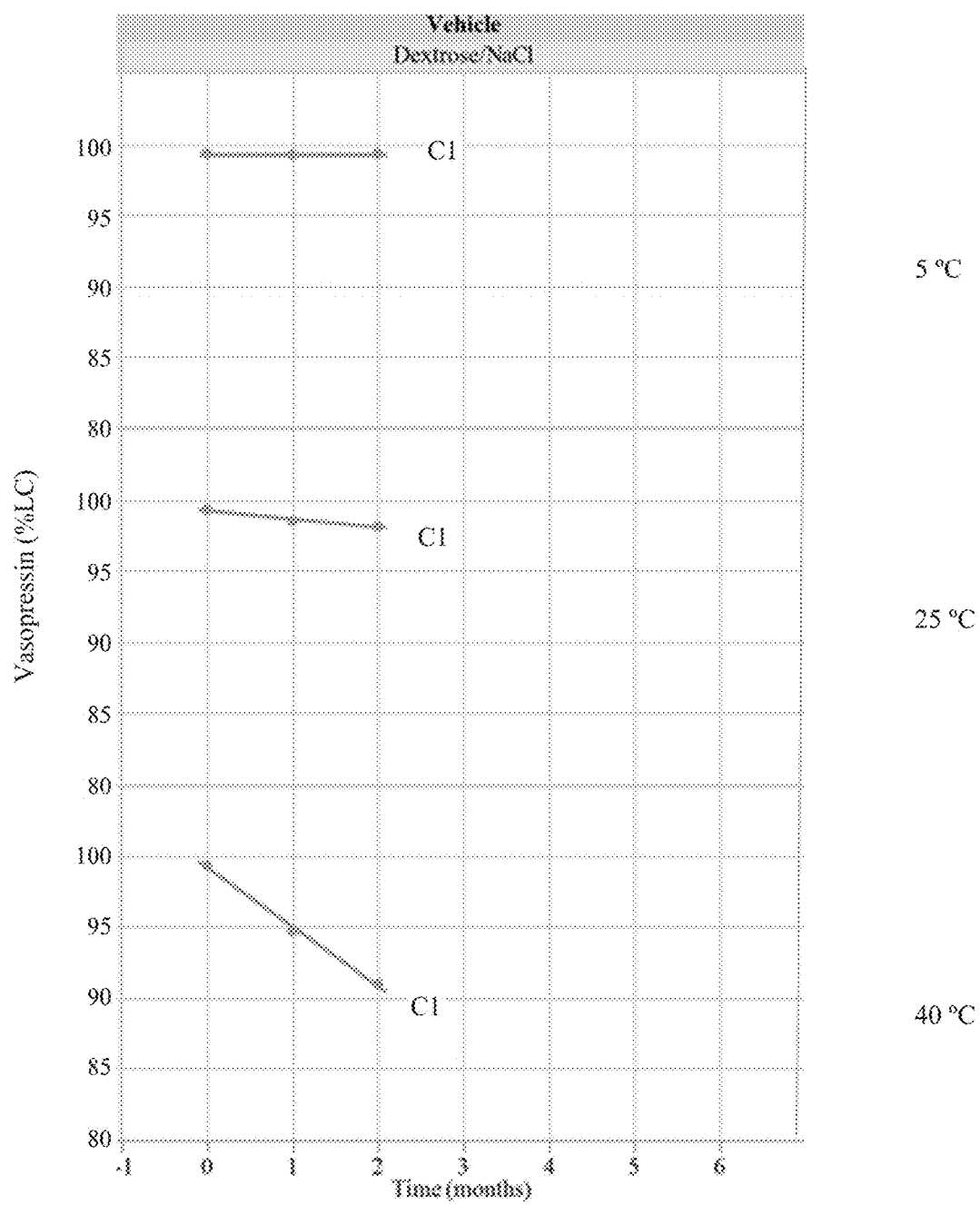
FIG. 30 shows the % LC of vasopressin after storage at 5° C., 25° C., and 40° C. of vasopressin formulations prepared in dextrose and sodium chloride.
Figure 31:
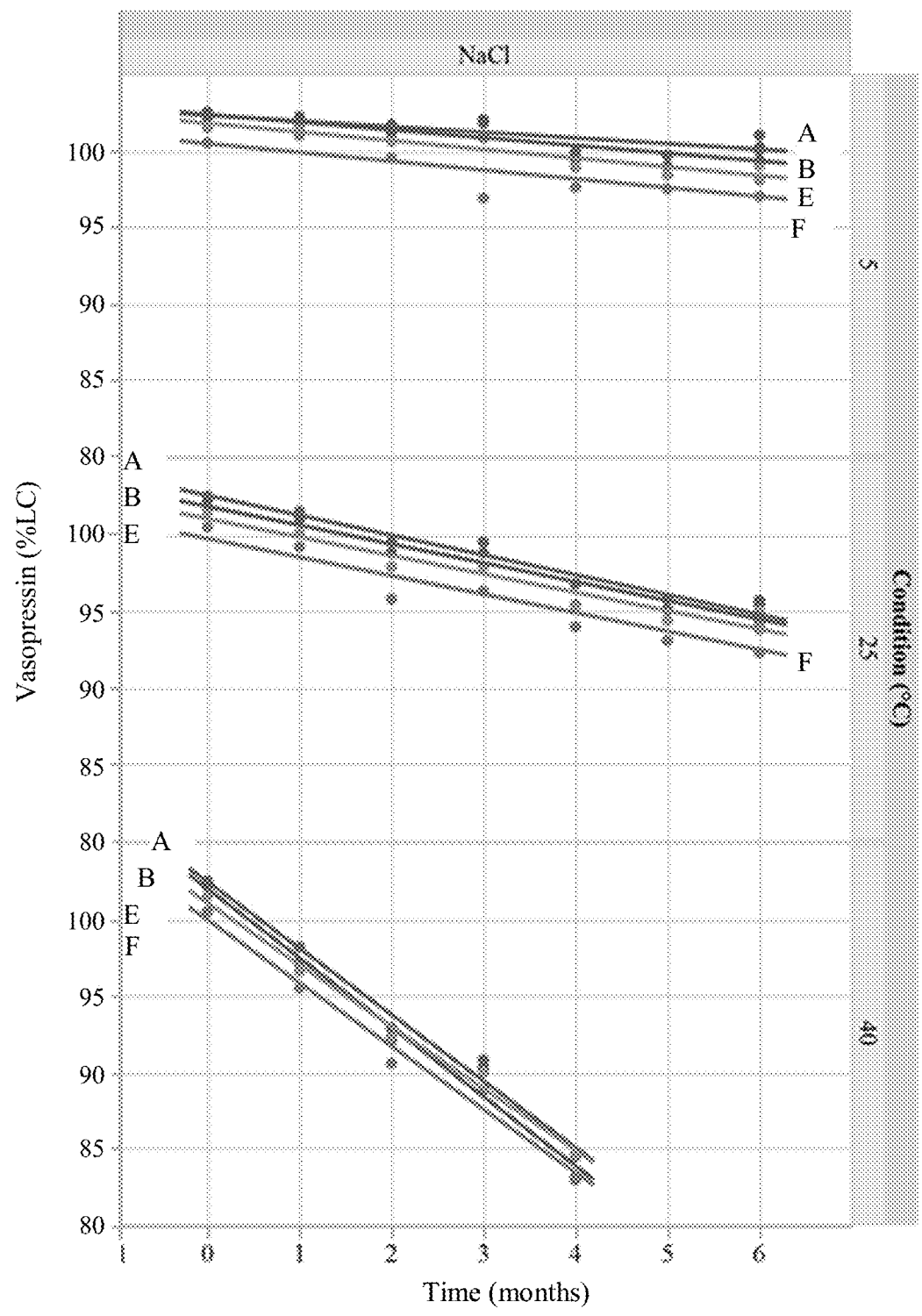
FIG. 31 shows the % LC of vasopressin after storage at 5° C., 25° C., and 40° C. of vasopressin formulations prepared in sodium chloride.
Figure 32:
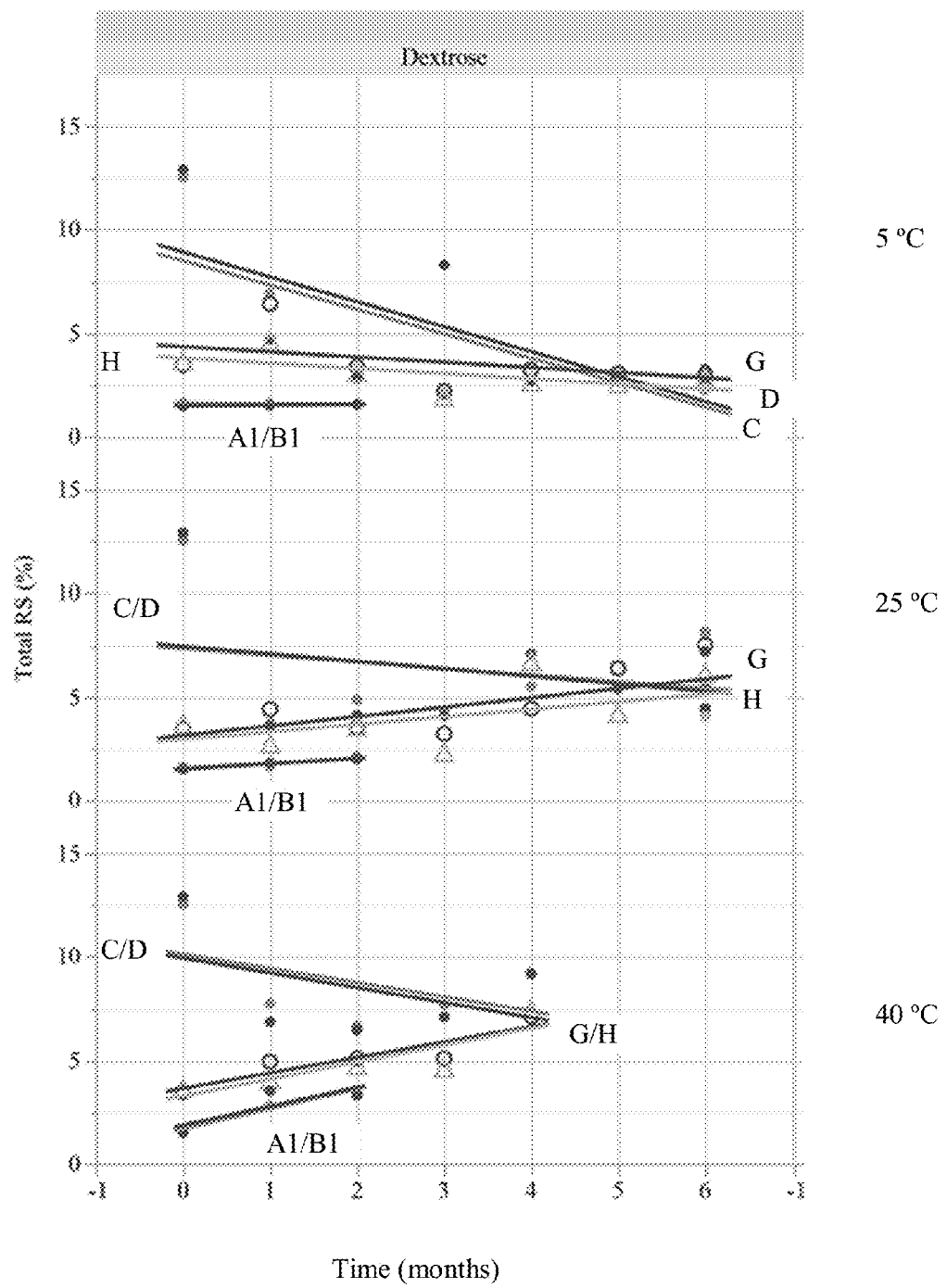
FIG. 32 shows the total impurities of vasopressin after storage at 5° C., 25° C., and 40° C. of vasopressin formulations prepared in dextrose.
Figure 33:
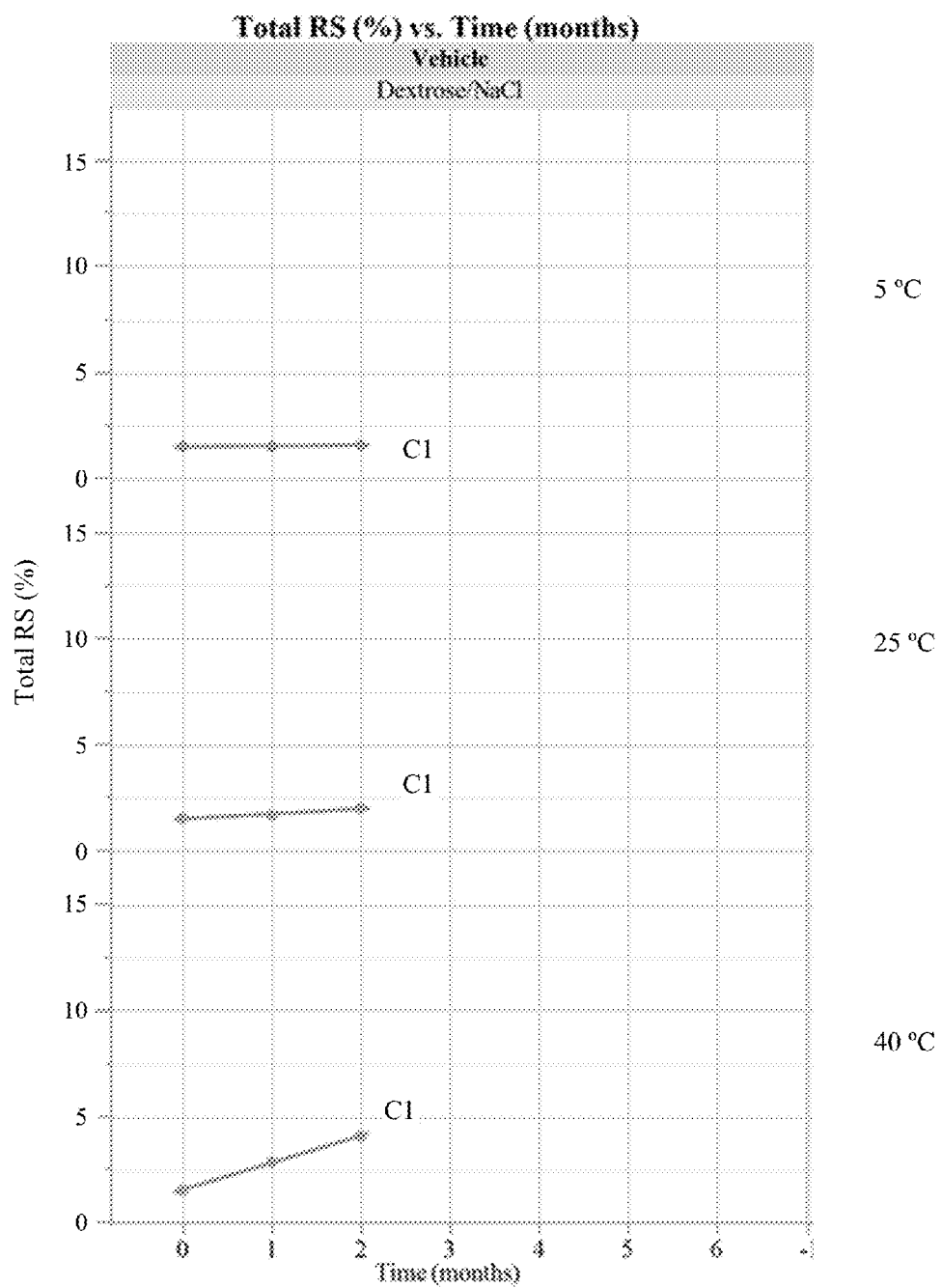
FIG. 33 shows the total impurities of vasopressin after storage at 5° C., 25° C., and 40° C. of vasopressin formulations prepared in dextrose and sodium chloride.
Figure 34:
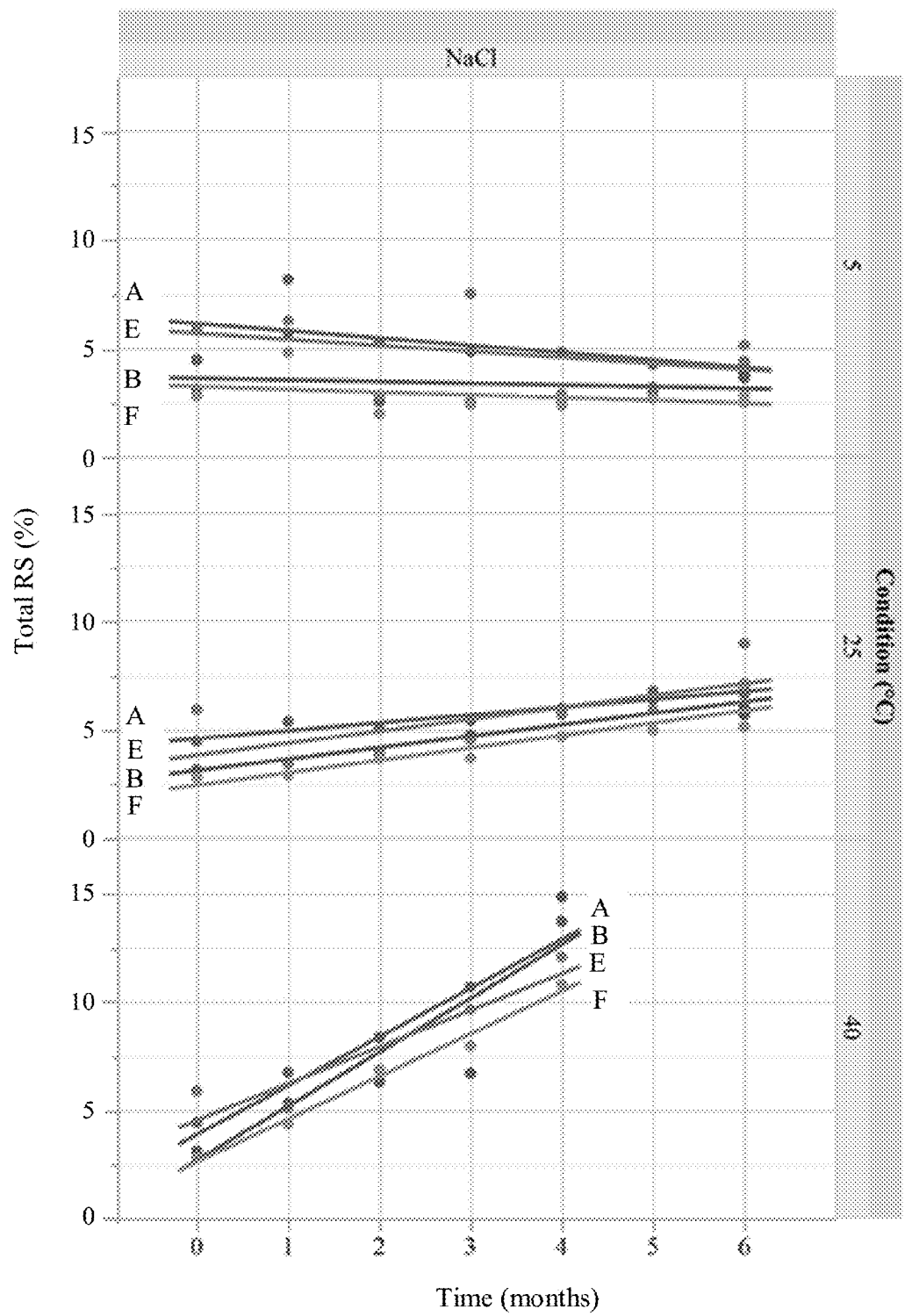
FIG. 34 shows the total impurities of vasopressin after storage at 5° C., 25° C., and 40° C. of vasopressin formulations prepared in sodium chloride.
Figure 35:
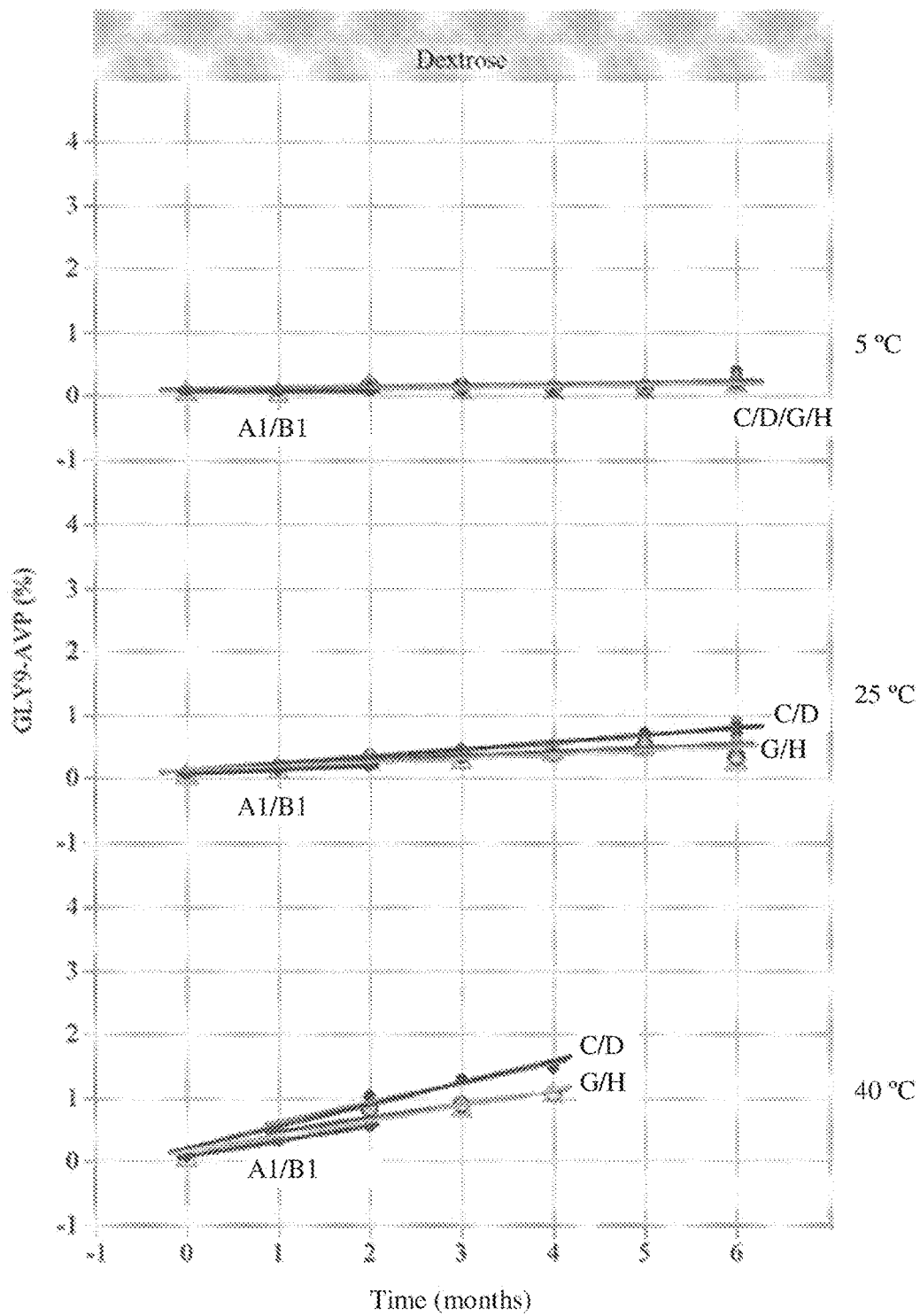
FIG. 35 shows the % Gly9-AVP of vasopressin after storage at 5° C., 25° C., and 40° C. of vasopressin formulations prepared in dextrose.
Figure 36:
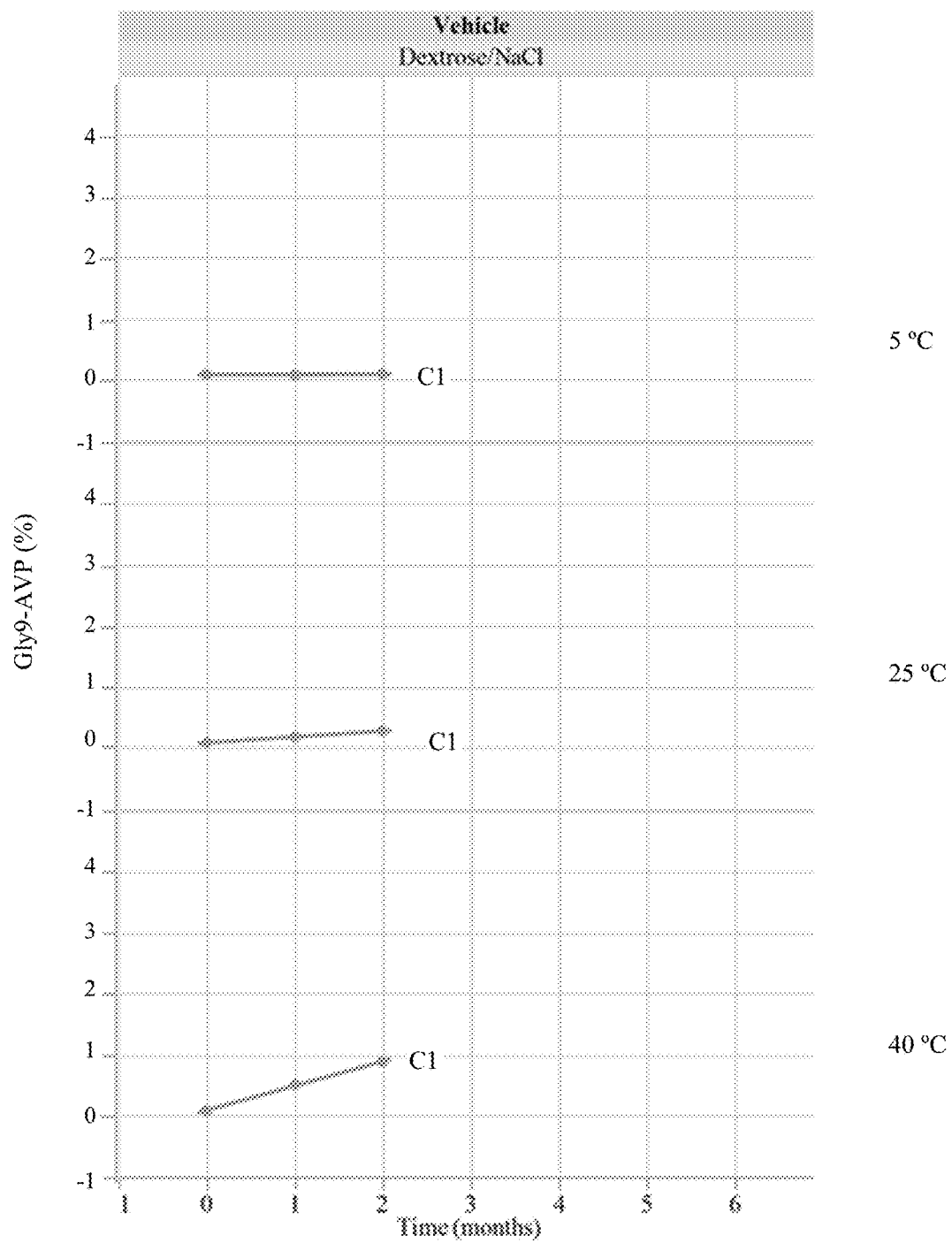
FIG. 36 shows the % Gly9-AVP of vasopressin after storage at 5° C., 25° C., and 40° C. of vasopressin formulations prepared in dextrose and sodium chloride.
Figure 37:
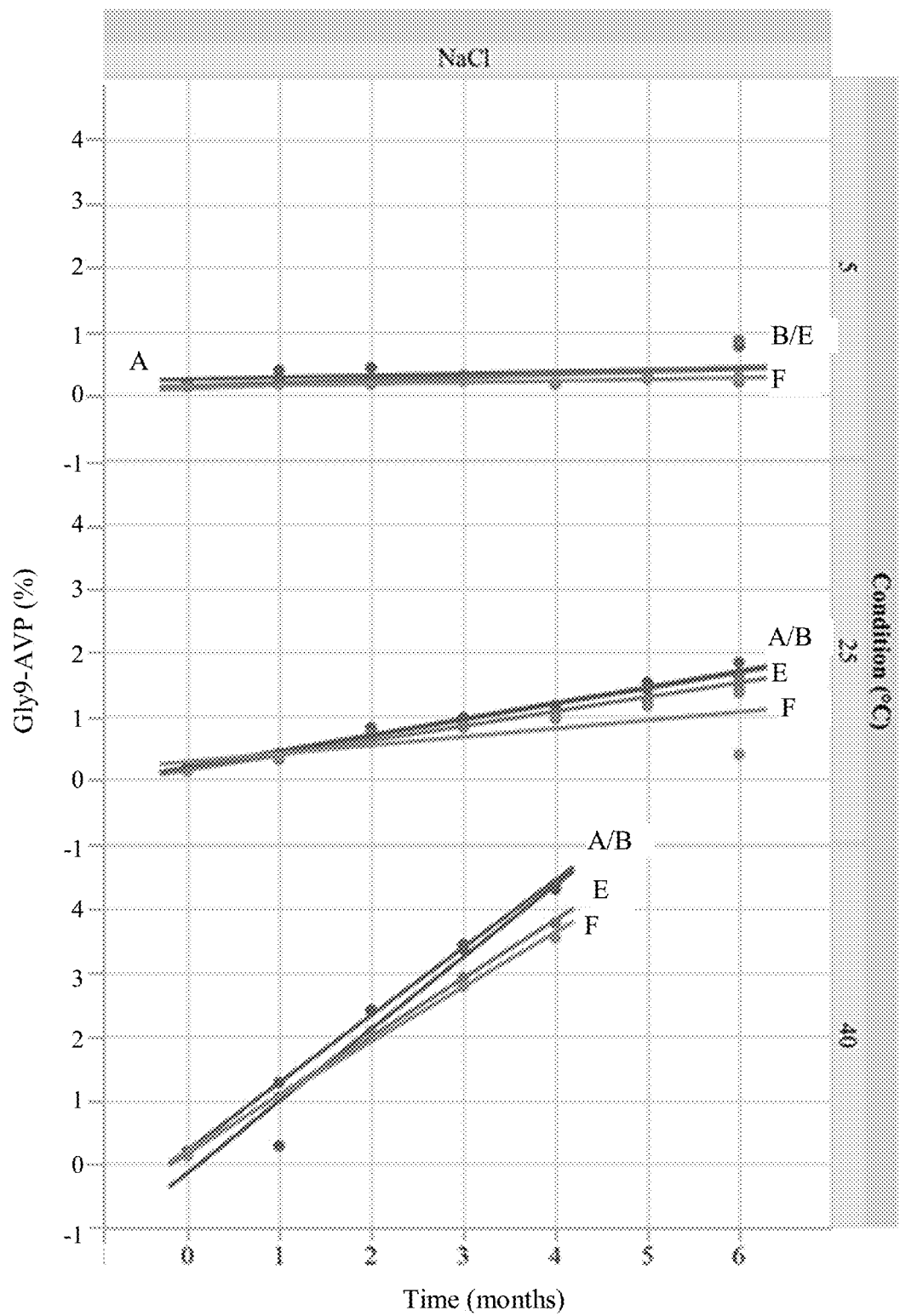
FIG. 37 shows the % Gly9-AVP of vasopressin after storage at 5° C., 25° C., and 40° C. of vasopressin formulations prepared in sodium chloride.
Figure 38:
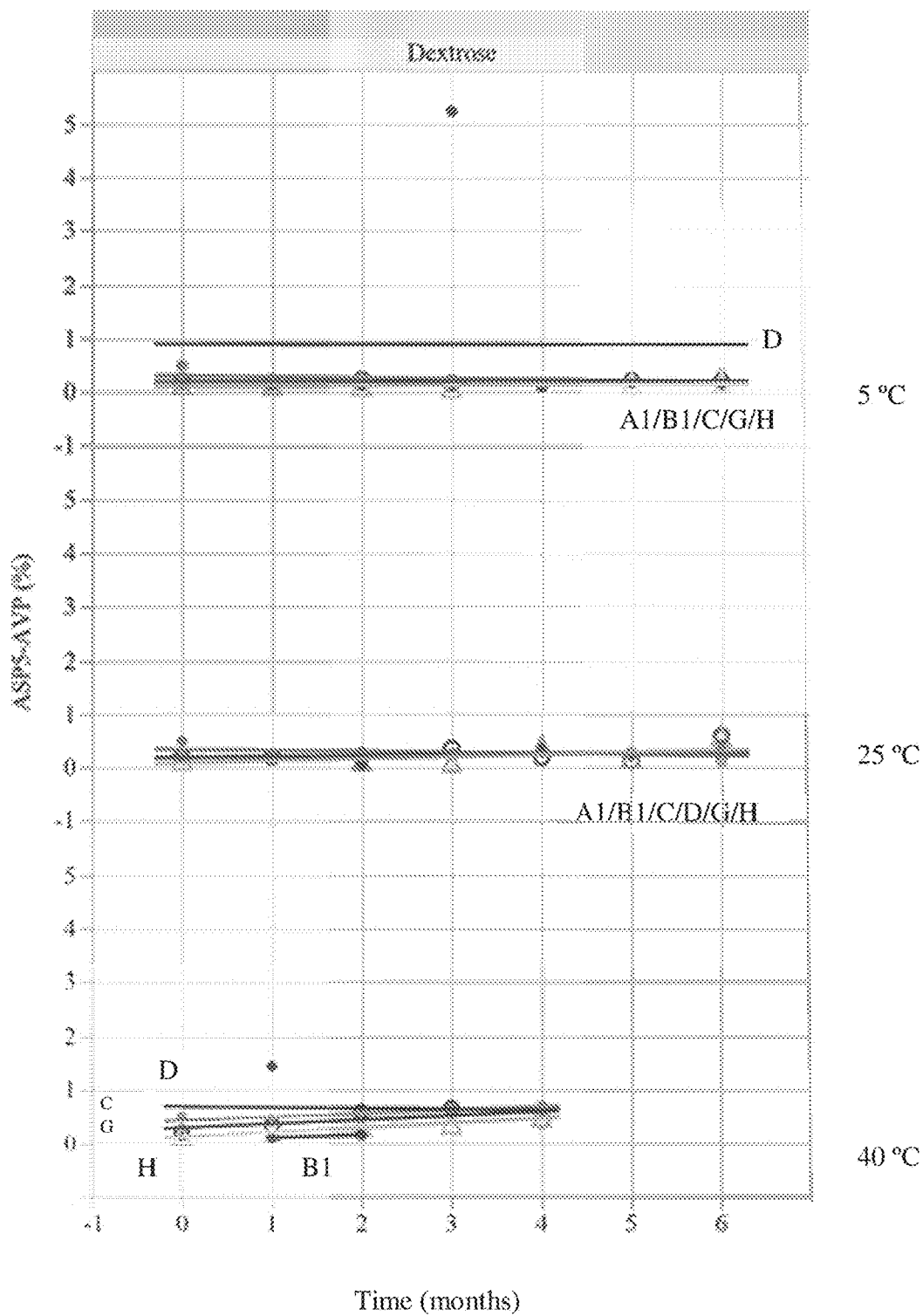
FIG. 38 shows the % Asp5-AVP of vasopressin after storage at 5° C., 25° C., and 40° C. of vasopressin formulations prepared in dextrose.
Figure 39:
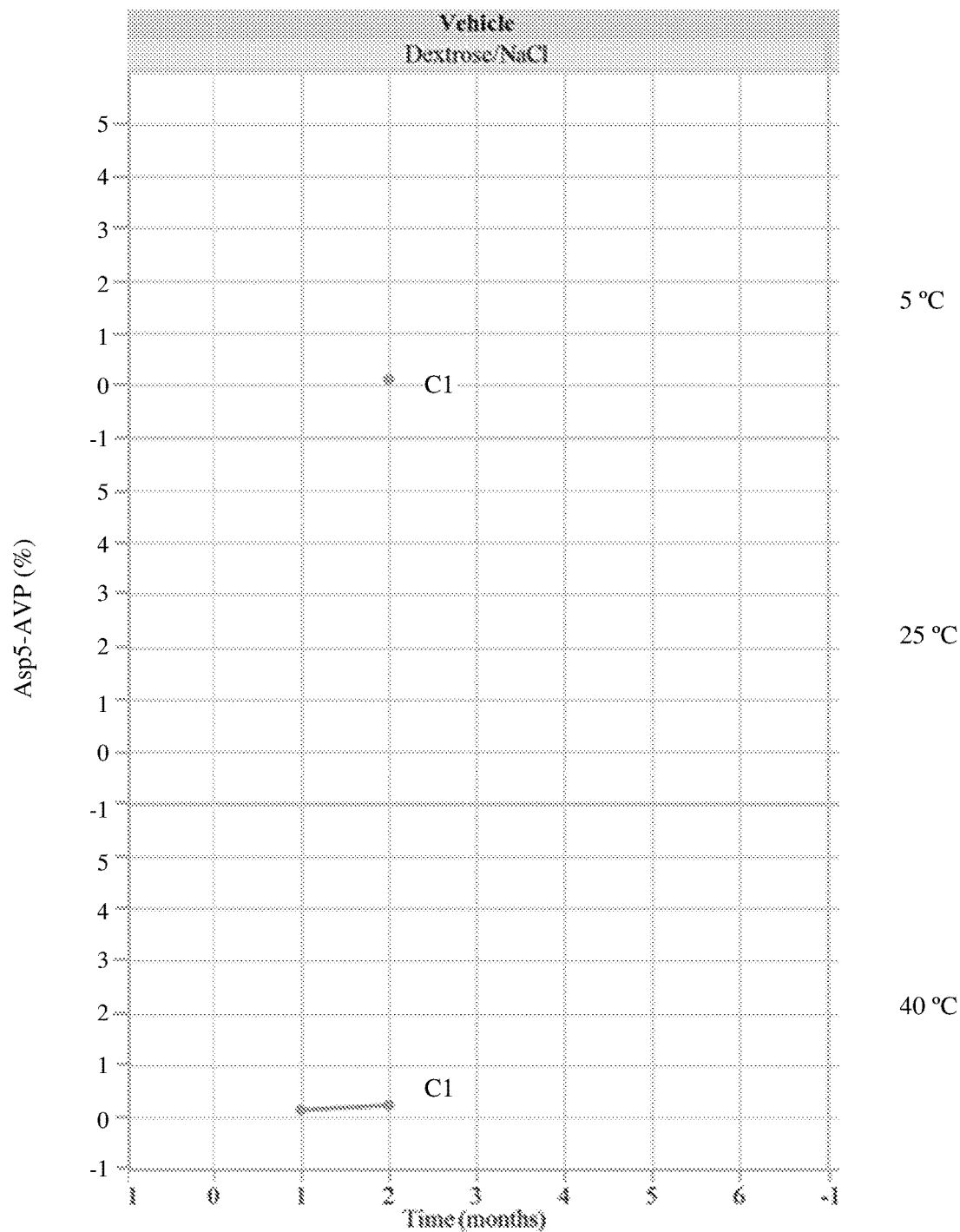
FIG. 39 shows the % Asp5-AVP of vasopressin after storage at 5° C., 25° C., and 40° C. of vasopressin formulations prepared in dextrose and sodium chloride.
Figure 40:
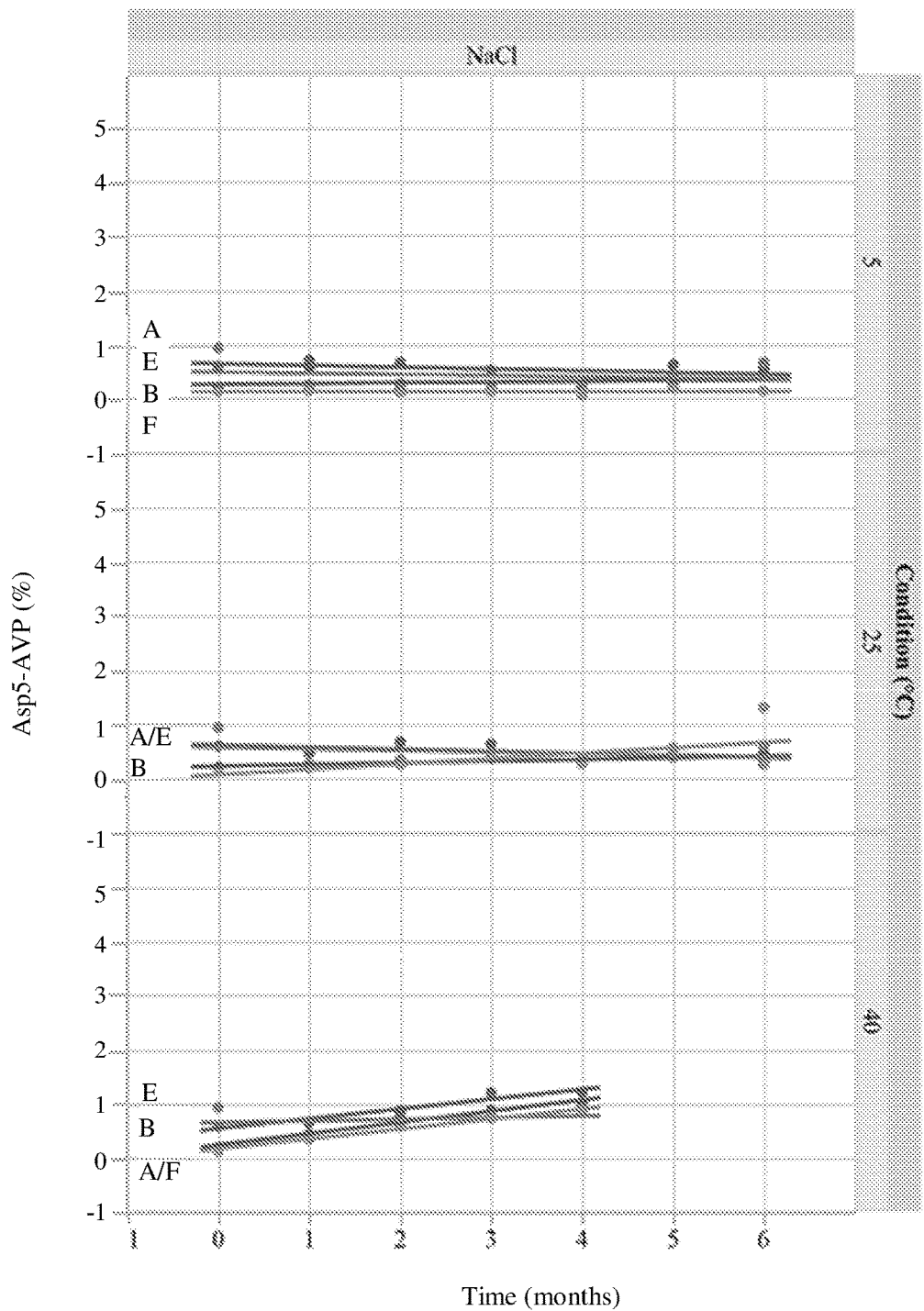
FIG. 40 shows the % Asp5-AVP of vasopressin after storage at 5° C., 25° C., and 40° C. of vasopressin formulations prepared in sodium chloride.
Figure 41:
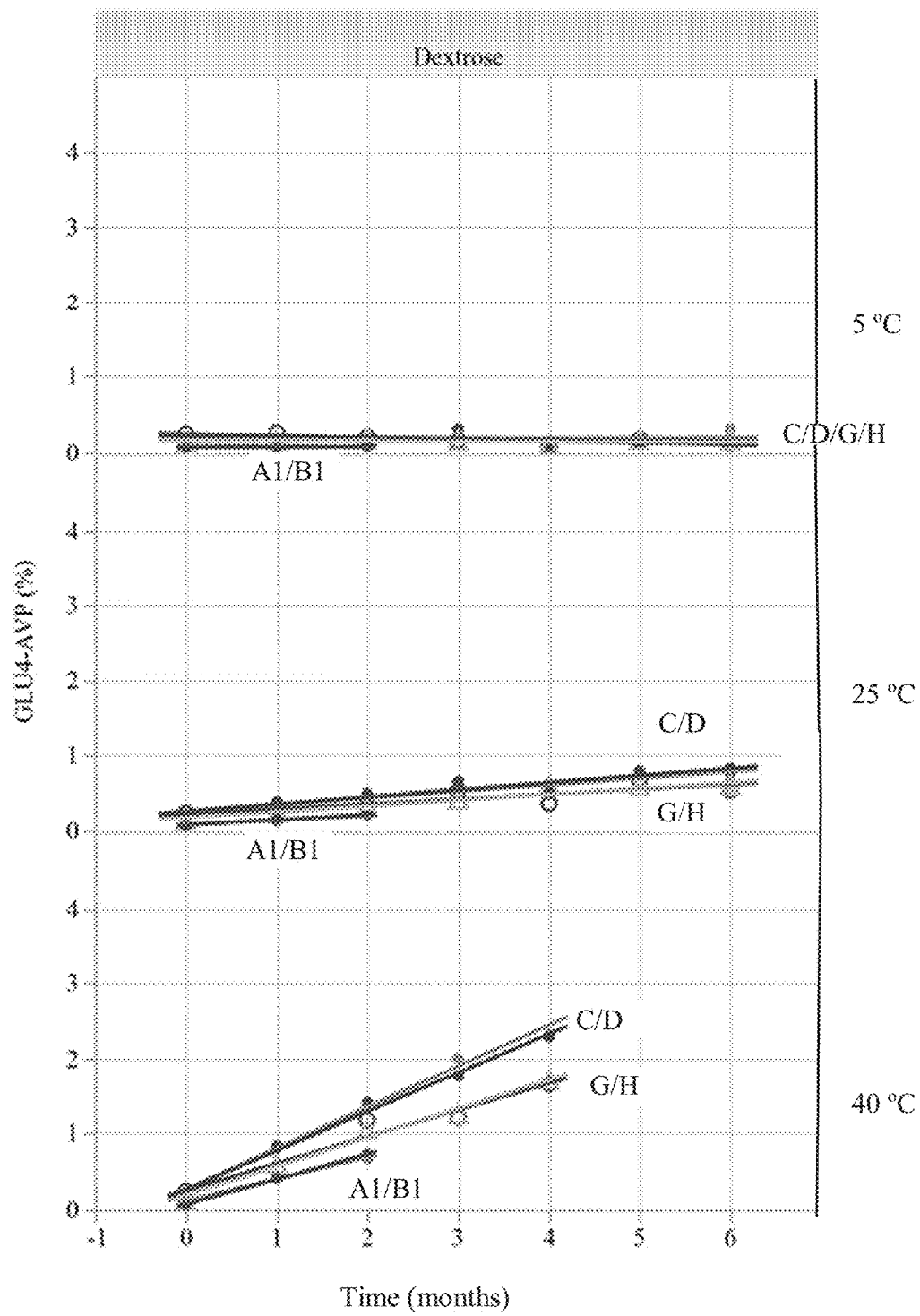
FIG. 41 shows the % Glu4-AVP of vasopressin after storage at 5° C., 25° C., and 40° C. of vasopressin formulations prepared in dextrose.
Figure 42:
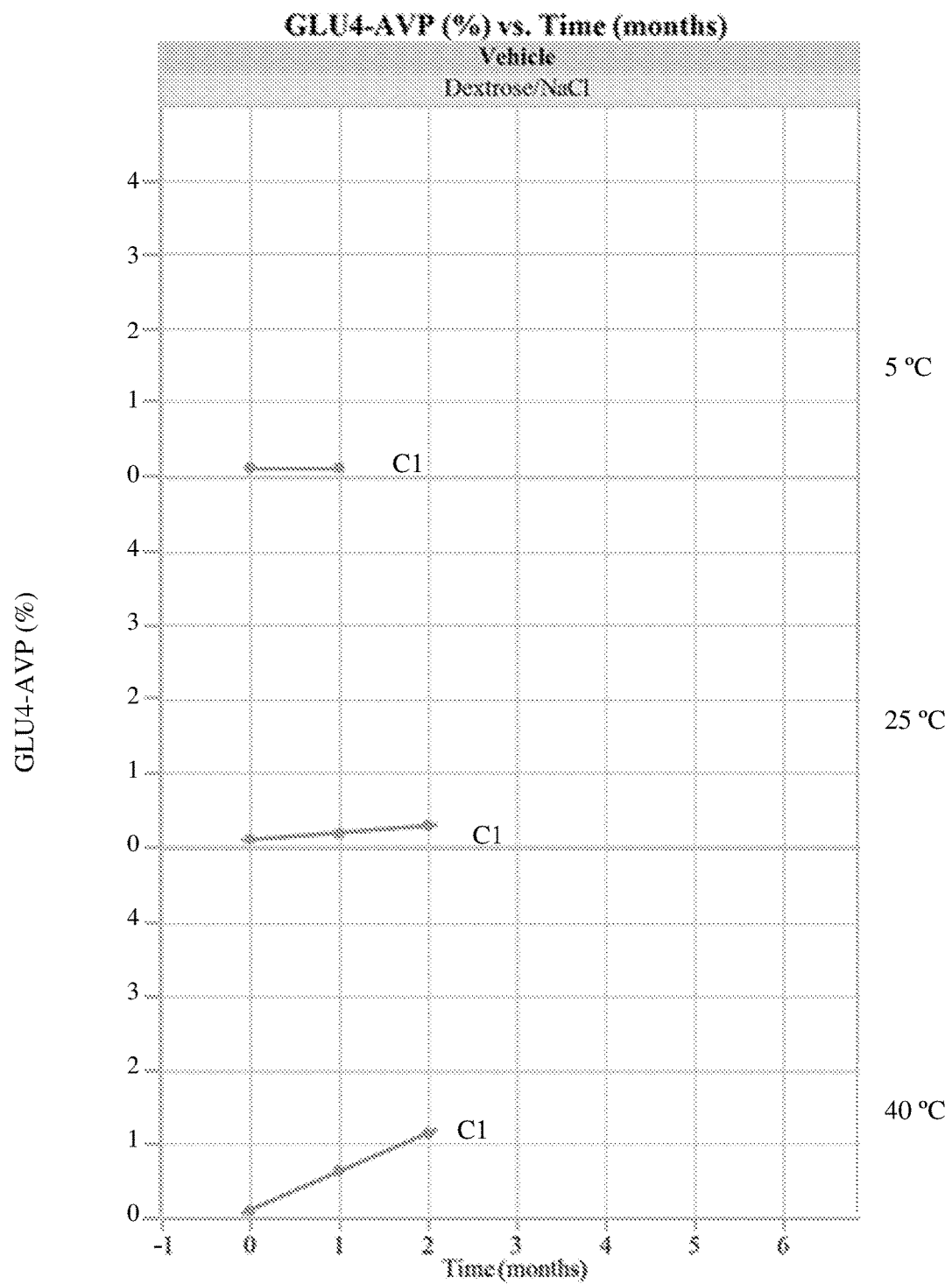
FIG. 42 shows the % Glu4-AVP of vasopressin after storage at 5° C., 25° C., and 40° C. of vasopressin formulations prepared in dextrose and sodium chloride.
Figure 43:
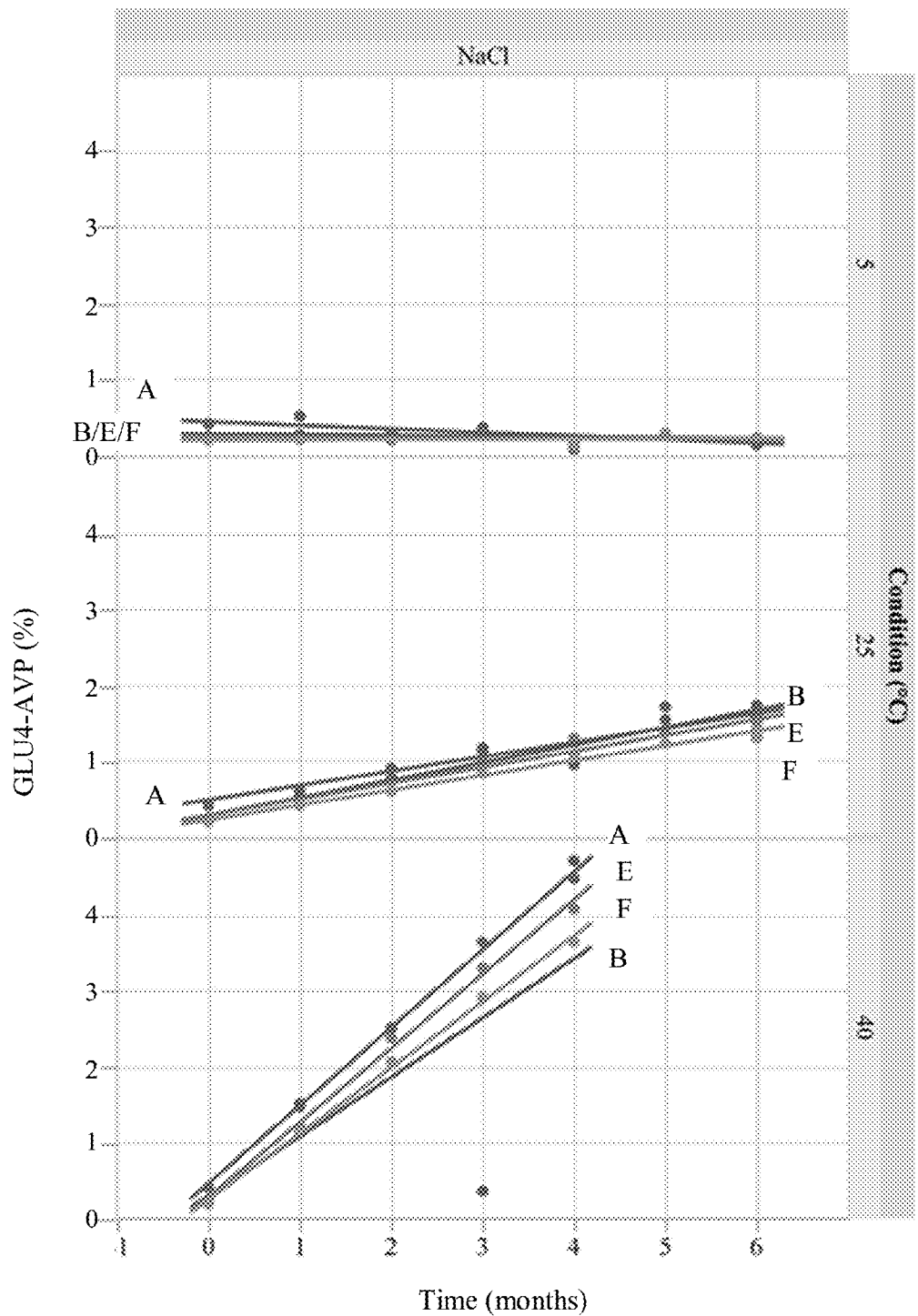
FIG. 43 shows the % Glu4-AVP of vasopressin after storage at 5° C., 25° C., and 40° C. of vasopressin formulations prepared in sodium chloride.
Figure 44:
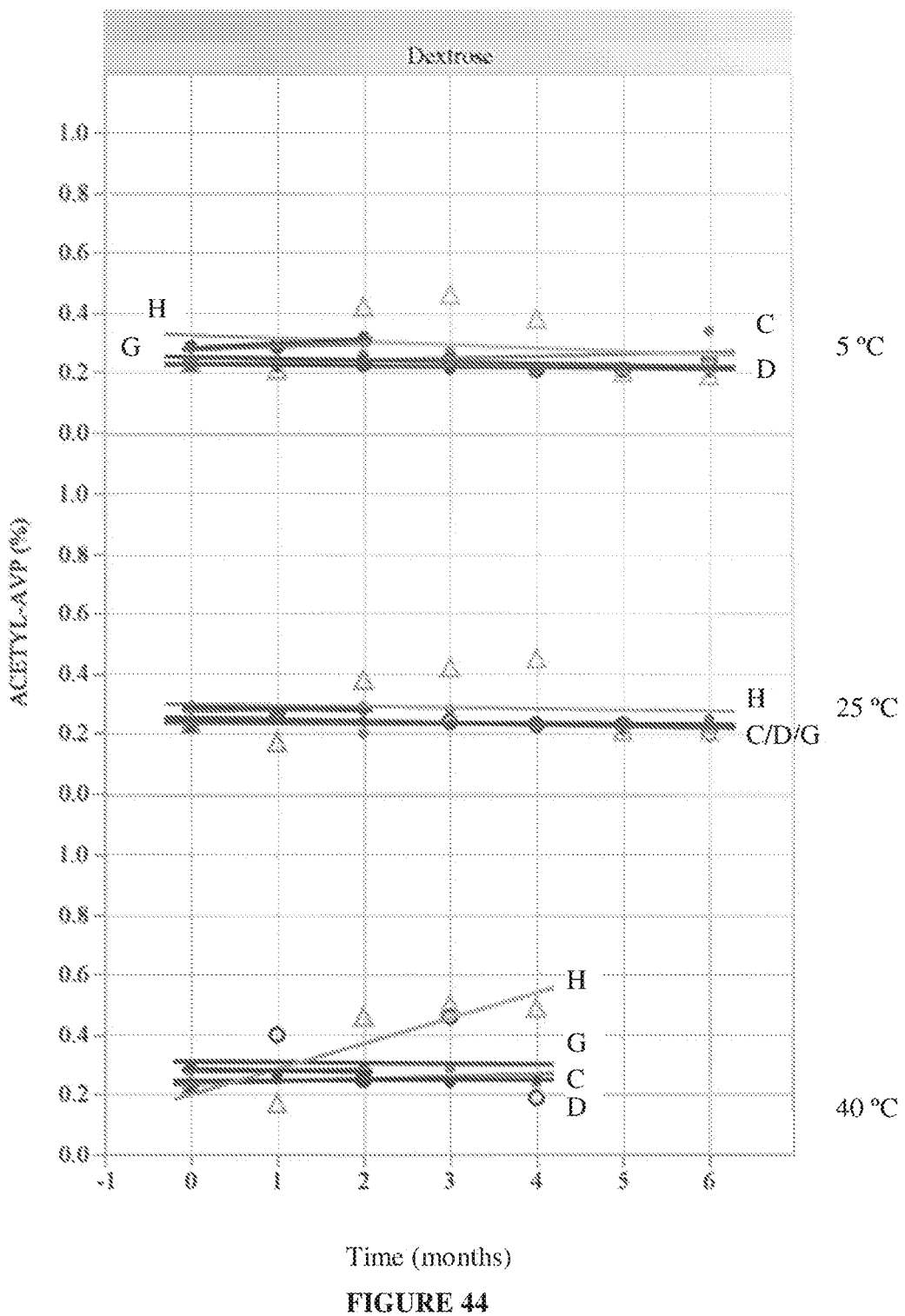
FIG. 44 shows the % Acetyl-AVP of vasopressin after storage at 5° C., 25° C., and 40° C. of vasopressin formulations prepared in dextrose.
Figure 45:
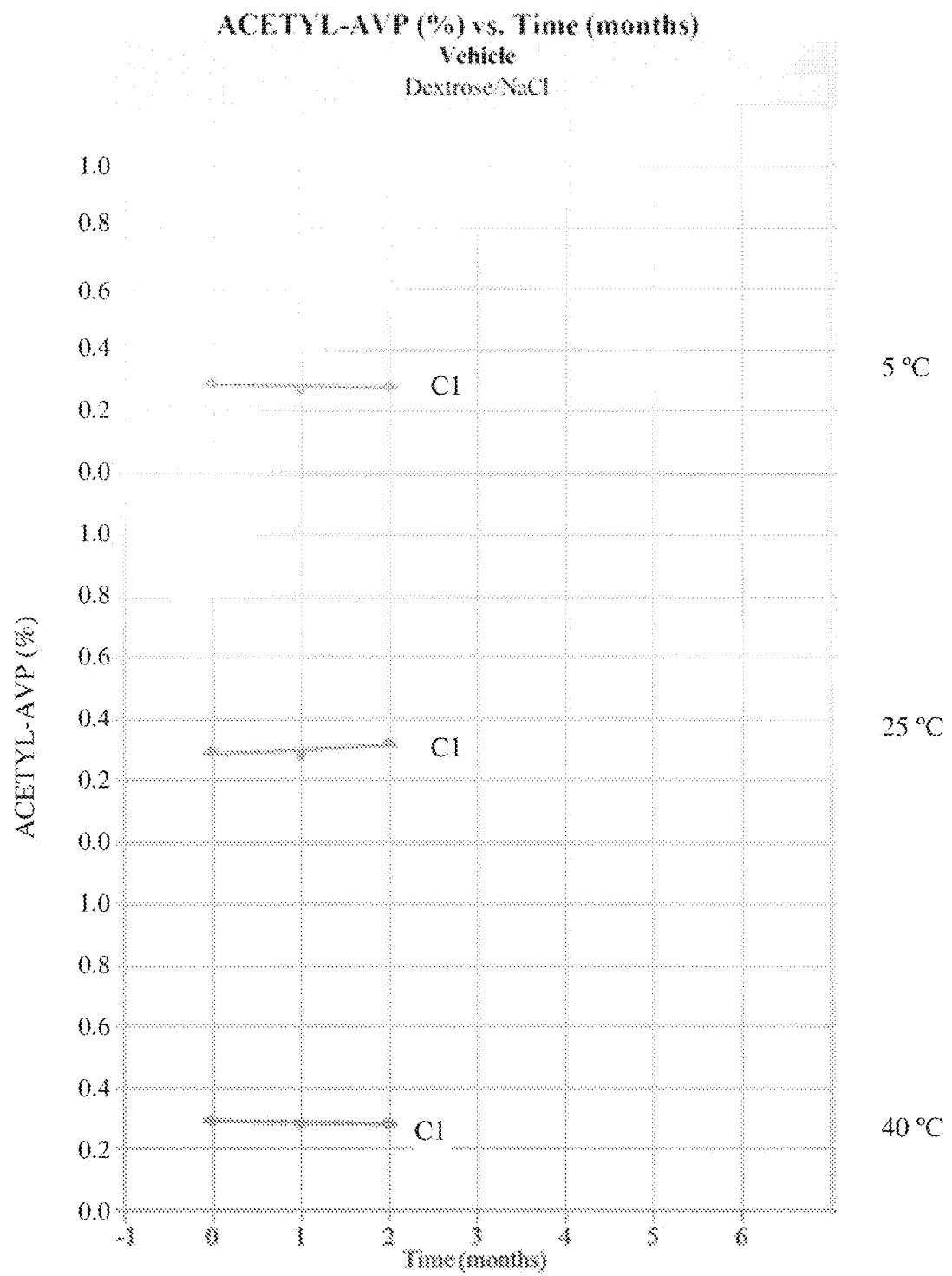
FIG. 45 shows the % Acetyl-AVP of vasopressin after storage at 5° C., 25° C., and 40° C. of vasopressin formulations prepared in dextrose and sodium chloride.
Figure 46:
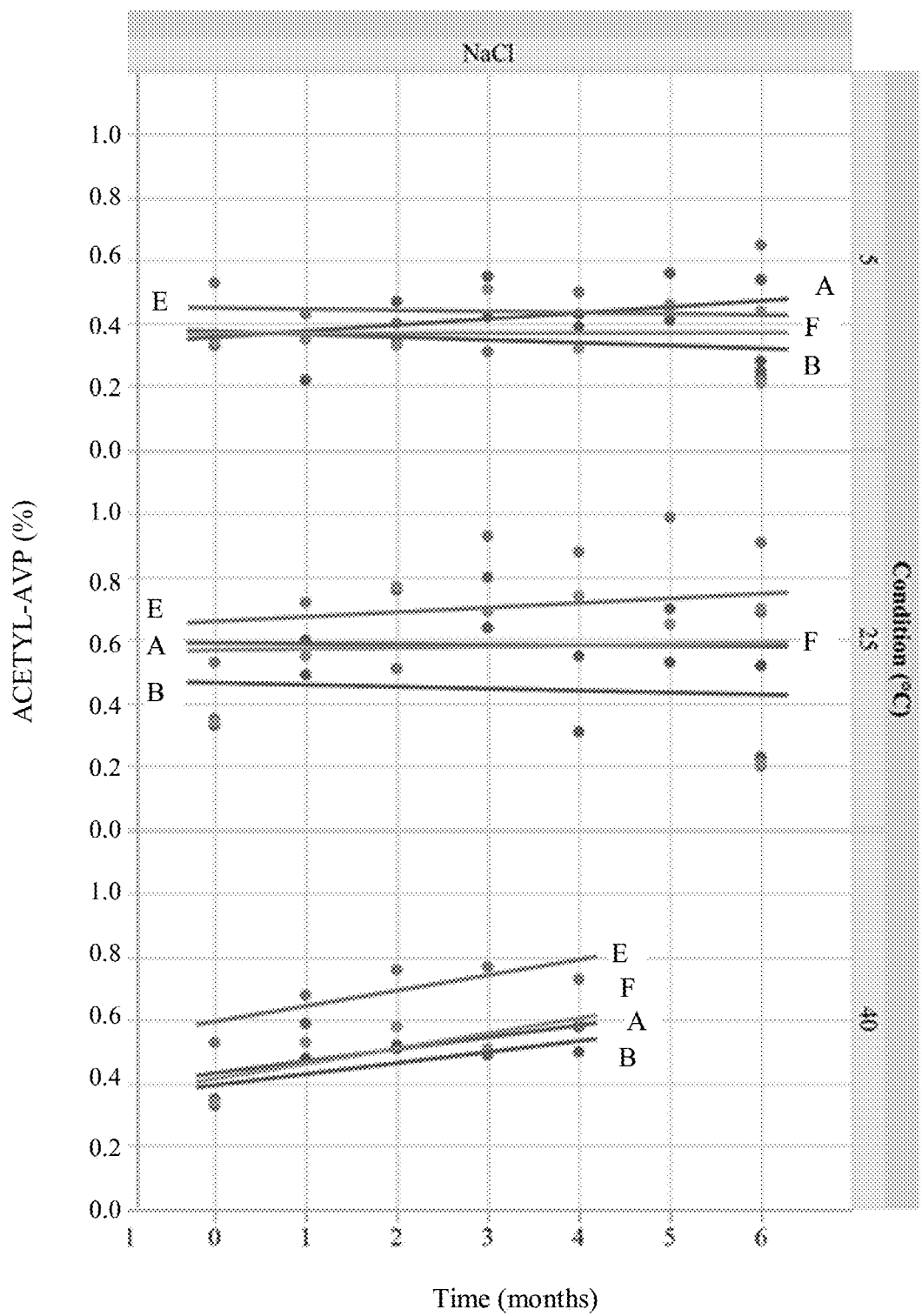
FIG. 46 shows the % Acetyl-AVP of vasopressin after storage at 5° C., 25° C., and 40° C. of vasopressin formulations prepared in sodium chloride.
Figure 47:
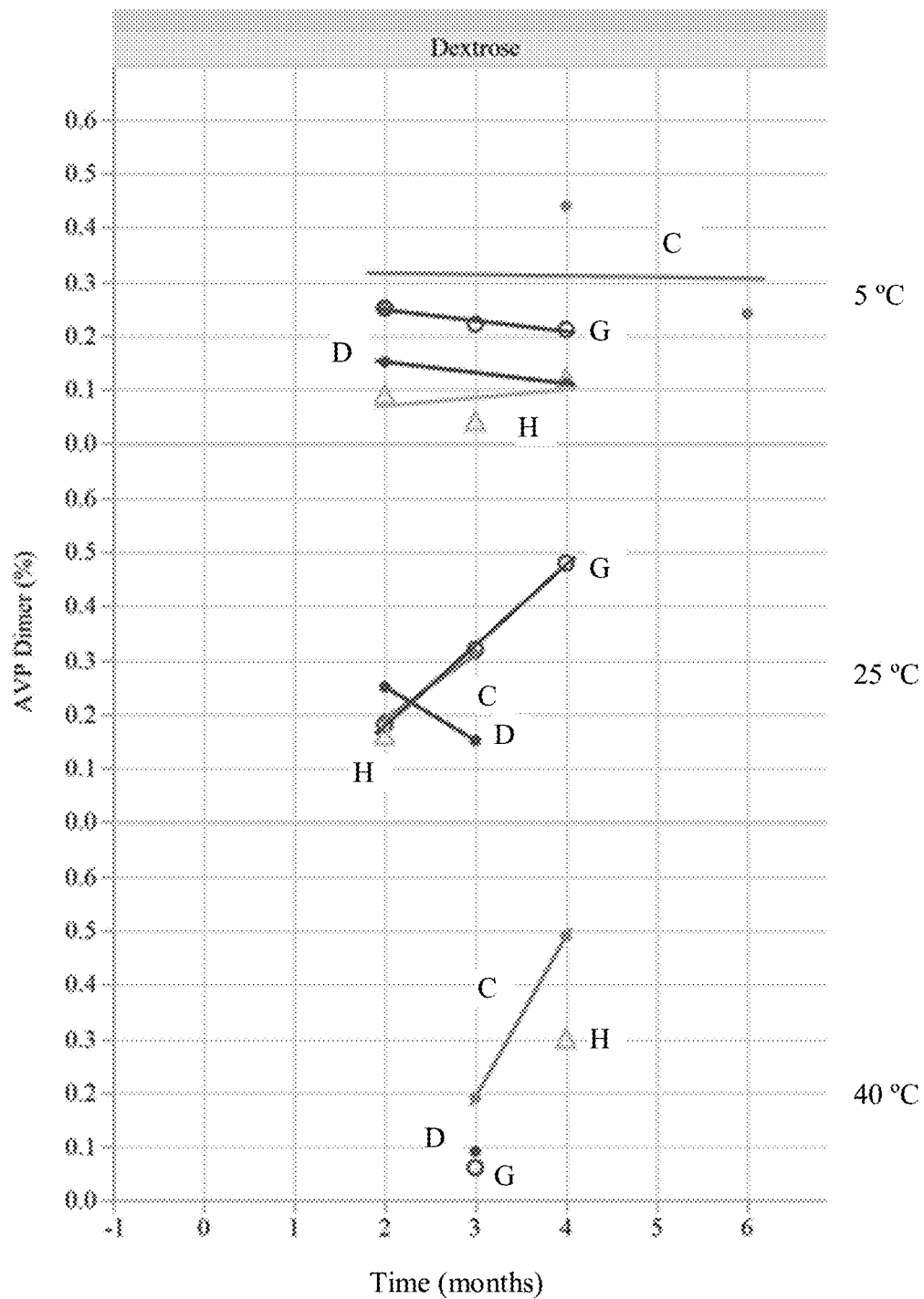
FIG. 47 shows the % AVP-dimer of vasopressin after storage at 5° C., 25° C., and 40° C. of vasopressin formulations prepared in dextrose.
Figure 48:
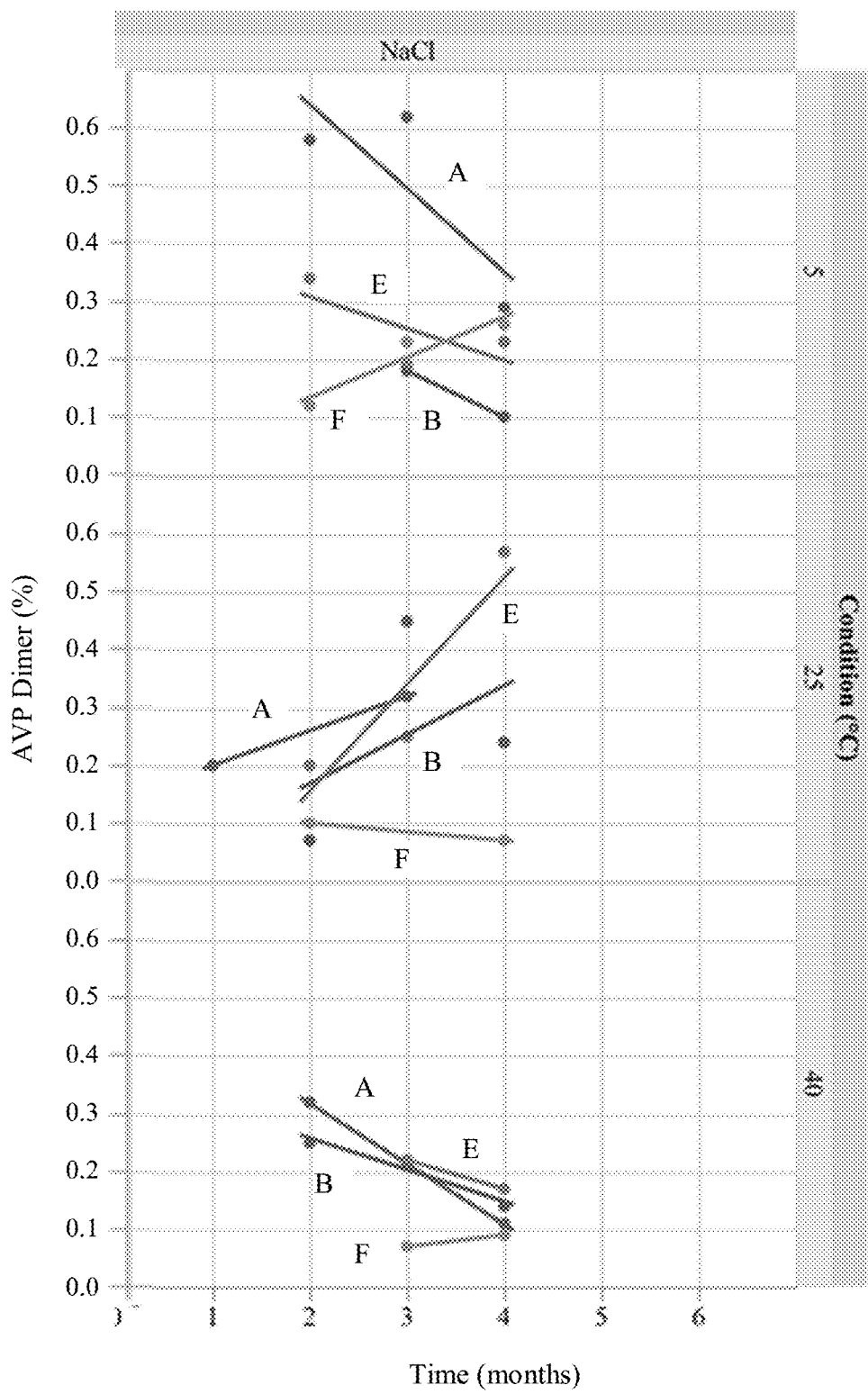
FIG. 48 shows the % AVP-dimer of vasopressin after storage at 5° C., 25° C., and 40° C. of vasopressin formulations prepared in sodium chloride.

The appearance for all of the tested lots through the duration of the experiment was clear and colorless. The results above provided an estimated shelf life at 5° C. of about 16.1 months (FIG. 27) and at 25° C. of about eight months (FIG. 28). The results indicated that the dextrose vehicle with 1 mM acetate buffer provided a lower rate of degradation and a lower rate of impurities accumulation for the vasopressin formulations at 5° C., 25° C., and 40° C. compared to NaCl or a combination of dextrose and NaCl in either 1 mM or 10 mM acetate buffer Graphical depictions of TABLES 66-72 are shown in FIGS. 29-48 below. FIGS. 29-31 show the vasopressin (% LC) levels in the samples prepared in dextrose, dextrose and NaCl, or NaCl. FIGS. 32-34 show the total impurities (total RS (%)) levels in the samples prepared in dextrose, dextrose and NaCl, or NaCl. FIGS. 35-37 show the Gly9-AVP levels in the samples prepared in dextrose, dextrose and NaCl, or NaCl. FIGS. 38-40 show the Asp5-AVP levels in the samples prepared in dextrose, dextrose and NaCl, or NaCl. FIGS. 41-43 show the Glu4-AVP levels in the samples prepared in dextrose, dextrose and NaCl, or NaCl. FIGS. 44-46 show the Acetyl-AVP levels in the samples prepared in dextrose, dextrose and NaCl, or NaCl. FIGS. 47-48 show the AVP dimer levels in the samples prepared in dextrose, dextrose and NaCl, or NaCl.

Based on the data from FIGS. 29-48, the estimated shelf-life at 5° C. is about 16.1 months, and the estimated shelf-life at 25° C. is about 8 months.

Figure 49:
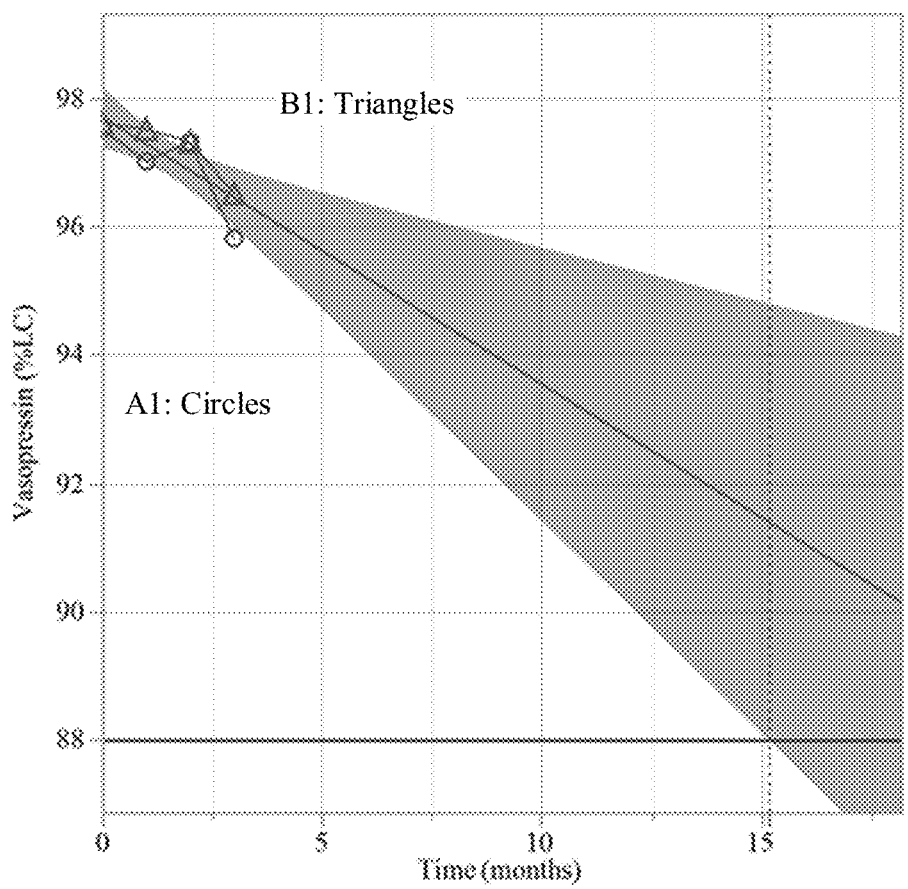
FIG. 49 depicts the estimated shelf-life of a vasopressin sample described herein at 5° C.
Figure 50:
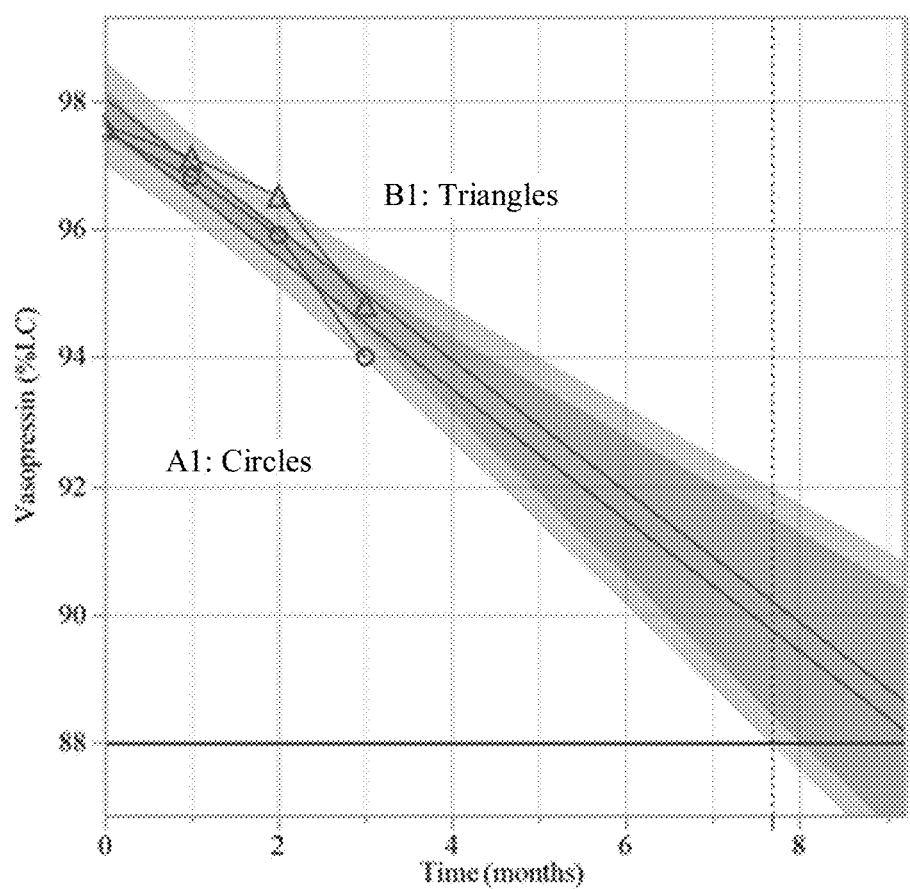
FIG. 50 depicts the estimated shelf-life of a vasopressin sample described herein at 25° C.

TABLES 73-75 display data of further studies on Formulations A1, B1, and C1 as detailed in TABLE 65. The appearance for all of the tested lots through the duration of the experiment was clear and colorless. The estimated shelf life at 5° C. of about 15 months and at 25° C. of about 7.7 months is shown below in FIG. 49 and FIG. 50, respectively. The results indicated that the dextrose vehicle provided a lower rate of degradation and a lower rate of impurities accumulation for the vasopressin formulations at 5° C., 25° C., and 40° C. compared to a combination of dextrose and NaCl.

Figure 51:
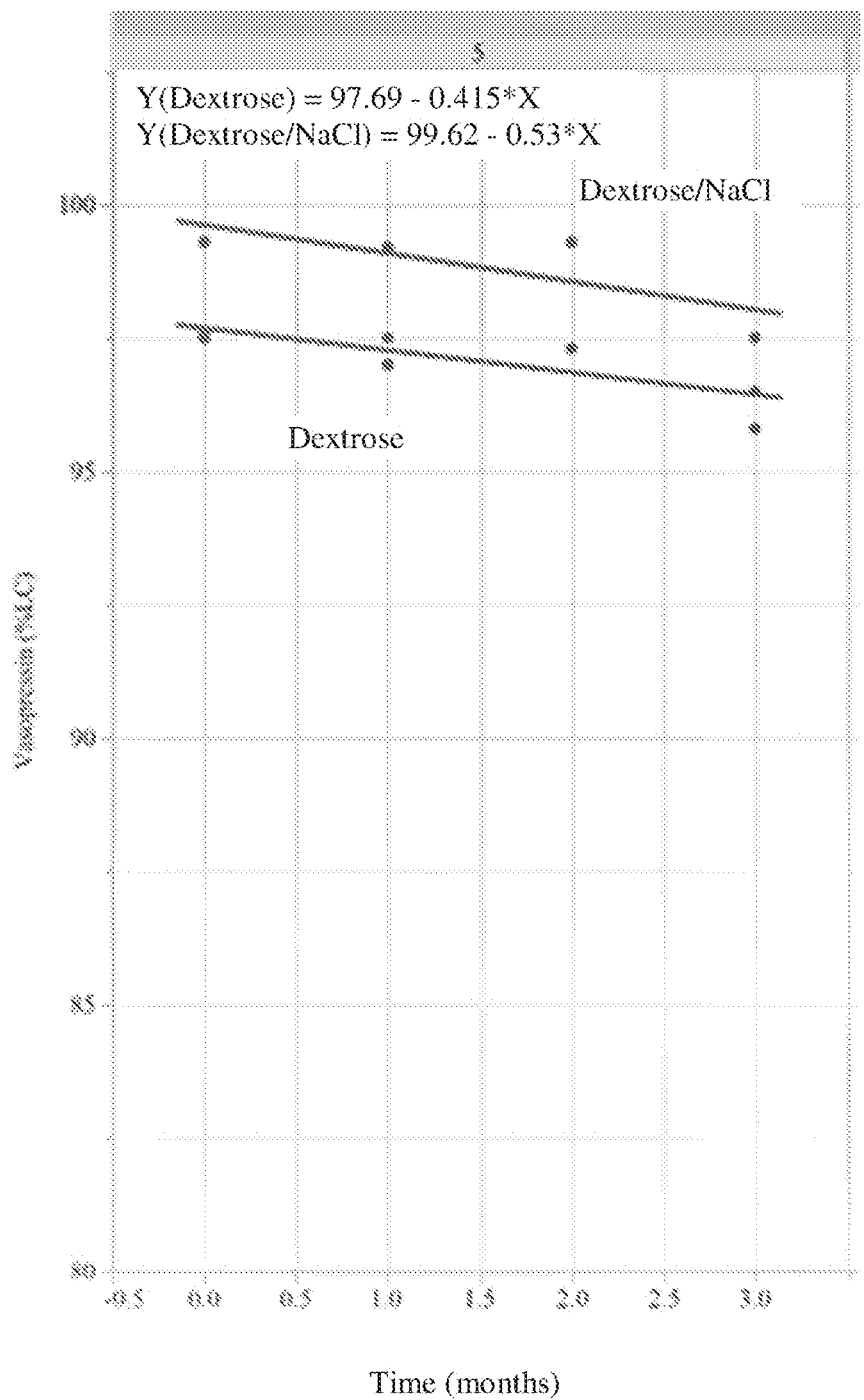
FIG. 51 shows the % LC of vasopressin after storage at 5° C. of vasopressin formulations prepared in dextrose or dextrose and sodium chloride.
Figure 52:
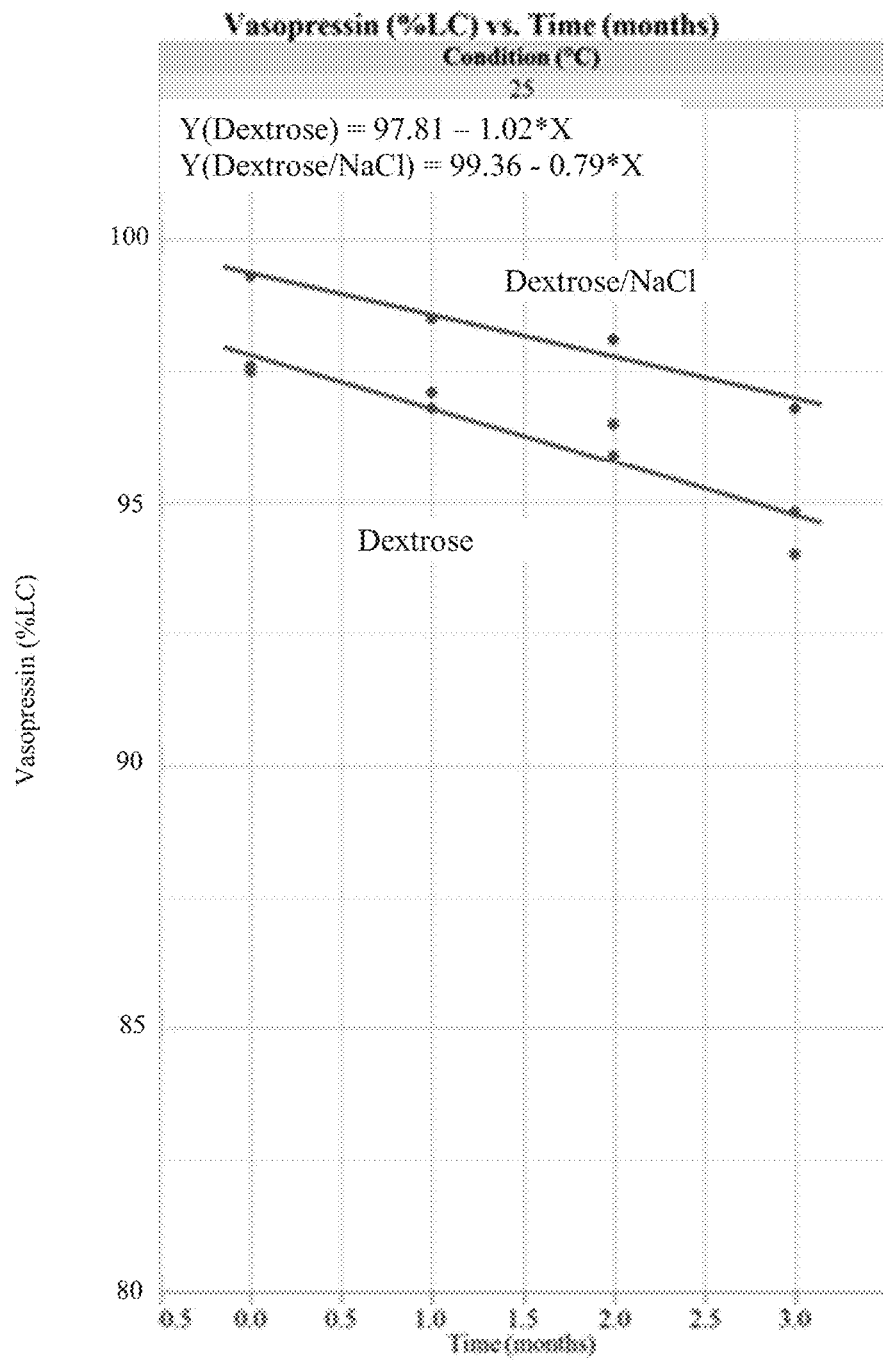
FIG. 52 shows the % LC of vasopressin after storage at 25° C. of vasopressin formulations prepared in dextrose or dextrose and sodium chloride.
Figure 53:
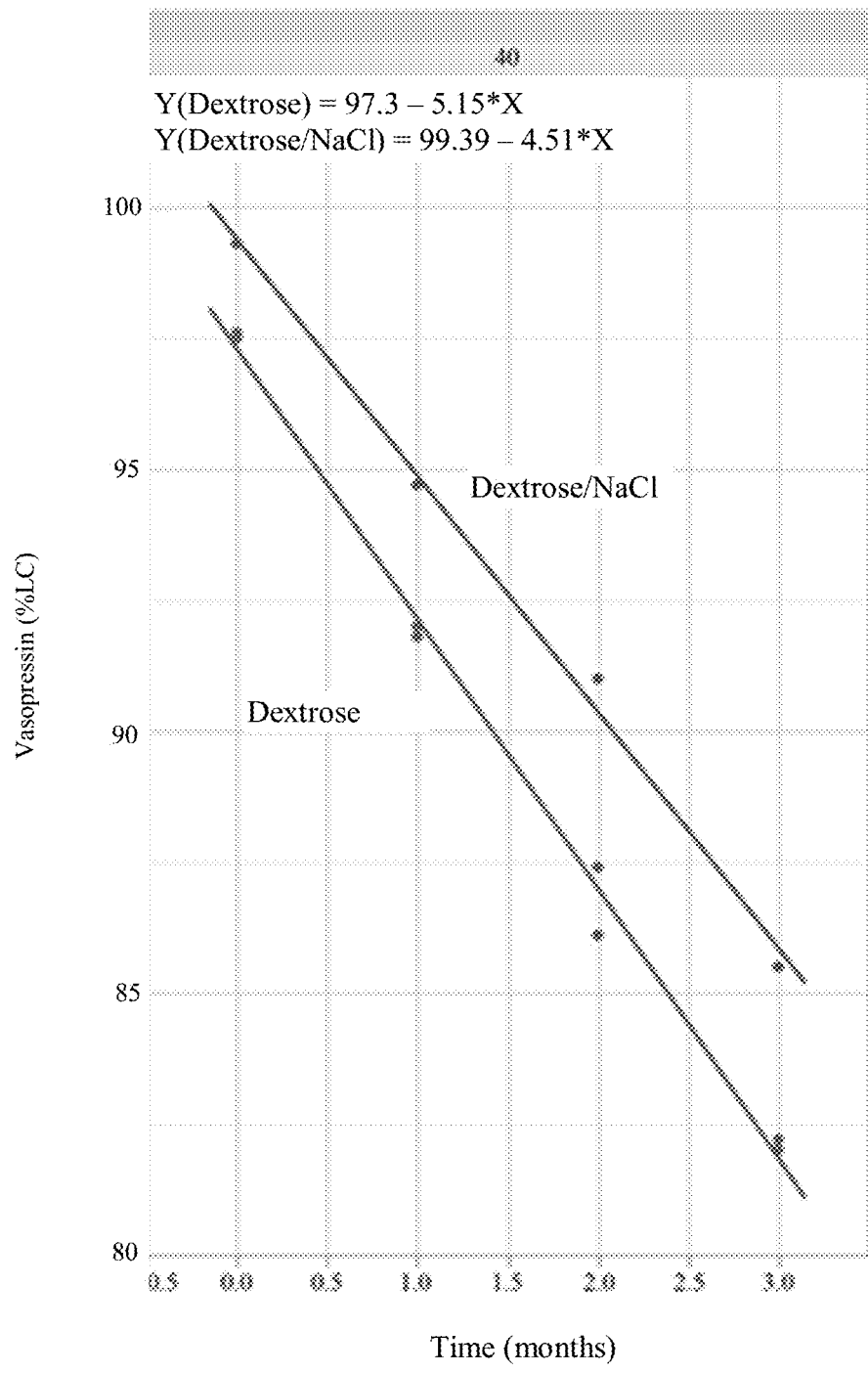
FIG. 53 shows the % LC of vasopressin after storage at 40° C. of vasopressin formulations prepared in dextrose or dextrose and sodium chloride.
Figure 54:
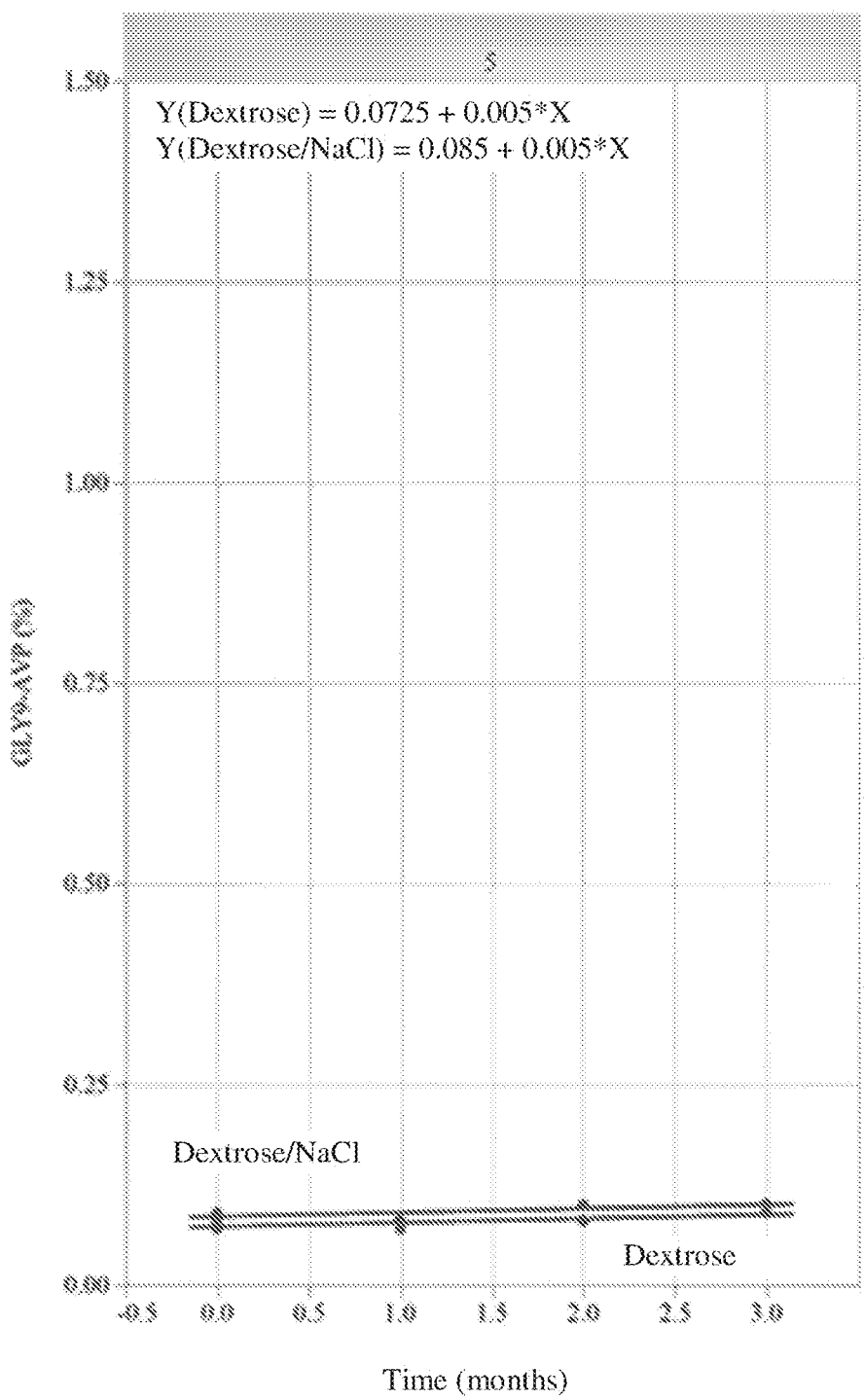
FIG. 54 shows the % Gly9-AVP of vasopressin after storage at 5° C. of vasopressin formulations prepared in dextrose or dextrose and sodium chloride.
Figure 55:
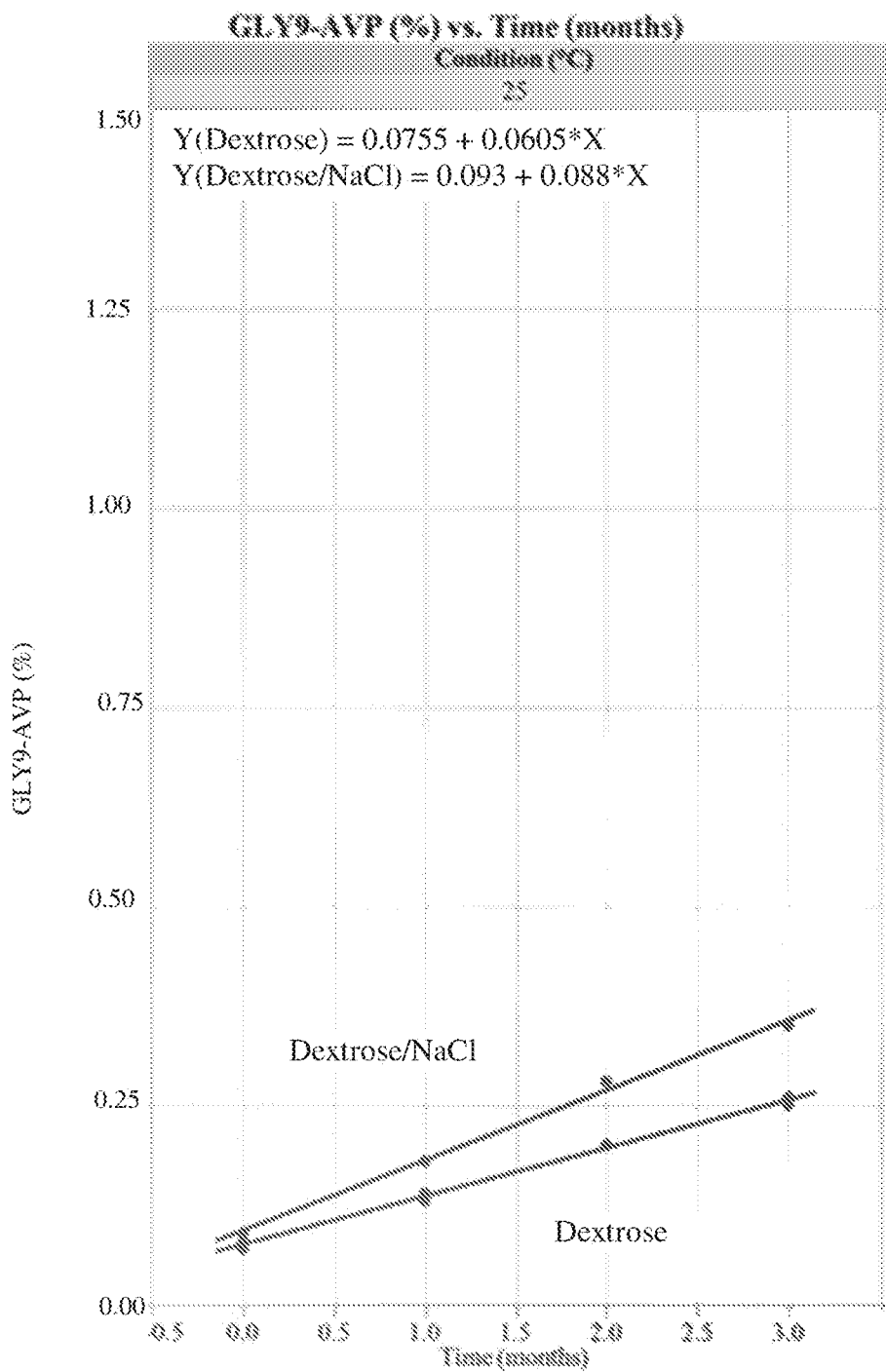
FIG. 55 shows the % Gly9-AVP of vasopressin after storage at 25° C. of vasopressin formulations prepared in dextrose or dextrose and sodium chloride.
Figure 56:
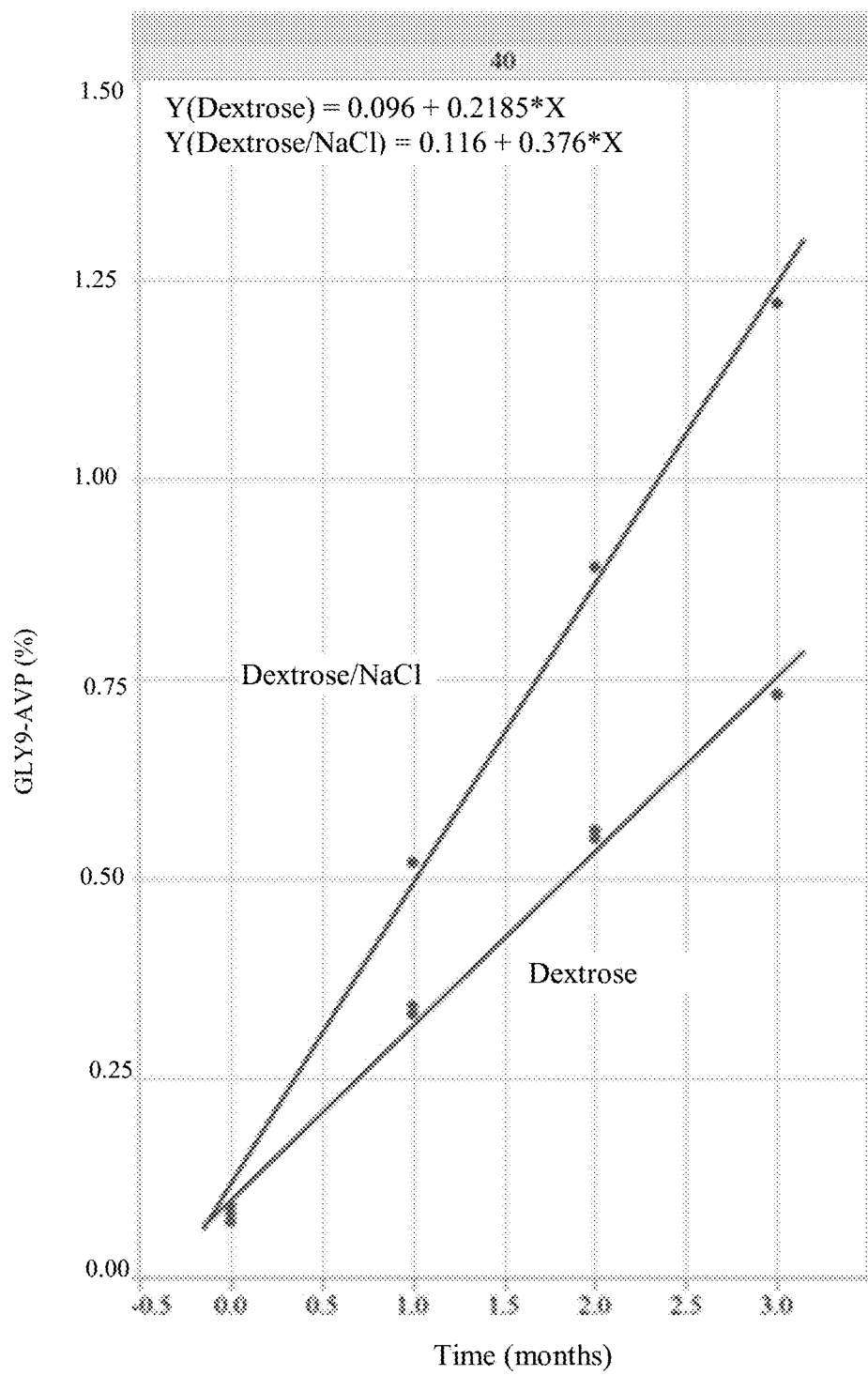
FIG. 56 shows the % Gly9-AVP of vasopressin after storage at 40° C. of vasopressin formulations prepared in dextrose or dextrose and sodium chloride.
Figure 57:
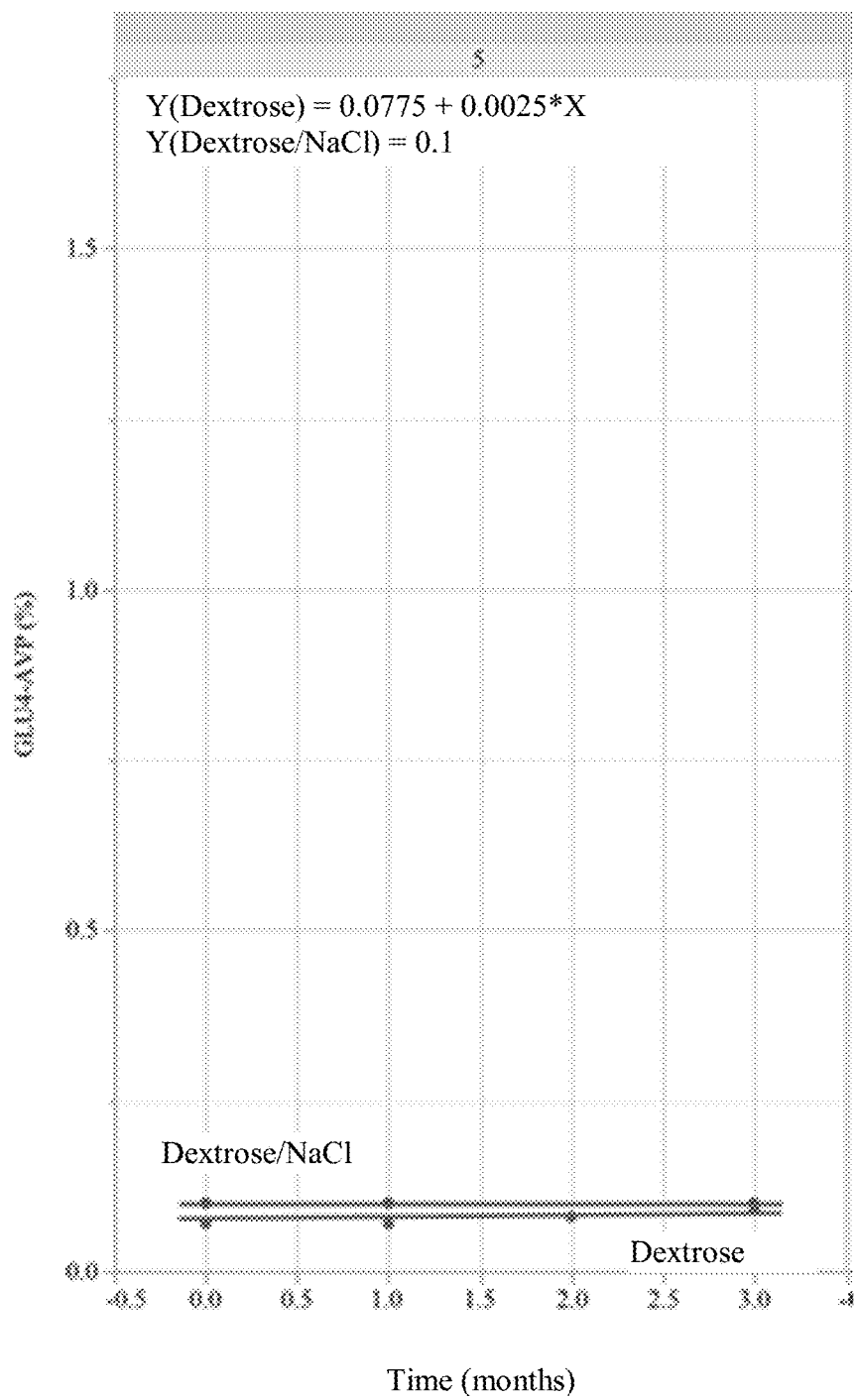
FIG. 57 shows the % Glu4-AVP of vasopressin after storage at 5° C. of vasopressin formulations prepared in dextrose or dextrose and sodium chloride.
Figure 58:
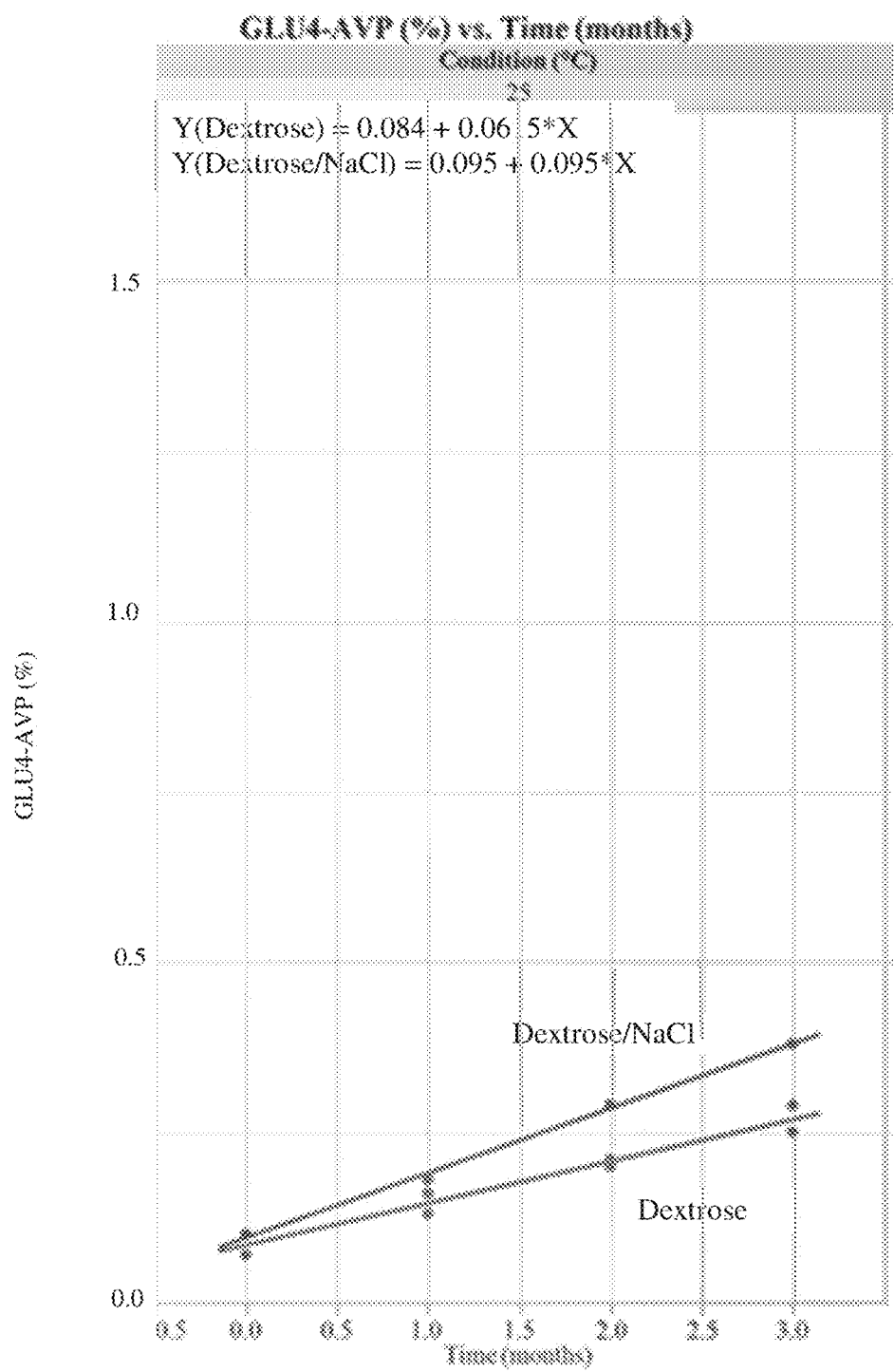
FIG. 58 shows the % Glu4-AVP of vasopressin after storage at 25° C. of vasopressin formulations prepared in dextrose or dextrose and sodium chloride.
Figure 59:
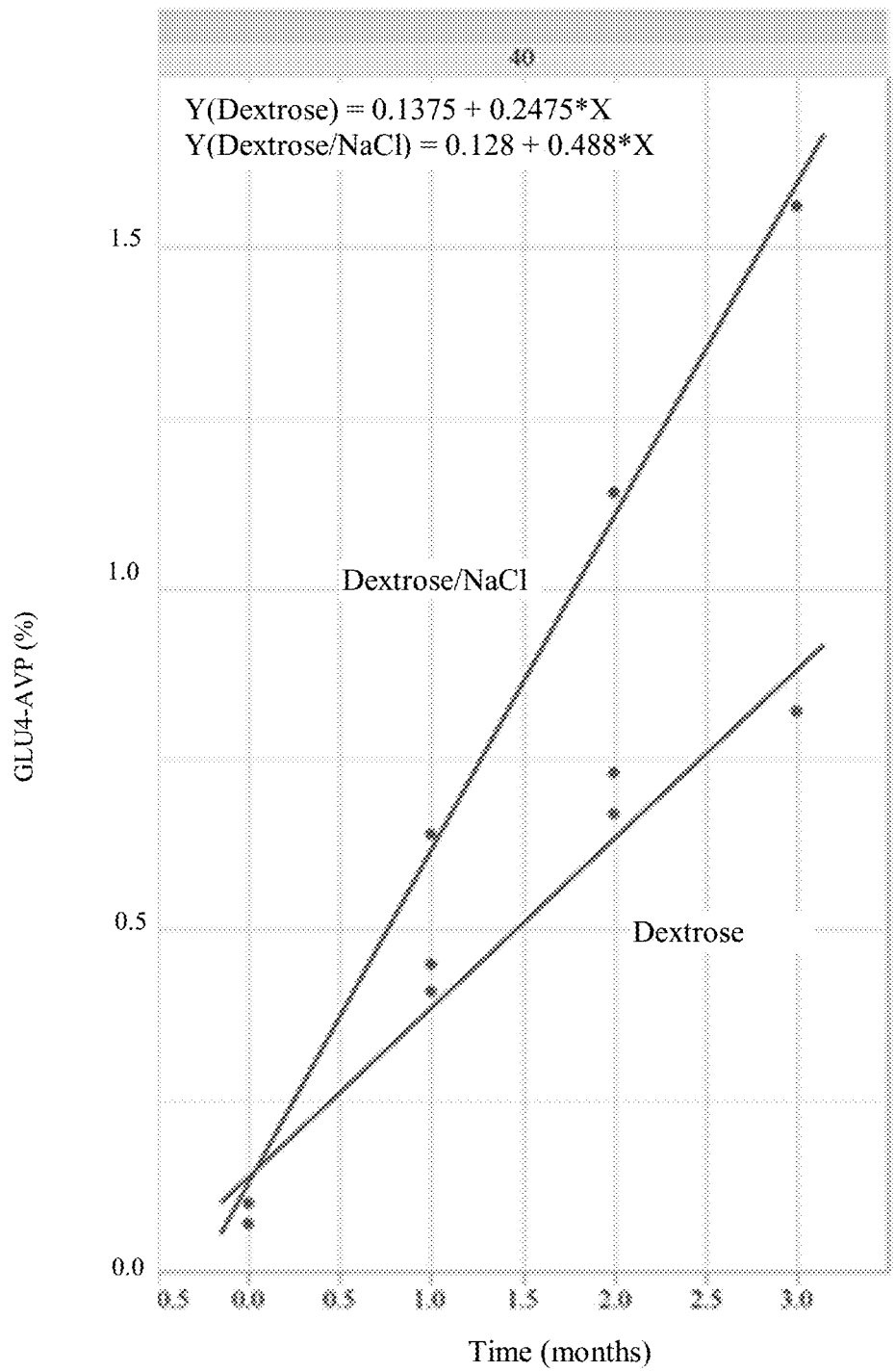
FIG. 59 shows the % Glu4-AVP of vasopressin after storage at 40° C. of vasopressin formulations prepared in dextrose or dextrose and sodium chloride.
Figure 60:
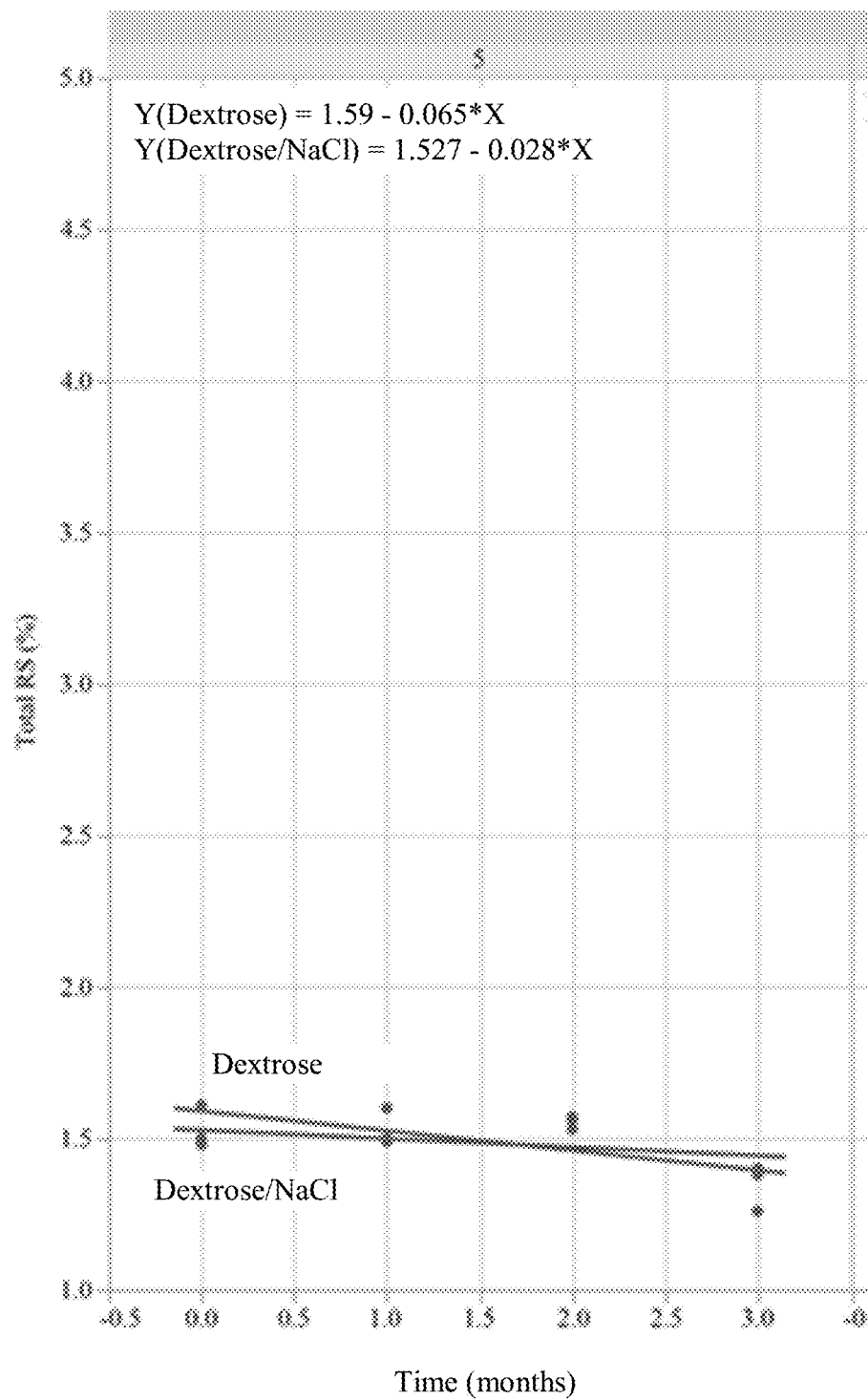
FIG. 60 shows the total impurities of vasopressin after storage at 5° C. of vasopressin formulations prepared in dextrose or dextrose and sodium chloride.
Figure 61:
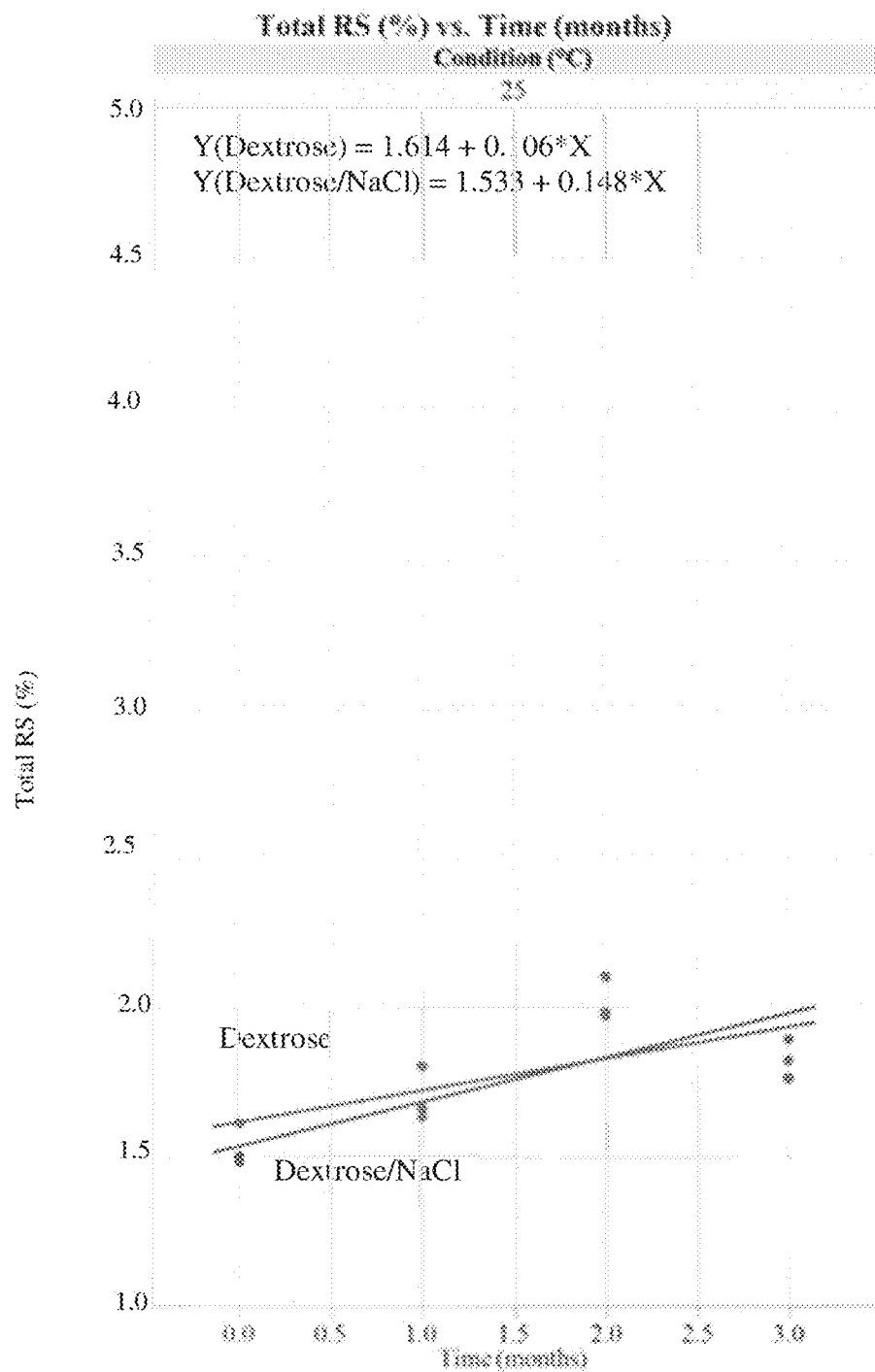
FIG. 61 shows the total impurities of vasopressin after storage at 25° C. of vasopressin formulations prepared in dextrose or dextrose and sodium chloride.
Figure 62:
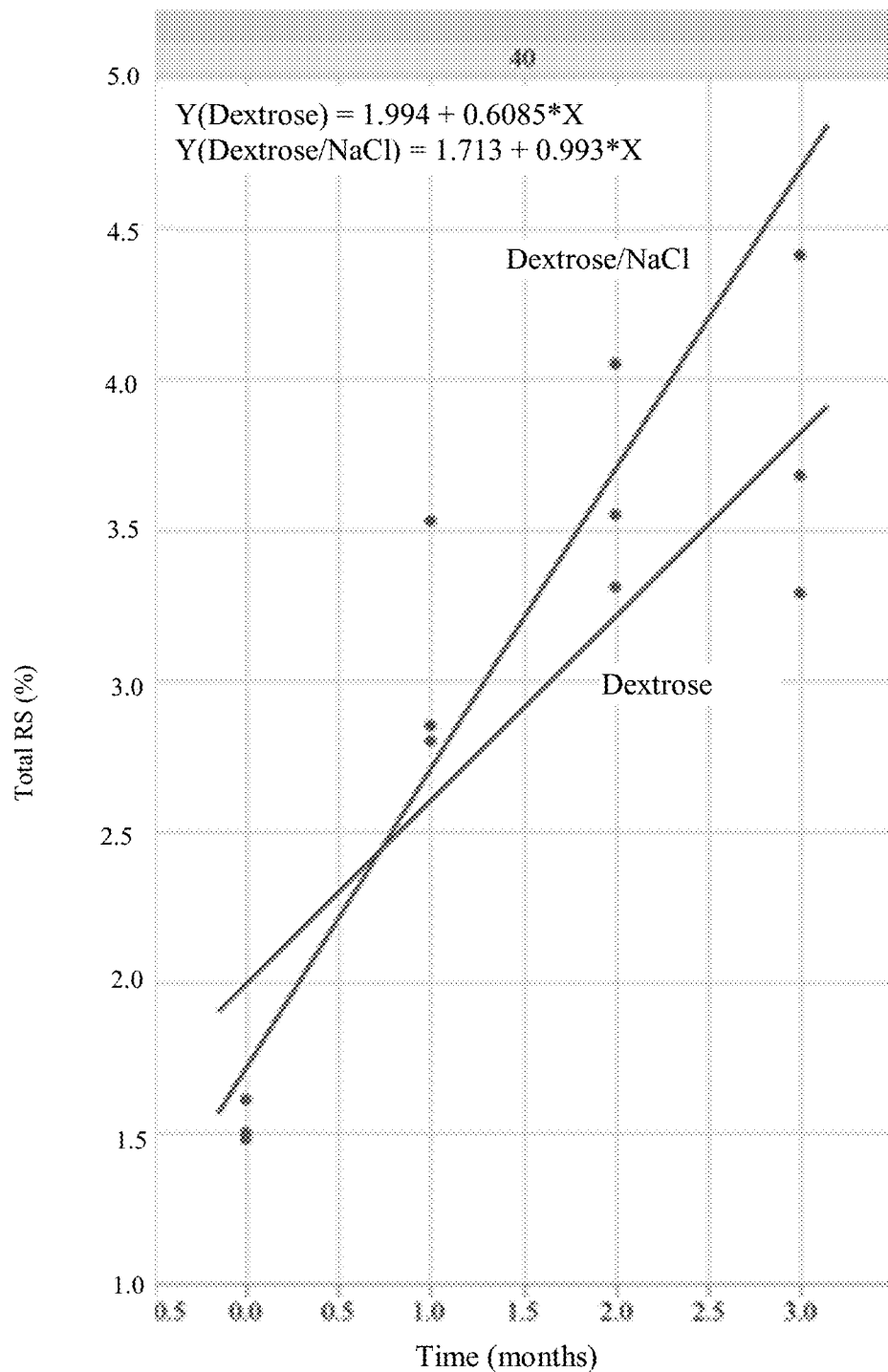
FIG. 62 shows the total impurities of vasopressin after storage at 40° C. of vasopressin formulations prepared in dextrose or dextrose and sodium chloride.

Graphical depictions of TABLES 73-75 are shown in FIGS. 51-62 below. FIGS. 51-53 show the vasopressin (% LC) levels in the samples prepared in dextrose or dextrose and NaCl at 5° C., 25° C., and 40° C., respectively. FIGS. 54-56 show the Gly9-AVP levels in the samples prepared in dextrose or dextrose and NaCl at 5° C., 25° C., and 40° C., respectively. FIGS. 57-59 show the Glu4-AVP levels in the samples prepared in dextrose or dextrose and NaCl at 5° C., 25° C., and 40° C., respectively. FIGS. 60-62 show the total impurities (% RS) levels in the samples prepared in dextrose or dextrose and NaCl at 5° C., 25° C., and 40° C., respectively.

EMBODIMENTS

The following non-limiting embodiments provide illustrative examples of the invention, but do not limit the scope of the invention.

In some embodiments, the invention provides a pharmaceutical composition comprising, in a unit dosage form: a) from about 0.01 mg/mL to about 0.07 mg/mL of vasopressin, or a pharmaceutically-acceptable salt thereof; and b) a polymeric pharmaceutically-acceptable excipient in an amount that is from about 1% to about 10% by mass of the unit dosage form or the pharmaceutically-acceptable salt thereof, wherein the unit dosage form exhibits from about 5% to about 10% less degradation of the vasopressin or the pharmaceutically-acceptable salt thereof after storage for about 1 week at about 60° C. than does a corresponding unit dosage form, wherein the corresponding unit dosage form consists essentially of: A) vasopressin, or a pharmaceutically-acceptable salt thereof; and B) a buffer having acidic pH. In some embodiments, the polymeric pharmaceutically-acceptable excipient comprises a polyalkylene oxide moiety. In some embodiments, the polymeric pharmaceutically-acceptable excipient is a polyethylene oxide. In some embodiments, the polymeric pharmaceutically-acceptable excipient is a poloxamer. In some embodiments, the unit dosage form has an amount of the polymeric pharmaceutically-acceptable excipient that is about 1% the amount of the vasopressin or the pharmaceutically-acceptable salt thereof. In some embodiments, the first unit dosage form exhibits about 10% less degradation of the vasopressin or the pharmaceutically-acceptable salt thereof after storage for about 1 week at about 60° C. than does the corresponding unit dosage form. In some embodiments, the unit dosage form further comprises SEQ ID NO. 2. In some embodiments, the composition further comprises SEQ ID NO. 3. In some embodiments, the composition further comprises SEQ ID NO. 4. In some embodiments, the unit dosage form is an injectable of about 1 mL volume. In some embodiments, the unit dosage form consists essentially of: a) about 0.04 mg/mL of vasopressin, or the pharmaceutically-acceptable salt thereof; b) the polymeric pharmaceutically-acceptable excipient in an amount that is from about 1% to about 10% by mass of the vasopressin or the pharmaceutically-acceptable salt thereof; and c) a plurality of peptides, wherein each of the peptides has from 88% to 90% sequence homology to the vasopressin or the pharmaceutically-acceptable salt thereof. In some embodiments, one of the plurality of peptides is SEQ ID NO.: 2. In some embodiments, one of the plurality of peptides is SEQ ID NO.:3. In some embodiments, wherein one of the plurality of peptides is SEQ ID NO.: 4. In some embodiments, the buffer has a pH of about 3.5.

Embodiment 1

A method of increasing blood pressure in a human in need thereof, the method comprising: intravenously administering to the human a pharmaceutical composition comprising, in a unit dosage form: i) from about 0.1 µg/mL to about 2 µg/mL of vasopressin or a pharmaceutically-acceptable salt thereof; and ii) acetic acid, sodium acetate, or a combination thereof, wherein: the pharmaceutical composition is at about room temperature; the administration to the human is longer than 18 hours; the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

Embodiment 2

The method of embodiment 1, wherein the administration to the human is for about one day.

Embodiment 3

The method of embodiment 1, wherein the administration to the human is for about one week.

Embodiment 4

The method of any one of embodiments 1-3, wherein the human's mean arterial blood pressure is increased within 15 minutes of administration.

Embodiment 5

The method of any one of embodiments 1-4, wherein the human's hypotension is associated with vasodilatory shock.

Embodiment 6

The method of embodiment 5, wherein the vasodilatory shock is post-cardiotomy shock.

Embodiment 7

The method of any one of embodiments 1-6, wherein the administration provides to the human from about 0.03 units of vasopressin or the pharmaceutically-acceptable salt thereof per minute to about 0.1 units of vasopressin or the pharmaceutically-acceptable salt thereof per minute Embodiment 8

The method of embodiment 5, wherein the vasodilatory shock is septic shock.

Embodiment 9

The method of any one of embodiments 1-8, wherein the administration provides to the human from about 0.01 units of vasopressin or the pharmaceutically-acceptable salt thereof per minute to about 0.07 units of vasopressin or the pharmaceutically-acceptable salt thereof per minute Embodiment 10

The method of any one of embodiments 1-9, wherein the unit dosage form further comprises dextrose.

Embodiment 11

The method of any one of embodiments 1-10, wherein the unit dosage form further comprises about 5% dextrose.

Embodiment 12

A method of increasing blood pressure in a human in need thereof, the method comprising: intravenously administering to the human a pharmaceutical composition that consists essentially of, in a unit dosage form: i) from about 0.1 µg/mL to about 2 µg/mL of vasopressin or a pharmaceutically-acceptable salt thereof; ii) dextrose; iii) acetic acid, sodium acetate, or a combination thereof; and iv) optionally hydrochloric acid or sodium hydroxide, wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

Embodiment 13

The method of embodiment 12, wherein the unit dosage form consists essentially of hydrochloric acid.

Embodiment 14

The method of embodiment 12, wherein the unit dosage form consists essentially of sodium hydroxide.

Embodiment 15

The method of any one of embodiments 12-14, wherein the human's mean arterial blood pressure is increased within 15 minutes of administration.

Embodiment 16

The method of any one of embodiments 12-15, wherein the human's hypotension is associated with vasodilatory shock.

Embodiment 17

The method of embodiment 16, wherein the vasodilatory shock is post-cardiotomy shock.

Embodiment 18

The method of any one of embodiments 12-17, wherein the administration provides to the human from about 0.03 units of vasopressin or the pharmaceutically-acceptable salt thereof per minute to about 0.1 units of vasopressin or the pharmaceutically-acceptable salt thereof per minute Embodiment 19

The method of embodiment 16, wherein the vasodilatory shock is septic shock.

Embodiment 20

The method of any one of embodiments 12-19 wherein the administration provides to the human from about 0.01 units of vasopressin or the pharmaceutically-acceptable salt thereof per minute to about 0.07 units of vasopressin or the pharmaceutically-acceptable salt thereof per minute.

Embodiment 21

The method of any one of embodiments 12-20, wherein the unit dosage form consists essentially of 5% dextrose.

Embodiment 22

A method of increasing blood pressure in a human in need thereof, the method comprising: a) storing at 5° C. for at least about one month a pharmaceutical composition for intravenous administration comprising, in a unit dosage form: i) from about 0.1 µg/mL to about 2 µg/mL of vasopressin or a pharmaceutically-acceptable salt thereof; ii) dextrose; and iii) acetic acid, sodium acetate, or a combination thereof, wherein the pharmaceutical composition exhibits no more than about 1% degradation of vasopressin or the pharmaceutically-acceptable salt thereof after the storage at 5° C. for about one month; and b) administering to the human the pharmaceutical composition, wherein the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

Embodiment 23

The method of embodiment 22, wherein the administration to the human is for about one day.

Embodiment 24

The method of embodiment 22, wherein the administration to the human is for about one week.

Embodiment 25

The method of any one of embodiments 22-24, wherein the human's mean arterial blood pressure is increased within 15 minutes of administration.

Embodiment 26

The method of any one of embodiments 22-25, wherein the human's hypotension is associated with vasodilatory shock.

Embodiment 27

The method of embodiment 26, wherein the vasodilatory shock is post-cardiotomy shock.

Embodiment 28

The method of any one of embodiments 22-27, wherein the administration provides to the human from about 0.03 units of vasopressin or the pharmaceutically-acceptable salt thereof per minute to about 0.1 units of vasopressin or the pharmaceutically-acceptable salt thereof per minute Embodiment 29

The method of embodiment 26, wherein the vasodilatory shock is septic shock.

Embodiment 30

The method of any one of embodiments 22-29, wherein the administration provides to the human from about 0.01 units of vasopressin or the pharmaceutically-acceptable salt thereof per minute to about 0.07 units of vasopressin or the pharmaceutically-acceptable salt thereof per minute.

Embodiment 31

The method of any one of embodiments 22-30, wherein the pharmaceutical composition exhibits no more than about 2% degradation of vasopressin or the pharmaceutically-acceptable salt thereof after storage of the pharmaceutical composition at 5° C. for about two months.

Embodiment 32

A method of increasing blood pressure in a human in need thereof, the method comprising: a) storing at 25° C. for at least about one month a pharmaceutical composition for intravenous administration comprising, in a unit dosage form: i) from about 0.1 µg/mL to about 2 µg/mL of vasopressin or a pharmaceutically-acceptable salt thereof; ii) dextrose; and iii) acetic acid, sodium acetate, or a combination thereof, wherein the pharmaceutical composition exhibits no more than about 2% degradation of vasopressin or the pharmaceutically-acceptable salt thereof after the storage at 25° C. for about one month; and b) administering to the human the pharmaceutical composition, wherein the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

Embodiment 33

The method of embodiment 32, wherein the human's mean arterial blood pressure is increased within 15 minutes of administration.

Embodiment 34

The method of any one of embodiments 32-33, wherein the human's hypotension is associated with vasodilatory shock.

Embodiment 35

The method of embodiment 34, wherein the vasodilatory shock is post-cardiotomy shock.

Embodiment 36

The method of any one of embodiments 32-35, wherein the administration provides to the human from about 0.03 units of vasopressin or the pharmaceutically-acceptable salt thereof per minute to about 0.1 units of vasopressin or the pharmaceutically-acceptable salt thereof per minute Embodiment 37

The method of embodiment 35, wherein the vasodilatory shock is septic shock.

Embodiment 38

The method of any one of embodiments 32-37, wherein the administration provides to the human from about 0.01 units of vasopressin or the pharmaceutically-acceptable salt thereof per minute to about 0.07 units of vasopressin or the pharmaceutically-acceptable salt thereof per minute.

Embodiment 39

The method of any one of embodiments 32-38, wherein the pharmaceutical composition exhibits no more than about 5% degradation after storage of the pharmaceutical composition at 25° C. for about two months.

What is claimed is:

1. A method of increasing blood pressure in a human in need thereof, the method comprising:
   a) providing a unit dosage form for intravenous administration, wherein the unit dosage form comprises:
      i) from about 0.1 units/mL to about 1 unit/mL of vasopressin or a pharmaceutically-acceptable salt thereof;
      ii) from about 1 mM to about 10 mM acetate buffer;
      iii) 0-2% vasopressin degradation products;
      iv) sodium chloride; and
      v) water; and
   b) storing the unit dosage form for at least about 24 hours at from about 0.1 units/ml to about 1 unit/ml of vasopressin or a pharmaceutically-acceptable salt thereof; and
   c) after the storing, administering the unit dosage form to the human by intravenous administration, wherein the unit dosage form that is administered to the human comprises from about 0.1 units/mL to about 1 unit/mL of vasopressin or the pharmaceutically-acceptable salt thereof; wherein:
   the unit dosage form has a pH of 3.4 to 3.8; the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

2. The method of claim 1, wherein the administration to the human is over about one day.

3. The method of claim 1, wherein the administration to the human is over about one week.

4. The method of claim 1, wherein the human's mean arterial blood pressure is increased within 15 minutes of administration.

5. The method of claim 1, wherein the human's hypotension is associated with vasodilatory shock.

6. The method of claim 5, wherein the vasodilatory shock is post-cardiotomy shock.

7. The method of claim 6, wherein the administration provides to the human from about 0.03 units of vasopressin or the pharmaceutically-acceptable salt thereof per minute to about 0.1 units of vasopressin or the pharmaceutically-acceptable salt thereof per minute.

8. The method of claim 5, wherein the vasodilatory shock is septic shock.

9. The method of claim 8, wherein the administration provides to the human from about 0.01 units of vasopressin or the pharmaceutically-acceptable salt thereof per minute to about 0.07 units of vasopressin or the pharmaceutically-acceptable salt thereof per minute.

10. The method of claim 1, wherein the pharmaceutically-acceptable salt thereof is present in the unit dosage form.

11. The method of claim 1, wherein the pharmaceutically-acceptable salt thereof is not present in the unit dosage form.

12. The method of claim 1, wherein the unit dosage form further comprises chlorobutanol.

13. The method of claim 1, wherein the unit dosage form comprises about 10 mM acetate buffer, and wherein the unit dosage form has a pH of 3.4 to 3.7.

14. The method of claim 1, wherein the unit dosage form comprises about 1 mM acetate buffer, and wherein the unit dosage form has a pH of 3.5 to 3.8.

* * * * *